(12) United States Patent
Weinstock et al.

(10) Patent No.: US 10,968,496 B2
(45) Date of Patent: Apr. 6, 2021

(54) RECOMBINANT VIBRIO NATRIEGENS ORGANISMS HAVING A MODIFIED OUTER MEMBRANE

(71) Applicant: Codex DNA, Inc., San Diego, CA (US)

(72) Inventors: Matthew T Weinstock, San Diego, CA (US); Daniel G. Gibson, Carlsbad, CA (US); Daniel Strimling, La Jolla, CA (US)

(73) Assignee: Codex DNA, Inc., San Diego, CA (US)

( * ) Notice: Subject to any disclaimer, the term of this patent is extended or adjusted under 35 U.S.C. 154(b) by 0 days.

(21) Appl. No.: 16/154,618

(22) Filed: Oct. 8, 2018

(65) Prior Publication Data

US 2019/0153554 A1  May 23, 2019

Related U.S. Application Data

(60) Provisional application No. 62/588,755, filed on Nov. 20, 2017.

(51) Int. Cl.
| | | |
|---|---|---|
| *C12R 1/63* | (2006.01) | |
| *C12N 15/74* | (2006.01) | |
| *C12N 9/10* | (2006.01) | |

(52) U.S. Cl.
CPC .............. *C12R 1/63* (2013.01); *C12N 9/1029* (2013.01); *C12N 15/74* (2013.01)

(58) Field of Classification Search
None
See application file for complete search history.

(56) References Cited

U.S. PATENT DOCUMENTS

| 10,377,997 B1* | 8/2019 | Weinstock ....... C12Y 207/0700 |
|---|---|---|
| 2010/0112002 A1 | 5/2010 | Lien et al. |
| 2010/0272758 A1 | 10/2010 | Woodard et al. |
| 2013/0230555 A1 | 9/2013 | Trent et al. |
| 2014/0221251 A1* | 8/2014 | Bramhill .................. C12N 9/52 506/14 |
| 2014/0328880 A1 | 11/2014 | Lien et al. |
| 2016/0228523 A1 | 8/2016 | Newman |

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Kizer et al. Appl Environ Microbiol. May 2008;74(10):3229-41. (Year: 2008).*
Prather et al. Curr Opin Biotechnol. Oct. 2008;19(5):468-74. (Year: 2008).*
Weinstock et al. Nat Methods. Oct. 2016;13(10):849-51 (Year: 2016).*
Lee et al. Vibrio natriegens, a new genomic powerhouse. bioRxiv Jun. 12, 2016, pp. 1-30 (Year: 2016).*
International Search Report dated Dec. 26, 2018, regarding PCT/US2018/054883.

* cited by examiner

*Primary Examiner* — Christian L Fronda
(74) *Attorney, Agent, or Firm* — DLA Piper LLP (US)

(57) ABSTRACT

The invention provides engineered *Vibrio* sp. organisms that comprise a genetic modification to either or both of the lpxL and/or lpxM genes. The organisms score substantially lower in an in vitro endotoxin assay versus the unmodified or wild type organism. The organisms preserve substantially the growth rate of the corresponding unmodified organisms. The organisms can also have an exogenous nucleic acid cloned in the organism, or an exogenous nucleic acid encoding a protein, polypeptide, or peptide expressed by the organism, and optionally secreted from the organism.

17 Claims, 8 Drawing Sheets
Specification includes a Sequence Listing.

| Strain | Media | Specific growth rate (hr-1) | |
|---|---|---|---|
| | | Flower well | Round bottom well |
| E. coli BL21(DE3) | LB media | 0.193 | 0.597 |
| | LBv2 media | 0.471 | 0.434 |
| E. coli ClearColi® BL21(DE3) | LB media | 0.106 | 0.16 |
| | LBv2 media | 0.089 | 0.149 |
| V. natriegens (wt) | LBv2 media | 0.758 | 0.903 |
| V. natriegens (ΔlpxL, ΔlpxM) | LBv2 media | 0.645 | 0.698 |

SEQUENCE LISTING

<160> NUMBER OF SEQ ID NOS: 288

<210> SEQ ID NO 1
<211> LENGTH: 922
<212> TYPE: PRT
<213> ORGANISM: Ruminococcus Sp.
<220> FEATURE:
<221> NAME/KEY: misc_feature
<223> OTHER INFORMATION: CDC65743_RspMmc2

<400> SEQUENCE: 1

```
Met Ala Lys Lys Asn Lys Met Lys Pro Arg Glu Leu Arg Glu Ala Gln
1               5                   10                  15

Lys Lys Ala Arg Gln Leu Lys Ala Ala Glu Ile Asn Asn Asn Ala Ala
            20                  25                  30

Pro Ala Ile Ala Ala Met Pro Ala Ala Glu Val Ile Ala Pro Val Ala
        35                  40                  45

Glu Lys Lys Lys Ser Ser Val Lys Ala Ala Gly Met Lys Ser Ile Leu
    50                  55                  60

Val Ser Glu Asn Lys Met Tyr Ile Thr Ser Phe Gly Lys Gly Asn Ser
65                  70                  75                  80

Ala Val Leu Glu Tyr Glu Val Asp Asn Asn Asp Tyr Asn Lys Thr Gln
                85                  90                  95

Leu Ser Ser Lys Asp Asn Ser Asn Ile Glu Leu Gly Asp Val Asn Glu
            100                 105                 110

Val Asn Ile Thr Phe Ser Ser Lys His Gly Phe Gly Ser Gly Val Glu
        115                 120                 125

Ile Asn Thr Ser Asn Pro Thr His Arg Ser Gly Glu Ser Ser Pro Val
130                 135                 140

Arg Gly Asp Met Leu Gly Leu Lys Ser Glu Leu Glu Lys Arg Phe Phe
145                 150                 155                 160

Gly Lys Thr Phe Asp Asp Asn Ile His Ile Gln Leu Ile Tyr Asn Ile
                165                 170                 175

Leu Asp Ile Glu Lys Ile Leu Ala Val Tyr Val Thr Asn Ile Val Tyr
            180                 185                 190

Ala Leu Asn Asn Met Leu Gly Ile Lys Asp Ser Glu Ser Tyr Asp Asp
        195                 200                 205

Phe Met Gly Tyr Leu Ser Ala Arg Asn Thr Tyr Glu Val Phe Thr His
210                 215                 220

Pro Asp Lys Ser Asn Leu Ser Asp Lys Val Lys Gly Asn Ile Lys Lys
225                 230                 235                 240

Ser Leu Ser Lys Phe Asn Asp Leu Leu Lys Thr Lys Arg Leu Gly Tyr
                245                 250                 255

Phe Gly Leu Glu Glu Pro Lys Thr Lys Asp Thr Arg Ala Ser Glu Ala
            260                 265                 270

Tyr Lys Lys Arg Val Tyr His Met Leu Ala Ile Val Gly Gln Ile Arg
        275                 280                 285

Gln Cys Val Phe His Asp Lys Ser Gly Ala Lys Arg Phe Asp Leu Tyr
290                 295                 300

Ser Phe Ile Asn Asn Ile Asp Pro Glu Tyr Arg Asp Thr Leu Asp Tyr
305                 310                 315                 320

Leu Val Glu Glu Arg Leu Lys Ser Ile Asn Lys Asp Phe Ile Glu Gly
                325                 330                 335

Asn Lys Val Asn Ile Ser Leu Leu Ile Asp Met Met Lys Gly Tyr Glu
            340                 345                 350

Ala Asp Asp Ile Ile Arg Leu Tyr Tyr Asp Phe Ile Val Leu Lys Ser
        355                 360                 365

Gln Lys Asn Leu Gly Phe Ser Ile Lys Lys Leu Arg Glu Lys Met Leu
370                 375                 380

Glu Glu Tyr Gly Phe Arg Phe Leu Asp Lys Gln Tyr Asp Ser Val Arg
385                 390                 395                 400
```

-continued

```
Ser Lys Met Tyr Lys Leu Met Asp Phe Leu Phe Cys Asn Tyr Tyr
            405                 410                 415

Arg Asn Asp Val Ala Ala Gly Glu Ala Leu Val Arg Lys Leu Arg Phe
            420                 425                 430

Ser Met Thr Asp Asp Glu Lys Glu Gly Ile Tyr Ala Asp Glu Ala Ala
            435                 440                 445

Lys Leu Trp Gly Lys Phe Arg Asn Asp Phe Glu Asn Ile Ala Asp His
450                 455                 460

Met Asn Gly Asp Val Ile Lys Glu Leu Gly Lys Ala Asp Met Asp Phe
465                 470                 475                 480

Asp Glu Lys Ile Leu Asp Ser Glu Lys Lys Asn Ala Ser Asp Leu Leu
                485                 490                 495

Tyr Phe Ser Lys Met Ile Tyr Met Leu Thr Tyr Phe Leu Asp Gly Lys
                500                 505                 510

Glu Ile Asn Asp Leu Leu Thr Thr Leu Ile Ser Lys Phe Asp Asn Ile
                515                 520                 525

Lys Glu Phe Leu Lys Ile Met Lys Ser Ser Ala Val Asp Val Glu Cys
                530                 535                 540

Glu Leu Thr Ala Gly Tyr Lys Leu Phe Asn Asp Ser Gln Arg Ile Thr
545                 550                 555                 560

Asn Glu Leu Phe Ile Val Lys Asn Ile Ala Ser Met Arg Lys Pro Ala
                565                 570                 575

Ala Ser Ala Lys Leu Thr Met Phe Arg Asp Ala Leu Thr Ile Leu Gly
                580                 585                 590

Ile Asp Asp Asn Ile Thr Asp Asp Arg Ile Ser Glu Ile Leu Lys Leu
                595                 600                 605

Lys Glu Lys Gly Lys Gly Ile His Gly Leu Arg Asn Phe Ile Thr Asn
610                 615                 620

Asn Val Ile Glu Ser Ser Arg Phe Val Tyr Leu Ile Lys Tyr Ala Asn
625                 630                 635                 640

Ala Gln Lys Ile Arg Glu Val Ala Lys Asp Glu Lys Val Val Met Phe
                645                 650                 655

Val Leu Gly Gly Ile Pro Asp Thr Gln Ile Glu Arg Tyr Tyr Lys Ser
                660                 665                 670

Cys Val Glu Phe Pro Asp Met Asn Ser Ser Leu Glu Ala Lys Arg Ser
                675                 680                 685

Glu Leu Ala Arg Met Ile Lys Asn Ile Ser Phe Asp Asp Phe Lys Asn
                690                 695                 700

Val Lys Gln Gln Ala Lys Gly Arg Glu Asn Val Ala Lys Glu Arg Ala
705                 710                 715                 720

Lys Ala Val Ile Gly Leu Tyr Leu Thr Val Met Tyr Leu Leu Val Lys
                725                 730                 735

Asn Leu Val Asn Val Asn Ala Arg Tyr Val Ile Ala Ile His Cys Leu
                740                 745                 750

Glu Arg Asp Phe Gly Leu Tyr Lys Glu Ile Pro Glu Leu Ala Ser
                755                 760                 765

Lys Asn Leu Lys Asn Asp Tyr Arg Ile Leu Ser Gln Thr Leu Cys Glu
                770                 775                 780

Leu Cys Asp Asp Arg Asn Glu Ser Ser Asn Leu Phe Leu Lys Lys Asn
785                 790                 795                 800

Lys Arg Leu Arg Lys Cys Val Glu Val Asp Ile Asn Asn Ala Asp Ser
                805                 810                 815

Ser Met Thr Arg Lys Tyr Arg Asn Cys Ile Ala His Leu Thr Val Val
```

```
                    820                 825                 830
Arg Glu Leu Lys Glu Tyr Ile Gly Asp Ile Arg Thr Val Asp Ser Tyr
                835                 840                 845

Phe Ser Ile Tyr His Tyr Val Met Gln Arg Cys Ile Thr Lys Arg Gly
            850                 855                 860

Asp Asp Thr Lys Gln Glu Lys Ile Lys Tyr Glu Asp Leu Leu
865                 870                 875                 880

Lys Asn His Gly Tyr Thr Lys Asp Phe Val Lys Ala Leu Asn Ser Pro
                885                 890                 895

Phe Gly Tyr Asn Ile Pro Arg Phe Lys Asn Leu Ser Ile Glu Gln Leu
            900                 905                 910

Phe Asp Arg Asn Glu Tyr Leu Thr Glu Lys
            915                 920

<210> SEQ ID NO 2
<211> LENGTH: 919
<212> TYPE: PRT
<213> ORGANISM: Ruminococcus Sp.
<220> FEATURE:
<221> NAME/KEY: misc_feature
<223> OTHER INFORMATION: SCJ78044_Rsp2Mmc2

<400> SEQUENCE: 2

Met Ala Lys Lys Asn Lys Met Lys Pro Arg Glu Leu Arg Glu Ala Gln
1               5                   10                  15

Lys Lys Ala Arg Gln Leu Lys Ala Ala Glu Ile Asn Asn Asn Ala Ala
                20                  25                  30

Pro Ala Ile Ala Ala Met Pro Ala Glu Val Ile Ala Pro Ala Ala
            35                  40                  45

Glu Lys Lys Lys Ser Ser Val Lys Ala Ala Gly Met Lys Ser Ile Leu
50                  55                  60

Val Ser Glu Asn Lys Met Tyr Ile Thr Ser Phe Gly Lys Gly Asn Ser
65                  70                  75                  80

Ala Val Leu Glu Tyr Glu Val Asp Asn Asn Asp Tyr Asn Gln Thr Gln
                85                  90                  95

Leu Ser Ser Lys Asp Asn Ser Asn Ile Gln Leu Gly Gly Val Asn Glu
            100                 105                 110

Val Asn Ile Thr Phe Ser Ser Lys His Gly Phe Glu Ser Gly Val Glu
            115                 120                 125

Ile Asn Thr Ser Asn Pro Thr His Arg Ser Gly Glu Ser Ser Pro Val
130                 135                 140

Arg Gly Asp Met Leu Gly Leu Lys Ser Glu Leu Glu Lys Arg Phe Phe
145                 150                 155                 160

Gly Lys Thr Phe Asp Asp Asn Ile His Ile Gln Leu Ile Tyr Asn Ile
                165                 170                 175

Leu Asp Ile Glu Lys Ile Leu Ala Val Tyr Val Thr Asn Ile Val Tyr
            180                 185                 190

Ala Leu Asn Asn Met Leu Gly Val Lys Gly Ser Glu His Asp Asp
            195                 200                 205

Phe Ile Gly Tyr Leu Ser Thr Asn Asn Ile Tyr Asp Val Phe Ile Asp
        210                 215                 220

Pro Asp Asn Ser Ser Leu Ser Asp Asp Lys Lys Ala Asn Val Arg Lys
225                 230                 235                 240

Ser Leu Ser Lys Phe Asn Ala Leu Leu Lys Thr Lys Arg Leu Gly Tyr
                245                 250                 255
```

-continued

Phe Gly Leu Glu Glu Pro Lys Thr Lys Asp Asn Arg Val Ser Gln Ala
              260                 265                 270

Tyr Lys Lys Arg Val Tyr His Met Leu Ala Ile Val Gly Gln Ile Arg
          275                 280                 285

Gln Cys Val Phe His Asp Lys Ser Gly Ala Lys Arg Phe Asp Leu Tyr
      290                 295                 300

Ser Phe Ile Asn Asn Ile Asp Pro Glu Tyr Arg Asp Thr Leu Asp Tyr
305                 310                 315                 320

Leu Val Glu Glu Arg Leu Lys Ser Ile Asn Lys Asp Phe Ile Glu Asp
                  325                 330                 335

Asn Lys Val Asn Ile Ser Leu Leu Ile Asp Met Met Lys Gly Tyr Glu
              340                 345                 350

Ala Asp Asp Ile Ile Arg Leu Tyr Tyr Asp Phe Ile Val Leu Lys Ser
          355                 360                 365

Gln Lys Asn Leu Gly Phe Ser Ile Lys Lys Leu Arg Glu Lys Met Leu
      370                 375                 380

Asp Glu Tyr Gly Phe Arg Phe Lys Asp Lys Gln Tyr Asp Ser Val Arg
385                 390                 395                 400

Ser Lys Met Tyr Lys Leu Met Asp Phe Leu Leu Phe Cys Asn Tyr Tyr
                  405                 410                 415

Arg Asn Asp Ile Ala Ala Gly Glu Ser Leu Val Arg Lys Leu Arg Phe
              420                 425                 430

Ser Met Thr Asp Asp Lys Glu Gly Ile Tyr Ala Asp Glu Ala Ala
          435                 440                 445

Lys Leu Trp Gly Lys Phe Arg Asn Asp Phe Glu Asn Ile Ala Asp His
      450                 455                 460

Met Asn Gly Asp Val Ile Lys Glu Leu Gly Lys Ala Asp Met Asp Phe
465                 470                 475                 480

Asp Glu Lys Ile Leu Asp Ser Glu Lys Lys Asn Ala Ser Asp Leu Leu
                  485                 490                 495

Tyr Phe Ser Lys Met Ile Tyr Met Leu Thr Tyr Phe Leu Asp Gly Lys
              500                 505                 510

Glu Ile Asn Asp Leu Leu Thr Thr Leu Ile Ser Lys Phe Asp Asn Ile
          515                 520                 525

Lys Glu Phe Leu Lys Ile Met Lys Ser Ser Ala Val Asp Val Glu Cys
      530                 535                 540

Glu Leu Thr Ala Gly Tyr Lys Leu Phe Asn Asp Ser Gln Arg Ile Thr
545                 550                 555                 560

Asn Glu Leu Phe Ile Val Lys Asn Ile Ala Ser Met Arg Lys Pro Ala
                  565                 570                 575

Ala Ser Ala Lys Leu Thr Met Phe Arg Asp Ala Leu Thr Ile Leu Gly
              580                 585                 590

Ile Asp Asp Lys Ile Thr Asp Asp Arg Ile Ser Gly Ile Leu Lys Leu
          595                 600                 605

Lys Glu Lys Gly Lys Gly Ile His Gly Leu Arg Asn Phe Ile Thr Asn
      610                 615                 620

Asn Val Ile Glu Ser Ser Arg Phe Val Tyr Leu Ile Lys Tyr Ala Asn
625                 630                 635                 640

Ala Gln Lys Ile Arg Glu Val Ala Lys Asn Glu Lys Val Val Met Phe
                  645                 650                 655

Val Leu Gly Gly Ile Pro Asp Thr Gln Ile Glu Arg Tyr Tyr Lys Ser
              660                 665                 670

Cys Val Glu Phe Pro Asp Met Asn Ser Ser Leu Gly Val Lys Arg Ser

```
                    675                 680                 685
Glu Leu Ala Arg Met Ile Lys Asn Ile Ser Phe Asp Asp Phe Lys Asn
    690                 695                 700

Val Lys Gln Gln Ala Lys Gly Arg Glu Asn Val Ala Lys Glu Arg Ala
705                 710                 715                 720

Lys Ala Val Ile Gly Leu Tyr Leu Thr Val Met Tyr Leu Leu Val Lys
                725                 730                 735

Asn Leu Val Asn Val Asn Ala Arg Tyr Val Ile Ala Ile His Cys Leu
            740                 745                 750

Glu Arg Asp Phe Gly Leu Tyr Lys Glu Ile Ile Pro Glu Leu Ala Ser
        755                 760                 765

Lys Asn Leu Lys Asn Asp Tyr Arg Ile Leu Ser Gln Thr Leu Cys Glu
    770                 775                 780

Leu Cys Asp Lys Ser Pro Asn Leu Phe Leu Lys Lys Asn Glu Arg Leu
785                 790                 795                 800

Arg Lys Cys Val Glu Val Asp Ile Asn Asn Ala Asp Ser Ser Met Thr
                805                 810                 815

Arg Lys Tyr Arg Asn Cys Ile Ala His Leu Thr Val Val Arg Glu Leu
            820                 825                 830

Lys Glu Tyr Ile Gly Asp Ile Cys Thr Val Asp Ser Tyr Phe Ser Ile
        835                 840                 845

Tyr His Tyr Val Met Gln Arg Cys Ile Thr Lys Arg Glu Asn Asp Thr
    850                 855                 860

Lys Gln Glu Glu Lys Ile Lys Tyr Glu Asp Asp Leu Leu Lys Asn His
865                 870                 875                 880

Gly Tyr Thr Lys Asp Phe Val Lys Ala Leu Asn Ser Pro Phe Gly Tyr
                885                 890                 895

Asn Ile Pro Arg Phe Lys Asn Leu Ser Ile Glu Gln Leu Phe Asp Arg
            900                 905                 910

Asn Glu Tyr Leu Thr Glu Lys
        915

<210> SEQ ID NO 3
<211> LENGTH: 946
<212> TYPE: PRT
<213> ORGANISM: Eubacterium siraeum
<220> FEATURE:
<221> NAME/KEY: misc_feature
<223> OTHER INFORMATION: SG3METG5565466_Es6Mmc2

<400> SEQUENCE: 3

Met Lys Lys Arg Glu Glu Cys Leu Gly Ser Arg Glu Glu Leu Glu Gln
1               5                   10                  15

Lys Asn Leu Lys Lys Trp Glu Glu Thr Asn Ala Glu Asn Arg Arg Ser
            20                  25                  30

Arg Ala Lys Ala Val Gly Val Lys Ser Val Phe Val Val Gly Glu Asp
        35                  40                  45

Leu Tyr Leu Ala Thr Phe Gly Asn Gly Asn Glu Thr Leu Leu Glu Lys
    50                  55                  60

Lys Ile Thr Pro Asp Gly Thr Ile Thr Ser Phe Ser Lys Glu Glu Ala
65                  70                  75                  80

Phe Thr Ala Lys Leu Lys Phe Ala Gln Thr Glu Ser Thr Glu Ala Thr
                85                  90                  95

Ser Ile Gly Ile Ser Asn Gly Arg Ile Val Leu Pro Glu Val Pro Val
            100                 105                 110
```

-continued

```
Asp Asn Pro Cys Tyr Ala Ala Pro Gln Ala Lys Thr Ala Lys Lys Val
            115                 120                 125
Ala Gly Glu Asp Leu Leu Gln Leu Lys Glu Val Leu Glu Lys Arg Tyr
        130                 135                 140
Phe Gly Cys Ser Phe Asp Asp Leu His Ile Arg Leu Ile Tyr Asn
145                 150                 155                 160
Ile Leu Asp Ile Glu Lys Ile Leu Ala Glu Tyr Val Thr Asn Ala Val
                165                 170                 175
Phe Ser Ile Asp Asn Val Ser Gly Asn Ala His Asp Phe Leu Gly Tyr
            180                 185                 190
Leu Ser Thr Arg Asn Ser Tyr Asp Ala Phe Met His Pro Glu Lys Tyr
        195                 200                 205
Pro Glu His Phe Glu Asn Lys Ser Asp Leu Ile Glu Arg Val Arg Lys
    210                 215                 220
Gln Gly Asp Asp Phe Leu Ala Phe Val Asp Asn Lys Arg Ile Gly Tyr
225                 230                 235                 240
Phe Gly Lys Ala Phe Phe Tyr Gln Asp Gly Arg Lys Glu Ile Glu Lys
                245                 250                 255
Pro Asp Gly Glu Ile Tyr His Leu Leu Thr Leu Ile Gly Ser Leu Arg
            260                 265                 270
Gln Trp Ile Thr His Ser Asp Glu Arg Glu Glu Gly Thr Ser Arg Thr
        275                 280                 285
Trp Leu Tyr Gln Leu Glu Lys Phe Leu Leu Pro Glu Tyr Gln Glu Thr
    290                 295                 300
Met Asn Val Asn Tyr Asn Asp Ile Val Lys Glu Leu Thr Thr Asn Phe
305                 310                 315                 320
Thr Lys Thr Asn Ala Thr Asn Leu Asn Phe Leu Ala Glu Leu Leu His
                325                 330                 335
Val Pro Val Lys Ala Ile Ala Glu Ser Tyr Phe Arg Phe Ala Ile Thr
            340                 345                 350
Lys Glu Tyr Lys Asn Leu Gly Phe Cys Ile Lys Thr Ile Arg Glu Ile
        355                 360                 365
Leu Leu Lys Arg Arg Glu Leu Ser Asp Ile Lys Glu Asn His Ala Val
    370                 375                 380
Tyr Asp Ser Ile Arg Ser Lys Leu Tyr Lys Met Met Asp Phe Val Leu
385                 390                 395                 400
Val His Ala Tyr Glu Ser Glu Gly Lys Lys Glu Ala Glu Glu Leu
                405                 410                 415
Ala Ser Ser Leu Arg Phe Ala Leu Thr Glu Glu Lys Glu Ser Ile
        420                 425                 430
Tyr Leu Asn Glu Ala Glu Arg Leu Trp Lys Met Tyr Gly Asp Lys Leu
    435                 440                 445
Leu Lys Ile Lys Asp Phe Lys Gly Ser Gln Val Asn Leu Tyr Ser Tyr
    450                 455                 460
Lys Ser Lys Pro Val Asp Val Gln Leu Pro Ala Ile Leu Lys Pro Ala
465                 470                 475                 480
Lys Glu Val Thr Cys Phe Thr Lys Leu Met Tyr Ile Leu Thr Met Phe
                485                 490                 495
Leu Asp Gly Lys Glu Ile Asn Asp Leu Leu Thr Leu Ile Asn Lys
            500                 505                 510
Phe Asp Asn Ile Asn Ser Leu Leu Lys Thr Met Glu Gln Leu Glu Leu
        515                 520                 525
Gln Thr Ala Phe Val Lys Glu Tyr Thr Phe Phe Ser Gln Ser Gln Arg
```

```
                535                540
Leu Cys Ala Glu Ile Thr Gln Leu Lys Ser Phe Ala Arg Met Gly Lys
545                 550                 555                 560

Pro Val Ser Asn Ala Lys Glu Ala Met Met Ile Asp Ala Ile Gln Ile
                565                 570                 575

Leu Gly Thr Asp Lys Thr Glu Lys Glu Leu Glu Thr Met Ala Lys Arg
            580                 585                 590

Phe Phe Arg Asp Gly Asn Gly Lys Leu Leu Lys Gly Gln His Gly
            595                 600                 605

Met Arg Asn Phe Ile Ala Ser Asn Val Ile Ser Asn Ala Arg Phe His
    610                 615                 620

Tyr Leu Ile Arg Tyr Gly Lys Pro Asp Lys Leu His Lys Leu Ala Gln
625                 630                 635                 640

Asn Glu Ala Val Val Lys Phe Val Leu His Asn Ile Ala Lys Ser Gln
                645                 650                 655

Lys Lys Gln Gly Gln Leu Gly Lys Asn Gln Ile Asp Arg Tyr Tyr Glu
                660                 665                 670

Thr Cys Gly Gly Lys Gln Thr Asn Ala Ser Thr Glu Glu Lys Ile Asp
            675                 680                 685

Phe Leu Ser Ser Ile Leu Thr Gly Met Asn Tyr Asp Gln Phe Gln Asp
    690                 695                 700

Val Lys Gln Ser Asp Gln Arg Ala Thr Pro Gln Glu Arg Arg Asp Lys
705                 710                 715                 720

Glu Lys Tyr Lys Ala Val Ile Ser Leu Tyr Leu Thr Val Leu Tyr Leu
                725                 730                 735

Phe Val Lys Asn Leu Val Asn Ile Asn Ala Arg Tyr Val Ile Gly Phe
                740                 745                 750

His Cys Leu Glu Arg Asp Ala Gln Leu Tyr Ser Gln Lys Phe Gly Ser
            755                 760                 765

Ser Ile Asn Ile Arg Lys Arg Tyr Thr Lys Leu Thr Glu Thr Ile Leu
    770                 775                 780

Gly Tyr Glu Ala Asp Glu Arg Ala Arg Lys Lys Asp Arg Arg Thr Ile
785                 790                 795                 800

Tyr Glu Lys Ala Ala Ala Lys Asn Arg His Leu Lys Asn Val Lys
                805                 810                 815

Trp Asn Cys Lys Thr Arg Glu Asn Leu Glu Arg Ala Asp Ala Asn Ala
            820                 825                 830

Ile Arg Glu Phe Arg Asn Thr Ile Ala His Leu Gly Val Val Arg Asp
    835                 840                 845

Ala Asp Arg Ser Ile Ala Gly Ile Gly Thr Val Thr Cys Tyr Phe Asp
850                 855                 860

Cys Tyr His Tyr Leu Val Gln Lys Glu Leu Ser Ser Leu Lys Asp
865                 870                 875                 880

Lys Asn Ala Tyr Thr Glu Glu Tyr Leu Lys Lys Val Asn Lys Tyr His
                885                 890                 895

Ser Tyr Cys Arg Asp Phe Leu His Val Leu Cys Leu Pro Phe Ala Tyr
            900                 905                 910

Ser Ile Pro Arg Tyr Lys Asn Leu Ser Ile Ala Glu Leu Phe Asp Arg
            915                 920                 925

Asn Asn Leu Ala Glu Glu Pro Lys Glu Thr Asn Ser Ala Val Ala Val
    930                 935                 940

Thr Val
945
```

<210> SEQ ID NO 4
<211> LENGTH: 1057
<212> TYPE: PRT
<213> ORGANISM: Eubacterium siraeum
<220> FEATURE:
<221> NAME/KEY: misc_feature
<223> OTHER INFORMATION: SG3METG12187448_EsMmc2

<400> SEQUENCE: 4

```
Met Glu Glu Thr Lys Val Thr Lys Glu Thr Thr Ile Glu Lys Gln Ser
1               5                   10                  15

Thr Lys Arg His Lys Gln Lys Ser Lys Lys Thr Ala Thr Lys Met Ser
            20                  25                  30

Gly Leu Lys Ser Ala Leu Val Ile Asn Asn His Glu Met Leu Leu Thr
        35                  40                  45

Ser Phe Gly Lys Gly Asn Asn Ala Ile Ala Glu Lys Arg Tyr Ile Leu
    50                  55                  60

Asp Gly Asp Ile Glu Thr Ile Asn Asn Lys Asn Lys Lys Phe Asp Ala
65                  70                  75                  80

Asn Asn Asp Ser Lys Val Val Ile Lys Gly Ile Ser Asn Pro Asn
                85                  90                  95

Gly Gln Leu Thr Asn Pro Leu Phe Asp Gln Ser Pro Thr Ala Ile Gln
            100                 105                 110

Pro Asn Arg Thr Ser Gly Asn Asp Met Ile Gly Ile Arg Arg Met Leu
        115                 120                 125

Glu Arg Lys Tyr Phe Val His Asn Glu Glu Asn Lys Glu Phe Gln Asp
    130                 135                 140

Asn Ile Arg Ile Gln Ile Ala Tyr Cys Ile Leu Asp Ile Glu Lys Ile
145                 150                 155                 160

Leu Met Pro His Ile Asn Asn Ile Cys Phe Glu Ile Asn Asn Met Leu
                165                 170                 175

Arg Leu Glu Gly Tyr Gln Glu Asp Ser Phe Met Gly Ser Phe Asn Leu
            180                 185                 190

Tyr Lys Pro Tyr Asp Ala Phe Ile Ala Thr Thr Asp Asp Lys Glu Ser
        195                 200                 205

Ser Arg Arg Asp Asn Phe Ala Lys Leu Met Thr Ser Lys Gln Val Arg
    210                 215                 220

Tyr Leu Gly Asn Ala Leu Tyr Ser Asp Ser Leu Ser Asn Leu Thr Lys
225                 230                 235                 240

Asp Glu Ile Leu Asp Gly Lys Arg Ser Lys Glu Leu Lys Lys Tyr Tyr
                245                 250                 255

Gln Glu Leu Cys Leu Leu Gly Met Val Arg Gln Ser Met Ile His Ser
            260                 265                 270

Asn Gln Phe Asn Ser Ser Ile Tyr Thr Leu Asp Ser Ser Tyr Asp Ser
        275                 280                 285

Thr Met Asn Thr Ala Glu Leu Leu Gly Lys Gly Asp Asp Ser Ser Leu
    290                 295                 300

Val Ala Leu Ala Thr Asp Ala Arg Val Glu Ala Arg Ala Ile Leu Asp
305                 310                 315                 320

Glu Ile Tyr Lys Lys Gly Val Asp Ser Ile Asn Asn Ser Phe Leu Ser
                325                 330                 335

Asn Ser Ile Asn Asp Leu Glu Asn Leu Phe Lys Ile Tyr Lys Cys Asp
            340                 345                 350

Ser Ser Glu Lys Lys Thr Glu Leu Ile Lys Gln Tyr Tyr Asp Phe Cys
```

-continued

```
            355                 360                 365
Ile Arg Lys Pro Gln Met Asn Met Gly Phe Ser Ile Thr Thr Ile Arg
            370                 375                 380
Glu Gly Met Phe Thr Arg Cys Ser Glu Ala Asn Thr Leu Leu Leu Cys
385                 390                 395                 400
Asp Glu Gly Ser Thr Val Lys Leu Asn Val His Asp Thr Met Lys Ser
                    405                 410                 415
Lys Phe Tyr Lys Asn Leu Asp Phe Met Ile Tyr Lys Tyr Tyr Lys Tyr
                420                 425                 430
Glu Asn Pro Glu Lys Gly Glu Lys Leu Ile Glu Asp Leu Arg Ser Lys
            435                 440                 445
Ile Lys Gly Lys Lys Lys Glu Asp Glu Asp Lys Lys Gln Arg Tyr Ala
        450                 455                 460
Glu Glu Ser Ala Cys Ile Leu Lys Ala Lys Arg Asp Ile Ile Lys Lys
465                 470                 475                 480
Asp Leu Thr Glu Ala Ala Asn Lys Asp Leu Phe Ala Asp Leu Val Lys
                    485                 490                 495
Ser Asn Lys Asn Glu Lys Gln Lys Phe Lys Asn Glu Tyr Glu Glu Leu
                500                 505                 510
Leu Lys Pro Phe Met Ile Pro Val Lys Val Asp Tyr Phe Ser Glu Leu
            515                 520                 525
Ile Tyr Leu Val Thr Arg Phe Leu Ser Gly Lys Glu Ile Asn Asp Leu
        530                 535                 540
Leu Thr Gln Leu Ile Asn Lys Phe Glu Asn Ile Ala Ala Phe Ile Arg
545                 550                 555                 560
Met Tyr Gln Asn Asp Gln Gly Lys Leu Glu Phe Thr Ala Asn Tyr Lys
                    565                 570                 575
Met Phe Glu Ile Asp Pro Gln Lys Asp Ile Pro Lys Asp Gly Lys Arg
                580                 585                 590
Val Leu Ser Gly Ser Ala Lys Ile Ala Tyr Tyr Leu Arg Thr Ile Asn
            595                 600                 605
Tyr Ile Ala Arg Met Glu Ser Phe Glu Ile Lys Ser Asp Lys Thr Ala
        610                 615                 620
Ile Asn Asp Ala Ile Ser Leu Leu Gly Tyr Asn Ser Asn Glu His Arg
625                 630                 635                 640
Asp Glu Phe Ile Thr Tyr Thr Met Ala Lys His Val Val Asp Lys Tyr
                    645                 650                 655
Gln Asn Thr Asp Tyr Gln Lys Ile Val Lys Asp Phe Leu Ser Ala Asn
                660                 665                 670
Lys Thr Leu Asp Cys Lys Ser Lys Asn Met Gln Ala Phe Val Ser Glu
            675                 680                 685
Leu Lys Asn Ala His Leu Ser Glu Asn Tyr Glu Gln Arg Glu Lys Glu
        690                 695                 700
Ile Tyr Glu Leu Ala Asp Thr Asn Leu Pro Ala Tyr Phe Ser Glu Glu
705                 710                 715                 720
Asp Lys Glu Lys Leu Ala Arg Tyr Ile Val His Ser Asp Gly Thr Tyr
                    725                 730                 735
Lys Lys Phe Leu Lys Glu Ser Tyr Ala Ile Glu Glu Leu Pro Asn
                740                 745                 750
Glu Gly Phe Arg Asn Phe Ile Ser Asn Val Ile Asn Ser Arg Arg
            755                 760                 765
Phe Asn Tyr Ile Met Arg Phe Cys Asn Pro Glu Lys Ile Ala Asn Ile
        770                 775                 780
```

Gly Lys Asn Lys Val Leu Ile Ser Phe Ala Leu Ser Ser Leu Ala Glu
785                 790                 795                 800

Lys Thr Asp Met Ile Ala Lys Tyr Tyr Arg Val Phe Cys Asp Arg Ile
                805                 810                 815

Asp Asp Gln Lys Thr Met Glu Asp Tyr Leu Val Asn Lys Leu Thr Lys
            820                 825                 830

Ile Ser Tyr Thr Glu Phe Leu Asn Val Asn Gln Lys Ala Asn Ala Glu
        835                 840                 845

Lys Asn Lys Glu Lys Asp Arg Ser Gln Lys Leu Ile Gly Leu Tyr Ile
850                 855                 860

Thr Leu Leu Tyr Glu Ile Val Lys Asn Leu Val Asn Ile Asn Ser Arg
865                 870                 875                 880

Tyr Asn Ile Ala Phe Gln Arg Cys Asp Asn Asp Ser Ile Met Ile Leu
                885                 890                 895

Gln Gly Gln Tyr Asp Glu Arg Ala Val Gln Glu Ser Lys Leu Thr Lys
            900                 905                 910

Lys Phe Ile Ser Asn Gln Lys Leu Asn Ser Tyr Ser Cys Arg Tyr Leu
        915                 920                 925

Thr His Asn Ile Ser Gln Leu Asp Arg Cys Asn Asp Phe Ile Arg Gln
930                 935                 940

Tyr Arg Asn Lys Val Ala His Leu Glu Val Val Ser Asn Ile Asp Glu
945                 950                 955                 960

Tyr Leu Ser Gly Ile Lys His Ile Glu Ser Tyr Tyr Ala Leu Tyr His
                965                 970                 975

Tyr Leu Met Gln Lys Cys Leu Leu Lys Asn Tyr Arg Ile Glu Asp His
            980                 985                 990

Ser Gln Asn Glu Tyr Lys Asn Leu Asn Asp Phe Ser Ser Lys Leu Asp
        995                 1000                1005

Lys His Gly Thr Tyr Val Lys Asp Phe Val Lys Ala Leu Asn Val
    1010                1015                1020

Pro Phe Gly Tyr Asn Leu Pro Arg Tyr Lys Asn Leu Ser Ile Asp
    1025                1030                1035

Glu Leu Phe Asp Arg Asn Lys Leu Lys Thr Gly Gly Thr Ile Glu
    1040                1045                1050

Met Lys Gly Glu
    1055

<210> SEQ ID NO 5
<211> LENGTH: 953
<212> TYPE: PRT
<213> ORGANISM: Ruminococcus flavefaciens
<220> FEATURE:
<221> NAME/KEY: misc_feature
<223> OTHER INFORMATION: SG3METG14260312_Rf3Mmc2

<400> SEQUENCE: 5

Met Ile Glu Lys Lys Lys Ser Tyr Ala Lys Gly Met Gly Leu Lys Ser
1               5                   10                  15

Thr Leu Val Ser Asp Ser Lys Val Tyr Met Thr Ser Phe Gly Asn Gly
            20                  25                  30

Asn Asp Ala Arg Leu Glu Lys Val Glu Asn Asn Ala Ile Ser Cys
        35                  40                  45

Leu Val Asp Lys Lys Glu Ala Phe Val Ala Glu Ile Thr Asp Lys Asn
50                  55                  60

Ala Gly Tyr Lys Ile Ile Asn Lys Lys Phe Gly His Pro Lys Gly Tyr

```
            65                  70                  75                  80
Asp Val Val Ala Asn Asn Pro Leu Tyr Thr Gly Pro Val Gln Gln Asp
                    85                  90                  95
Met Leu Gly Leu Lys Glu Thr Leu Glu Lys Arg Tyr Phe Gly Ser Ser
                100                 105                 110
Val Ser Gly Asn Asp Asn Ile Cys Ile Gln Val Ile His Asn Ile Leu
                115                 120                 125
Asp Ile Glu Lys Ile Leu Ala Glu Tyr Ile Thr Asn Ala Ala Tyr Ala
            130                 135                 140
Val Asn Asn Ile Ala Gly Leu Asp Lys Asp Ile Ile Gly Phe Gly Lys
145                 150                 155                 160
Phe Ser Thr Val Tyr Thr Phe Asp Glu Phe Arg Asn Ser Ser Glu Phe
                    165                 170                 175
Lys Cys Val Tyr Glu Glu Phe Lys Arg Phe Ile Asn Asn Ser Arg Phe
                180                 185                 190
Gly Tyr Phe Gly Lys Ala Phe Phe Tyr Lys Asn Lys Lys Asp Tyr Ser
                195                 200                 205
Leu Lys Lys Asn Ser Gln Cys Tyr His Ile Leu Ala Leu Leu Ser Gly
            210                 215                 220
Leu Arg Asn Trp Val Val His Asn Asn Glu Val Glu Ser Lys Ile Asp
225                 230                 235                 240
Arg Lys Trp Leu Tyr Asn Leu Asp Lys Asn Leu Asp Lys Glu Tyr Ile
                    245                 250                 255
Thr Thr Leu Asp Tyr Met Tyr Ser Asp Ile Ala Asp Glu Leu Thr Lys
                260                 265                 270
Ser Phe Ser Lys Asn Ser Ala Ala Asn Val Asn Tyr Ile Ala Glu Ile
                275                 280                 285
Leu Asn Ile Asp Ser Lys Thr Phe Ala Glu Gln Tyr Phe Arg Phe Ser
            290                 295                 300
Ile Met Lys Glu Gln Lys Asn Leu Gly Phe Thr Leu Thr Lys Leu Arg
305                 310                 315                 320
Glu Cys Met Leu Asp Arg Glu Glu Leu Ser Asp Ile Arg Asp Asn His
                    325                 330                 335
Lys Glu Phe Asp Ser Ile Arg Ser Lys Leu Tyr Thr Met Met Asp Phe
                340                 345                 350
Val Ile Tyr Arg Tyr Tyr Ile Glu Glu Ala Lys Lys Ile Glu Asn Glu
                355                 360                 365
Asn Lys Thr Leu Ser Asp Asp Lys Lys Lys Leu Ser Glu Lys Asp Ile
            370                 375                 380
Phe Ile Ile Ser Leu Arg Gly Ser Phe Ser Glu Glu Gln Lys Asp Lys
385                 390                 395                 400
Leu Tyr Ser Asp Glu Ala Glu Arg Leu Trp Ala Lys Leu Gly Lys Leu
                    405                 410                 415
Met Leu Asp Ile Lys Lys Phe Gln Gly Tyr Arg Thr Asp Lys Tyr Lys
                420                 425                 430
Glu Lys Gly Ala Pro Ile Leu Asn Arg Ile Leu Pro Glu Ser Glu Asp
                435                 440                 445
Val Ser Thr Phe Ser Lys Leu Met Tyr Ala Leu Thr Met Phe Leu Asp
            450                 455                 460
Gly Lys Glu Ile Asn Glu Leu Leu Thr Thr Leu Ile Asn Lys Phe Asp
465                 470                 475                 480
Asn Ile Gln Ser Met Leu Lys Ile Met Pro Leu Ile Gly Val Asn Ala
                    485                 490                 495
```

```
Lys Phe Ser Ser Asp Tyr Ala Phe Phe Asn Asn Ser Glu Lys Ile Ala
              500                 505                 510

Asp Glu Leu Lys Leu Ile Lys Ser Phe Ala Arg Met Gly Glu Pro Val
        515                 520                 525

Ala Ser Thr Lys Arg Asp Met Met Ile Asp Ala Ile Lys Ile Leu Gly
530                 535                 540

Thr Asp Leu Asp Asp Asn Glu Leu Lys Lys Arg Ala Asp Ser Phe Phe
545                 550                 555                 560

Lys Asp Ser Asn Gly Lys Met Leu Ala Lys Gly Lys His Gly Met Arg
                565                 570                 575

Asn Phe Ile Ile Asn Asn Val Val Asn Lys Arg Phe His Tyr Ile
                580                 585                 590

Ile Arg Tyr Gly Asp Pro Ala His Leu His Glu Ile Ala Lys Asn Glu
            595                 600                 605

Ala Val Val Arg Phe Val Leu Gly Arg Ile Ala Asp Ile Gln Lys Lys
        610                 615                 620

Gln Gly Lys Cys Gly Lys Asn Gln Ile Asp Arg Tyr Tyr Glu Ile Cys
625                 630                 635                 640

Ile Gly Asn Asp Tyr Gly Lys Ser Val Ser Glu Lys Ile Asp Ala Leu
                645                 650                 655

Thr Lys Val Ile Ile Asn Met Asn Tyr Asp Gln Phe Glu Ala Lys Arg
                660                 665                 670

Lys Val Ile Glu Asn Ser Lys Arg Asp Asn Ala Glu Arg Glu Lys Tyr
            675                 680                 685

Lys Lys Ile Ile Ser Leu Tyr Leu Thr Val Ile Tyr Gln Ile Leu Lys
        690                 695                 700

Asn Leu Val Asn Val Asn Ser Arg Tyr Val Ile Gly Phe His Cys Val
705                 710                 715                 720

Glu Arg Asp Ala Gln Leu Tyr Met Glu Lys Gly Tyr Asp Ile Asn Leu
                725                 730                 735

Lys Lys Leu Gly Asn Asn Gly Phe Thr Ser Val Thr Lys Leu Cys Val
                740                 745                 750

Gly Ile Ala Asp Asp Pro Val Lys Tyr Lys Asn Val Glu Ile Glu
            755                 760                 765

Leu Lys Glu Arg Ala Leu Ala Ser Phe Asp Ala Leu Glu Lys Glu Asn
770                 775                 780

Pro Glu Leu Tyr Lys Lys Tyr Asn Met Tyr Ser Glu Lys Gln Lys Glu
785                 790                 795                 800

Ala Glu Leu Glu Lys Gln Ile Lys Arg Glu Lys Ala Lys Thr Ala Leu
                805                 810                 815

Asn Ala His Leu Arg Asn Thr Lys Trp Asn Asp Arg Val Arg Glu Asn
            820                 825                 830

Ile Arg Asn Thr Glu Lys Asp Ala Cys Lys Gln Phe Arg Asn Lys Ala
        835                 840                 845

Asp His Leu Glu Val Ala Arg Tyr Ala His Lys Tyr Ile Asn Asp Ile
850                 855                 860

Ser Glu Val Asn Ser Tyr Phe Gln Leu Tyr His Tyr Ile Met Gln Arg
865                 870                 875                 880

Ile Ile Ile Asp Ser Ser Gly Asn Asn Ala Asn Gly Met Met Lys Lys
                885                 890                 895

Tyr Tyr Glu Ser Val Ile Ser Asp Lys Lys Tyr Asn Asp Arg Leu Leu
            900                 905                 910
```

-continued

```
Lys Leu Leu Cys Val Pro Phe Gly Tyr Cys Ile Pro Arg Phe Lys Asn
            915                 920                 925

Leu Ser Ile Glu Ala Leu Phe Asp Lys Asn Glu Ala Ala Lys Tyr Asp
            930                 935                 940

Lys Met Lys Lys Val Ala Val Arg
945                 950

<210> SEQ ID NO 6
<211> LENGTH: 911
<212> TYPE: PRT
<213> ORGANISM: Eubacterium siraeum
<220> FEATURE:
<221> NAME/KEY: misc_feature
<223> OTHER INFORMATION: SG3METG14270245_Es2Mmc2

<400> SEQUENCE: 6

Met Val Met Glu Asn Lys Glu Asn Ile Gly Lys Val Glu Asn Gln Asn
1               5                   10                  15

His Lys Lys Arg Ser Gly Ala Lys Ala Ser Gly Leu Lys Ser Thr Phe
            20                  25                  30

Ala Leu Gly Glu Asn Arg Val Leu Met Thr Ser Phe Gly Lys Gly Asn
            35                  40                  45

Glu Ala Ile Pro Glu Lys Leu Ile Val Asp Gly Ala Val Thr Asp Tyr
    50                  55                  60

Glu Lys Asn Leu Glu Val Thr Pro Leu Lys Lys Asp Phe Lys Val Lys
65                  70                  75                  80

Gly Lys His Phe Asn Asn Pro Ile Val Ala Ser Asp Pro Tyr Arg Arg
                85                  90                  95

Thr Lys Val Gly Lys Asp Val Ile Asp Arg Lys Glu Val Leu Glu Gln
            100                 105                 110

Lys Tyr Tyr Gly Arg Thr Phe Asp Asp Asn Ile His Ile Gln Leu Ile
            115                 120                 125

Tyr Asn Ile Met Asp Ile Glu Lys Ile Leu Ser Val His Ile Asn Asn
        130                 135                 140

Ile Leu Tyr Gly Leu Asn Asn Val Leu Asn Arg Asn Ser Asp Asp Ala
145                 150                 155                 160

Ser Asp Ile Ile Gly Met Met Arg Ser Lys Pro Tyr Ser Asp Phe Cys
                165                 170                 175

Val Ala Asn Asp Thr Tyr Glu Gln Phe Lys Gly His Leu Lys Asn Ser
            180                 185                 190

Gln Leu Ser Tyr Tyr Gly Thr Ala Phe Tyr Lys Thr Gly Phe Asp Ile
            195                 200                 205

Lys Ala Lys Lys Glu Arg Val Leu Lys Arg Asp Glu Lys Asp Ile Tyr
        210                 215                 220

Tyr Ile Leu Ser Leu Leu Ser Thr Val Arg Gln Phe Leu Ala His Lys
225                 230                 235                 240

Ser Asp Asp Asn Arg Asn Ser Lys Lys Asp Asn Tyr Gln Val Ala Leu
                245                 250                 255

Tyr Thr Phe Asp Glu Glu Phe Asp Asn Leu Tyr Lys Glu Lys Asn Ile
            260                 265                 270

Val Phe Arg Lys Asp Ala Arg Lys Val Leu Asp Gly Leu Tyr Asp Ser
            275                 280                 285

Arg Val Ile Ser Leu Asn Glu Ser Phe Leu Lys Asn Ala Lys Lys Asp
        290                 295                 300

Leu Thr Ile Leu Phe Lys Ala Tyr Gly Ile Glu Asn Arg Gly Asp Lys
305                 310                 315                 320
```

-continued

```
Met Lys Leu Ile Arg Glu Tyr Tyr Asp Phe Leu Ile Arg Lys Ser Tyr
            325                 330                 335

Lys Asn Leu Gly Phe Ser Leu Lys Leu Leu Arg Glu Cys Ile Ile Ser
            340                 345                 350

Glu Asn Arg Trp Ile Ser Gly Lys Lys Tyr Asp Thr Met Arg Ser Arg
            355                 360                 365

Leu Asn Arg Leu Phe Asp Phe Val Val Tyr Lys Tyr Tyr Glu Glu Asn
            370                 375                 380

Gln Thr Arg Ala Thr Val Leu Val Glu Lys Leu Arg Ala His Ser Cys
385                 390                 395                 400

Gln Glu Glu Lys Asp Arg Ile Tyr Ile Asp Glu Ser Leu Val Leu Trp
                405                 410                 415

Lys Gly Ile Lys Ser Ile Val Ser Asp Lys Ile Leu Ala Glu Met Asn
            420                 425                 430

Gly Lys Asn Leu Ala Thr Met Arg Ile Asp Pro Ala Ile Gly Glu Thr
            435                 440                 445

Ser Ile Glu Arg Leu Thr Ala Pro Glu Trp Lys Pro Ile Val Thr Thr
    450                 455                 460

Ala Thr Tyr Phe Thr Lys Ile Val Tyr Leu Leu Thr Leu Phe Leu Asp
465                 470                 475                 480

Gly Lys Glu Ile Asn Asp Met Val Thr Thr Leu Ile Asn Lys Phe Glu
                485                 490                 495

Asn Ile Ala Ser Phe Asn Glu Val Leu Ser Ser Ala Gly Cys Gln Thr
            500                 505                 510

Gln Ile Asn Arg Glu Tyr Leu Ile Phe Glu Asn Ser Glu Glu Val Ser
            515                 520                 525

Lys Glu Leu Arg Val Leu Asn Ser Phe Ala Arg Met Glu Val Pro Asp
530                 535                 540

Ala Ser Thr Asn Arg Glu Met Phe Val Glu Ala Ala Lys Ile Leu Gly
545                 550                 555                 560

Tyr Asp Ala Gly Arg Lys Asn Leu Glu Gln Tyr Phe Asp Thr Leu Leu
                565                 570                 575

Asp Lys Asn Ala Ser Lys Ala Glu Lys Gly Phe Arg Asn Phe Ile Arg
            580                 585                 590

Asn Asn Val Ile Asn Ser Leu Arg Phe Lys Tyr Leu Ile Lys Tyr Cys
            595                 600                 605

Asn Ile Glu Asp Val Lys Cys Phe Ser Lys Asn Lys Ser Leu Val Glu
    610                 615                 620

Phe Val Met Lys Ser Ile Pro Glu Ala Gln Ile Leu Arg Tyr Tyr Lys
625                 630                 635                 640

Ser Cys Ile Asn Glu Phe Ala Asp Lys Tyr Ser Asp Asn Met Arg Ser
                645                 650                 655

Glu Leu Ser Asp Val Ile Val Ser Met Ser Phe Glu Lys Leu Lys Gly
            660                 665                 670

Val Val Gln Gln Ala Asn Arg Asn Thr Lys Glu Glu Lys Glu Lys Leu
            675                 680                 685

Gln Lys Gln Asn Val Ile Arg Leu Tyr Leu Thr Val Cys Tyr Leu Phe
    690                 695                 700

Phe Lys Asn Leu Val Tyr Val Asn Ser Arg Tyr Phe Leu Ala Phe Tyr
705                 710                 715                 720

Cys Leu Glu Arg Asp Met Lys Leu Trp Asp Tyr Glu Lys Pro Gly Phe
                725                 730                 735
```

-continued

```
Ser Glu Ser Tyr Asn Ser Tyr Asn Thr Leu Thr Glu Lys Phe Ile Glu
                740                 745                 750

Glu Asp Lys Ile Arg Arg Thr Ala Lys Arg Lys Val Ile Asp Asp
            755                 760                 765

Ser Gly Asn Val Arg Tyr Glu Glu Val Ser Glu Lys His Ile Pro Ala
770                 775                 780

Val Tyr Leu Lys Asn Asn Leu Glu Asn Ser Asp Asn Ala Val Ile His
785                 790                 795                 800

Ala Phe Arg Asn Ser Ala Glu His Met Asn Ala Val Arg Arg Cys Ser
                805                 810                 815

Lys Tyr Leu Gly Ser Ile Ser Ser Val Glu Ser Tyr Phe Glu Ile Tyr
            820                 825                 830

His Tyr Ile Thr Gln Cys Tyr Leu Arg Glu Cys Leu Met Asn Ser Asp
        835                 840                 845

Asn Val Lys Asn Pro Lys Ile Val Glu Tyr Phe Glu Asn Val Glu Lys
    850                 855                 860

Tyr Arg Lys Tyr Ser Lys Asp Phe Val Lys Ala Leu Cys Ile Pro Phe
865                 870                 875                 880

Gly Tyr Asn Leu Ala Arg Phe Lys Asn Leu Ser Ile Asp Gly Leu Phe
                885                 890                 895

Asp Met His Asp Glu Arg Glu Asp Lys Lys Thr Gly Ile Asp Asp
            900                 905                 910

<210> SEQ ID NO 7
<211> LENGTH: 913
<212> TYPE: PRT
<213> ORGANISM: Ruminococcus Sp.
<220> FEATURE:
<221> NAME/KEY: misc_feature
<223> OTHER INFORMATION: SG3METG14353528_Rs5Mmc2

<400> SEQUENCE: 7

Met Ser Ser Lys Lys Thr Asn Thr Lys Arg Leu Gly Ile Lys Ser Ile
1               5                   10                  15

Phe Ala His Ala Gly Asp Gln Leu Thr Met Thr Glu Phe Gly Arg Gly
            20                  25                  30

Asn Lys Ala Glu Ile Gly Phe His Ala Gly Glu Arg Gly Arg Asp Leu
        35                  40                  45

Ala Cys Pro His Arg Thr Lys Asn Phe Thr Val Asn Gln Ile Asp Glu
    50                  55                  60

Leu Ile Asp Leu Glu Lys Gly Ser Leu Glu Leu Leu Asn Asn Pro
65                  70                  75                  80

Ala Glu Lys Val Gln Glu Asp Tyr Leu Gln Leu Lys Gly Glu Leu Glu
                85                  90                  95

Lys Leu Phe Phe Gly Gln Glu Phe Pro His Asp Asn Val Arg Ile Gln
            100                 105                 110

Ile Ile His Asn Ile Leu Asp Ile Leu Lys Ile Phe Gly Leu Tyr Val
        115                 120                 125

Asn Asp Ile Ile Tyr Thr Val Asn Asn Leu Ser Asp Glu Pro Thr Asp
    130                 135                 140

Ile Ile Gly Leu Gly Asp Gly Lys Lys Gln Glu Ala Leu Lys Lys Met
145                 150                 155                 160

Thr Pro Tyr Phe Gly Tyr Phe Gly Asp Ala Phe Lys Val Leu Pro Lys
                165                 170                 175

Leu Lys Asn Gly Lys Gln Asn Ser Asn Glu Asp Met Glu Arg Ile Asn
            180                 185                 190
```

```
Asp His Asn Leu Asn Val Leu Arg Ile Leu Gly Asp Leu Arg Gln Trp
    195                 200                 205

Ser Ala His Phe Lys Thr Lys Lys Asp Ala Val Lys Lys Phe Ile Phe
210                 215                 220

Ser Ser Lys Tyr Gly Leu Ile Gln Pro Glu Gly Met Gln Lys Glu Glu
225                 230                 235                 240

Ile Ser Asn Glu Gly Val Lys Trp Glu Thr Ile Lys Asn Leu Tyr Cys
                245                 250                 255

Lys Arg Ile Asp Ala Val Asn Lys Asp Phe Phe Asp His Ser Lys Met
                260                 265                 270

Asn Leu Asn Ile Ile Phe Asp Leu Leu Gly Ile Thr Glu Thr Ala Asp
                275                 280                 285

Lys Val Asp Ile Val Gln Glu Tyr Tyr Arg Phe Ser Ile Leu Lys Glu
            290                 295                 300

Gly Lys Asn Leu Gly Val Asn Met Thr Lys Leu Arg Glu Phe Ile Val
305                 310                 315                 320

Asp Lys Tyr Tyr Pro Gln Leu Lys Asp Lys Met His Asp Ser Tyr Arg
                325                 330                 335

His Lys Ile Tyr Thr Ile Thr Asp Phe Val Leu Phe Arg Leu Leu Asn
            340                 345                 350

Asn Ser Asp Leu Leu Asp Ile Ile Ile Pro Glu Leu Arg Lys Ala Pro
            355                 360                 365

Asn Glu Glu Lys Lys Glu Ser Ile Tyr Arg Ser Phe Ser Cys Asn Val
        370                 375                 380

Trp Lys Met Ala Gln Gly Gln Leu Lys Pro Phe Phe Glu Lys Phe His
385                 390                 395                 400

Gly Arg Phe Pro Lys Phe Ser Thr Asp Thr Asp Pro Ser Leu Asn Ile
                405                 410                 415

Asp Arg Val Lys Ile Asn Thr Lys Glu Thr Tyr Pro Phe Val Met Val
                420                 425                 430

Leu Ser Phe Met Cys Asn Phe Leu Glu Gly Lys Glu Ile Asn Glu Leu
            435                 440                 445

Leu Thr Ala Tyr Ile His Lys Phe Glu Asn Ile Gln Ser Phe Ile Asp
    450                 455                 460

Thr Leu Lys Asn Leu Asp Asp Thr Pro Glu Phe Lys Ser Lys Met Phe
465                 470                 475                 480

Asp Met Phe Asn Ala Glu Asn His Glu Trp Ala Gly Lys Ile Ala Gln
                485                 490                 495

Gln Leu Arg Val Leu Ala Ser Ile Gly Lys Met Lys Pro Asp Leu Asn
                500                 505                 510

Gly Ala Lys Arg Leu Leu Tyr Lys Ala Ala Ile Gln Thr Leu Gly Ile
            515                 520                 525

Pro Asp Asp Ser Glu Tyr Ile Thr Asp Lys Trp Leu Glu Glu Asn Val
530                 535                 540

Leu Leu Asp Gln Ser Asp Lys Glu Arg Tyr Ala Ala Arg Lys Thr Glu
545                 550                 555                 560

Thr Asn Pro Phe Arg Asn Phe Ile Ala Gly Asn Val Ile Ser Ser Arg
                565                 570                 575

Arg Phe Met Tyr Leu Val Arg Tyr Thr Lys Pro Arg Thr Val Arg Ala
                580                 585                 590

Leu Met Gln Asn Gln Ala Ile Val Arg Tyr Val Leu Thr Arg Leu Pro
            595                 600                 605
```

Val Ala Gln Ile Asp Ser Tyr Cys Ser Asn Leu Leu Asp Lys Met Gln
610                 615                 620

Gly Ser Val Ser Leu Asp Gln Lys Tyr Asp Leu Leu Thr Asn Lys Leu
625                 630                 635                 640

Ser Gly Leu Ser Phe Glu Ser Tyr Val Asp Ser Arg His Gly Ile Ile
            645                 650                 655

Glu Asn Ser Arg Lys His Ser Gln Lys Asn Ile Glu Ile Glu Arg Leu
            660                 665                 670

Lys Gly Leu Thr Ser Leu Tyr Leu Thr Val Ala Tyr Ala Ile Lys
                675                 680                 685

Asn Leu Val Lys Thr Asn Ala Arg Tyr Tyr Ile Ala Tyr Ser Ile Phe
690                 695                 700

Glu Arg Asp Arg Phe Leu Phe Glu Lys Asp Lys Glu Ala Val Thr
705                 710                 715                 720

Lys Tyr Asp Val Lys Tyr Asn Asn Gly Ser Lys Pro Cys Gln Tyr Phe
                725                 730                 735

Ser Leu Val Gln Tyr Tyr Leu Asp Lys Glu Ile Ala Gln Asp Tyr Lys
            740                 745                 750

Pro Glu Pro Gly Gln Pro Phe Asp Arg Glu Ala Cys Arg Lys His Leu
        755                 760                 765

Asp Gly Ile His Arg His Phe Ser Lys Lys Trp Arg Glu Ile Phe Lys
770                 775                 780

Asn Glu Leu Asp Glu Ala Lys Lys Val Asn Pro Thr Gly Tyr Leu Leu
785                 790                 795                 800

Thr Ser Val Arg Asn Asp Ala Glu His Leu Asn Val Leu Thr Ser Leu
                805                 810                 815

His Asp His Ile Gly Asp Phe Leu Lys Asn Asn His Arg Arg Met Lys
            820                 825                 830

Ser Tyr Phe Glu Leu Tyr His Phe Ile Leu Gln Lys Met Met Cys Asn
        835                 840                 845

Asp Pro Gly Leu Ser Ile Gly Asp His Trp Arg Arg Pro Ile Glu Lys
850                 855                 860

Tyr Gly Glu Pro Cys Leu Asp Leu Ile Lys Val Ala Tyr Val Ser Leu
865                 870                 875                 880

Gly Tyr Asn Leu Ala Arg Tyr Lys Asn Leu Thr Val Glu Ala Leu Phe
                885                 890                 895

Asp Arg Asp Ser Asp Asp Gly Lys Ala Leu Gln Glu Arg Gln Lys Lys
            900                 905                 910

Arg

<210> SEQ ID NO 8
<211> LENGTH: 956
<212> TYPE: PRT
<213> ORGANISM: Ruminococcus Sp.
<220> FEATURE:
<221> NAME/KEY: misc_feature
<223> OTHER INFORMATION: SG3METG14417906_Rs4Mmc2

<400> SEQUENCE: 8

Met Ser Glu Ser Asn Asn Val Ala Asn Leu Asp Ser Leu Lys Gly Leu
1               5                   10                  15

Lys Gly Ala Leu Gly Lys Asn Arg Lys Lys Thr Lys Ser Lys Met Ile
            20                  25                  30

Gly Val Lys Ser Thr Phe Val Thr Pro Gln Gly Val Ala Val Ser Ser
        35                  40                  45

```
Phe Ala Asp Val Lys Asn Asp Arg Gly Glu Lys Val Pro Asn Val Glu
     50                  55                  60
Leu Ile Thr Ser Arg Asp Gly Ser Glu Thr Phe Arg Glu Ala Leu Arg
 65                  70                  75                  80
Leu Phe Arg Ser Ala Ser Val Ser Pro Asp Ala Val Asn Leu Val Gly
                 85                  90                  95
Thr Leu Gly Glu Val Glu Leu Glu Asn Pro Ala Ile Arg Leu Ser Arg
                100                 105                 110
Gly Asp Tyr Val Gly Ile Lys Ala Ala Met Glu Arg Lys Tyr Phe Gly
            115                 120                 125
Arg Glu Phe Pro Glu Asp Asn Ile His Val Gln Ile Ala Tyr Asn Ile
130                 135                 140
Ala Asp Ile Lys Lys His Leu Met His Phe Ile Asn Gln Ile Ile Tyr
145                 150                 155                 160
Val Phe Tyr Asn Ile Asn Arg Thr Thr Ile Ser Tyr Asp Ser Tyr Asn
                165                 170                 175
Asp Leu Ile Gly Thr Val Tyr Ala Phe Ala Ser Leu Asp Asp Gln Arg
            180                 185                 190
Val Asn Thr Glu Asn Ala Ala Ala Val Arg Arg Ala Glu Glu Arg Gln
            195                 200                 205
Leu Leu Leu Asp Gly Val Tyr Phe Tyr Asp Ala Tyr Phe Pro Gly Val
210                 215                 220
Phe Arg Leu Pro Arg Lys Asp Ser Lys Leu Asp Ala Ala Ala Glu Lys
225                 230                 235                 240
Leu Lys Cys Asp Arg Tyr Asn Phe Asn Ile Leu Arg Leu Leu Ser Val
                245                 250                 255
Ile Arg Gln Ala Cys Glu His Glu Lys Leu Gly Ser Ala Ser Ala Glu
            260                 265                 270
Ala Leu Leu Tyr Asp Leu Thr Ala Ala Leu Arg Gly Glu Ser Asp Glu
            275                 280                 285
Leu Leu Arg Leu Leu Asp Asn Leu Tyr Lys Lys Val Pro Asp Leu Ile
290                 295                 300
Asn Arg Glu Phe Ser Gly Thr Pro Lys Ile Val Gly Ser Ser Ala Asn
305                 310                 315                 320
Asn Leu Tyr Ile Leu Ser Arg Ile Phe Pro Asp Met Pro Cys Glu Val
                325                 330                 335
Leu Leu Glu Lys Tyr Tyr Arg Tyr Thr Val Ile Lys Glu His Asn Thr
            340                 345                 350
Ile Gly Val Asn Leu Arg Leu Leu Arg Glu Ile Ile Arg Gln Phe
            355                 360                 365
Met Pro Glu Ile Ser Asp Arg Lys Tyr Asp Thr Ser Arg Gly Lys Leu
370                 375                 380
Tyr Thr Val Leu Gly Phe Met Leu Ala Glu Trp Leu Val Gly Ser Glu
385                 390                 395                 400
Tyr Ile Thr Asp Thr Val Ser Ser Leu Arg Ala Asn Ser Thr Glu Glu
                405                 410                 415
Gly Arg Val Ser Ile Tyr Leu Ser Leu Ala Glu Ala Val Phe Gly Glu
            420                 425                 430
Tyr Gly Ser Ala Leu Arg Ser Ala Leu Ala Val Phe Asp Arg Glu Met
            435                 440                 445
Tyr Asn Lys Phe Lys Ser Lys Pro Asn Phe Ser Val Asp Val Thr Asp
450                 455                 460
Lys Pro Tyr Ala Leu Asp Gly Ser Gln Gly Leu Tyr Phe Ser Lys Leu
```

```
            465                 470                 475                 480
        Val Leu Phe Met Thr Lys Phe Leu Asp Gly Lys Glu Ile Asn Glu Leu
                        485                 490                 495

Leu Ala Gly Leu Ile Ser Arg Phe Glu Asn Ile Gln Asp Leu Leu Tyr
                        500                 505                 510

Cys Ala Asp Glu Cys Gly Val Pro Val Arg Phe Gly Asp Gly Tyr Ser
                        515                 520                 525

Met Phe Ala Asp Ala Gly Arg Ala Ala Ala Glu Leu Arg Leu Val Lys
                        530                 535                 540

Asn Ile Ala Arg Met Lys Pro Glu Ala Lys Asn Phe Lys Asn Cys Met
        545                 550                 555                 560

Leu Val Asp Ala Val Asn Ile Leu Gly Ile Asn Glu Ser Val Leu Asp
                        565                 570                 575

Ala Glu Glu Cys Thr Asp Glu Asp Leu Lys Ala Thr Asn Thr Thr Phe
                        580                 585                 590

Leu Lys Arg Ile His Gly Glu Gly Asp Arg Ala Asn His Gln Val Arg
                        595                 600                 605

Asn Phe Leu Ile Asn Asn Val Ile Lys Ser Arg Trp Phe Phe Tyr Ile
                        610                 615                 620

Ala Arg Tyr Thr Lys Pro Ser Gln Cys Arg Ser Ile Ile Lys Ser Glu
        625                 630                 635                 640

Lys Leu Val Ala Phe Val Leu Arg Glu Ile Pro Asp Asp Gln Ile Lys
                        645                 650                 655

Arg Tyr Tyr Lys Ser Ile Thr Gly Tyr Asn Ala Gln Asp Leu Gly Arg
                        660                 665                 670

Ala Arg Ala Glu Leu Gln Arg Leu Val Gly Phe Ser Val Asn Arg
                        675                 680                 685

Leu Leu Asp Thr Val Glu Asp Met Pro Lys Gly Ala Tyr Arg Asp Thr
                        690                 695                 700

Arg Glu Asn Ser Glu Lys Gln Lys Asn Lys Ala Ile Val Gly Leu Tyr
        705                 710                 715                 720

Leu Thr Val Ile Tyr Leu Ala Ile Lys Ser Val Val Lys Val Asn Ser
                        725                 730                 735

Val Phe Ser Ile Ala Phe Ser Cys Leu Glu Arg Asp Leu Ser Leu Lys
                        740                 745                 750

Gly His Ser Asn Asp Thr Arg Leu Ala Ile Thr Glu Glu Met Leu Ala
                        755                 760                 765

Gln Asp Lys Glu Arg Val Asp Ser Tyr Thr Ala Leu Arg Asn Ser Ile
        770                 775                 780

Arg Asp Asn Glu Ala Leu Thr Lys Asp Gly Lys Arg Val Glu Tyr Lys
        785                 790                 795                 800

Ala Leu Lys Ser Ile Leu Lys Glu Met His Tyr Asp Leu His Ser Tyr
                        805                 810                 815

His Cys Val Lys Ala Asn Tyr Asp Asn Ala Ile Asn Leu Arg Cys Gly
                        820                 825                 830

Asp Ala Asp Leu Ile Ile Ala Met Tyr Arg Asn Ala Val Ala His Leu
                        835                 840                 845

Asn Ile Pro Val Arg Phe Ala Ser Tyr Leu Ser Asp Met Lys Glu Ile
                        850                 855                 860

Thr Ser Tyr Tyr Ser Ile Phe Val Tyr Ala Leu Glu Arg Tyr Ile Val
        865                 870                 875                 880

Asp Ser Gln Ile Arg Asn Ile Asp Gly Arg Ser Gln Thr Phe Ala Ala
                        885                 890                 895
```

```
Leu Ile Arg Arg Phe Ala Asp Thr Leu Arg Gly Ile Pro Ser Lys
            900                 905                 910

Asp Met Leu Trp Ile Ile Asn Thr Pro Phe Ala Tyr Asn Leu Ala Arg
        915                 920                 925

Tyr Lys Asn Leu Ser Ile Glu Asp Leu Phe Tyr Gly Arg Cys Ser Gly
        930                 935                 940

Gln Lys Leu Glu Gly Val Ser Gly Ser Asp Pro Val
945                 950                 955

<210> SEQ ID NO 9
<211> LENGTH: 970
<212> TYPE: PRT
<213> ORGANISM: Ruminococcus Sp.
<220> FEATURE:
<221> NAME/KEY: misc_feature
<223> OTHER INFORMATION: SG3METG14534299_Rs2Mmc2

<400> SEQUENCE: 9

Met Asn Asp Asn Ile Lys Arg Ser Thr Gln Met Asp Ser Thr Asn Ala
1               5                   10                  15

Pro Arg Asn Asp Gln Pro Thr Ser Asn Lys Ala Lys Thr Asn Pro Gly
            20                  25                  30

Ser Lys Ala Lys Lys Ser Lys Ala Lys Ala Gly Val Lys Ser Ala
        35                  40                  45

Phe Val Leu Thr Thr Asp Lys Val Val Thr Thr Ala Phe Gly Arg Gly
50                  55                  60

Asn Asp Ala Leu Leu Ala Ala Lys Ile Thr Asn Thr Ser Asn Ile Glu
65                  70                  75                  80

Pro Leu Ala Pro Val Ser Ser Tyr Thr Leu Ser Pro Ala Ser Ala Tyr
                85                  90                  95

Lys Asn Arg Lys Glu Arg Arg Gln Ala His Phe Lys Ala Gly Gly Ser
            100                 105                 110

Ser Glu Asn Trp Lys Thr Ser Ala Leu Ala Thr Thr Gln Pro Asp Lys
        115                 120                 125

Tyr Gly Ile Arg Ser Lys Leu Ile Ser Pro Ala Pro Gly Gly Ser Pro
    130                 135                 140

Thr Val Arg Asp Asn Pro Leu Lys Ala Ala Pro Thr Asp Gln Leu His
145                 150                 155                 160

Ala Lys Glu Phe Leu Glu Lys Glu Val Phe Gly Gln Thr Phe Ala Asp
                165                 170                 175

Thr Leu His Ile Gln Ile Ala Tyr Gln Thr Leu Asp Ile Asn Lys Ile
            180                 185                 190

Phe Thr Pro His Ile Ala Asn Leu Val Tyr Val Leu Asn Asn Leu Ser
        195                 200                 205

Arg Asn Glu Lys Met Ile Ala Asp Asp Phe Val Gly Ala Leu Pro Glu
    210                 215                 220

Asp Ile Lys Asp Lys Ser Trp Lys Lys Tyr Ile Ala Trp Lys Glu Ala
225                 230                 235                 240

Ala Glu Pro Ser Phe Ile Tyr Phe Gly Asp Ala Phe Pro Gln Arg Pro
                245                 250                 255

Lys Ala Ala Lys Asn Asp Ser Asn Ala Lys Lys Ala Glu Lys Asp Lys
            260                 265                 270

Arg Tyr Asp Asp Thr Val Trp Cys Thr Val His Ala Val Ser Ser Leu
        275                 280                 285

Arg Ala Ser Ile Thr His Ala Ser Lys Asp Asn Tyr Leu Leu His Pro
```

```
            290                 295                 300
Glu Lys Leu Pro Ala Glu Thr Lys Lys Leu Ile Glu Gly Ile Tyr Ala
305                 310                 315                 320

Ala Arg Ile Glu Asp Leu Asn Lys Asn Phe Ile Ala Met Ser Gly Lys
                325                 330                 335

Ser Asn Leu Pro Ile Leu Phe Ser Phe Tyr Asp Ala Asp Thr Ala Gly
                340                 345                 350

Lys Lys Ala Ala Ile Thr Cys Asp Tyr Tyr Asp Phe Ile Val Lys Lys
            355                 360                 365

Leu Ser Lys Asn Met Gly Phe Ser Leu Arg Thr Val Arg Glu Glu Met
370                 375                 380

Leu Arg Arg Asp Asp Asp Gly Gln Arg Leu Ala Ser Asp Asp Tyr Ser
385                 390                 395                 400

Thr Val Arg His Lys Leu Tyr Ser Leu Leu Asp Phe Ile Leu Tyr Arg
                405                 410                 415

His Phe Thr His Ser Pro Gln Ala Ser Thr Gln Pro Glu Lys Ile Ile
                420                 425                 430

Glu Asn Leu Arg Gly Ala Thr Glu Asp Val Tyr Lys Gln Ala Val Tyr
            435                 440                 445

Lys Gln Val Ala Arg Asp Val Trp Asn Ala Leu Ser Ala Asp Ile Arg
450                 455                 460

Gln Lys Leu Met Pro Leu Ile Asp Gly Ile Lys His Glu Gln Gly Cys
465                 470                 475                 480

Ala Pro Leu Ser Lys Glu Met Ala Ala Leu Glu Gly Ala Ile Ala
                485                 490                 495

Lys Val Lys Ile Thr Pro Asp Asp Thr Thr Leu Phe Ser Lys Leu Ile
                500                 505                 510

Tyr Phe Ile Thr Arg Phe Leu Asp Gly Lys Glu Ile Asn Asp Leu Leu
            515                 520                 525

Thr Thr Leu Ile His Thr Phe Glu Asn Ile Gln Ser Phe Arg Asp Leu
530                 535                 540

Glu Arg Lys Leu Cys Asp Lys Gly Glu Leu Pro Ala Phe Ala Glu Phe
545                 550                 555                 560

Thr Ser Ala Tyr Glu Leu Phe Asn Glu Ser Gly Lys Ile Ala Lys Glu
                565                 570                 575

Leu Arg Val Val Asn Ser Phe Ala Arg Met Ser Arg Glu Leu Pro His
                580                 585                 590

Ile Gly Arg Gln Gln Tyr Leu Asp Ala Ala His Val Leu Gly Ile Lys
            595                 600                 605

Asp Ala Pro Asp Asn Glu Gly Asp Lys Val Lys Glu Tyr Val Ser Arg
610                 615                 620

Val Leu Lys Leu Ala Glu Lys Gly Lys Val Asp Lys Ser Phe Arg Asn
625                 630                 635                 640

Phe Ile Ala Lys Asn Val Ile Glu Ser Asp Arg Phe Lys Tyr Ile Val
                645                 650                 655

Arg Tyr Val Asn Pro Leu Thr Ala Ser Lys Leu Ala Ser Asp Asn Met
                660                 665                 670

Leu Arg Phe Val Leu Lys Arg Ile Leu Gln Asn Asp Gln Arg Leu
            675                 680                 685

Lys Glu His Ala Gly Arg Asn Gly Gln Lys Ser Ile Ile Asp Arg Tyr
690                 695                 700

Ala Glu Thr Leu Gly Ile Arg Thr Ser Leu Pro Pro Glu Gln Lys Ile
705                 710                 715                 720
```

Asp Ala Leu Ala Lys Ala Ile Lys Gly Ile Ser Phe Glu Thr Phe Met
            725                 730                 735

Asn Val Lys Gln Gln Pro Gly Lys Asn Gln Gly Glu Val Arg Glu Lys
            740                 745                 750

Glu Arg Leu Leu Ala Leu Val Arg Leu Tyr Leu Val Ile Leu Tyr His
            755                 760                 765

Ile Val Lys Asn Leu Val Tyr Ile Asn Ala Arg Tyr Ile Ile Ala Ile
            770                 775                 780

Gln Arg Leu Glu Ser Asp Arg Ile Leu His Gly Glu Ala Arg Asn Val
785                 790                 795                 800

Val Lys Asn Ser Gly Phe Thr Lys Leu Ser Arg Lys Phe Ala Asp Glu
            805                 810                 815

Lys Trp Leu Asn Pro Lys Met Cys Arg Cys Leu Cys Asn Asn Met Ala
            820                 825                 830

Asp Asp Lys Tyr Asn Asp Trp Ile Phe Ile Ala Tyr Arg Asn Ala Ile
            835                 840                 845

Ala His Phe Lys Val Leu Ala Asn Ala Gly Glu Ser His Lys Ala Met
            850                 855                 860

Gly Arg Ile Pro Ser Trp Phe Ala Leu Tyr His Tyr Val Met Gln Ser
865                 870                 875                 880

Ser Cys Ile Leu Asp Tyr Leu Leu Ala Arg Asp Asp Asn Trp Asn Asp
            885                 890                 895

Lys Lys Gly Thr Pro Glu Glu Lys Arg Gln Leu Gln Val Ser Ile Asp
            900                 905                 910

Ile Tyr Lys Gly Met Leu Glu Gln Val Glu Glu Asn Gly Asn Tyr Gly
            915                 920                 925

Lys Asp Leu Leu Trp Ser Leu Asn Ala Pro Phe Gly Tyr Asn Leu Ser
            930                 935                 940

Arg Tyr Lys Asn Leu Ser Met Glu Val Leu Phe Asp Arg Asn Glu Arg
945                 950                 955                 960

Pro Leu Glu Glu Pro Asp Gly Met Asp Thr
            965                 970

<210> SEQ ID NO 10
<211> LENGTH: 940
<212> TYPE: PRT
<213> ORGANISM: Eubacterium siraeum
<220> FEATURE:
<221> NAME/KEY: misc_feature
<223> OTHER INFORMATION: SG3METG15604602_Es5Mmc2

<400> SEQUENCE: 10

Met Ala Lys Lys Lys Met Ser Cys Lys Glu Val Arg Glu Gln Lys Lys
1 5 10 15

Leu Met Asp Lys Ala Lys Tyr Ser Ala Glu Gln Ala Glu Arg Asp Arg
20 25 30

Val Lys Lys Glu Ala Glu Asp Ala Ala Glu Met Glu Lys Ala Lys Gln
35 40 45

Ala Phe Ser Ser Lys Tyr Lys Ser Met Ser Gly Glu Lys Ser Glu Lys
50 55 60

Lys Ser Val Ala Lys Ala Val Gly Ile Lys Ser Val Phe Ala Val Asp
65 70 75 80

Asp Ala Val Tyr Met Thr Ser Phe Gly Lys Gly Asn Asp Ala Val Leu
85 90 95

Glu Lys Lys Ile Ile Ser Asp Asn Tyr Gln Ser Ile Asn Thr Ala Asp

```
            100                 105                 110
Pro Ala Phe Thr Leu Thr Asp Val Asn Thr Val Asn Tyr Lys Ala Ser
            115                 120                 125

Gly Gly Arg Ile Arg Asn Leu Thr Ala Thr Asp Asn Pro Leu His
130                 135                 140

Gln Ser Gly Gly Ser Val Asp Ser Ile Pro Thr Asp Met Leu Cys Leu
145                 150                 155                 160

Lys Asn Lys Leu Glu Glu Arg Phe Tyr Gly Arg Ser Phe Asp Asn Asp
                165                 170                 175

Asn Ile His Ile Gln Leu Ile Tyr Asn Ile Leu Asp Ile Glu Lys Ile
            180                 185                 190

Ile Ala Glu Tyr Ala Thr Asn Ala Val Tyr Ala Ile Asp Asn Leu Phe
            195                 200                 205

Arg Lys Thr Glu Ser Glu Leu Arg Asn Asp Phe Ile Gly Gly Ile Ser
    210                 215                 220

Ala Lys Tyr Thr Tyr Asp Asp Leu Ser Asp Thr Lys Lys Glu Leu
225                 230                 235                 240

Lys Thr Leu Met Ser Gly Ser Arg Ile Gly Tyr Phe Gly Asn Ala Phe
                245                 250                 255

Tyr Gly Cys Glu Ile Asp Glu Lys Thr Gly Lys Val Lys His Arg Asp
                260                 265                 270

Glu Arg Asp Cys Tyr Asn Ile Leu Ala Leu Ile Gly Ser Leu Arg Gln
            275                 280                 285

Trp Ser Phe His Gly Asp Glu Lys Asn Asp Pro Thr Trp Leu Tyr Cys
    290                 295                 300

Leu Asp Ser Ile Asp Gly Glu Phe Arg Gly Ile Leu Asp Lys Leu Tyr
305                 310                 315                 320

Asp Glu Ala Val Phe Arg Val Asn Ser Asp Phe Val Asn Thr Asn Lys
                325                 330                 335

Val Asn Ile Gln Ile Leu Lys Glu Leu Phe Pro Asp Asp Lys Asn Ile
            340                 345                 350

Ala Gly Lys Tyr Tyr Gln Phe Leu Val Thr Lys Lys Tyr Lys Asn Ile
            355                 360                 365

Gly Phe Ser Ile Lys Lys Leu Arg Glu Met Met Val Glu Asn Ala Thr
    370                 375                 380

Val Lys Asp Glu Arg Tyr Asp Ser Val Arg Ser Lys Ala Tyr Lys Leu
385                 390                 395                 400

Ile Asp Phe Val Ile Trp His Gly Tyr Leu His Glu Asp Lys Ala Lys
                405                 410                 415

Val Ser Glu Leu Val Asn Gly Leu Arg Gly Ser Leu Ser Asp Glu Glu
            420                 425                 430

Lys Glu Arg Val Tyr His Ala Glu Ala Leu Arg Leu Trp Lys Lys Leu
            435                 440                 445

Lys Gly Thr Ile Ile Asp Asn Ile Met Pro Ala Val Asn Gly Arg Asn
    450                 455                 460

Ile Lys Ala Leu Gln Gln His Tyr Ile Lys Asp Ala Val Ser Gly Glu
465                 470                 475                 480

Met Leu Ile Lys Gly Ser Lys Asp Val Ser Tyr Phe Thr Lys Leu Met
                485                 490                 495

Tyr Leu Leu Thr Leu Phe Ile Asp Gly Lys Glu Ile Asn Asp Leu Leu
            500                 505                 510

Thr Thr Leu Ile Asn Lys Phe Asp Asn Ile Arg Ser Phe Asn Glu Thr
    515                 520                 525
```

```
Met Arg Ser Leu Gly Leu Val Ala Glu Phe Ser Ala Gly Tyr Ser Phe
    530                 535                 540

Phe Lys Asn Ser Asp Val Ile Phe Lys Glu Leu Ser Glu Leu Asn Ser
545                 550                 555                 560

Phe Ala Lys Met Cys Pro Val Asp Val Ser Ala Lys Arg Ala Met Tyr
                565                 570                 575

Cys Asp Ala Ile Asp Val Leu Gly Ile Glu Ser Asp Met Ser Ala Asp
                580                 585                 590

Glu Phe Tyr Ser Met Ile Asn Lys Met Leu Cys Leu Asp Ala Asn Gly
        595                 600                 605

Lys Pro Ile Arg Asp Lys Ser Lys Asp Ser Gly Leu Arg Asn Phe
    610                 615                 620

Ile Ala Asn Asn Val Ile Glu Ser Ala Arg Phe Arg Tyr Leu Ile Arg
625                 630                 635                 640

Tyr Gly Asn Thr Lys Lys Ile Lys Ser Leu Ala Lys Cys Glu Ala Ala
                645                 650                 655

Val Gly Phe Val Leu Ser Gly Ile Pro Asp Glu Gln Ile Glu Arg Tyr
                660                 665                 670

Tyr Arg Thr Cys His Asp Ile Ala Asp Glu Pro Ala Phe Asn Tyr Asp
        675                 680                 685

Glu Lys Arg Arg Tyr Leu Thr Lys Val Ile Lys Glu Met Ser Phe Glu
    690                 695                 700

Lys Ile Arg Asn Ala Gly Thr Val Gln Lys Ser Asn Ala Ser Ala Leu
705                 710                 715                 720

Asp Met Asp Ser Glu Lys Lys Arg Arg Tyr Gln Ala Val Val Arg Leu
                725                 730                 735

Tyr Leu Thr Val Met Tyr Leu Met Leu Lys Asn Leu Val Asn Val Asn
                740                 745                 750

Ser Arg Tyr Val Met Gly Phe His Cys Leu Glu Arg Asp Ala Leu Tyr
        755                 760                 765

Tyr Gly Val Lys Ile Asp Arg Tyr Cys Asp Leu Arg Asn Leu Val Phe
    770                 775                 780

Glu Leu Met Gly Thr Ser Asp Pro Gly Lys Ala Glu Asn Ala Gly Asn
785                 790                 795                 800

Arg Tyr Leu Arg Asn Lys Arg Trp Tyr Gly Ile Ile Phe Glu Asn Leu
                805                 810                 815

Gln His Ser Asp Lys Asn Thr Val Arg Glu Phe Arg Asn Thr Ala Ala
                820                 825                 830

His Leu Asn Ala Ile Arg Asn Ile Asp Glu Asn Ile Val Gly Ile Ala
        835                 840                 845

His Val Asn Ser Tyr Phe Glu Leu Tyr His Tyr Ile Val Gln Arg His
    850                 855                 860

Ile Tyr Asn Ile Gly Ile Lys Asn Pro Ser Asn Ser Thr Ser Glu Tyr
865                 870                 875                 880

Leu Asp Lys Leu Asn Ser Phe His Thr Tyr Asn Lys Asp Phe Val Lys
                885                 890                 895

Ala Tyr Cys Ser Pro Met Ala Tyr Asn Leu Val Arg Tyr Lys Asn Leu
                900                 905                 910

Thr Ile Asp Gly Leu Phe Asp Arg Asn Phe Arg Ala Asp Thr Asp Ser
        915                 920                 925

Ser Asp Lys Ser Ser Lys Asp Asp Leu Ile Cys Val
    930                 935                 940
```

<210> SEQ ID NO 11
<211> LENGTH: 933
<212> TYPE: PRT
<213> ORGANISM: Eubacterium siraeum
<220> FEATURE:
<221> NAME/KEY: misc_feature
<223> OTHER INFORMATION: SG3METG15632563_Es7Mmc2

<400> SEQUENCE: 11

```
Met Arg Lys Lys Met Ser Lys Ala Glu Leu Arg Glu Lys Arg Asn Leu
1               5                   10                  15

Asp Lys Lys Glu Lys Tyr Lys Lys Gln Asp Glu Glu Gln Lys Leu Lys
            20                  25                  30

Lys Asp Met Gln Glu Gln Gln Glu Tyr Phe Ala Ala Asn Pro Asp Arg
        35                  40                  45

Ser Lys Ser Leu Ala Lys Ala Ala Gly Val Lys Ser Val Phe Ala Val
    50                  55                  60

Asn Asp Ala Val Tyr Met Thr Ser Phe Gly Lys Gly Asn Asp Ala Val
65                  70                  75                  80

Leu Glu Lys Lys Ile Val Gly Val Asp Arg Lys Tyr Glu Ala Asn Pro
                85                  90                  95

Ala Ala Tyr Glu Phe Val Asp Val Ser Glu Ala Lys Tyr Thr Val Lys
            100                 105                 110

Gly Lys Arg Gly Arg Pro Leu Phe Ala Val Thr Asp Asn Pro Leu Arg
        115                 120                 125

His Asp Asp Gly Met Ser Val Pro Thr Asp Met Leu Cys Leu Lys Thr
    130                 135                 140

Thr Leu Glu Arg Ala Phe Phe Gly Arg Glu Phe Asp Asp Ser Leu His
145                 150                 155                 160

Ile Gln Leu Ile Tyr Asn Ile Leu Asp Ile Glu Lys Ile Leu Ala Val
                165                 170                 175

Tyr Ser Thr Asn Ala Val Tyr Ala Leu Asn Asn Met Phe Ala Asp Asp
            180                 185                 190

Ser Pro Glu Asn Trp Asp Phe Phe Ser Asn Met Thr Thr Asp Lys Thr
        195                 200                 205

Phe Glu Glu Phe Ser Leu Lys Glu Thr Asp Leu Ala Lys Phe Arg Glu
    210                 215                 220

Phe Thr Lys Leu Pro Arg Leu Gly Tyr Phe Ala Asp Ala Phe Tyr Asp
225                 230                 235                 240

Gly Gly Gly Gly Val Gly Lys Lys Ala Ser Arg Arg Ser Glu Asn Glu
                245                 250                 255

Ile Tyr Ala Ile Leu Ala Met Leu Ala Lys Leu Arg His Trp Cys Val
            260                 265                 270

His Ser Glu Lys Gly Glu Ala Glu Ser Trp Leu Tyr Lys Leu Asp Glu
        275                 280                 285

Pro Gly Ser Leu His Arg Glu Phe Thr Asp Val Leu Asp Lys Leu Tyr
    290                 295                 300

Asp Arg Ala Val Thr Glu Ile Asn Gly Gly Phe Ala Glu Thr Asn Lys
305                 310                 315                 320

Val Asn Leu Gln Ile Leu Gln Glu Ile Cys Arg Asp Ser Asp Leu Pro
                325                 330                 335

Gly Leu Ala Arg Glu Tyr Tyr Glu Phe Leu Ile Thr Lys Lys Tyr Lys
            340                 345                 350

Asn Thr Gly Phe Ser Ile Lys Thr Leu Arg Glu Lys Met Ile Ala Gly
        355                 360                 365
```

-continued

```
Tyr Ala Ala Glu His Asp Gly Ile Phe Ser Gly Lys Asp Leu Asp His
    370                 375                 380

Ile Arg Asn Lys Leu Tyr Gln Met Thr Asp Phe Leu Val Tyr Arg Gly
385                 390                 395                 400

Tyr Gln Thr Glu Asp Ser Gly Arg Ala Asp Glu Leu Val Glu Arg Leu
                405                 410                 415

Arg Asn Cys Val Asn Glu Asp Lys Glu Ser Ala Tyr Ser Val Glu
                420                 425                 430

Ala Ser Tyr Leu Ser Gly Lys Tyr Arg Trp Gln Val Gly Arg Ile Ala
            435                 440                 445

Asp Ser Leu Ser Gly Gly Asn Ile Lys Lys Leu Gln Lys Asn Ser Val
    450                 455                 460

Ser Val Pro Asp Ser Gly Leu Gln Ser Cys Phe Ile Ser Thr Ala Gly
465                 470                 475                 480

Lys Val Ser Asn Phe Thr Lys Leu Ile Tyr Leu Leu Thr Arg Phe Ile
                485                 490                 495

Asn Gly Lys Glu Ile Asn Asp Leu Leu Thr Thr Leu Ile Asn Lys Phe
            500                 505                 510

Asp Asn Ile Arg Ser Phe Leu Arg Leu Met Asp Glu Leu Gly Leu Glu
    515                 520                 525

Arg Gly Phe Thr Asp Ser Tyr Gly Phe Phe Ala Asp Ser Ser Arg Tyr
530                 535                 540

Leu Gly Glu Leu Thr Glu Leu Asn Ser Phe Ala Arg Ser Cys Ser Phe
545                 550                 555                 560

Asp Ile Ser Ala Lys Arg Ser Met Tyr Leu Asp Ala Leu Ala Ile Leu
                565                 570                 575

Gly Ala Asp Ala Asp Leu Ile Gly Gly Glu Val Asp Glu Ile Leu Gln
            580                 585                 590

Leu Asp Glu Asn Gly Lys Lys Leu Pro Lys Ala Asp Asn Gly Leu Arg
    595                 600                 605

Asn Phe Ile Ile Ser Asn Val Ile Ser Ser Asn Arg Phe Lys Tyr Leu
610                 615                 620

Val Arg Tyr Gly Asn Pro Glu Lys Ile Arg Lys Thr Ala Arg Cys Glu
625                 630                 635                 640

Ala Ala Val Arg Phe Val Leu Asp Gly Ile Pro Asp Glu Gln Ile Thr
                645                 650                 655

Arg Tyr Tyr Gly Ser Cys Tyr Pro Glu Arg Val Pro Glu Tyr Ala Gly
            660                 665                 670

Gly Ala Asp Leu Asn Lys Glu Arg Ser Glu Leu Ala Ala Ala Val Ser
    675                 680                 685

Gly Ile Ser Phe Asp Gln Phe Arg Asp Ala Gly Lys Val Gln Arg Val
690                 695                 700

Asn Ala Asp Ser Asp Thr Gln Asp Ala Glu Ile Lys Arg Arg Asn Gln
705                 710                 715                 720

Ala Val Ile Arg Leu Tyr Leu Thr Val Met Tyr Leu Met Leu Lys Asn
                725                 730                 735

Leu Val Asn Val Asn Ala Arg Tyr Val Ile Gly Phe His Cys Leu Glu
            740                 745                 750

Arg Asp Ala Lys Leu Tyr Arg Gln Arg Asn Val Tyr Gln Gly Asn Ile
    755                 760                 765

Ser Asn Asp Arg Thr Tyr Leu Thr Thr Ala Val Met Asp Ile Glu Arg
770                 775                 780
```

```
Leu Lys Ser Gly Glu Leu Pro Asp Ser Cys Asp Pro Asp Lys Ala Lys
785                 790                 795                 800

Asn Ala Lys Asn Arg His Leu Arg Asn Glu Arg Trp Tyr Gly Ile Val
                805                 810                 815

Phe Asp Asn Leu Lys Lys Ser Asp Lys Ile Val Val Thr Glu Phe Arg
            820                 825                 830

Asn Thr Val Cys His Leu Asn Ala Ile Arg Asn Ile Asp Glu Asn Ile
        835                 840                 845

Ala Gly Ile Lys Ser Val Lys Asn Tyr Phe Ser Leu Tyr His Tyr Ile
850                 855                 860

Ile Gln Arg His Ile Arg Asn Tyr Val Asn Lys Asn Ser Lys Pro Phe
865                 870                 875                 880

Ser Ser Asn Thr Ile Ser Tyr Leu Ser Ser Leu Glu Lys Tyr Gly Thr
                885                 890                 895

Tyr Cys Lys Asp Phe Val Lys Ala Tyr Cys Thr Pro Phe Ala Tyr Asn
            900                 905                 910

Leu Val Arg Tyr Lys Asn Leu Thr Ile Asp Gly Gln Phe Asp Arg Asn
        915                 920                 925

Glu Pro Lys Val Lys
    930

<210> SEQ ID NO 12
<211> LENGTH: 906
<212> TYPE: PRT
<213> ORGANISM: Eubacterium siraeum
<220> FEATURE:
<221> NAME/KEY: misc_feature
<223> OTHER INFORMATION: SG3METG15637593_Es3Mmc2

<400> SEQUENCE: 12

Met Glu Arg Glu Val Lys Lys Pro Pro Lys Ser Leu Ala Lys Ala
1               5                   10                  15

Ala Gly Leu Lys Ser Thr Phe Val Ile Ser Pro Gln Glu Lys Glu Leu
            20                  25                  30

Ala Met Thr Ala Phe Gly Arg Gly Asn Asp Ala Leu Leu Gln Lys Arg
        35                  40                  45

Ile Val Asp Gly Val Val Arg Asp Val Ala Gly Glu Lys Gln Gln Phe
50                  55                  60

Gln Val Gln Arg Gln Asp Glu Ser Arg Phe Arg Leu Gln Asn Ser Arg
65                  70                  75                  80

Leu Ala Asp Arg Thr Val Thr Ala Asp Pro Leu His Arg Ala Glu
                85                  90                  95

Ala Pro His Arg Gln Pro Leu Gly Ala Gly Met Asp Gln Leu Arg Arg
            100                 105                 110

Lys Ala Val Leu Glu Gln Lys Tyr Phe Gly Arg Thr Phe Asp Asp Asn
        115                 120                 125

Ile His Ile Gln Leu Ile Tyr Asn Ile Leu Asp Ile His Lys Met Leu
    130                 135                 140

Ala Val Pro Ala Asn His Ile Val His Thr Leu Asn Leu Gly Gly
145                 150                 155                 160

Tyr Gly Glu Thr Asp Phe Val Gly Met Leu Pro Ala Gly Leu Pro Tyr
                165                 170                 175

Asp Lys Leu Arg Val Val Lys Lys Asn Gly Asp Thr Val Asp Ile
            180                 185                 190

Lys Ala Asp Ile Ala Ala Tyr Ala Lys Arg Pro Gln Leu Ala Tyr Leu
        195                 200                 205
```

Gly Ala Ala Phe Tyr Asp Val Thr Pro Gly Lys Ser Lys Arg Asp Ala
            210                 215                 220

Ala Arg Gly Arg Val Lys Arg Glu Gln Asp Val Tyr Thr Ile Leu Ser
225                 230                 235                 240

Leu Met Ser Leu Leu Arg Gln Phe Cys Ala His Asp Ser Val Arg Ile
                245                 250                 255

Trp Gly Gln Asn Thr Pro Ala Ala Leu Tyr His Leu Gln Ala Leu Pro
            260                 265                 270

Gln Asp Met Lys Asp Leu Leu Asp Asp Gly Trp Arg Ala Leu Gly
        275                 280                 285

Gly Val Asn Asp His Phe Leu Asp Thr Asn Lys Val Asn Leu Leu Thr
    290                 295                 300

Leu Phe Glu Tyr Tyr Gly Ala Glu Thr Lys Gln Glu Arg Val Val Leu
305                 310                 315                 320

Thr Gln Asp Phe Tyr Arg Phe Val Val Leu Lys Glu Gln Lys Asn Met
                325                 330                 335

Gly Phe Ser Leu Arg Arg Leu Arg Glu Leu Leu Lys Leu Pro Asp
            340                 345                 350

Ala Ala Tyr Leu Thr Gly Gln Glu Tyr Asp Ser Val Arg Gln Lys Leu
                355                 360                 365

Tyr Met Leu Leu Asp Phe Leu Leu Cys Arg Leu Tyr Ala Gln Glu Arg
370                 375                 380

Ala Asp Arg Cys Glu Glu Leu Val Ser Ala Leu Arg Cys Ala Leu Ser
385                 390                 395                 400

Asp Glu Glu Lys Gly Ala Val Tyr Gln Ala Ala Ala Leu Trp
                405                 410                 415

Gln Ala Leu Gly Asp Thr Leu Arg Arg Glu Leu Leu Pro Leu Leu Lys
            420                 425                 430

Gly Lys Lys Leu Gln Asp Lys Asp Lys Lys Pro Asp Glu Leu Gly
            435                 440                 445

Leu Ser Arg Asp Val Leu Asp Gly Val Leu Phe Arg Pro Ala Gln Gln
450                 455                 460

Gly Asn Arg Ala Asn Ala Asp Tyr Phe Cys Arg Leu Met His Leu Ser
465                 470                 475                 480

Thr Trp Phe Met Asp Gly Lys Glu Ile Asn Thr Leu Leu Thr Thr Leu
                485                 490                 495

Ile Ser Lys Leu Glu Asn Ile Asp Ser Leu Arg Ser Val Leu Glu Ser
            500                 505                 510

Met Gly Leu Ala Cys Ser Phe Val Pro Ala Tyr Ala Met Phe Asp His
        515                 520                 525

Ser Arg Tyr Ile Ala Gly Gln Leu Arg Val Val Asn Asn Ile Ala Arg
530                 535                 540

Met Arg Lys Pro Ala Ile Gly Ala Lys Arg Glu Met Tyr Arg Ala Ala
545                 550                 555                 560

Val Val Leu Leu Gly Val Asp Ser Pro Glu Ala Ala Ala Ile Thr
                565                 570                 575

Asp Asp Leu Leu Gln Ile Asp Pro Glu Thr Gly Lys Val Arg Pro Arg
            580                 585                 590

Gly Asp Ser Ala Arg Asp Thr Gly Leu Arg Asn Phe Ile Ala Asn Asn
        595                 600                 605

Val Val Glu Ser Arg Arg Phe Thr Tyr Leu Leu Arg Tyr Met Thr Pro
610                 615                 620

```
Glu Gln Ala Arg Val Leu Ala Gln Asn Glu Lys Leu Ile Ala Phe Val
625                 630                 635                 640

Leu Ser Thr Val Pro Asp Thr Gln Leu Glu Arg Tyr Cys Arg Thr Cys
            645                 650                 655

Gly Arg Glu Asp Ile Thr Asp Arg Pro Ala Gln Ile Arg Tyr Leu Thr
                660                 665                 670

Ala Gln Ile Met Gly Val Arg Tyr Glu Ser Phe Thr Asp Val Glu Gln
            675                 680                 685

Arg Gly Arg Gly Asp Asn Pro Lys Lys Glu Arg Tyr Lys Ala Leu Ile
        690                 695                 700

Gly Leu Tyr Leu Thr Val Leu Tyr Leu Ala Val Lys Asn Met Val Asn
705                 710                 715                 720

Cys Asn Ala Arg Tyr Val Ile Ala Phe Tyr Cys Arg Asp Arg Asp Thr
                725                 730                 735

Ala Leu Tyr Gln Lys Glu Val Cys Trp Tyr Asp Leu Glu Glu Asp Lys
            740                 745                 750

Lys Ser Gly Lys Gln Arg Gln Val Glu Asp Tyr Thr Ala Leu Thr Arg
        755                 760                 765

Tyr Phe Val Ser Gln Gly Tyr Leu Asn Arg His Ala Cys Gly Tyr Leu
770                 775                 780

Arg Ser Asn Met Asn Gly Val Gly Asn Gly Leu Leu Val Ala Tyr Arg
785                 790                 795                 800

Asn Ala Val Asp His Leu Asn Val Ile Pro Pro Leu Gly Ser Leu Cys
                805                 810                 815

Arg Asp Ile Gly Arg Val Asp Ser Tyr Phe Ala Leu Tyr His Tyr Ala
            820                 825                 830

Val Gln Gln Tyr Leu Asn Gly Arg Tyr Tyr Lys Thr Pro Arg Glu
        835                 840                 845

Gln Glu Leu Phe Ala Ala Met Ala Gln His Arg Thr Trp Cys Ser Asp
850                 855                 860

Leu Val Lys Ala Leu Asn Thr Pro Phe Gly Tyr Asn Leu Ala Arg Tyr
865                 870                 875                 880

Lys Asn Leu Ser Ile Asp Gly Leu Phe Asp Arg Glu Gly Asp His Val
                885                 890                 895

Val Arg Glu Asp Gly Glu Lys Pro Ala Glu
            900                 905

<210> SEQ ID NO 13
<211> LENGTH: 906
<212> TYPE: PRT
<213> ORGANISM: Ruminococcus Sp.
<220> FEATURE:
<221> NAME/KEY: misc_feature
<223> OTHER INFORMATION: SG3METS659628_Rs6Mmc2

<400> SEQUENCE: 13

Met Ser Lys Asn Lys Lys Thr Arg Ala Lys Arg Met Gly Val Lys Ser
1               5                   10                  15

Val Phe Ala His Gly Glu Lys Gly Arg Leu Ala Ile Thr Ser Phe Gly
                20                  25                  30

Lys Gly Asn Arg Ala Glu Leu Val Val Asp Thr Asp Ser Arg Gly Lys
            35                  40                  45

Ser Leu Cys Leu Pro His Arg Val Pro Gly Ser Val Thr Ile Asp Arg
        50                  55                  60

Ile Asp Glu Glu Ile Gly Leu Ser Arg Ser Thr Leu Glu Ala Leu Val
65                  70                  75                  80
```

```
Asn Asn Pro Ala Glu Arg Asp Ser Asp Asp Tyr Leu Gly Leu Lys Gly
             85                  90                  95

Glu Leu Glu Glu Met Phe Phe Gly Glu Lys Phe Pro Arg Asp Thr Val
        100                 105                 110

Arg Ile Gln Ile Ile His Asn Ile Leu Asp Ile Leu Lys Ile Leu Gly
        115                 120                 125

Leu Tyr Val Gly Asp Ile Val Tyr Cys Ile Asn Asn Leu Gln Asp Val
    130                 135                 140

Pro Ile Pro Asp Asp Gln Ile Gly Lys Ser Leu Cys Asn Glu Lys Lys
145                 150                 155                 160

Val Glu Asp Ile Leu Arg Cys Met Glu Pro Phe Leu Gly Tyr Phe Gly
                165                 170                 175

Glu Ala Phe Arg Ala Arg Pro Gln Met Lys Val Lys Lys Pro Ala Ala
            180                 185                 190

Ala Gly Lys Gln Met Arg Asp Glu Arg Phe Ser His Asn Lys Asn Ala
        195                 200                 205

Ile Tyr Ile Leu Ser Thr Ile Arg His Asn Thr Ala His Phe Lys Lys
    210                 215                 220

Ser Phe Phe Phe Gln Lys Asp Leu Asn Lys Lys Phe Thr Gly Ala
225                 230                 235                 240

Ser Gly Ser Trp Lys Ile Val Glu Glu Asn Tyr Lys Asn Leu Ile Asp
                245                 250                 255

Arg Ile Asn Ser Lys Phe Val Ser Asn Ser Ile Asn Leu Arg Ile
            260                 265                 270

Leu Phe Glu Leu Leu Ser Ala Glu Ser Leu Ala Glu Gln Thr Ala Ile
        275                 280                 285

Ala Glu Glu Tyr Tyr Cys Phe Ser Ile Leu Lys Lys Gly Lys Asn Leu
    290                 295                 300

Gly Ile Gly Met Lys Lys Leu Arg Glu Tyr Ile Ile Glu Leu Cys Cys
305                 310                 315                 320

Pro Glu Ile Lys Asn Lys Val Tyr Asp Ser Tyr Arg Ser Lys Leu Tyr
                325                 330                 335

Thr Ile Leu Asp Tyr Leu Leu Tyr Arg Thr Ile Cys Asp Ser Asp Glu
            340                 345                 350

Leu Val Leu Met Val Glu Glu Leu Arg Glu Thr Ala Asp Glu Asp Ala
        355                 360                 365

Lys Glu Arg Leu Tyr Arg Asn Asn Ala Val Val Phe Trp Glu Lys Ile
    370                 375                 380

Glu Gln Tyr Val His Pro Phe Leu Glu Lys Phe Lys Asp Gly Phe Pro
385                 390                 395                 400

Val Phe Ser Ser Asp Lys Tyr Pro Ala Ser Leu Ile Asp Lys Val Ala
                405                 410                 415

Leu Lys Ala Asp Gly Val Pro Phe Val Gln Leu Leu Ala Phe Leu Cys
            420                 425                 430

Asp Phe Trp Glu Gly Lys Glu Ile Asn Glu Ile Leu Ser Ala Tyr Ile
        435                 440                 445

His Lys Phe Glu Asn Ile Gln Ala Phe Ile Asp Thr Leu Glu Asn Leu
    450                 455                 460

Gly Glu Arg Leu Glu Phe Lys Ala Cys Pro Ile Phe Asn Glu Pro Arg
465                 470                 475                 480

Ile Ala Glu Arg Val Ala Ala Glu Leu Arg Ile Leu Ala Ser Ile Gly
                485                 490                 495
```

```
Lys Met Lys Pro Asp Leu Ser Ser Val Lys Arg Pro Leu Tyr Lys Ala
            500                 505                 510

Ala Ile Ala Phe Leu Gly Val Asn Glu Ser His Glu Cys Leu Thr Asp
            515                 520                 525

Glu Trp Leu Ala Glu Asn Leu Leu Asp Gly Glu Ala Pro Arg Glu
        530                 535                 540

Lys Lys Glu Ser Thr Asn Pro Phe Arg Asn Phe Ile Val Asn Asn Val
545                 550                 555                 560

Ile Lys Ser Arg Arg Phe Met Tyr Leu Val Arg Tyr Thr Lys Pro Gln
                565                 570                 575

Thr Val His Ala Leu Met Gly Asn Arg Glu Ile Val Arg Tyr Val Leu
            580                 585                 590

Thr Arg Leu Pro Glu Lys Gln Val Asp Thr Tyr Tyr Glu Asn Ile Glu
        595                 600                 605

Glu Pro Asn Glu Asn Asp Ala Leu Glu Asp Lys Ile Arg Ala Leu Thr
    610                 615                 620

Ala Ala Leu Thr Asn Phe Ser Phe Glu Asn Leu Arg Arg Gln Lys Glu
625                 630                 635                 640

Arg Ile Val Glu Asn Ser Leu Leu Gly Ala Ser Glu Lys Ile Leu Glu
                645                 650                 655

Ile Glu Gln Leu Lys Ala Leu Thr Gly Leu Tyr Leu Thr Val Ala Tyr
            660                 665                 670

Val Ala Val Lys Asn Leu Ile Lys Thr Asn Ala Arg Tyr Tyr Ile Ala
        675                 680                 685

Phe Ser Ala Phe Glu Arg Asp Tyr Glu Leu Phe Leu Gln Lys Asp Lys
    690                 695                 700

Ser Thr Ile Glu Asp Leu Arg Ile Leu Leu Pro Phe Leu Gly Lys Lys
705                 710                 715                 720

Gly Lys Asn Thr Trp Asn Glu Cys Leu Ala Leu Thr Arg Tyr Phe Leu
                725                 730                 735

Lys Lys Glu Glu Glu Asn Asp Tyr His Pro Pro Gly Lys Pro Phe
            740                 745                 750

Asp Lys Glu Ala Cys Arg Lys His Leu Asp Ser Ile Lys Arg His Phe
        755                 760                 765

Ser Lys Lys Trp Arg Glu Ile Phe Gln Thr Ala Ile Asn Asp Ala Leu
770                 775                 780

Gln Ile Ser Asn Thr Gly Tyr Leu Pro Ile Val Arg Asn His Ala
785                 790                 795                 800

Ala His Leu Asn Val Leu Ser Ala Gln Ala Leu Lys Tyr Val Ser Glu
            805                 810                 815

Phe Arg Ala Lys Arg Pro Gly Met Gln Ser Tyr Phe Glu Leu Tyr His
        820                 825                 830

Phe Leu Leu Gln Lys Leu Met Cys Glu Asn Pro Ser Leu Asn Ile Leu
    835                 840                 845

Pro Glu His Gln Lys Tyr Leu Asn Ala Gly Val Pro Cys Leu Asp Leu
    850                 855                 860

Ile Lys Ile Ala Tyr Val Ser Leu Gly Tyr Asn Leu Pro Arg Phe Lys
865                 870                 875                 880

Asn Leu Thr Ile Glu Ala Leu Phe Asp Glu Asp Ser Glu Ser Gly Lys
                885                 890                 895

Glu Arg Ile Glu Arg Arg Lys Ser Lys Arg
            900                 905
```

<210> SEQ ID NO 14
<211> LENGTH: 954
<212> TYPE: PRT
<213> ORGANISM: Eubacterium siraeum
<220> FEATURE:
<221> NAME/KEY: misc_feature
<223> OTHER INFORMATION: SG4METG13463921_Es4Mmc2

<400> SEQUENCE: 14

```
Met Gly Lys Lys Ile His Ala Arg Asp Leu Arg Glu Gln Arg Lys Thr
1               5                   10                  15

Asp Arg Thr Glu Lys Phe Ala Asp Gln Asn Lys Lys Arg Glu Ala Glu
            20                  25                  30

Arg Ala Val Gln Lys Lys Asp Ala Ala Val Ser Val Lys Ser Val Ser
        35                  40                  45

Ser Val Ser Ser Lys Lys Asp Asn Val Thr Lys Ser Met Ala Lys Ala
    50                  55                  60

Ala Gly Val Lys Ser Val Phe Ala Val Gly Asn Thr Val Tyr Met Thr
65                  70                  75                  80

Ser Phe Gly Arg Gly Asn Asp Ala Val Leu Glu Gln Lys Ile Val Asp
                85                  90                  95

Thr Ser His Glu Pro Leu Asn Ile Asp Asp Pro Ala Tyr Gln Leu Asn
            100                 105                 110

Val Val Thr Met Asn Gly Tyr Ser Val Thr Gly His Arg Gly Glu Thr
        115                 120                 125

Val Ser Ala Val Thr Asp Asn Pro Leu Arg Arg Phe Asn Gly Gly Lys
    130                 135                 140

Lys Asp Glu Pro Glu Gln Ser Val Pro Thr Asp Met Leu Cys Leu Lys
145                 150                 155                 160

Pro Thr Leu Glu Lys Lys Phe Gly Lys Glu Phe Asn Asp Asn Ile
                165                 170                 175

His Ile Gln Leu Ile Tyr Asn Ile Leu Asp Ile Glu Lys Ile Leu Ala
            180                 185                 190

Val Tyr Ser Thr Asn Ala Ile Tyr Ala Leu Asn Asn Met Ser Ala Asp
        195                 200                 205

Glu Asn Ile Glu Asn Ser Asp Phe Phe Met Lys Arg Thr Thr Asp Glu
    210                 215                 220

Thr Phe Asp Asp Phe Glu Lys Lys Lys Glu Ser Thr Asn Ser Arg Glu
225                 230                 235                 240

Lys Ala Asp Phe Asp Ala Phe Glu Lys Phe Ile Gly Asn Tyr Arg Leu
                245                 250                 255

Ala Tyr Phe Ala Asp Ala Phe Tyr Val Asn Lys Lys Asn Pro Lys Gly
            260                 265                 270

Lys Ala Arg Asn Val Leu Arg Glu Asp Lys Glu Leu Tyr Ser Val Leu
        275                 280                 285

Thr Leu Ile Gly Lys Leu Arg His Trp Cys Val His Ser Glu Glu Gly
    290                 295                 300

Arg Ala Glu Phe Trp Leu Tyr Lys Leu Asp Glu Leu Lys Asp Asp Phe
305                 310                 315                 320

Lys Asn Val Leu Asp Val Val Tyr Asn Arg Pro Val Glu Glu Ile Asn
                325                 330                 335

Asn Arg Phe Ile Glu Asn Asn Lys Val Asn Ile Gln Ile Leu Gly Ser
            340                 345                 350

Val Tyr Lys Asn Thr Asp Ile Ala Glu Leu Val Arg Ser Tyr Tyr Glu
        355                 360                 365
```

-continued

```
Phe Leu Ile Thr Lys Lys Tyr Lys Asn Met Gly Phe Ser Ile Lys Lys
    370                 375                 380
Leu Arg Glu Ser Met Leu Glu Gly Lys Gly Tyr Ala Asp Lys Glu Tyr
385                 390                 395                 400
Asp Ser Val Arg Asn Lys Leu Tyr Gln Met Thr Asp Phe Ile Leu Tyr
                405                 410                 415
Thr Gly Tyr Ile Asn Glu Asp Ser Asp Arg Ala Asp Asp Leu Val Asn
            420                 425                 430
Thr Leu Arg Ser Ser Leu Lys Glu Asp Asp Lys Thr Thr Val Tyr Cys
        435                 440                 445
Lys Glu Ala Asp Tyr Leu Trp Lys Lys Tyr Cys Glu Ser Ile Arg Glu
450                 455                 460
Val Ala Glu Ala Leu Asp Gly Asp Asn Ile Lys Arg Leu Ser Lys Ser
465                 470                 475                 480
Asn Ile Glu Ile Arg Asp Asn Glu Leu Arg Lys Cys Phe Ile Ser Tyr
                485                 490                 495
Ala Asp Ser Val Ser Glu Phe Thr Lys Leu Ile Tyr Leu Leu Thr Arg
            500                 505                 510
Phe Leu Ser Gly Lys Glu Ile Asn Asp Leu Val Thr Thr Leu Ile Asn
        515                 520                 525
Lys Phe Asp Asn Ile Arg Ser Phe Leu Glu Ile Leu Asp Glu Leu Gly
530                 535                 540
Leu Asp Arg Thr Phe Thr Ala Glu Tyr Ser Phe Glu Gly Ser Thr
545                 550                 555                 560
Lys Tyr Leu Ala Glu Leu Val Glu Leu Asn Ser Phe Val Lys Ser Cys
                565                 570                 575
Ser Phe Asp Ile Asn Ala Lys Arg Thr Met Tyr Arg Asp Ala Leu Asp
            580                 585                 590
Ile Leu Gly Ile Lys Ser Gly Lys Thr Glu Glu Asp Ile Glu Lys Met
        595                 600                 605
Ile Asp Asn Ile Leu Gln Ile Asp Ala Asn Gly Asp Lys Lys Leu Lys
610                 615                 620
Lys Asn Asn Gly Leu Arg Asn Phe Ile Ala Ser Asn Val Ile Asp Ser
625                 630                 635                 640
Asn Arg Phe Lys Tyr Leu Val Arg Tyr Gly Asn Pro Lys Lys Ile Arg
                645                 650                 655
Glu Thr Ala Lys Cys Lys Pro Ala Val Arg Phe Val Leu Asn Glu Ile
            660                 665                 670
Pro Asp Ala Gln Ile Glu Arg Tyr Tyr Glu Ala Cys Cys Pro Lys Asn
        675                 680                 685
Thr Ala Leu Cys Ser Ala Asn Lys Arg Arg Glu Lys Leu Ala Asp Met
690                 695                 700
Ile Ala Glu Ile Lys Phe Glu Asn Phe Ser Asp Ala Gly Asn Tyr Gln
705                 710                 715                 720
Lys Ala Asn Val Thr Ser Lys Thr His Glu Ala Glu Ile Lys Arg Lys
                725                 730                 735
Asn Gln Ala Ile Ile Arg Leu Tyr Leu Thr Val Met Tyr Ile Met Leu
            740                 745                 750
Lys Asn Leu Val Asn Val Asn Ala Arg Tyr Val Ile Ala Phe His Cys
        755                 760                 765
Val Glu Arg Asp Thr Lys Leu Tyr Ala Glu Ser Gly Leu Glu Val Gly
770                 775                 780
Asn Ile Glu Lys Asn Lys Thr Asn Leu Thr Met Ala Val Met Gly Val
```

```
            785                 790                 795                 800
Lys Leu Glu Asn Gly Ile Ile Lys Thr Glu Phe Asp Lys Ser Leu Ala
                805                 810                 815

Glu Asn Ala Ala Asn Arg Tyr Leu Arg Asn Ala Arg Trp Tyr Lys Leu
            820                 825                 830

Ile Leu Asp Asn Leu Lys Lys Ser Glu Arg Ala Val Val Asn Glu Phe
                835                 840                 845

Arg Asn Thr Val Cys His Leu Asn Ala Ile Arg Asn Ile Asn Ile Asn
            850                 855                 860

Ile Asp Gly Ile Lys Glu Val Glu Asn Tyr Phe Ala Leu Tyr His Tyr
865                 870                 875                 880

Leu Ile Gln Lys His Leu Glu Asn Arg Phe Ala Asp Lys Lys Val Glu
                885                 890                 895

Arg Asp Thr Gly Asp Phe Ile Ser Lys Leu Glu Glu His Lys Thr Tyr
            900                 905                 910

Cys Lys Asp Phe Val Lys Ala Tyr Cys Thr Pro Phe Gly Tyr Asn Leu
                915                 920                 925

Val Arg Tyr Lys Asn Leu Thr Ile Asp Gly Leu Phe Asp Lys Asn Tyr
            930                 935                 940

Pro Gly Lys Asp Asp Ser Asp Lys Gln Lys
945                 950
```

```
<210> SEQ ID NO 15
<211> LENGTH: 900
<212> TYPE: PRT
<213> ORGANISM: Ruminococcus bicirculans
<220> FEATURE:
<221> NAME/KEY: misc_feature
<223> OTHER INFORMATION: SG4METG13543898_Rb2Mmc2

<400> SEQUENCE: 15

Met Ala Asp Ile Asp Lys Lys Lys Ser Ala Lys Ala Ala Gly Leu
1               5                   10                  15

Lys Ser Thr Phe Val Leu Glu Asn Asn Lys Leu Leu Met Thr Ser Phe
                20                  25                  30

Gly Asn Gly Asn Lys Ala Val Ile Glu Lys Ile Ile Asp Glu Lys Val
            35                  40                  45

Asp Ser Ile Asn Lys Pro Glu Val Phe Ser Val Thr Pro Cys Asp Lys
        50                  55                  60

Lys Phe Glu Leu Gln Pro Ala Lys Arg Gly Leu Ala Ala Asp Ser Leu
65                  70                  75                  80

Val Asp Asn Pro Leu Lys Ser Lys Lys Thr Ala Gly Asp Asp Ala Ile
                85                  90                  95

His Cys Arg Lys Phe Leu Glu Arg Gln Phe Asp Gly Asn Thr Phe
            100                 105                 110

Asn Asp Asn Ile His Ile Gln Leu Ile Tyr Asn Ile Leu Asp Ile Glu
        115                 120                 125

Lys Ile Leu Ser Val His Val Asn Asp Ile Val Tyr Ser Val Asn Asn
                130                 135                 140

Ile Leu Ser Arg Gly Glu Gly Met Glu Tyr Asn Asp Tyr Ile Gly Thr
145                 150                 155                 160

Leu Asn Leu Lys Ser Phe Glu Thr Tyr Lys Asn Asn Leu Val Asn Lys
                165                 170                 175

Lys Lys Phe Asp Leu Asp Arg Val Lys Lys Ile Pro Gln Leu Ala Tyr
            180                 185                 190
```

-continued

Phe Gly Ser Ala Phe Tyr Asn Thr Pro Glu Asp Thr Ser Ala Lys Ile
            195                 200                 205

Thr Lys Thr Lys Ile Lys Ser Asp Glu Glu Ile Tyr Tyr Thr Phe Met
    210                 215                 220

Leu Leu Ser Thr Ala Arg Asn Phe Ser Ala His Tyr Leu Asp Arg Asp
225                 230                 235                 240

Arg Ala Lys Ser Ser Asp Ala Glu Asp Phe Asp Gly Thr Ser Val Ile
                245                 250                 255

Met Tyr Asn Leu Asp Asn Glu Glu Leu Tyr Asn Glu Lys Val His Met
            260                 265                 270

Val Leu Thr Gly Met Lys Lys Val Leu Asp Ala Asn Phe Asn Lys Lys
        275                 280                 285

Val Glu His Leu Asn Asn Ser Phe Ile Lys Asn Ser Ala Lys Asp Phe
    290                 295                 300

Val Ile Leu Cys Glu Val Leu Gly Ile Lys Ser Arg Asp Glu Lys Thr
305                 310                 315                 320

Lys Phe Val Lys Asp Tyr Tyr Asp Phe Ile Val Arg Lys Asn Tyr Lys
                325                 330                 335

His Leu Gly Phe Ser Val Lys Glu Leu Arg Glu Leu Leu Phe Ala Asn
            340                 345                 350

His Asp Ser Asn Lys Tyr Ile Lys Glu Phe Asp Lys Ile Ser Asn Lys
        355                 360                 365

Lys Phe Asp Ser Val Arg Ser Arg Leu Asn Arg Leu Ala Asp Tyr Ile
    370                 375                 380

Ile Tyr Asp Tyr Tyr Asn Lys Asn Asn Ala Lys Val Ser Asp Leu Val
385                 390                 395                 400

Lys Tyr Leu Arg Ala Ala Ala Asp Asp Glu Gln Lys Lys Lys Ile Tyr
                405                 410                 415

Leu Asn Glu Ser Ile Asn Leu Val Lys Ser Gly Ile Leu Glu Arg Ile
            420                 425                 430

Lys Lys Ile Leu Pro Lys Leu Asn Gly Lys Ile Ile Gly Asn Met Gln
        435                 440                 445

Pro Asp Ser Thr Ile Thr Ala Ser Met Leu His Asn Thr Gly Lys Asp
    450                 455                 460

Trp His Pro Ile Ser Glu Asn Ala His Tyr Phe Thr Lys Trp Ile Tyr
465                 470                 475                 480

Thr Leu Thr Leu Phe Met Asp Gly Lys Glu Ile Asn Asp Leu Val Thr
                485                 490                 495

Thr Leu Ile Asn Lys Phe Asp Asn Ile Ala Ser Phe Ile Glu Val Leu
            500                 505                 510

Lys Ser Gln Ser Val Cys Thr His Phe Ser Glu Glu Arg Lys Met Phe
        515                 520                 525

Ile Asp Ser Ala Glu Ile Cys Ser Glu Leu Ser Ala Met Asn Ser Phe
    530                 535                 540

Ala Arg Met Glu Ala Pro Gly Ala Ser Ser Lys Arg Ala Met Phe Val
545                 550                 555                 560

Glu Ala Ala Arg Ile Leu Gly Asp Asn Arg Ser Lys Glu Glu Leu Glu
                565                 570                 575

Glu Tyr Phe Asp Thr Leu Phe Asp Lys Ser Ala Ser Lys Lys Glu Lys
            580                 585                 590

Gly Phe Arg Asn Phe Ile Arg Asn Asn Val Val Asp Ser Asn Arg Phe
        595                 600                 605

Lys Tyr Leu Thr Arg Tyr Thr Asp Thr Ser Ser Val Lys Ala Phe Ser

```
                    610               615               620
Asn Asn Lys Ala Leu Val Lys Phe Ala Ile Lys Asp Ile Pro Pro Glu
625                 630               635               640

Gln Ile Leu Arg Tyr Tyr Asn Ser Cys Phe Gly Ala Ser Glu Arg Tyr
                    645               650               655

Tyr Asn Asp Gly Met Ser Asp Lys Leu Val Glu Ala Ile Gly Lys Ile
                660               665               670

Asn Leu Met Gln Phe Asn Gly Val Ile Gln Gln Ala Asp Arg Asn Met
                675               680               685

Leu Pro Glu Glu Lys Lys Lys Ala Asn Ala Gln Lys Glu Lys Tyr Lys
            690               695               700

Ser Ile Ile Arg Leu Tyr Leu Thr Val Cys Tyr Leu Phe Phe Lys Asn
705                 710               715               720

Leu Val Tyr Val Asn Ser Arg Tyr Tyr Ser Ala Phe Tyr Asn Leu Glu
                    725               730               735

Lys Asp Arg Ser Leu Phe Glu Ile Asn Gly Glu Leu Lys Pro Thr Gly
                740               745               750

Lys Phe Asp Glu Gly His Tyr Thr Gly Leu Val Lys Leu Phe Ile Asn
            755               760               765

Asn Gly Trp Ile Asn Pro Arg Ala Ser Ala Tyr Leu Thr Val Asn Leu
            770               775               780

Ala Asn Ser Asp Glu Thr Ala Ile Arg Thr Phe Arg Asn Thr Ala Glu
785                 790               795               800

His Leu Glu Ala Leu Arg Asn Val Asp Lys Tyr Leu Asn Asp Leu Lys
                    805               810               815

Gln Phe Asp Ser Tyr Phe Glu Ile Tyr His Tyr Ile Thr Gln Arg Asn
                820               825               830

Ile Lys Glu Lys Cys Glu Met Pro Lys Glu Gln Thr Val Lys Tyr Asn
            835               840               845

Asn Asp Leu Leu Lys Tyr His Gly Tyr Ser Lys Asp Phe Val Lys Ala
            850               855               860

Leu Cys Val Pro Phe Gly Tyr Asn Leu Pro Arg Phe Lys Asn Leu Ser
865                 870               875               880

Ile Asp Ala Leu Phe Asp Lys Asn Asp Lys Arg Glu Lys Leu Lys Lys
                    885               890               895

Gly Phe Glu Asp
            900

<210> SEQ ID NO 16
<211> LENGTH: 937
<212> TYPE: PRT
<213> ORGANISM: Ruminococcus flavefaciens
<220> FEATURE:
<221> NAME/KEY: misc_feature
<223> OTHER INFORMATION: SG5METG11978931_Rf5Mmc2

<400> SEQUENCE: 16

Met Ala Lys Lys Lys Arg Ile Thr Ala Lys Glu Arg Lys Gln Asn His
1               5                   10                  15

Arg Glu Ser Leu Met Lys Lys Ala Asp Ser Asn Ala Glu Lys Glu Lys
                20                  25                  30

Ala Lys Glu Pro Val Val Glu Asn Lys Pro Asp Thr Ala Ile Ser Lys
            35                  40                  45

Asp Asn Thr Pro Lys Pro Asn Lys Glu Ile Lys Lys Ser Lys Ala Lys
        50                  55                  60
```

```
Leu Ala Gly Val Lys Trp Val Ile Lys Ala Asn Asp Val Ala Tyr
 65                  70                  75                  80

Ile Ser Ser Phe Gly Lys Gly Asn Asn Ser Val Leu Glu Lys Arg Ile
                 85                  90                  95

Met Gly Asp Val Ser Ser Asn Val Asn Lys Asp Ser His Met Tyr Val
            100                 105                 110

Asn Pro Lys Tyr Thr Lys Asn Tyr Glu Ile Lys Asn Gly Phe Ser
        115                 120                 125

Ser Gly Ser Ser Leu Val Thr Tyr Pro Asn Lys Pro Lys Asn Ser
    130                 135                 140

Gly Met Asp Ala Leu Cys Leu Lys Pro Tyr Phe Glu Lys Asp Phe Phe
145                 150                 155                 160

Gly His Ile Phe Thr Asp Asn Met His Ile Gln Ala Ile Tyr Asn Ile
                165                 170                 175

Phe Asp Ile Glu Lys Ile Leu Ala Lys His Ile Thr Asn Ile Ile Tyr
            180                 185                 190

Thr Val Asn Ser Phe Asp Arg Asn Tyr Asn Gln Ser Gly Asn Asp Thr
        195                 200                 205

Ile Gly Phe Asp Ile Asn Tyr Arg Val Pro Tyr Ser Glu Tyr Gly Gly
    210                 215                 220

Gly Lys Asp Ser Asn Gly Glu Pro Lys Asn Gln Ser Lys Trp Glu Lys
225                 230                 235                 240

Arg Asp Asn Phe Ile Lys Phe Tyr Asn Glu Ser Lys Pro His Leu Gly
                245                 250                 255

Tyr Tyr Glu Asn Ile Phe Tyr Asp His Gly Lys Pro Ile Ser Glu Glu
            260                 265                 270

Lys Phe Tyr Asn Tyr Leu Asn Ile Leu Asn Phe Ile Arg Asn Asn Thr
        275                 280                 285

Phe His Tyr Lys Asp Asp Ile Glu Leu Tyr Ser Glu Asn Tyr Ser
    290                 295                 300

Glu Glu Phe Val Phe Ile Asn Cys Leu Asn Lys Phe Val Lys Asn Lys
305                 310                 315                 320

Phe Lys Asn Val Asn Lys Asn Phe Ile Ser Asn Glu Lys Asn Asn Leu
                325                 330                 335

Tyr Ile Ile Leu Asn Ala Tyr Gly Lys Asp Thr Glu Asn Val Glu Val
            340                 345                 350

Val Lys Lys Tyr Ser Lys Glu Leu Tyr Lys Leu Ser Val Leu Lys Thr
        355                 360                 365

Asn Lys Asn Leu Gly Val Asn Val Lys Lys Leu Arg Glu Ser Ala Ile
    370                 375                 380

Glu Asn Gly Tyr Cys Pro Leu Pro Tyr Asp Lys Glu Lys Glu Val Ala
385                 390                 395                 400

Lys Leu Ser Ser Val Lys His Lys Leu Tyr Lys Thr Tyr Asp Phe Val
                405                 410                 415

Ile Thr His Tyr Leu Asn Ser Asn Asp Lys Leu Leu Glu Ile Val
            420                 425                 430

Glu Thr Leu Arg Leu Ser Lys Asn Asp Glu Lys Glu Asn Val Tyr
        435                 440                 445

Lys Lys Tyr Ala Glu Lys Leu Phe Lys Ala Asp Val Ile Asn Pro
    450                 455                 460

Ile Lys Ala Ile Ser Lys Leu Phe Ala Glu Lys Gly Asn Lys Leu Phe
465                 470                 475                 480

Lys Glu Lys Val Ile Ile Lys Lys Glu Tyr Val Glu Asp Ile Ser Ile
```

```
                485                 490                 495
Asp Lys Asn Ile Tyr Asp Phe Thr Lys Val Ile Phe Phe Met Thr Cys
            500                 505                 510

Phe Leu Asp Gly Lys Glu Ile Asn Asp Leu Leu Thr Asn Ile Ile Ser
            515                 520                 525

Lys Leu Gln Val Ile Glu Asp His Asn Asn Val Ile Lys Phe Ile Ala
            530                 535                 540

Glu Asn Asp Asp Ala Val Tyr Lys Asp Tyr Ser Asp Lys Tyr Ala Ile
545                 550                 555                 560

Phe Arg Asn Val Gly Lys Ile Ala Thr Glu Leu Glu Ala Ile Lys Ser
                565                 570                 575

Ile Ala Arg Met Glu Asn Lys Ile Glu Asn Ala Pro Gln Glu Pro Leu
            580                 585                 590

Leu Asn Asp Ala Leu Leu Ala Leu Gly Val Ser Lys Thr Asp Leu Glu
            595                 600                 605

Asn Thr Tyr Asn Lys Tyr Phe Asp Ser Lys Glu Lys Ala Asp Lys Gln
            610                 615                 620

Ser Gln Lys Val Ser Thr Phe Leu Met Asn Asn Val Ile Asn Asn Asn
625                 630                 635                 640

Arg Phe Lys Tyr Val Ile Lys Tyr Ile Asn Pro Ala Asp Ile Asn Gly
                645                 650                 655

Leu Ala Lys Asn Arg Tyr Leu Val Lys Phe Val Leu Ser Lys Ile Pro
            660                 665                 670

Glu Glu Gln Ile Asp Ser Tyr Tyr Lys Leu Phe Ser Asn Glu Glu Glu
            675                 680                 685

Pro Ser Cys Glu Glu Lys Ile Lys Leu Leu Thr Lys Lys Ile Ser Lys
            690                 695                 700

Leu Asn Phe Gln Thr Leu Phe Glu Asn Asn Lys Ile Pro Asn Val Glu
705                 710                 715                 720

Lys Glu Lys Lys Lys Ala Ile Ile Thr Leu Tyr Phe Thr Ile Val Tyr
                725                 730                 735

Ile Leu Val Lys Asn Leu Val Asn Ile Asn Gly Leu Tyr Thr Leu Ala
            740                 745                 750

Leu Tyr Phe Val Glu Arg Asp Arg Tyr Phe Tyr Lys Lys Ile Cys Gly
            755                 760                 765

Lys Lys Asp Lys Lys Ser Tyr Glu Asp Val Asp Tyr Leu Leu Leu
            770                 775                 780

Pro Glu Ile Phe Ser Gly Ser Lys Tyr Arg Glu Glu Thr Lys Asn Leu
785                 790                 795                 800

Lys Leu Pro Lys Glu Lys Asp Arg Asp Ile Met Lys Lys Tyr Leu Pro
            805                 810                 815

Asn Asp Lys Asp Arg Glu Lys Tyr Asn Lys Phe Phe Thr Ala Tyr Arg
            820                 825                 830

Asn Asn Ile Val His Leu Asn Ile Ile Ala Lys Leu Ser Glu Leu Thr
            835                 840                 845

Lys Asn Ile Asp Lys Asp Ile Asn Ser Tyr Phe Asp Ile Tyr His Tyr
            850                 855                 860

Cys Thr Gln Arg Val Met Phe Asn Tyr Cys Lys Glu Lys Asn Asp Val
865                 870                 875                 880

Val Leu Ala Lys Met Lys Asp Leu Ala His Ile Lys Ser Asp Cys Asp
                885                 890                 895

Glu Phe Ser Ser Lys His Thr Tyr Pro Phe Ser Ser Ala Val Leu Arg
            900                 905                 910
```

Phe Met Asn Leu Pro Phe Ala Tyr Asn Val Pro Arg Phe Lys Asn Leu
        915                 920                 925

Ser Tyr Lys Lys Phe Phe Asp Lys Gln
        930                 935

<210> SEQ ID NO 17
<211> LENGTH: 946
<212> TYPE: PRT
<213> ORGANISM: Eubacterium siraeum
<220> FEATURE:
<221> NAME/KEY: misc_feature
<223> OTHER INFORMATION: SG5METT12020113_Es8Mmc2

<400> SEQUENCE: 17

Met Lys Lys Arg Glu Glu Cys Leu Gly Ser Arg Glu Leu Glu Gln
1               5                   10                  15

Lys Asn Leu Lys Lys Trp Glu Glu Thr Asn Ala Glu Asn Arg Arg Ser
            20                  25                  30

Arg Ala Lys Ala Val Gly Val Lys Ser Val Phe Val Val Gly Glu Asp
        35                  40                  45

Leu Tyr Leu Ala Thr Phe Gly Asn Gly Asn Glu Thr Leu Leu Glu Lys
    50                  55                  60

Lys Ile Thr Pro Asp Gly Thr Ile Thr Ser Phe Ser Lys Glu Glu Ala
65              70                  75                  80

Phe Thr Ala Lys Leu Lys Phe Ala Gln Thr Glu Ser Thr Glu Ala Thr
                85                  90                  95

Ser Ile Gly Ile Ser Asn Gly Arg Ile Val Leu Pro Glu Val Pro Val
            100                 105                 110

Asp Asn Pro Cys Tyr Ala Ala Pro Gln Ala Lys Thr Ala Lys Lys Val
        115                 120                 125

Ala Gly Glu Asp Leu Leu Gln Leu Lys Glu Val Leu Glu Lys Arg Tyr
    130                 135                 140

Phe Gly Cys Ser Phe Asp Asp Asp Leu His Ile Arg Leu Ile Tyr Asn
145                 150                 155                 160

Ile Leu Asp Ile Glu Lys Ile Leu Ala Glu Tyr Val Thr Asn Ala Val
                165                 170                 175

Phe Ser Ile Asp Asn Val Ser Gly Asn Ala His Asp Phe Leu Gly Tyr
            180                 185                 190

Leu Ser Thr Arg Asn Ser Tyr Asp Ala Phe Met His Pro Glu Lys Tyr
        195                 200                 205

Pro Glu His Phe Glu Asn Lys Ser Asp Leu Ile Glu Arg Val Arg Lys
    210                 215                 220

Gln Gly Asp Asp Phe Leu Ala Phe Val Asp Asn Lys Arg Ile Gly Tyr
225                 230                 235                 240

Phe Gly Lys Ala Phe Phe Tyr Gln Asp Gly Arg Lys Glu Ile Glu Lys
                245                 250                 255

Pro Asp Gly Glu Ile Tyr His Leu Leu Thr Leu Ile Gly Ser Leu Arg
            260                 265                 270

Gln Trp Ile Thr His Ser Asp Glu Arg Glu Glu Gly Thr Ser Arg Thr
        275                 280                 285

Trp Leu Tyr Gln Leu Glu Lys Phe Leu Leu Pro Glu Tyr Gln Glu Thr
    290                 295                 300

Met Asn Val Asn Tyr Asn Asp Ile Val Lys Glu Leu Thr Thr Asn Phe
305                 310                 315                 320

Thr Lys Thr Asn Ala Thr Asn Leu Asn Phe Leu Ala Glu Leu Leu His

```
                  325                 330                 335
Val Pro Val Lys Ala Ile Ala Glu Ser Tyr Phe Arg Phe Ala Ile Thr
                340                 345                 350
Lys Glu Tyr Lys Asn Leu Gly Phe Cys Ile Lys Thr Ile Arg Glu Ile
                355                 360                 365
Leu Leu Lys Arg Arg Glu Leu Ser Asp Ile Lys Glu Asn His Ala Val
                370                 375                 380
Tyr Asp Ser Ile Arg Ser Lys Leu Tyr Lys Met Met Asp Phe Val Leu
385                 390                 395                 400
Val His Ala Tyr Glu Ser Glu Glu Gly Lys Lys Glu Ala Glu Glu Leu
                405                 410                 415
Ala Ser Ser Leu Arg Phe Ala Leu Thr Glu Glu Lys Glu Ser Ile
                420                 425                 430
Tyr Leu Asn Glu Ala Glu Arg Leu Trp Lys Met Tyr Gly Asp Lys Leu
                435                 440                 445
Leu Lys Ile Lys Asp Phe Lys Gly Ser Gln Val Asn Leu Tyr Ser Tyr
                450                 455                 460
Lys Ser Lys Pro Val Asp Val Gln Leu Pro Ala Ile Leu Lys Pro Ala
465                 470                 475                 480
Lys Glu Val Thr Cys Phe Thr Lys Leu Met Tyr Ile Leu Thr Met Phe
                485                 490                 495
Leu Asp Gly Lys Glu Ile Asn Asp Leu Leu Thr Thr Leu Ile Asn Lys
                500                 505                 510
Phe Asp Asn Ile Asn Ser Leu Leu Lys Thr Met Glu Gln Leu Glu Leu
                515                 520                 525
Gln Thr Ala Phe Val Lys Glu Tyr Thr Phe Phe Ser Gln Ser Gln Arg
                530                 535                 540
Leu Cys Ala Glu Ile Thr Gln Leu Lys Ser Phe Ala Arg Met Gly Lys
545                 550                 555                 560
Pro Val Ser Asn Ala Lys Glu Ala Met Met Ile Asp Ala Ile Gln Ile
                565                 570                 575
Leu Gly Thr Asp Lys Thr Glu Lys Glu Leu Glu Thr Met Ala Lys Arg
                580                 585                 590
Phe Phe Arg Asp Gly Asn Gly Lys Leu Leu Lys Gly Gln His Gly
                595                 600                 605
Met Arg Asn Phe Ile Ala Ser Asn Val Ile Ser Asn Ala Arg Phe His
                610                 615                 620
Tyr Leu Ile Arg Tyr Gly Lys Pro Asp Lys Leu His Lys Leu Ala Gln
625                 630                 635                 640
Asn Glu Ala Val Val Lys Phe Val Leu His Asn Ile Ala Lys Ser Gln
                645                 650                 655
Lys Lys Gln Gly Gln Leu Gly Lys Asn Gln Ile Asp Arg Tyr Tyr Glu
                660                 665                 670
Thr Cys Gly Gly Lys Gln Thr Asn Ala Ser Thr Glu Glu Lys Ile Asp
                675                 680                 685
Phe Leu Ser Ser Ile Leu Thr Gly Met Asn Tyr Asp Gln Phe Gln Asp
                690                 695                 700
Val Lys Gln Ser Asp Gln Arg Ala Thr Pro Gln Glu Arg Arg Asp Lys
705                 710                 715                 720
Glu Lys Tyr Lys Ala Val Ile Ser Leu Tyr Leu Thr Val Leu Tyr Leu
                725                 730                 735
Phe Val Lys Asn Leu Val Asn Ile Asn Ala Arg Tyr Val Ile Gly Phe
                740                 745                 750
```

His Cys Leu Glu Arg Asp Ala Gln Leu Tyr Ser Gln Lys Phe Gly Ser
                755                 760                 765

Ser Ile Asn Ile Arg Lys Arg Tyr Thr Lys Leu Thr Glu Thr Ile Leu
        770                 775                 780

Gly Tyr Glu Ala Asp Glu Arg Ala Arg Lys Lys Asp Arg Arg Thr Ile
785                 790                 795                 800

Tyr Glu Lys Ala Ala Ala Lys Asn Arg His Leu Lys Asn Val Lys
                805                 810                 815

Trp Asn Cys Lys Thr Arg Glu Asn Leu Glu Arg Ala Asp Ala Asn Ala
                820                 825                 830

Ile Arg Glu Phe Arg Asn Thr Ile Ala His Leu Gly Val Asp Arg Asp
                835                 840                 845

Ala Asp Arg Ser Ile Ala Gly Ile Gly Thr Val Thr Cys Tyr Phe Asp
                850                 855                 860

Cys Tyr His Tyr Leu Val Gln Lys Glu Leu Glu Ser Ser Leu Lys Asp
865                 870                 875                 880

Lys Asn Ala Tyr Thr Glu Glu Tyr Leu Lys Lys Val Asn Lys Tyr His
                885                 890                 895

Ser Tyr Cys Arg Asp Phe Leu His Val Leu Cys Leu Pro Phe Ala Tyr
                900                 905                 910

Ser Ile Pro Arg Tyr Lys Asn Leu Ser Ile Ala Glu Leu Phe Asp Arg
                915                 920                 925

Asn Asn Leu Ala Glu Glu Pro Lys Thr Asn Ser Ala Val Ala Val
                930                 935                 940

Thr Val
945

<210> SEQ ID NO 18
<211> LENGTH: 923
<212> TYPE: PRT
<213> ORGANISM: Ruminococcus Sp.
<220> FEATURE:
<221> NAME/KEY: misc_feature
<223> OTHER INFORMATION: SG9METT10694578_Rs7Mmc2

<400> SEQUENCE: 18

Met Ser Lys Asn Lys Lys Thr Lys Ala Lys Arg Met Gly Ile Lys Ser
1               5                   10                  15

Ile Phe Leu Tyr Lys Glu Gly Arg Leu Ala Ile Met Ala Phe Gly Lys
                20                  25                  30

Gly Asn Arg Ala Glu Ile Ala Val Asp Ala Asp Ala Arg Gly Glu Asp
            35                  40                  45

Ile Leu Leu Pro Phe Gln Thr Lys His Arg Phe Arg Val Gln Asn Ile
        50                  55                  60

Asp Glu Asn Ile Asp Val Lys Cys Gly Asp Leu Glu Ser Leu Leu Thr
65                  70                  75                  80

Asn Pro Ala Thr Ala Asp Leu Gly Asp Tyr Leu Gln Leu Lys Gly Arg
                85                  90                  95

Leu Glu Leu His Phe Phe Gly Arg Lys Phe Pro His Asp Asn Val Arg
                100                 105                 110

Ile Gln Leu Ile Tyr Asn Ile Leu Asp Ile Leu Lys Ile Leu Gly Leu
            115                 120                 125

Tyr Val Asn Asp Ala Ile Phe Ser Val Asn Asn Leu Gln Ser Glu Glu
        130                 135                 140

Asn Pro Gln Asp Val Val Gly Leu Ala Met Gly Glu Ile Lys Pro Ile

```
            145                 150                 155                 160
        Asp Cys Glu Lys Glu Ala Lys Val Arg Lys Ile Leu Lys Asp Met Lys
                        165                 170                 175
        Pro Leu Leu Gly Phe Gly Asp Ala Phe Leu Leu Pro Ala Pro Lys
                        180                 185                 190
        Pro Lys Lys Gly Ile Asn Phe Glu Pro Glu Leu Thr Ala Ile Glu Lys
                        195                 200                 205
        Glu Asn Leu Ile Asn Leu His Asn Glu Asn Val Leu Leu Ile Leu Gly
        210                 215                 220
        Thr Leu Arg Gln Arg Thr Met His Phe Arg Glu Gly Asp Phe Phe Phe
        225                 230                 235                 240
        Arg Glu Asp Met Asp Lys Asn Phe Thr Gly Ser Asp Gly Lys Lys His
                        245                 250                 255
        Gly Asn Trp Asp Ala Ile Glu Lys Asn Tyr Gly Lys Met Ile Asn Lys
                        260                 265                 270
        Ile Asn Val Gly Phe Ile Lys Asn Ser Ser Thr Asn Leu Arg Ile Leu
                        275                 280                 285
        Phe Asp Ile Tyr Pro Gln Thr Ser Glu Ile Glu Ile Thr Glu Glu Tyr
        290                 295                 300
        Tyr Arg Phe Ser Ile Leu Lys Gln Gly Arg Asn Leu Gly Val Asn Met
        305                 310                 315                 320
        Lys Lys Leu Arg Glu Lys Ile Val Glu Lys Phe Cys Pro Glu Ile Lys
                        325                 330                 335
        Asn Lys Lys His Asp Ser Tyr Arg Ser Lys Leu Tyr Thr Ile Leu Asp
                        340                 345                 350
        Tyr Ile Leu Phe Arg Glu Ile Gly Asn Thr Asn Asp Leu Val Ala Met
                        355                 360                 365
        Val Asp Arg Leu Arg Glu Thr Ser Asp Glu Glu Met Lys Glu Glu Leu
                        370                 375                 380
        Tyr Asn Lys His Ala Asn Ile Phe Trp Lys Lys Ile Lys Ile Gln Phe
        385                 390                 395                 400
        Leu Thr Phe Phe Glu Lys Phe Lys Asn Gly Phe Pro Glu Phe Arg Thr
                        405                 410                 415
        Asp Ala Ile Asp Pro Ser Tyr Ile Glu Asn Val Lys Leu Asn Glu Asp
                        420                 425                 430
        Gly Val Pro Phe Val Gln Leu Met Ala Phe Leu Cys Asn Phe Leu Asp
                        435                 440                 445
        Gly Lys Glu Ile Asn Glu Leu Leu Thr Ala Phe Ile Asn Lys Phe Glu
                        450                 455                 460
        Asn Ile His Ser Phe Ile Glu Thr Ile Glu Lys Leu Gly Glu Lys Val
        465                 470                 475                 480
        Glu Phe Thr Asn Cys Thr Leu Phe Asn Gln Asn Gly Leu Ser Leu Arg
                        485                 490                 495
        Ile Ala Asn Glu Leu Arg Val Leu Ala Ser Ile Ala Lys Met Lys Pro
                        500                 505                 510
        Asp Leu Lys Asp Val Lys Arg Pro Ala Tyr Lys Ala Ala Ile Glu Met
                        515                 520                 525
        Leu Gly Val Ser Glu Asn Ser Lys Phe Leu Ala Asn Lys Trp Leu Glu
                        530                 535                 540
        Lys Asn Leu Leu Leu Asn Glu Ser Ala Ser Asp Glu Glu Arg Lys Ser
        545                 550                 555                 560
        Thr Asn Pro Phe Arg Asn Phe Ile Val Asn Asn Val Ile His Ser Arg
                        565                 570                 575
```

Arg Phe Ala Tyr Leu Val Arg Tyr Ala Lys Pro Lys Ser Val Arg Ala
            580                 585                 590

Val Met Asn Asn Arg Ser Ile Val Tyr Val Leu Ser Arg Leu Pro
    595                 600                 605

Glu Lys Gln Ile Glu Arg Tyr Tyr Glu Asn Ile Ala Glu Ser Leu Asp
610                 615                 620

Asp Ala Thr Glu Ile Pro Ser Leu Gln Ala Met Ile Asn Arg Leu Gly
625                 630                 635                 640

Asn Gln Leu Val Gly Phe Ser Phe Asp Lys Leu Asn Glu Asn Arg His
                645                 650                 655

Gly Ile Val Arg Asn Ser Asn Leu Ser Ser Gly Asn Lys Asn Val Glu
            660                 665                 670

Ile Glu Arg Leu Lys Ala Leu Thr Gly Leu Tyr Leu Thr Val Ala Tyr
        675                 680                 685

Val Ala Ile Lys Asn Leu Val Lys Ile Asn Ala Arg Tyr Tyr Ile Ala
    690                 695                 700

Phe Gly Ile Phe Glu Arg Asp Tyr Thr Leu Phe Ser Arg Gly Glu Lys
705                 710                 715                 720

Gly Asn Glu Lys Lys Asn Pro Asp Val Glu Lys Phe Cys Ile Pro Phe
                725                 730                 735

Glu Ile Asn Gly Lys Lys Cys Ser Cys Glu Leu Phe Ser Leu Thr Glu
            740                 745                 750

Tyr Phe Leu Glu Lys Glu Gly Glu Asn Asp Tyr His Gln Gln Gln Asp
        755                 760                 765

Gln Pro Phe Asp Lys Glu Ala Cys Arg Lys His Leu Asp Ser Ile Arg
    770                 775                 780

Arg His Phe Thr Lys Lys Trp Arg Val Ile Phe Arg Gln Glu Ile Asp
785                 790                 795                 800

Asp Ala Lys Ala Ile His Pro Thr Gly Leu Leu Val Ser Ala Val Arg
                805                 810                 815

Asn His Ala Ala His Leu Asn Val Leu His Ala Leu Gln Lys Tyr Val
            820                 825                 830

Ala Asp Phe His Lys Ile Arg Pro Asp Met Ser Ser Tyr Phe Glu Leu
        835                 840                 845

Tyr His Phe Leu Ile Gln Lys Leu Phe Leu Glu Glu Asp Ser Leu Asn
    850                 855                 860

Ile Pro Asp Val His Lys Lys Arg Ile Asn Ala Gly Val Pro Ser Arg
865                 870                 875                 880

Asp Leu Ile His Val Ala Tyr Val Ser Leu Gly Tyr Asn Leu Pro Arg
                885                 890                 895

Tyr Lys Asn Leu Thr Thr Glu Ala Leu Phe Asp Lys Asp Ser Glu Ser
            900                 905                 910

Ala Lys Val Gly Glu Glu Lys Lys Ser Arg Lys
        915                 920

<210> SEQ ID NO 19
<211> LENGTH: 849
<212> TYPE: PRT
<213> ORGANISM: Ruminococcus Sp.
<220> FEATURE:
<221> NAME/KEY: misc_feature
<223> OTHER INFORMATION: SG10METT22022681_RuMmc2

<400> SEQUENCE: 19

Met Ala Gln Lys Lys Thr Ser Ala Lys Arg Ile Gly Leu Lys Ser Ile

```
1               5                   10                  15
Phe Gln Thr Gly Lys Lys Ala Tyr Leu Ala Gly Phe Gly Lys Asn Asn
                20                  25                  30
Lys Asn Val Ile Glu Lys Lys Tyr Phe Glu Asn Ser Ile Ser Asn Glu
                35                  40                  45
Thr Gln Asn Pro Ala Phe Asp Ala Arg Leu Asp Glu Asn Ser Asn Phe
                50                  55                  60
Ile Leu Glu Lys Asn Asn Leu Ser Ala Ser Tyr Ile Asn Pro Val His
65                  70                  75                  80
Gln Thr Pro Lys Arg Glu Phe Leu Lys Glu Asn Leu Glu Lys Phe Tyr
                85                  90                  95
Phe Gly Asn Val Ser Asn Gly Asn Ile Pro Ile Gln Ile Ala Tyr Tyr
                100                 105                 110
Val Arg Ser Ile Glu Lys Leu Phe Ala Leu Tyr Ile Asn Asp Ile Ile
                115                 120                 125
Tyr Ala Leu Asp Asn Leu Asn Ile Asn Arg Lys Ser Ile Leu Asn Ile
                130                 135                 140
Ser Ser Asp Glu His Arg Asn Asp Val Leu Gly Asn Asp Ile Lys Thr
145                 150                 155                 160
Asn Val Lys Phe Ser Thr Leu Ile Ser Asn Ile Gln Thr Lys Asn Glu
                165                 170                 175
Tyr Phe Ser Lys Ser Asn Arg Ile Val Asn Phe Leu Lys Asn Leu Lys
                180                 185                 190
Cys Tyr Glu Gly Met Phe Glu Asn Leu Phe Asn Arg Val Ser Thr Asp
                195                 200                 205
Val Gly Val Ser Asp Lys Asp Ala Lys Leu Asn Gln Ile Tyr Lys Thr
                210                 215                 220
Met Gln Val Ile Ser Phe Val Arg Asn Asn Ile Ile His Gly Glu Asn
225                 230                 235                 240
Asn Ile Phe Lys Asn Ile Asn Asn Ser Leu Val Lys Thr Thr Ala Ile
                245                 250                 255
Glu Ile Tyr Lys Asn Ala His Thr Val Phe Leu Lys Ser Phe Lys Ala
                260                 265                 270
Asn Ser Gln Thr Asn Val Phe Ile Leu Asn Arg Ile Phe Gly Thr Asp
                275                 280                 285
Ile Ser Lys Arg Tyr Tyr Asp Phe Ala Tyr Thr Lys Asp Tyr Lys Asn
                290                 295                 300
Leu Gly Leu Ser Ile Lys Lys Ile Arg Glu Gln Ile Phe Glu Val Arg
305                 310                 315                 320
Asn Leu Lys Glu Ser Phe Gly Ile Glu Glu Tyr Ser Lys Ile Lys Ser
                325                 330                 335
Lys Leu Asn Thr Leu Tyr Asp Phe Val Gln Asp Tyr Leu Lys Glu
                340                 345                 350
Asn Glu Glu Tyr Leu Ser Ser Cys Val Asn Ser Gln Arg Glu Met Leu
                355                 360                 365
Glu Glu Tyr Lys Glu Gln Asn Tyr Thr Lys Ile Ala Thr Asp Leu Ile
                370                 375                 380
Thr Lys Leu Ser Lys Gln Phe Val Ile Asp Ile Cys Leu Asn
385                 390                 395                 400
Phe Glu Lys Phe Lys Thr Glu Asn Gln Lys Ala Ile Ser Gln Val Lys
                405                 410                 415
Phe Asp Val Asn Glu Arg Ala Phe Gly Glu Asn Thr Val Ile Ala Ala
                420                 425                 430
```

-continued

```
Leu Val Tyr Val Met Cys Arg Phe Leu Ser Glu Lys Glu Ile Asn Glu
            435                 440                 445

Phe Val Thr Gly Leu Val Asn Asn Leu Ile Asn Ile Gln Ser Leu Ile
    450                 455                 460

Glu Thr Phe Glu Glu Val Glu Pro Asn Ser Lys Glu Leu Ser Tyr Phe
465                 470                 475                 480

Val Asn Asn Phe Glu Val Phe Lys Asn Ile Pro Asp Leu Val Tyr Glu
                485                 490                 495

Leu Gln Thr Ile Leu Thr Val Ser Lys Gln Arg Lys Ile Glu Ile Lys
                500                 505                 510

Arg Val Lys Asn Lys Asn Gln Gln Val Asp Cys Thr Tyr Thr Tyr Leu
                515                 520                 525

Glu Glu Ala Tyr Leu Leu Leu Ser Asp Asn Ser Leu Ser Phe Glu Glu
                530                 535                 540

Val Lys Asn Asp Lys Phe Leu Cys Asn Phe Leu Lys Asn Asn Ile Val
545                 550                 555                 560

Lys Ser Asn Lys Phe Ser Tyr Ile Leu Arg Tyr Asn Asn Leu Lys Asn
                565                 570                 575

Cys Lys Leu Leu Phe Lys Asn Lys Glu Phe Val Lys Tyr Val Ile Met
                580                 585                 590

Ser Gln Val Ser Lys Thr Gln Leu Glu Arg His Phe Leu Leu Ala Lys
                595                 600                 605

Thr Phe Ser Val Ser Ala Gln Ser Val Asp Glu Leu Cys Glu His Leu
        610                 615                 620

Ser Asn Ile Ser Leu Lys Thr Met Thr Ser Lys Gln Glu Ser Ala Glu
625                 630                 635                 640

Tyr Cys Glu Phe Ile Lys Ser Leu Thr Gln Leu Tyr Met Thr Ile Ile
                645                 650                 655

Tyr Leu Thr Thr Lys Ser Leu Val Arg Ile Asn Ser Leu Tyr Cys Ile
            660                 665                 670

Ala Trp Leu Ser Tyr Glu Gln Asp Met Phe Tyr Ile Ser Lys Asn Pro
            675                 680                 685

Gln Lys Val Ile Asn Arg Phe Asn Val Val Arg Glu Asn Gln Thr Thr
            690                 695                 700

Lys Pro Asn Glu Ile Glu Tyr Asn Asn Ser Ile Thr Gln Arg Ala Leu
705                 710                 715                 720

Phe Glu Asn Lys Leu Tyr Gly Lys His Asn Glu Pro Phe Ile Thr Tyr
                725                 730                 735

Leu Lys Glu His Phe Ile Cys Leu Asp Asn Glu Lys Thr Ile Phe Glu
            740                 745                 750

Lys Val Arg Asn His Val Met His Leu Ala Val Ile Asp Lys Val Phe
            755                 760                 765

Leu Lys Leu Glu Lys Tyr Asn Ser Lys Asp Ser Thr Tyr Phe Ser Leu
    770                 775                 780

Tyr Asn Phe Val Leu Gln Cys Leu Val Cys Asp Gly Val Glu Glu Leu
785                 790                 795                 800

Ser Tyr Cys Glu Lys Asn Phe Leu Ser Lys Gly Asn Tyr Ser Lys Asp
                805                 810                 815

Leu Val Gln Ile Leu Asn Met Pro Phe Ala Tyr Asn Ile Ala Arg Phe
                820                 825                 830

Lys Ala Leu Thr Asn Glu Lys Ile Phe Ser Lys Val Gln Lys Phe Gly
            835                 840                 845
```

Asn

<210> SEQ ID NO 20
<211> LENGTH: 891
<212> TYPE: PRT
<213> ORGANISM: Ruminococcus Sp.
<220> FEATURE:
<221> NAME/KEY: misc_feature
<223> OTHER INFORMATION: SG10METT22038604_Rs9Mmc2

<400> SEQUENCE: 20

Met Ser Glu Lys Arg Phe Ser Lys Thr Lys Ala Ala Gly Leu Lys Ser
1               5                   10                  15

Ser Leu Ala Asp Lys Asp Lys Leu Tyr Leu Thr Ser Phe Gly Lys Gly
            20                  25                  30

Asn Lys Ala Ile Leu Glu Lys Glu Ile Lys Gly Ser Gln Ile Lys Asp
        35                  40                  45

Ile His Met Glu Lys His Phe Asp Ala Ser Val Ile Ser Asn Lys Lys
    50                  55                  60

Phe Asn Ile Ser Gly Arg Val Val Lys Asp Ala Val Ser Asp Asn Leu
65                  70                  75                  80

Phe Ser Asn Ser Glu Ile Gly Ile Asp Arg Leu His Leu Lys Asp Lys
                85                  90                  95

Leu Glu Lys Met Phe Phe Gly Asp Thr Phe Pro Gly Glu Asn Ile His
            100                 105                 110

Ile Gln Ile Ala Tyr Asn Ile Leu Asp Ile Lys Lys Ile Leu Ser Val
        115                 120                 125

Tyr Val Asn Asn Val Ile Phe Thr Ile Asn Asn Leu Arg Arg Ile Glu
130                 135                 140

Lys Val Asn Asp Asp Lys Asp Tyr Ile Gly Met Leu Tyr Thr Phe Asn
145                 150                 155                 160

Thr Tyr Ser Asn Leu Ile Asp Asn Cys Ser Ile Cys Lys Asp Lys Asn
                165                 170                 175

Ser Cys Glu Tyr Cys Leu Ala Lys Phe Ser Lys Asn Ser Val Thr Pro
            180                 185                 190

His Asp Lys Lys Cys Lys Ser Thr Lys Ala Tyr Leu Glu Phe Met Asp
        195                 200                 205

Leu Ile Glu Gln Tyr Ser Cys Tyr Phe Lys Glu Phe Tyr Tyr Thr Gly
    210                 215                 220

Asn Phe Lys Thr Val Thr Gly Lys Asn Gly Lys Lys Gln Val Asp Ile
225                 230                 235                 240

Gln Arg Asn Lys Lys Asp Thr Tyr Asn Ile Leu Arg Val Ile Gly Cys
                245                 250                 255

Leu Arg Gln Phe Cys Ile His Asp Asn Asn Pro Leu Ser Asp Phe Leu
            260                 265                 270

Tyr Val Pro Val Lys Asp Asn Glu Met Lys Glu Leu Val Asp Arg Leu
        275                 280                 285

Tyr Arg Gly Lys Val Asp Thr Ile Asn Lys Asp Phe Ile Lys Asn Asn
    290                 295                 300

Arg Arg Thr Asn Leu Pro Ile Leu Phe Asp Ile Phe Asp Cys Arg Asn
305                 310                 315                 320

Asp Ser Gln Lys Ala Glu Leu Thr Lys Glu Phe Tyr Asp Phe Val Ile
                325                 330                 335

Cys Lys Glu His Lys Asn Leu Gly Phe Asn Val Lys Thr Leu Arg Glu
            340                 345                 350

```
Asn Met Leu Glu Ser Glu Glu Leu Ser Tyr Ile Arg Asp Lys Gln Tyr
            355                 360                 365

Asp Ser Val Arg Gly Lys Leu Phe Thr Leu Phe Asp Phe Ile Leu Tyr
            370                 375                 380

Lys Tyr Tyr Lys Asp Thr Val Leu Gln Glu Asp Ile Ile Lys Asn Leu
385                 390                 395                 400

Arg Glu Cys Met Ser Glu Glu Lys Asp Ala Val Tyr Lys Lys Gln
            405                 410                 415

Ala Gln Asp Ala Val Glu Asn Leu Gly Ser Val Ile Asn Thr Lys Leu
            420                 425                 430

Val Thr Lys Met Asn Gly Asp Leu Lys Asn Gln Asn His Gln Lys
            435                 440                 445

Thr Met Ile Asp Asn Arg Trp Ile Glu Ser Val Lys Ile Ser Asp Asn
        450                 455                 460

Ala Thr Asp Phe Ser Lys Ile Ile Tyr Ile Leu Thr Leu Phe Leu Asp
465                 470                 475                 480

Gly Lys Glu Ile Asn Glu Leu Leu Ser Ser Leu Ile Asn Lys Leu Glu
            485                 490                 495

Asn Ile Ala Ser Phe Val Asp Val Leu Lys Glu Leu Asn Ile His Cys
            500                 505                 510

Ser Phe Lys Ser Asp Tyr Ser Ile Leu Asn Asn Cys Tyr Lys Ile Ser
        515                 520                 525

Gly Glu Leu Arg Lys Val Lys Ser Phe Ala Arg Met Gln Lys Glu Met
            530                 535                 540

Asn Lys Tyr Ser Arg Gly Val Tyr Ile Asp Ala Val Glu Ile Leu Gly
545                 550                 555                 560

Ile Asp Lys Lys Asn Val Asn Leu Ser Gln Glu Gln Asp Glu Glu Glu
                565                 570                 575

Leu Met Glu Glu Phe Phe Ile Asn Asn Asp Asn Asn Val Arg Asn
            580                 585                 590

Phe Ile Ile Asn Asn Leu Ile Lys Ser Asn Arg Phe Ile Tyr Leu Met
        595                 600                 605

Arg Tyr Ser Asn Pro Lys Arg Ile Arg Lys Leu Ala Thr Asn Ile Cys
610                 615                 620

Leu Val Lys Phe Val Leu Asp Gly Ile Pro Glu Ser Gln Ile Asn Arg
625                 630                 635                 640

Tyr Phe Lys Ser Val Thr Gly Val Asp Ala Asp Arg Ala Thr Leu Glu
                645                 650                 655

Glu Gln Ile Asn Glu Leu Ala Lys Arg Ile Ser Glu Val Asn Phe Asn
            660                 665                 670

Gln Phe Val Asn Val Lys Gln Lys Ser Arg Asn Pro Gln Asp Asn Ile
            675                 680                 685

Arg Lys Glu Gln Met Lys Ala Ile Ile Gly Leu Tyr Leu Thr Val Leu
690                 695                 700

Tyr Leu Val Thr Lys Asn Ile Val Lys Val Asn Ala Arg Tyr Thr Ile
705                 710                 715                 720

Ala Ile Asn Cys Phe Glu Arg Asp Asn Ala Phe Tyr Gly Ile Asn Asn
                725                 730                 735

Gly Tyr Gln Thr Pro Thr Ala Leu Thr Asp Lys Phe Ile Glu Lys Gly
            740                 745                 750

Trp Ser Lys Asp Ser Trp Ile Asp Asn Gln Gly Lys Lys Cys Asp Met
        755                 760                 765

Ser Asp Tyr Lys Glu Phe Leu Leu Thr Asp Met Phe Lys Leu Tyr Arg
```

```
                    770                 775                 780
Asn Asn Ala Ala His Leu Asn Val Ile Thr Lys Ala Ser Ser Tyr Leu
785                 790                 795                 800

Glu Leu Asn Ala Asn Pro Asp Val Lys Ile Thr Lys Ile Lys Ser Tyr
                805                 810                 815

Tyr Gln Leu Tyr His Ser Ile Met Gln Arg Tyr Ile Met Ser Glu Tyr
                820                 825                 830

Val Phe Ser Lys Gly Asn Gln Lys Ala Tyr Glu Tyr Val Val Asn Ala
                835                 840                 845

Val Gly Gln Ala Lys Lys Tyr Gly Ser Tyr Ser Lys Asp Leu Val Lys
850                 855                 860

Val Leu Asn Tyr Pro Phe Ala Tyr Asn Leu Ala Arg Tyr Lys Asn Leu
865                 870                 875                 880

Thr Asn Glu Lys Ile Phe Asp Ala Asp Arg Gly
                885                 890

<210> SEQ ID NO 21
<211> LENGTH: 961
<212> TYPE: PRT
<213> ORGANISM: Ruminococcus flavefaciens
<220> FEATURE:
<221> NAME/KEY: misc_feature
<223> OTHER INFORMATION: SG10METT22060065_Rf10Mmc2

<400> SEQUENCE: 21

Met Lys Lys Lys Ile Lys Ala Lys Asp Leu Arg Glu Met Lys Lys Ala
1               5                   10                  15

Glu Gln Lys Glu Arg Phe Ser Ser Asn Val Val Lys Ala Asp Asp Ile
                20                  25                  30

Lys Glu Glu Lys Ile Lys Ile Ser Glu Thr Val Ile Glu Lys Thr Glu
            35                  40                  45

Glu Lys Thr Glu Gln Lys Leu Lys Ser Lys Ser Lys Ala Ala Gly Leu
        50                  55                  60

Lys Ser Thr Leu Val Ser Gly Lys Asp Ile Tyr Leu Thr Ser Phe Gly
65                  70                  75                  80

Lys Gly Asn Lys Ala Val Val Glu His Lys Ile Asp Ala Asp Asp Ser
                85                  90                  95

Tyr Ser Val Thr Lys Ile Ser Glu Glu Pro Thr Leu Ser Val Asn Asp
                100                 105                 110

Val Asp Asn Lys Asp Ile Ser Phe Ser Ser Asp Arg Pro Phe Gly Arg
            115                 120                 125

Asp Glu Lys Leu Leu Ala Ala Asn Pro Ile Val Gly Asn Ser Val Arg
        130                 135                 140

Gly Asp Asn Leu Gly Leu Lys Glu Lys Leu Glu Gln Lys Tyr Phe Asp
145                 150                 155                 160

Asp Thr Phe Asn Asp Asn Ile His Ile Gln Ile Ile Tyr Asn Ile Met
                165                 170                 175

Asp Ile Glu Lys Ile Leu Ala Val Tyr Ser Thr Ser Ile Ala Thr Thr
                180                 185                 190

Ile Asn Gly Met Leu Ser Asp Glu Leu Thr Asp Asp Lys Asp Phe Ile
            195                 200                 205

Gly Tyr Met Ser Thr Lys Asn Thr Tyr Asp Val Phe Leu Asp Pro Asp
        210                 215                 220

Lys Asn Pro Glu Leu Asp Lys Lys Lys Asp Asn Ile Asn Asp Ser
225                 230                 235                 240
```

-continued

Arg Gly Gln Phe Glu Asp Leu Leu Lys Thr Asn Arg Leu Gly Tyr Phe
            245                 250                 255
Gly Phe Asp Tyr Asn Pro Glu Glu Asn Lys His Ile Tyr His Leu Met
        260                 265                 270
Gly Phe Ala Gly Ser Leu Arg Gln Trp Ser Val His Asp Lys Gly Asn
    275                 280                 285
Trp Ile Tyr Lys Phe Gly Val Ala Pro Glu Tyr Leu Asp Thr Leu
290                 295                 300
Asp Tyr Tyr Phe Glu Asn Arg Tyr Thr Glu Leu Asn Asp Glu Phe Ile
305                 310                 315                 320
Ser Gly Lys Lys Asn Asp Lys Asp Val Gly Asn Arg Val Asn Leu
            325                 330                 335
Phe Ile Leu Ile Asp Asp Leu Thr Asp Gly Leu Thr Asp Asp Leu Lys
            340                 345                 350
Lys Ser Lys Lys Cys Glu Ile Cys Arg Leu Tyr Arg Glu Phe Ile Ile
        355                 360                 365
Glu Lys Thr Tyr Lys Asn Met Gly Phe Ser Ile Lys Lys Leu Arg Glu
    370                 375                 380
Asn Met Leu Thr Leu Glu Gly Gly Asp Lys Ile Thr Asp Glu Ser Met
385                 390                 395                 400
Asn Ser Val Arg Ser Lys Leu Tyr Lys Leu Ile Asp Phe Cys Ile Tyr
            405                 410                 415
Tyr Gly Tyr Tyr Lys Asp Glu Lys Arg Val Glu Lys Asn Val Arg Thr
            420                 425                 430
Leu Arg Ala Cys Met Thr Asp Ser Asp Lys Glu Ile Phe Tyr Lys Lys
        435                 440                 445
Glu Ala Glu Arg Leu Trp Ala Glu Asn Lys Asn Arg Phe Ile Ser Phe
    450                 455                 460
Ala Asn Lys Leu Thr Lys Arg Asn Ile Asp Lys Leu Arg Lys Arg Asp
465                 470                 475                 480
Thr Ser Glu Phe Leu Ser Ser Tyr Glu Lys Lys Ala Asn Lys Ser Phe
            485                 490                 495
Ser His Phe Ser Lys Leu Met Tyr Cys Met Cys Phe Phe Leu Asp Gly
        500                 505                 510
Lys Glu Ile Asn Asp Leu Leu Thr Thr Leu Ile Asn Lys Phe Asp Val
    515                 520                 525
Ile Ala Asn Leu Val Lys Thr Ala Lys Glu Ile Gly Val Glu Val Lys
530                 535                 540
Phe Lys Asp Asn Tyr Gly Phe Phe Asn Asn Ile Ser Lys Tyr Val
545                 550                 555                 560
Lys Glu Leu Asn Ile Val Lys Asn Ile Ala Arg Met Lys Lys Pro Ser
            565                 570                 575
Ala Asn Val Lys Lys Thr Met Tyr Arg Asp Ala Leu Tyr Ile Leu Gly
        580                 585                 590
Ile Pro Ser Asp Met Ser Lys Glu Leu Asn Asp Lys Ile Ala Asp
    595                 600                 605
Met Leu Lys Gly Thr Glu Asp Lys Ser Thr Lys Thr Gly Met Arg His
610                 615                 620
Asp Phe Arg Asn Phe Ile Lys Asn Asn Val Ile Asn Ser Ser Arg Phe
625                 630                 635                 640
Ile Tyr Ile Ile Lys Tyr Cys Asp Pro Lys Ser Ala Arg Lys Ile Ala
            645                 650                 655
Ser Asn Arg Lys Val Val Glu Phe Val Leu Arg Glu Ser Met Pro Glu

```
            660                 665                 670
Ser Ile Ile Glu Arg Tyr Tyr Lys Ser Cys Ile Glu Pro Gly Phe Ile
            675                 680                 685

Val Glu Ser Asp Ser Leu Asn Glu Lys Ile Met Lys Leu Ser Lys Val
            690                 695                 700

Ile Thr Glu Met Asn Phe Gly Lys Phe Glu Asp Ile Val Gln Asp Pro
705                 710                 715                 720

Arg Tyr Arg Asn Phe Asp Gly Glu Thr Lys Thr Arg Tyr Ile Ala Val
                725                 730                 735

Ile Gly Leu Tyr Leu Asn Val Val Tyr Gln Ile Ile Lys Asn Leu Val
            740                 745                 750

Asn Val Asn Ala Arg Tyr Val Met Gly Phe His Ser Leu Glu Arg Asp
            755                 760                 765

Met Glu Tyr Met Gly Phe Lys Asp Lys Tyr Asn Arg Thr Cys Ile Thr
            770                 775                 780

Arg Lys Ile Leu Glu Glu Thr Glu Gly Ala Lys Asp Lys Asn Ser Glu
785                 790                 795                 800

Glu Asn Lys Leu Lys Asn Arg Tyr Leu Ala Lys Asn Met His Tyr Arg
                805                 810                 815

Lys Cys Ile Asp Asp Ile Glu Asn Ser Asp Glu Ser Ala Ile Asn
            820                 825                 830

Leu Tyr Arg Asn Val Ala His Leu Lys Val Ile Lys Arg Cys Ala
            835                 840                 845

Leu Tyr Ile Gly Asp Ile Glu Tyr Ile Asn Ser Tyr Phe Gly Leu Tyr
            850                 855                 860

His Tyr Ile Met Gln Arg Cys Ile Ala Asp Gly Asn Tyr Asp Lys Tyr
865                 870                 875                 880

Lys Lys Lys Tyr Asn Gly Tyr Asn Ser Glu His Asp Tyr Phe Ile Lys
                885                 890                 895

Cys Asn Pro His Leu Glu Asp Lys Thr Lys Phe Glu Lys Thr Lys Lys
            900                 905                 910

Tyr Leu Ala Ser Leu Ser Glu Tyr Asn Thr Tyr Val Lys Asp Phe Val
            915                 920                 925

Lys Ala Leu Asn Val Pro Phe Gly Tyr Asn Ala Pro Arg Phe Lys Asn
            930                 935                 940

Leu Ser Ile Glu Glu Leu Phe Asp Lys Asn Ser Lys Lys Leu Asp
945                 950                 955                 960

Lys

<210> SEQ ID NO 22
<211> LENGTH: 914
<212> TYPE: PRT
<213> ORGANISM: Ruminococcus flavefaciens
<220> FEATURE:
<221> NAME/KEY: misc_feature
<223> OTHER INFORMATION: SG10METT22076049_Rf7Mmc2

<400> SEQUENCE: 22

Met Ala Lys Lys Met Asn Ala Lys Glu Lys Arg Glu Ala Ala Lys Ala
1               5                   10                  15

Glu Ala Glu Ala Glu Lys Lys Lys Ala Asp Leu Lys Ala Phe Ser
            20                  25                  30

Ala Asp Gln Lys Ser Arg Asn Lys Leu Asp Lys Cys Asn Arg Lys Ser
            35                  40                  45

Leu Ala Lys Ala Ala Gly Leu Lys Ser Thr Phe Ala Val Gly Asn Asp
```

```
              50                  55                  60
Leu Tyr Met Thr Ser Phe Gly Lys Gly Asn Asp Ala Ile Val Glu Lys
 65                  70                  75                  80

Lys Ile Ser Gly Thr Thr Val Thr Asn Leu Asn Tyr Gln Lys Glu Ser
                     85                  90                  95

Phe Thr Val Asn Lys Asp Ser Ile Thr Asp Met Thr Val Pro Ile Gln
                    100                 105                 110

Ser Asn Arg Ile Ala Phe Leu Asn Ser Gln Ala Asp Asn Pro Leu Tyr
                115                 120                 125

Arg Lys Gly Ser Glu Asn Lys Ile Gln Pro Asp Lys Leu Leu Leu Lys
                130                 135                 140

Asp Thr Leu Glu Lys Asn Tyr Phe Gly Lys Thr Phe Asn Asp Thr Leu
145                 150                 155                 160

His Ile Gln Leu Ile Tyr Asn Ile Leu Asp Ile Glu Lys Ile Leu Thr
                165                 170                 175

Val His Ser Val Asn Thr Val Tyr Ala Leu Asn Asn Leu Phe Gly Thr
                180                 185                 190

Glu Thr Ala Glu Ile Asn Asp Leu Ile Gly Ala Leu Ser Tyr Gln Lys
                195                 200                 205

Thr Tyr Asn Glu Phe Met Gln Thr Ser Ser Gln Lys Asn Ile Glu Leu
                210                 215                 220

Phe Glu Lys Phe Tyr Asn Leu Lys Thr Leu Gly Tyr Tyr Gly Asn Ile
225                 230                 235                 240

Phe Phe Lys Gly Asn Asn Lys Arg Ser Arg Lys Glu Ile Tyr Asp Ile
                245                 250                 255

Ile Ala Leu Ile Ala Thr Ile Arg Gln Trp Cys Ile His Phe Glu Glu
                260                 265                 270

Asp Lys Lys Asn Trp Leu Tyr Asn Val Gln Lys Val Leu Ser Pro Glu
                275                 280                 285

Tyr Ile Tyr Ile Leu Asp Asp Val Tyr Asp Ser Leu Val Glu Lys Ile
                290                 295                 300

Asn Lys Asn Phe Val Lys Asp Asn Lys Val Asn Ile Ile Met Leu Ser
305                 310                 315                 320

Asp Ile Leu Asn Met Lys Ser Glu Glu Lys Phe Arg Glu Leu Ile Lys
                325                 330                 335

Gln Tyr Tyr Lys Phe Ile Val Thr Lys Glu Gln Lys Leu Leu Gly Phe
                340                 345                 350

Ser Ile Lys Lys Leu Arg Glu Ala Met Leu Glu Asp Thr Ile Phe Lys
                355                 360                 365

Thr Asp Lys Lys Tyr Asp Ser Ile Arg Ser Lys Leu Tyr Lys Leu Ile
                370                 375                 380

Asp Phe Ile Leu Phe Tyr Lys Tyr Thr Thr Val Asp Ser Glu Lys Glu
385                 390                 395                 400

Tyr Ser Ile Asp Met Ile Asp Gln Leu Arg Ala Ala Val Ser Pro Glu
                405                 410                 415

Arg Lys Glu Gln Ile Tyr Lys Ser Glu Ser Glu Arg Leu Trp Lys Leu
                420                 425                 430

Tyr Lys Asn Ile Ile Met Asn Glu Ile Lys Pro Leu Leu Ser Glu Ser
                435                 440                 445

Ser Ile Ser Lys Leu Lys Lys Asn Lys Asp Tyr Asp Asn Ile Asn Ile
                450                 455                 460

Lys Asp Ile Val Ser Val Glu Thr Ala Asn Val Ser His Phe Ser Lys
465                 470                 475                 480
```

```
Ile Ile Tyr Leu Leu Ala Gln Phe Ile Asp Gly Lys Glu Val Asn Asp
            485                 490                 495

Leu Thr Thr Thr Leu Ile Asn Lys Phe Asp Asn Ile Arg Ser Phe Ile
            500                 505                 510

Lys Thr Ala Glu Asp Ile Gly Ile Glu Cys Asn Phe Leu Asn Glu Tyr
            515                 520                 525

Lys Phe Phe Asn Thr Ala Asn Thr Leu Lys Asn Glu Leu His Leu Ile
            530                 535                 540

Lys Asn Leu Thr Gly Met Gly Tyr Tyr Asp Val Ser Val Lys His Gln
545                 550                 555                 560

Met Tyr Lys Asp Ala Ile Asp Ile Leu Gly Ile Asn Asp Asn Val Ser
            565                 570                 575

Asp Asp Glu Ile Leu His Ile Ile Asp Asp Asn Ile Leu Phe Leu Gly
            580                 585                 590

Pro Asp Gly Lys Pro Leu Lys Asp Lys Lys Gly Lys Arg Gly Met Arg
            595                 600                 605

Asn Phe Ile Ile Ser Asn Val Ile Glu Ser Ser Arg Phe Arg Tyr Leu
            610                 615                 620

Val Lys Tyr Cys Asn Pro Lys Lys Ile Arg Lys Ile Ala Asn Asn Glu
625                 630                 635                 640

Lys Leu Val Lys Phe Val Met Gly Arg Ile Thr Glu Thr Gln Leu Glu
            645                 650                 655

Arg Tyr Tyr Tyr Ser Cys Asn Pro Glu Lys Gly Thr Tyr Pro Gly His
            660                 665                 670

Asp Gln Ala Val Asn Asn Leu Thr His Ile Ile Thr His Met Thr Phe
            675                 680                 685

Asp Asp Phe Gln Asn Val Lys Gln Asn Val Asn Ala Asp Gly Asp Asn
            690                 695                 700

Glu Asp Ser Lys Glu Lys Met Lys Tyr Gln Thr Ile Ile Ser Leu Tyr
705                 710                 715                 720

Leu Thr Ile Cys Tyr His Leu Val Lys Asn Leu Val Asn Ile Asn Ala
            725                 730                 735

Arg Tyr Ala Ile Ala Phe His Ser Leu Glu Arg Asp Ala Arg Leu Tyr
            740                 745                 750

Asn Leu Asn Leu Asn His Ser Asp Leu Met Asn Asp Gln Ser Ala Leu
            755                 760                 765

Val Lys Lys Ile Leu Ser Asp Ser Tyr Glu Thr Ala Gly Asn Leu His
770                 775                 780

Leu Arg Asn Lys Lys Trp Tyr Leu Thr Thr Lys Glu Asn Leu Glu Arg
785                 790                 795                 800

Tyr Asn Ala Glu Ala Ser Lys Asn Phe Arg Asn Ala Val Ala His Leu
            805                 810                 815

Asn Pro Ile Arg Asn Ala Asp Leu Phe Ile Gly Asp Ile Lys Asn Ile
            820                 825                 830

Thr Ser Tyr Tyr Asp Ile Tyr His Tyr Ile Leu Gln Lys Ser Ile Phe
            835                 840                 845

Lys Arg Met Asn Lys Gln Leu Ser Gly Lys Leu Cys Glu Tyr Asn Glu
            850                 855                 860

Ala Val Asn Lys Tyr His Asn Tyr Asn Lys Asp Phe Val Lys Ala Leu
865                 870                 875                 880

Cys Val Pro Phe Ala Tyr Asn Ile Val Arg Phe Lys Ser Leu Ser Ile
            885                 890                 895
```

```
Cys Glu Leu Phe Asp Arg Asn Ala Pro Glu Lys Glu Gln Lys Glu Thr
                900                 905                 910

Lys Asn

<210> SEQ ID NO 23
<211> LENGTH: 926
<212> TYPE: PRT
<213> ORGANISM: Eubacterium siraeum
<220> FEATURE:
<221> NAME/KEY: misc_feature
<223> OTHER INFORMATION: SG10METT23049739_Eb2Mmc2

<400> SEQUENCE: 23

Met Leu Asp Met Ser Val Asp Pro Met Asp Ile Arg Glu Gly Glu Ile
1               5                   10                  15

Pro Val Arg Glu Gly Arg Glu Gln Glu Ala Thr Gly Lys Leu Thr Ala
                20                  25                  30

Ser Gly Glu Lys Asn Ser Gly Ala Val Arg Lys Ser Arg Ala Lys Ala
            35                  40                  45

Ala Gly Leu Lys Ser Thr Phe Ile Leu Asn Glu Glu Ser Leu Leu Met
    50                  55                  60

Thr Ser Phe Gly Lys Gly Asn Asp Ala Lys Pro Glu Lys Gln Ile Thr
65                  70                  75                  80

Gly Asn Gln Ile Thr Ser Val Ser Ser Glu Pro Ala Phe Ser Thr Arg
                85                  90                  95

Leu Leu Pro His Gln Phe Glu Ile Ser Gly Arg Leu Ser Ala Val Ser
                100                 105                 110

Asp Asp Pro Leu His Ser Gly Gln Gly Ala Arg Thr Ala Met Arg Arg
            115                 120                 125

Glu Arg Asp Ser Gly Gln Gly Val Gly Gln Ser Val Gly Phe Leu Arg
    130                 135                 140

Glu Ser Leu Glu Lys Lys Phe Tyr Gly Gln Thr Phe Ala Asp Asn Ile
145                 150                 155                 160

His Ile Gln Leu Ile Tyr Asn Ile Leu Asp Ile Glu Lys Leu Leu Ala
                165                 170                 175

Ala His Ile Asn His Ile Cys Tyr Glu Val Asn Asn Leu Phe Arg Asn
                180                 185                 190

Ala Leu Ser Glu Thr Trp Asp Phe Val Gly Tyr Leu Ser Leu Asn Val
            195                 200                 205

Pro Tyr Asp Asp Phe Arg Ser Gly Arg Ala Glu His Ala Lys Ala Ala
    210                 215                 220

Glu Asn Asn Lys Val Ser Cys Glu His Phe Asp Tyr Leu Met Gln Asn
225                 230                 235                 240

Ala Arg Gln Ile Trp Tyr Phe Pro Ser Ala Phe Tyr Gly Trp Met Tyr
                245                 250                 255

Ser Pro Ala Asn Ala Asn Leu Lys Asp Ser Lys Thr Arg Gln Tyr Trp
                260                 265                 270

Asn Trp Trp Asn Asn Tyr Tyr Arg Leu Cys Leu Leu Gly Met Thr Arg
            275                 280                 285

Gln Ala Met Ser His Glu Tyr Phe Ser Ala Ala Lys Asn Ile Tyr Met
    290                 295                 300

Leu Asp Ala Gln Tyr Asp Gly Arg Phe Asp Ser Asp Pro Leu Arg Lys
305                 310                 315                 320

Ala Ala Arg Lys Asp Ala Arg Lys Met Leu Asp Ala Leu Tyr Gly Ser
                325                 330                 335
```

```
Arg Val Arg Glu Leu Asn Asp Asn Phe Leu Ser Leu Ala Lys Val Asp
            340                 345                 350

Leu Gly Leu Leu Phe Asp Ala Tyr Arg Met Thr Lys Lys Asp Asp Lys
        355                 360                 365

Ala Asp Leu Leu Gly Asp Tyr Tyr Arg Phe Thr Val Arg Lys Glu Phe
370                 375                 380

Lys Asn Leu Gly Phe Ser Ile Lys Arg Leu Arg Glu Ile Leu Leu Thr
385                 390                 395                 400

His Ile Glu Asp Gln Glu Asn Arg Lys Val Lys Gly Lys Gly Tyr Asp
                405                 410                 415

Ser Val Arg His Lys Met Tyr Lys Leu Phe Asp Phe Val Leu Phe Arg
        420                 425                 430

Tyr Tyr Arg Thr His Ser Ala Ala Gln Asp Glu Leu Val Ser Asn Leu
        435                 440                 445

Arg Ser Ala Met Ser Glu Ala Glu Lys Glu Ala Val Tyr Thr Lys Ala
        450                 455                 460

Ala Val Asn Leu Trp Pro Lys Ile Arg Gly Ile Phe Leu Lys Gly Ile
465                 470                 475                 480

Leu Pro Lys Met Asn Gly Lys Asp Ile Arg Glu Ile Lys Thr Glu Arg
                485                 490                 495

Glu Asp Pro Asp Ile Ser Ala Glu Met Leu Ala Asp Arg Ile Gly Gln
                500                 505                 510

Asn Ala His Thr Phe Ser Lys Leu Ile Tyr Leu Leu Thr Leu Tyr Leu
            515                 520                 525

Asp Gly Lys Glu Ile Asn Asp Leu Leu Thr Gly Leu Ile Asn Lys Leu
        530                 535                 540

Glu Asn Ile Gln Ser Phe Gln Ser Val Leu Glu Trp Gln Lys Leu Pro
545                 550                 555                 560

Cys Arg Leu Val Asp Glu Phe Ser Ile Phe Glu Ser Gly Arg Leu
                565                 570                 575

Ala Ala Glu Leu Arg Ile Val Asn Ser Phe Ala Arg Met Glu Lys Ala
            580                 585                 590

Asp Ala Asn Ala Lys Lys Val Met Phe Met Glu Ala Ala Gln Val Leu
            595                 600                 605

Gly Asp Ser Arg Ser Glu Glu Glu Leu Ser Val Tyr Phe Asp Gly Leu
        610                 615                 620

Leu Asp Gln Ser Ser Arg Pro His Leu Arg Asn Gly Lys Arg Asp Asn
625                 630                 635                 640

Arg Phe Arg Asn Phe Ile Cys Asn Asn Val Ile Glu Ser Pro Arg Phe
                645                 650                 655

Arg Tyr Leu Val Arg Tyr Ala Asp Pro Lys Ser Val Arg Lys Ile Ile
                660                 665                 670

Ser Asn Arg Ala Val Val Lys Leu Val Leu Asn Asp Ile Pro Asp Ala
        675                 680                 685

Gln Ile Thr Arg Tyr Tyr Glu Thr Cys Met Gly Ala Lys Glu Thr Phe
                690                 695                 700

Phe Asp Gly Met Arg Asp Thr Leu Ala Asp Lys Leu Ala Gly Ile Thr
705                 710                 715                 720

Phe Leu Glu Phe Lys His Ala Thr Ser Gly Asn Gly Leu Pro Glu Glu
                725                 730                 735

Glu Lys Arg Glu Asn Glu Arg Met Lys Gly Leu Ile Arg Leu Tyr Leu
            740                 745                 750

Thr Val Leu Tyr Leu Leu Val Lys Asn Leu Val Tyr Ile Asn Ser Arg
```

```
            755                 760                 765
Tyr Thr Leu Ala Phe His Cys Leu Glu Arg Asp Tyr Asn Leu Ile Tyr
    770                 775                 780

Gly Lys Ser Ile Lys Asp Ser Lys Tyr Leu Ala Leu Thr Arg Glu Ala
785                 790                 795                 800

Val Asp Lys Lys Arg Leu Asn Arg His Ser Ala Gln Tyr Met Gln Gln
                805                 810                 815

Asn Met Glu Asn Ala Asp Ile Arg Leu Ile Arg Asp Tyr Arg Asn Lys
            820                 825                 830

Val Ala His Leu Asn Thr Val Arg Asn Ala Ala Lys Tyr Ile Gly Asp
        835                 840                 845

Leu Arg Val Ala Asn Ser Tyr Phe Glu Ile Tyr His Tyr Leu Met Gln
    850                 855                 860

Arg Ser Leu Gln Glu Ser Phe Arg Asn Thr Ser Gly Lys Lys Tyr
865                 870                 875                 880

Phe Ala Ala Leu Asp Lys His Arg Ala Tyr Cys Lys Asp Phe Val Lys
                885                 890                 895

Ala Leu Asn Thr Pro Phe Gly Tyr Asn Leu Ala Arg Tyr Lys Asn Leu
            900                 905                 910

Ser Ile Asp Gly Leu Phe Asp Arg Asn Arg Pro Gly Lys Glu
        915                 920                 925
```

<210> SEQ ID NO 24
<211> LENGTH: 948
<212> TYPE: PRT
<213> ORGANISM: Eubacterium siraeum
<220> FEATURE:
<221> NAME/KEY: misc_feature
<223> OTHER INFORMATION: SG10METT28285540_Eb4Mmc2

<400> SEQUENCE: 24

Met Lys Lys Lys Pro Ser Ile Lys Glu Gln Arg Glu Gln Gln Lys Asn
1 5 10 15

Ala Gln Ser Ala Gln His Arg Gln Ala Glu Asn Ala Lys Lys Leu Ala
20 25 30

Glu Gln Lys Ala Met Glu Glu Ala Ala Arg Leu Lys Ala Glu Ala Glu
35 40 45

Arg Lys Lys Gln Leu Glu Val Met Arg Ser Gln Leu Ser Ala Asp Asn
50 55 60

Ser Arg Ser Met Lys Thr Lys Ala Lys Ala Ala Gly Leu Lys Ser Ile
65 70 75 80

Phe Thr Leu Lys Gln Gly Thr Leu Leu Met Thr Ser Phe Gly Arg Gly
85 90 95

Asn Asp Ala Leu Leu Glu Lys Arg Val Ile Ser Gly Lys Val Glu Asp
100 105 110

Met Arg Ser Pro Ala Ser Phe Ala Ala Leu Pro Asp Gly Lys Leu Phe
115 120 125

Arg Ile Asp Gly Arg Val Pro Gly Ala Val Ser Asp Asn Pro Ile Ala
130 135 140

Glu Lys Lys Ser Ala Glu Arg Arg Pro Gly Asp Asp Leu Val Phe Asn
145 150 155 160

Arg Val Phe Leu Glu Lys Arg Phe Phe Asn Arg Thr Phe Glu Asp Asn
165 170 175

Ile His Ile Gln Leu Ala Tyr Asn Ala Leu Asp Ile Glu Lys Ile Leu
180 185 190

```
Ala Val His Ile Asn Asn Ile Val Phe Thr Leu Asn Met Leu Arg
        195                 200             205
Asp Glu Asp Ile Asn Tyr Cys Asp Val Val Gly Asn Met Gly Met Ser
        210                 215             220
Cys Ser Tyr Asp Asn Phe Pro Ala Ser Lys Pro Lys Tyr Asn Glu Leu
225                 230                 235                 240
Phe Asn Arg Leu Cys Leu Gln Pro Gln Leu Ser Tyr Phe Gly Ile Thr
                245                 250                 255
Val Lys Asn Pro Asn Ala Pro Val Arg Lys Gly Lys Lys Pro Pro Lys
                260                 265                 270
Asn Glu Ala Leu Glu Ile Thr Gln Lys Gln Phe Tyr Tyr Met Leu Cys
                275                 280             285
Leu Leu Gly Asn Leu Arg Gln Ala Met Ala His Ser Thr Glu Glu Asn
        290                 295             300
Leu Leu Arg Leu Tyr Ser Met His Thr Met Lys Lys Ser Asp Ile Asn
305                 310                 315                 320
Ser Gly Ala Ile Asp Val Leu Asp Thr Ile Tyr Asn Asp Arg Val Lys
                325                 330                 335
Arg Leu Asn Asp Asp Phe Ile Lys Asp Ala Asn Lys Arg Asp Leu Ser
                340                 345                 350
Leu Leu Phe Lys Ala Phe Asp Val Ala Glu Ser Asn Lys Ala Glu Tyr
            355                 360                 365
Val Arg Ala Tyr Tyr Asp Phe Met Val Arg Lys Gln Tyr Lys Asn Thr
        370                 375                 380
Gly Phe Ser Ile Lys Thr Leu Arg Glu Ile Met Glu Thr Cys Ile Asp
385                 390                 395                 400
Glu Ala Lys Glu Ile Lys Asp Lys Lys Tyr Asp Thr Gly Arg Arg Lys
                405                 410                 415
Leu Asn Arg Leu Tyr Asp Phe Ala Leu Phe Arg Tyr Tyr Gln Asp His
                420                 425                 430
Ala Asp Glu Ser Leu Arg Leu Val Glu Ala Leu Arg Ala Ser Met Ser
        435                 440                 445
Glu Gln Asp Lys Thr Asp Ile Tyr Leu Ala Glu Ala Met Arg Met Trp
        450                 455                 460
Pro Ile Val Arg Ser Thr Val Glu His Ile Met Pro Asn Val Thr
465                 470                 475                 480
Glu Arg Thr Leu Glu Asn Glu Cys Gln Asp Ala Tyr Val Glu Ala His
                485                 490                 495
Lys Asp Thr Ile Leu Gly Asp Ile Gln Ile Gly Thr Glu Ala Asp Tyr
                500                 505                 510
Phe Cys Lys Tyr Ile Tyr Leu Leu Thr Arg Phe Leu Asp Gly Lys Glu
        515                 520                 525
Ile Asn Asp Leu Leu Thr Thr Leu Ile Asn Lys Phe Glu Asn Ile Ala
530                 535                 540
Ser Phe Asn Asp Val Ile Glu Gln Glu Gly Leu Ala Val Pro Phe Ala
545                 550                 555                 560
Ala Thr Tyr Lys Ile Phe Ala Cys Ala Gln Lys Ile Ala Asp Glu Leu
                565                 570                 575
Arg Val Ile Asn Ser Phe Ala Arg Met Ser Gln Glu Ser Gly Asp Ala
                580                 585                 590
Lys Arg Thr Leu Phe Val Glu Ala Ala Gln Leu Leu Gly Cys Lys Ala
            595                 600                 605
Ser Glu Ala Asp Leu Glu Asp Tyr Val Gln Arg Tyr Leu Leu Asp Asn
```

```
                    610                 615                 620
Asn Gly Lys Leu Thr Ala Lys Gly Lys Ala Asp Lys Gly Phe Arg Asn
625                 630                 635                 640

Phe Ile Ala Asn Asn Val Val Glu Ser Asp Arg Phe Arg Tyr Leu Val
                    645                 650                 655

Arg Tyr Gly Asn Pro Lys Thr Leu Asn Met Leu Gly His Cys Arg Asn
                660                 665                 670

Val Met Arg Phe Gly Leu Asp Ser Ile Lys Asp Gln Ile Val Arg
            675                 680                 685

Tyr Tyr Asn Ser Tyr Thr Leu Leu Asn Asp Glu Tyr His Glu Gly Met
            690                 695                 700

Arg Asp Tyr Leu Cys Asp Arg Leu Val Gly Ile Thr Leu Glu Asp Phe
705                 710                 715                 720

Glu Asn Val Asn Gln Ser Ala Lys Ser Gly Phe Glu Ala Asp Glu Lys
                725                 730                 735

Glu Arg Tyr Lys Ser Leu Ile Arg Leu Tyr Leu Thr Val Leu Tyr Leu
                740                 745                 750

Ile Val Lys Asn Leu Val Tyr Val Asn Ser Arg Tyr Phe Leu Ala Phe
                755                 760                 765

His Cys Val Glu Arg Asp Ser Asp Leu Gln Gly Met Lys Val Ser Asn
770                 775                 780

Arg Asp Phe Thr Ala Phe Ala Arg Asn Phe His Gln His Glu Ser
785                 790                 795                 800

Ser Phe Lys Lys Arg Val Arg Glu Tyr Ile Ala Leu Asn Met Ser Asn
                805                 810                 815

Ser Asp Pro Asn Leu Val Arg Met Tyr Arg Asn Ala Val Glu His Leu
                820                 825                 830

Asn Ala Val Arg Asn Ala Gly Val Tyr Val Gly Ser Val Ser Lys Ile
                835                 840                 845

Asp Ser Trp Phe Ser Leu Tyr His Tyr Leu Val Gln Arg Ser Val Tyr
850                 855                 860

Val Asn Tyr Lys Asn Glu Ile Ala Ser Asn Ala Asp Tyr Thr Ile Asn
865                 870                 875                 880

Pro Val Thr Glu Lys Tyr Phe Glu Met Leu Leu Lys Tyr Asn Thr Tyr
                885                 890                 895

Val Lys Asp Phe Val Lys Ala Leu Asn Val Pro Phe Ala Tyr Asn Leu
                900                 905                 910

Ala Arg Tyr Lys Asn Leu Ser Ile Asp Asp Leu Phe Asp Arg Asn Asn
                915                 920                 925

Tyr Leu Pro Asp Lys Gln Gly Asp Ile Ile Val Lys Pro Glu Phe Glu
930                 935                 940

Pro Val Val Glu
945

<210> SEQ ID NO 25
<211> LENGTH: 959
<212> TYPE: PRT
<213> ORGANISM: Eubacterium siraeum
<220> FEATURE:
<221> NAME/KEY: misc_feature
<223> OTHER INFORMATION: SG10METT28423427_Eb6Mmc2

<400> SEQUENCE: 25

Met Ala Gly Asn Asn Lys Lys Gln Glu Glu Leu Asp Lys Ala Lys Met
1               5                   10                  15
```

```
Trp Arg Leu Lys Glu Phe Gln Ala Pro Val Gln Thr Ser Glu Ser Glu
            20                  25                  30

Leu Arg Ile Lys Leu Val Arg Glu Arg Lys Ala Lys Gln Ala Gln Glu
         35                  40                  45

Gly Val Lys Lys His Ala Pro Lys Ala Ala Gly Val Lys Ser Val Phe
     50                  55                  60

Thr Leu Asn Gly Gln Gly Ser Leu Leu Met Thr Ser Phe Gly Arg Gly
 65                  70                  75                  80

Asn Asp Ala Leu Pro Glu Lys Leu Val Glu Asn Asp Lys Ile Ile Thr
                 85                  90                  95

Ile Pro Ser Asp Pro Ala Tyr Ser Ala Glu His Ala Asp Ile Arg Phe
            100                 105                 110

Lys Val Arg Gly Arg Val Gly Val Asn Ala Met Val Asp Asp Pro Thr
        115                 120                 125

His Ser Gln Met Asp Ala Gly Thr Asp Phe Ile Gly Leu Lys Asp Lys
    130                 135                 140

Ile Glu Ser Arg Phe Phe Gly Lys Thr Tyr Glu Asp Asn Ile His Ile
145                 150                 155                 160

Gln Leu Ala His Asn Ile Gln Asp Ile Glu Lys Ile Leu Ala Val His
                165                 170                 175

Ile Asn Asn Ile Ile Tyr Glu Leu Asn Asn Met Leu Arg Gly Asp Asp
            180                 185                 190

Ala Asp Tyr Ile Asp Val Ile Gly Tyr Leu Gly Val Gly Lys Thr Trp
        195                 200                 205

Glu Gln Phe Arg Lys Gly Asp Lys Asp Leu Val Ala Leu Val Asp Lys
    210                 215                 220

Leu Leu Arg Ser Pro Gln Leu Ser Tyr Phe Gly Thr Ile Leu Tyr Asp
225                 230                 235                 240

Pro Gln Leu Val Lys Asn Leu Ser Lys Ala Ser Asn Asp Tyr Lys Lys
                245                 250                 255

Ala Glu Ala Arg Gln Ala Leu Asp Ala Lys His Glu Ser Ala Tyr Asn
            260                 265                 270

Val Leu Ser Leu Leu Gly Met Thr Arg Gln Ala Leu Ala His Asp Ser
        275                 280                 285

Thr Ile Leu Tyr Thr Leu Asp Arg Glu Lys Leu Ser Glu Lys Thr Asn
    290                 295                 300

Glu Arg Val Lys Ala Gly Gln Val Ala Asn Ala Arg Thr Glu Leu Tyr
305                 310                 315                 320

Lys Val Tyr Ser Glu Arg Ile Asn Ser Ile Asn Lys Asp Phe Leu Ser
                325                 330                 335

Lys Ser Ala Phe Asp Ile Asn Met Leu Ile Ser Ile Phe Asn Ala Ile
            340                 345                 350

Asp Val Glu Glu Lys Lys Leu Val Ser Ser Tyr Tyr Asn Phe Val
        355                 360                 365

Val Thr Lys Ala Tyr Lys Asn Gln Gly Phe Ser Phe Thr Arg Ile Arg
    370                 375                 380

Glu Asn Met Leu Val Ser Thr Lys Ala Ala Cys Leu Ala Asn Glu Lys
385                 390                 395                 400

Tyr Asp Ser Met Arg Gly Arg Leu Tyr Arg Thr Phe Asp Phe Val Leu
                405                 410                 415

Tyr Lys His Tyr Glu Asp Asn Pro Ala Glu Ala Ala Leu Val Glu
            420                 425                 430

Lys Leu Arg Ala Thr Met Asn Ser Gln Glu Lys Glu Ala Ile Tyr Ala
```

```
            435                 440                 445
Asp Glu Ala Lys Arg Val Trp Ala Cys Ile Glu Lys Thr Val Leu Asn
450                 455                 460

Glu Ile Leu Pro Trp Met Ser Pro Ser Leu Met Lys Asn Lys Ala Pro
465                 470                 475                 480

Leu Asp Ser Asp Val Thr Pro Glu Met Leu Ser Gly Val Leu Leu Ala
                    485                 490                 495

Pro Ser Asn Thr Ser Glu Phe Ser Met Leu Met Tyr Leu Ile Ser Cys
                500                 505                 510

Phe Gln Asp Gly Lys Glu Ile Asn Asp Leu Leu Thr Thr Leu Ile Asn
            515                 520                 525

Lys Phe Asp Asn Ile Ala Ser Phe Cys Ala Ile Leu Arg Lys Gln Lys
            530                 535                 540

Leu Pro Ile Glu Phe Thr Pro Gly Tyr Glu Met Phe Lys Asn Ser Ser
545                 550                 555                 560

Arg Ile Ser Gln Glu Leu Arg Asn Ile Asn Ser Ile Ala Arg Met Glu
                565                 570                 575

Leu Lys Thr Gln Pro Asp Ala Lys Arg Thr Leu Phe Val Glu Ala Ala
                580                 585                 590

Asn Ile Leu Gly Tyr Pro Gly Ser Asp Asp Leu Leu Lys Tyr Val
            595                 600                 605

Asp Gln Met Leu Asn Ile Ala Ser Pro Arg Lys Asp Phe Arg Asn Phe
610                 615                 620

Ile Ala Ser Asn Val Ile Glu Ser Asp Arg Phe Lys Tyr Leu Val Arg
625                 630                 635                 640

Tyr Gly Asn Val Lys Lys Leu Arg Ala Leu Ala Ser Asn Arg Ala Val
                645                 650                 655

Ile Asp Phe Val Leu Lys Asp Ile Pro Asp Thr Gln Ile Val His Tyr
                660                 665                 670

His Asn Ser Cys Phe Gly Thr Ala Ala Lys Glu Cys Ala Pro Asn Met
            675                 680                 685

Arg Lys Asp Ile Ala Gly Ile Leu Leu Asn Leu Lys Phe Ala Asp Phe
690                 695                 700

Ala Asn Val Asn Asn Arg Val Met Ala Ala Asn Pro Gly Met Ala Lys
705                 710                 715                 720

Ala Tyr Ser Asp Lys Ser Lys Lys Gln Ala Ile Ile Ser Leu Tyr Leu
                725                 730                 735

Thr Val Leu Tyr Leu Ile Val Lys Asn Met Val Tyr Val Asn Ser Arg
                740                 745                 750

Tyr Phe Met Ala Phe His Cys Leu Glu Arg Asp Val Ser Thr Ala Asp
            755                 760                 765

Lys Gly Arg Tyr Lys Ala Ser Leu Gly Thr Asp Gly Asp Asn Arg Ser
            770                 775                 780

Phe Ala Tyr Asp Thr Val Ile Ser Asp Asp Ser Ala Arg Pro Cys
785                 790                 795                 800

Val Cys Lys Val Asn Gly Arg Ala Arg Lys Tyr Ile Lys Val Asn Tyr
                805                 810                 815

Val Asn Ser Asp Val Trp Ala Thr Arg Ala Phe Arg Asn Ser Val Glu
                820                 825                 830

His Leu Lys Ala Val Arg Ser Ile Ser Asp Tyr Ile Gly Asp Ile Lys
            835                 840                 845

His Phe Asp Ser Trp Phe Glu Leu Tyr His Tyr Val Met Gln Arg Gly
850                 855                 860
```

```
Leu Glu Lys Gln Tyr Glu Tyr Asp Ser Thr Thr Leu Ser Lys His Pro
865                 870                 875                 880

Asp Asn Gly Gln Thr Ile Ile Ser Ala Glu Cys Leu Thr Gly Lys Thr
            885                 890                 895

Leu Lys Tyr Ile Gly Ser Val Lys Ala Cys Arg Val Tyr Ser Lys Asp
        900                 905                 910

Phe Val Lys Ala Tyr Cys Val Pro Phe Ala Tyr Asn Leu Pro Arg Tyr
        915                 920                 925

Lys Asn Leu Thr Ile Asn Glu Leu Phe Asp Lys Asn Arg Pro Ala Glu
        930                 935                 940

Ser Lys Ala Cys Gly Lys Thr Asp Arg Leu Gly Glu Glu Gln
945                 950                 955
```

<210> SEQ ID NO 26
<211> LENGTH: 960
<212> TYPE: PRT
<213> ORGANISM: Eubacterium siraeum
<220> FEATURE:
<221> NAME/KEY: misc_feature
<223> OTHER INFORMATION: SG11METT28163212_Eb5Mmc2

<400> SEQUENCE: 26

```
Met Lys Lys Lys Thr Asn Asp Ile Arg Ala Ala Arg Glu Gln Ala Lys
1               5                   10                  15

Gln Gln Asn Ala Gln Lys Phe Lys Asn Asp Ala Lys Arg Lys Gln
            20                  25                  30

Glu Glu Glu Glu Lys Arg Ile Lys Asp Ala Glu Ala Ala Ala Lys
            35                  40                  45

Lys Glu Glu Ala Leu Leu Ala Arg Ile Lys Ala Glu His Pro Glu Ile
    50                  55                  60

Thr Asp Lys Arg Ile Lys Ser Ser Ala Lys Ala Ala Gly Leu Lys Ser
65                  70                  75                  80

Thr Phe Met Val Gly Lys Asp Lys Leu Leu Met Thr Ser Phe Gly Lys
                85                  90                  95

Gly Asn Glu Ala Val Pro Glu Lys Arg Val Gln Gly Ala Glu Ile Thr
            100                 105                 110

Asp Val Asn Phe Pro Gly Met Phe Thr Leu Glu Arg Ser Thr Asp Ala
        115                 120                 125

Lys Ala Ser Gly Phe Val Ile Ser Gly Arg Val Asp Ala Tyr Thr Asp
    130                 135                 140

Asp Pro Leu Asn Ser Arg Lys Lys Pro Gly Asp Asp Leu Ile His Asn
145                 150                 155                 160

Arg Ala Gln Leu Glu Arg Arg Tyr Phe Gly Thr Thr Phe Pro Asp Asn
                165                 170                 175

Ile His Ile Gln Leu Ile Tyr Asn Ile Leu Asp Ile Asp Lys Ile Leu
            180                 185                 190

Thr Glu His Ile Asn Asn Ile Val Tyr Thr Val Asn Asn Leu Phe Arg
        195                 200                 205

Lys Glu Glu Glu Asp Asn His Asp Ile Ile Gly Gln Leu Phe Gly Leu
    210                 215                 220

Asn Glu Met Ser Phe Glu Gln Phe Glu Leu Thr Leu Asn Ala Pro Tyr
225                 230                 235                 240

Asn Lys Asn Thr Ala Lys Ala Arg Ser Ile Asp Arg Phe Leu Asn Ser
                245                 250                 255

Pro Tyr Leu Gly Tyr Phe Gly Asn Thr Val Tyr Asn Lys Gln Leu Ile
```

-continued

```
                260                 265                 270
Asp Ala Ala Asn Glu Asn Lys Val Asn Ala Ala Leu Arg Ser Tyr
            275                 280                 285
Arg Lys Arg Asn Tyr Tyr Leu Leu Leu Leu Ser Met Thr Arg Gln
            290                 295                 300
Ser Leu Ala His Asn Asn Ala Asp Leu Phe Thr Leu Glu Pro Glu Cys
305                 310                 315                 320
Gly Ser Ala Ala Thr Pro Ser Asn Met Ala Ala Arg Lys Ala Leu
                325                 330                 335
Asn Asp Ile Phe Asp Asp Lys Val Asp Lys Leu Asn Arg Glu Phe Leu
                340                 345                 350
Ser Thr Ser Ala Lys Asn Leu Arg Ile Leu Phe Lys Ile Leu Arg Cys
            355                 360                 365
Val Ser Glu Ala Asp Lys Thr Arg Val Ala Arg Asp Tyr Tyr Asp Phe
            370                 375                 380
Ser Val Arg Lys Thr Tyr Lys Asn Met Gly Phe Ser Met Lys Thr Leu
385                 390                 395                 400
Arg Glu Glu Met Leu Glu Leu Glu Gly Ala Arg Asp Met Arg Ser Met
                405                 410                 415
Glu Tyr Asp Thr Val Arg Ser Lys Met Tyr Asn Leu Leu Asp Phe Ile
                420                 425                 430
Ile Tyr Glu Arg Tyr Leu Gly Ser Glu Lys Ala Ala Gly Glu Lys Leu
            435                 440                 445
Val Asn Glu Leu Arg Ala Ala Pro Asn Asp Phe Asp Lys Arg Leu Cys
            450                 455                 460
Tyr Ala His Glu Ala Asp Arg Leu Trp Gln Ile Ile Arg Ser Asp Val
465                 470                 475                 480
Glu Asn Glu Leu Leu Pro Lys Met Asn Gly Asp Tyr Ile Lys Thr Leu
                485                 490                 495
Asp Asn Ala Val Pro Glu Leu Asp Glu Lys Ala Phe Ala Asp Val Leu
            500                 505                 510
Met Lys Pro Ser Val Ser Tyr Phe Ser Lys Leu Met Tyr Leu Leu Thr
            515                 520                 525
Thr Phe Ile Asp Gly Lys Glu Ile Asn Asp Leu Leu Thr Thr Leu Leu
            530                 535                 540
Ser Lys Phe Glu Asn Ile Gln Ser Phe Leu Thr Val Leu Glu Ser Cys
545                 550                 555                 560
Gly His Pro Ala Lys Phe Lys Pro Glu Tyr Gln Leu Leu Leu Arg Ser
                565                 570                 575
Gly Glu Ile Ala Asp Glu Leu Arg Phe Ile Asn Ser Phe Ala Arg Met
                580                 585                 590
Thr Gly Lys Glu Lys Arg Lys Pro Pro Gln Lys Lys Asp Ala Asn Ala
            595                 600                 605
Pro Arg Val Val Gly Phe Thr Glu Lys Ser Met Tyr Ile Asp Ala Ala
            610                 615                 620
Thr Val Leu Gly Tyr Asn Lys Gly Lys Glu Glu Leu Ile Ser Lys Leu
625                 630                 635                 640
Asp Gly Ala Ser Ser Gly Asp Lys Asp Lys Asp Gly Gly Phe Ser
                645                 650                 655
Ser Phe Leu Leu Asn Asn Val Leu Pro Ser Arg Phe Ala Tyr Leu
                660                 665                 670
Met Arg Tyr Ser Asn Ala Ala Asn Val Arg Arg Leu Ala Glu Asn Lys
            675                 680                 685
```

```
His Ile Val Ser Phe Val Leu Gly Gln Ile Pro Asp Ala Gln Ile Thr
    690                 695                 700

Arg Tyr Tyr Glu Ser Val Thr Gly Gly Glu Ala Cys Gly Ile Glu Thr
705                 710                 715                 720

Met Arg Gly Glu Leu Val Arg Leu Leu Thr Gly Leu Ser Phe Glu Glu
                725                 730                 735

Phe Ala Tyr Ile Gly Lys Gly Leu Asp Lys Ala Gly Tyr Arg Leu Ala
            740                 745                 750

Leu Glu Arg Lys Lys Ser Leu Val Gly Leu Tyr Phe Thr Val Leu Tyr
        755                 760                 765

Leu Leu Thr Lys Asn Leu Val Tyr Val Asn Ser Arg Tyr Phe Leu Ala
    770                 775                 780

Phe His Cys Ala Glu Arg Asp Ala Gln Ile Phe Asp Gly Leu Lys Tyr
785                 790                 795                 800

Thr Asp Asp Phe Ile Lys Asn Asp Arg Ala Val Phe Ala Arg Asp Phe
                805                 810                 815

Leu Asn Gln Tyr Pro Gly Lys Lys Arg Val Lys Ala Tyr Leu Asp Val
            820                 825                 830

Asn Met Ala Asn Ser Asp Ser Trp Ala Ile Arg Gln Phe Arg Asn Lys
        835                 840                 845

Thr Glu His Leu Asn Ala Val Arg Glu Ala Tyr Lys His Ala Gln Ser
    850                 855                 860

Ile Gly Ala Phe Lys Ser Tyr Phe Glu Leu Tyr His Tyr Leu Val Gln
865                 870                 875                 880

Cys Asp Ile Leu Glu Gln Tyr Thr Glu Ser Pro Thr Asn Leu His Gly
                885                 890                 895

Lys Thr Ala Val Tyr Phe Asp Leu Ile Gln Lys His His Thr Tyr Ser
            900                 905                 910

Lys Asp Phe Val Lys Ala Leu Cys Val Pro Phe Ala Tyr Asn Leu Pro
        915                 920                 925

Arg Phe Lys Asn Leu Ser Ile Glu Gly Leu Phe Asp Met Asn His Pro
    930                 935                 940

Gly Glu Asp Thr Met Pro Glu Lys Ile Arg Glu Met Gly Glu His Ala
945                 950                 955                 960

<210> SEQ ID NO 27
<211> LENGTH: 952
<212> TYPE: PRT
<213> ORGANISM: Eubacterium siraeum
<220> FEATURE:
<221> NAME/KEY: misc_feature
<223> OTHER INFORMATION: SG11METT28200818

<400> SEQUENCE: 27

Met Ala Lys Asp Lys Lys Gln Asp Arg Val Ile Gly Leu Gly Ala Leu
1               5                   10                  15

Ala Gly Ala Leu Gly Met Gly Thr Ala Glu Pro Lys Lys Glu Ala Lys
            20                  25                  30

Thr Glu Lys Lys Glu Lys Gln Pro Val Lys Pro Val Val Ala Glu Leu
        35                  40                  45

Ile Ser Leu Glu Gly Met Glu Glu Glu Lys Lys Ala Val Ala Ala Glu
    50                  55                  60

Gln Pro Lys Ala Glu Ile Gly Lys Lys Ser Ser Ser Lys Ala Ala Gly
65                  70                  75                  80

Val Lys Ser Val Phe Thr Met Gly Asp Gly Ser Leu Leu Met Thr Ser
```

```
                         85                  90                  95
Phe Gly Arg Gly Asn Ser Ala Val Leu Glu Lys Asn Val Thr Gly Asp
                100                 105                 110
Asn Glu Ile Asn Asp Ile Asn Thr Glu Ala Pro Val Tyr Ser Ala Lys
                115                 120                 125
Val Lys Glu Asn Gly Phe Thr Val Lys Gly Arg Ala Ser His Ala Gly
            130                 135                 140
Ser Val Asp Asp Pro Arg Lys Ser Glu Lys Arg Pro Asp Gln Ile Asp
145                 150                 155                 160
Cys Arg Glu Lys Ile Glu Gln Arg Phe Phe Gly Lys Thr Tyr Glu Asp
                165                 170                 175
Asn Ile His Ile Gln Met Ala Tyr Asn Ile Met Asp Ile Glu Lys Ile
                180                 185                 190
Leu Ala Val His Val Asn Asn Val Val Tyr Ala Leu Asn Asn Ile Leu
                195                 200                 205
Gly Asp Glu Glu Ala Phe Tyr Ala Asp Trp Ile Gly Phe Met Gly Trp
            210                 215                 220
Asp Lys Thr Tyr Glu Lys Ala Met Ser Ala Lys Glu Gly Asn Ser Arg
225                 230                 235                 240
Phe Val Ala Asp Cys Phe Lys Asn Leu Met Arg Ser Lys Arg Arg Ala
                245                 250                 255
Tyr Phe Gly Asp Val Leu Phe Asp Ala Gly Ile Ser Lys Ile Thr Lys
                260                 265                 270
Lys Glu Ile Lys Glu Ala Arg Ile Glu Glu Arg Lys Lys Ala Tyr
                275                 280                 285
Tyr Ile Cys Leu Leu Leu Gly Lys Ala Arg Gln Met Thr Ala His Asp
            290                 295                 300
Leu Ala Asp Thr Arg Ser Ala Leu Tyr Cys Leu Asp Glu Thr Phe Asp
305                 310                 315                 320
Ala Lys Cys Lys Asn Glu Ala Lys Glu Val Arg Ala Glu Val Arg Ala
                325                 330                 335
Val Leu Asp Glu Leu Tyr Tyr Ala Arg Val Ser Lys Leu Asn Ser Asp
            340                 345                 350
Phe Ile Asp Thr Ser Lys Lys Asp Leu Val Leu Leu Phe Arg Ala Phe
            355                 360                 365
Gly Ile Thr Glu Pro Ala Gln Lys Lys Glu Tyr Ala Gly Leu Tyr Tyr
            370                 375                 380
Asp Phe Val Val Arg Lys Asn Tyr Lys Phe Met Gly Phe Ser Ile Lys
385                 390                 395                 400
Glu Leu Arg Glu Val Ile Thr Lys Thr Ile Pro Glu Ala Ala Val Val
                405                 410                 415
Lys Asp Glu Lys Tyr Asp Thr Val Arg Gln Lys Leu Asn Arg Leu Phe
                420                 425                 430
Asp Phe Ala Ile Tyr Asp Tyr Arg Lys Asn Pro Ala Glu Ala Asp
            435                 440                 445
Ser Ile Val Cys Thr Leu Arg Ala Val Gln Ser Glu Thr Asp Lys Gln
            450                 455                 460
Leu Val Tyr Arg Arg Ser Ala Lys Gln Leu Trp Lys Ser Ile Arg Ala
465                 470                 475                 480
Thr Val Leu Asn His Ile Leu Pro Asn Met Asn Gly Asp Ala Ile Lys
                485                 490                 495
Ala Ile Val Ala Asp Arg Asp Ile Thr Ala Asp Ala Leu Lys Asp Val
            500                 505                 510
```

```
Leu Val Ser Pro Asn Ala Asp Tyr Phe Val Lys Phe Leu Tyr Met Leu
        515                 520                 525

Thr Arg Phe Gln Asn Gly Lys Glu Ile Asn Asp Leu Ile Thr Thr Cys
        530                 535                 540

Ile Asn Lys Phe Glu Asn Ile Ala Ser Phe Ile Ala Val Leu Glu Glu
545                 550                 555                 560

Lys His Ile Gly Arg Arg Phe Val Gln Glu Tyr Ser Val Phe Glu Arg
                565                 570                 575

Ser Ala Lys Ile Ala Ser Gln Leu Arg Glu Met Asn Asn Phe Ala Arg
                580                 585                 590

Met Ser Met Lys Ser Asp Glu Thr Ala Thr Lys Lys Ala Met Phe Glu
        595                 600                 605

Asp Ala Ala Leu Ile Leu Gly Tyr Glu Asn Ala Ala Glu Leu Asp Ser
        610                 615                 620

Met Leu Asp Arg Met Leu Asp Pro Lys Gly Thr Glu Lys Gly Phe Arg
625                 630                 635                 640

Asn Phe Ile Val Asn Asn Val Ile Glu Ser Val Arg Phe Asp Tyr Leu
                645                 650                 655

Val Arg Tyr Cys Asn Pro Thr Lys Val Arg Lys Leu Ala Ser Asn Ala
                660                 665                 670

Val Val Leu Gly Phe Val Leu Arg Gly Ile Pro Asp Asp Gln Ile Leu
        675                 680                 685

Arg Tyr Tyr Asn Ala Cys Thr Gly Ser Glu Ala Lys Glu Cys Thr Pro
        690                 695                 700

Arg Met Arg Asp Glu Leu Thr Lys Lys Leu Glu Gly Ile Ser Phe Asn
705                 710                 715                 720

Glu Phe Arg Asp Val His Gln Lys Asp Ala Thr Ala Thr Pro Ala Gln
                725                 730                 735

Ala Gln Asp Lys Val Arg Lys Gln Ala Ile Ile Arg Leu Tyr Leu Ala
        740                 745                 750

Val Leu Tyr Leu Leu Val Lys Asn Met Val Tyr Val Asn Ser Arg Tyr
        755                 760                 765

Phe Met Ala Phe His Cys Leu Glu Arg Asp Asn Ser Leu Tyr Thr Gly
        770                 775                 780

Ser Glu Ile Asn Lys Asn Asp Tyr Ala Ala Phe Ala Arg Ala Phe Met
785                 790                 795                 800

Gln Glu Glu Arg His Arg Lys Asn Ala Arg Ala Arg Tyr Leu Asp
                805                 810                 815

Val Asp Phe Ala Asn Ser Asp Pro Gln Ala Val His Glu Tyr Arg Asn
        820                 825                 830

Cys Val Glu His Leu Ser Ala Ile Arg Arg Met Asp Gly Tyr Ile Ala
        835                 840                 845

Asp Val Gly Lys Met Asp Ser Tyr Phe Asp Leu Tyr His Tyr Ile Val
        850                 855                 860

Gln Arg His Leu Ser Asp Gln His Asp Arg Ala Ile Arg Glu Asn Lys
865                 870                 875                 880

Tyr Gly Lys Ile Glu Asn Pro Lys Met Leu Gly Phe Ile Ala Asn Met
                885                 890                 895

Lys Arg Tyr Asn Gly Cys Ser Lys Asp Met Ile Lys Ala Leu Asn Val
                900                 905                 910

Pro Phe Ala Tyr Asn Leu Ala Arg Phe Lys Asn Leu Ser Val Asp Gly
        915                 920                 925
```

```
Leu Phe Asp Met Asn Asp Thr Arg Glu Lys Pro Lys Gly Lys Asn Cys
        930                 935                 940

Gly Met Glu Thr Glu Glu Ala Glu
945                 950
```

<210> SEQ ID NO 28
<211> LENGTH: 952
<212> TYPE: PRT
<213> ORGANISM: Ruminococcus flavefaciens
<220> FEATURE:
<221> NAME/KEY: misc_feature
<223> OTHER INFORMATION: SG11METT28950652_Rf9Mmc2

<400> SEQUENCE: 28

```
Met Lys Lys Lys Ile Lys Ala Lys Asp Leu Arg Glu Met Lys Lys Ala
1               5                   10                  15

Glu Gln Lys Glu Arg Phe Leu Ser Asn Val Val Lys Ala Asp Asp Val
            20                  25                  30

Lys Glu Glu Lys Ile Lys Thr Ser Glu Thr Val Ile Glu Lys Thr Glu
        35                  40                  45

Glu Lys Thr Glu Gln Lys Leu Lys Ser Lys Ser Lys Ala Ala Gly Leu
    50                  55                  60

Lys Ser Thr Leu Val Ser Gly Lys Asp Ile Tyr Leu Thr Ser Phe Gly
65                  70                  75                  80

Lys Gly Asn Lys Ala Val Val Glu His Lys Ile Asp Ala Asp Asp Ser
                85                  90                  95

Tyr Ser Val Thr Lys Ile Ser Glu Glu Pro Thr Leu Ser Val Asn Asp
            100                 105                 110

Val Asp Asn Lys Asp Ile Arg Phe Ser Ser Asp Arg Pro Phe Gly Arg
        115                 120                 125

Asp Glu Thr Leu Leu Ala Ala Asn Pro Ile Val Glu Asn Ser Val Arg
130                 135                 140

Gly Asp Asn Leu Gly Leu Lys Glu Lys Leu Glu Lys Lys Tyr Phe Gly
145                 150                 155                 160

Lys Thr Phe Asn Asp Asn Ile His Ile Gln Ile Ile Tyr Asn Ile Met
                165                 170                 175

Asp Ile Glu Lys Ile Leu Ala Val Tyr Ser Thr Ser Ile Ala Thr Thr
            180                 185                 190

Ile Asn Gly Met Leu Ser Asp Lys Leu Thr Asp Lys Asp Phe Ile
        195                 200                 205

Gly Tyr Met Ser Thr Lys Asn Thr Tyr Asp Val Phe Leu Asn Pro Asp
210                 215                 220

Lys Asn Pro Lys Leu Asp Lys Lys Lys Asp Asn Ile Asn Asp Ser
225                 230                 235                 240

Arg Glu Lys Phe Glu Asp Leu Leu Lys Thr Asn Arg Leu Gly Tyr Phe
                245                 250                 255

Gly Phe Asp Tyr Lys Phe Asn Lys Lys Asn Pro Asn Glu Ser Glu Glu
            260                 265                 270

Asn Lys Lys Arg Ile Tyr His Leu Met Gly Phe Ala Gly Ser Leu Arg
        275                 280                 285

Gln Trp Ser Val His Asn Glu Gly Asn Trp Ile Tyr Lys Phe His Ile
    290                 295                 300

Gly Glu Lys Asn Gly Gly Val Ala Lys Glu Tyr Leu Asp Thr Leu Asn
305                 310                 315                 320

His Tyr Phe Lys Asn Arg Tyr Asp Glu Leu Asn Asn Phe Ile Asp
                325                 330                 335
```

-continued

Gln Asn Lys Val Asn Leu Phe Met Leu Ile Asp Ala Leu Lys Glu Ser
              340                 345                 350

Asp Pro Glu Glu Ile Cys Ser Leu Tyr Arg Glu Phe Ile Ile Glu Lys
        355                 360                 365

Thr Tyr Lys Asn Met Gly Phe Ser Ile Lys Lys Leu Arg Glu Asn Met
    370                 375                 380

Leu Thr Leu Glu Gly Gly Asp Lys Ile Thr Asp Glu Ser Met Asn Ser
385                 390                 395                 400

Val Arg Ser Lys Leu Tyr Lys Leu Ile Asp Phe Cys Val Tyr Tyr Gly
                405                 410                 415

Tyr Tyr Lys Asp Glu Lys Arg Ile Glu Glu Asn Val Arg Thr Leu Arg
            420                 425                 430

Ala Cys Met Thr Asp Ser Asp Lys Glu Met Phe Tyr Glu Lys Glu Ala
        435                 440                 445

Glu Arg Leu Trp Ala Glu Asn Lys Asn Arg Phe Ile Arg Phe Ala Asn
    450                 455                 460

Glu Leu Thr Gly Ser Asn Ile Lys Lys Leu Gln Asp Lys Lys Ile Ser
465                 470                 475                 480

Glu Leu Pro Ser Gly Trp Arg Asn Asn Val Arg Thr Ser Glu Phe Ser
                485                 490                 495

Cys Phe Ser Lys Leu Met Tyr Cys Met Cys Phe Phe Leu Asp Gly Lys
            500                 505                 510

Glu Ile Asn Asp Leu Leu Thr Thr Leu Ile Asn Lys Phe Asp Val Ile
        515                 520                 525

Val Asn Leu Val Lys Thr Ala Lys Glu Ile Gly Ile Pro Val Glu Phe
    530                 535                 540

Asp Lys Lys Tyr Thr Phe Phe Asn Tyr Asn Leu Ile Asn Asn Glu Lys
545                 550                 555                 560

Lys Asp Ile Ser Ser Tyr Val Asp Glu Leu Asn Thr Val Lys Asn Ile
                565                 570                 575

Ala Arg Met Lys Lys Pro Ser Ala Asn Ala Lys Glu Thr Met Tyr Arg
            580                 585                 590

Asp Ala Leu Tyr Ile Leu Gly Ile Pro Ser Asp Met Ser Glu Lys Lys
        595                 600                 605

Leu Gly Asp Lys Ile Ala Asp Met Leu Asp Thr Ser Asp Lys Asn Lys
    610                 615                 620

Arg His Asp Phe Arg Asn Phe Ile Ala Asn Asn Val Ile Asn Ser Ser
625                 630                 635                 640

Arg Phe Ile Tyr Ile Ile Lys Tyr Cys Asp Pro Lys Ser Ala Arg Lys
                645                 650                 655

Ile Ala Ser Asn Arg Lys Val Val Glu Phe Val Leu Lys Glu Ser Met
            660                 665                 670

Pro Glu Ser Ile Ile Asp Arg Tyr Tyr Lys Ser Cys Ile Glu Pro Asp
        675                 680                 685

Phe Val Phe Glu Ser Asp Ser Leu Asn Glu Lys Ile Met Lys Leu Ser
    690                 695                 700

Lys Val Ile Thr Glu Met Asn Phe Gly Asn Phe Glu Asp Val Asp Gln
705                 710                 715                 720

Arg Ala Arg Gly Thr Leu Ala Gly Glu Thr Lys Thr Arg Tyr Ile Ala
                725                 730                 735

Val Ile Gly Leu Tyr Leu Asn Val Tyr Gln Ile Val Lys Asn Leu
            740                 745                 750

```
Val Asn Val Asn Ala Arg Tyr Val Met Gly Phe His Ser Leu Glu Arg
        755                 760                 765

Asp Met Gly Tyr Asn Gly Phe Lys Asp Glu Tyr Asn Arg Thr Cys Ile
    770                 775                 780

Thr Arg Lys Ile Leu Glu Glu Gly Asp Lys Thr Lys Asn Arg Tyr Leu
785                 790                 795                 800

Ala Lys Asn Met His Tyr Arg Glu Cys Ile Lys Val Asp Ile Glu Asn
                805                 810                 815

Ser Asp Glu Ser Ala Ile Asn Leu Tyr Arg Asn Asn Val Ala His Leu
            820                 825                 830

Lys Val Ile Lys Arg Cys Ala Arg Tyr Ile Gly Asp Ile Lys Tyr Ile
        835                 840                 845

Asn Ser Tyr Phe Gly Leu Tyr His Tyr Ile Met Gln Arg Cys Ile Ala
850                 855                 860

Asp Gly Asn Tyr Asn Lys Tyr Lys Glu Tyr Asn Gly Tyr Asn Ser
865                 870                 875                 880

Glu His Asp Tyr Phe Ile Lys Cys Asn Pro His Leu Glu Asp Lys Thr
                885                 890                 895

Asn Ser Glu Lys Thr Lys Glu Tyr Leu Ala Ser Leu Ser Glu Tyr Asn
            900                 905                 910

Thr Tyr Val Gly Asp Phe Val Lys Ala Leu Asn Ala Pro Phe Gly Tyr
        915                 920                 925

Asn Ala Pro Arg Phe Lys Asn Leu Ser Ile Glu Gly Arg Phe Asp Lys
    930                 935                 940

Asn Ser Lys Lys Lys Leu Asp Lys
945                 950

<210> SEQ ID NO 29
<211> LENGTH: 849
<212> TYPE: PRT
<213> ORGANISM: Ruminococcus Sp.
<220> FEATURE:
<221> NAME/KEY: misc_feature
<223> OTHER INFORMATION: SG11METT28951888_Ru2Mmc2

<400> SEQUENCE: 29

Met Ala Gln Lys Lys Thr Ser Ala Lys Arg Ile Gly Leu Lys Ser Ile
1               5                   10                  15

Phe Gln Thr Gly Lys Lys Ala Tyr Leu Ala Gly Phe Gly Lys Asn Asn
            20                  25                  30

Lys Asn Val Ile Glu Lys Lys Tyr Phe Glu Asn Ser Ile Ser Asn Glu
        35                  40                  45

Thr Gln Asn Pro Ala Phe Asp Ala Arg Leu Asp Glu Asn Ser Asn Phe
    50                  55                  60

Ile Leu Glu Lys Asn Asn Leu Ser Ala Ser Tyr Ile Asn Pro Val His
65                  70                  75                  80

Gln Thr Pro Lys Arg Glu Phe Leu Lys Glu Asn Leu Glu Lys Phe Tyr
                85                  90                  95

Phe Gly Asn Val Ser Asn Gly Asn Ile Pro Ile Gln Ile Ala Tyr Tyr
            100                 105                 110

Val Arg Ser Ile Glu Lys Leu Phe Ala Leu Tyr Ile Asn Asp Ile Ile
        115                 120                 125

Tyr Ala Leu Asp Asn Leu Asn Ile Asn Lys Lys Ser Ile Leu Asn Ile
    130                 135                 140

Ser Ser Asp Glu His Arg Asn Asp Val Leu Gly Asn Asp Ile Lys Thr
145                 150                 155                 160
```

```
Asn Val Lys Phe Ser Thr Leu Leu Ser Asn Ile Gln Thr Lys Asn Glu
                165                 170                 175

Tyr Phe Ser Lys Ser Asn Arg Ile Val Asn Phe Leu Lys Asn Leu Lys
                180                 185                 190

Cys Tyr Glu Gly Met Phe Glu Asn Leu Phe Asn Arg Val Ser Thr Asp
                195                 200                 205

Val Gly Val Ser Asp Lys Asp Ala Lys Leu Asn Gln Ile Tyr Lys Thr
            210                 215                 220

Met Gln Val Ile Ser Phe Val Arg Asn Asn Ile Ile His Gly Glu Asn
225                 230                 235                 240

Asn Ile Phe Lys Asn Ile Asn Asn Ser Leu Val Lys Thr Thr Ala Ile
                245                 250                 255

Glu Ile Tyr Lys Asn Ala His Thr Val Phe Leu Lys Ser Phe Lys Ala
                260                 265                 270

Asn Ser Gln Thr Asn Val Phe Ile Leu Asn Lys Ile Phe Gly Thr Asp
            275                 280                 285

Ile Ser Lys Arg Tyr Tyr Asp Phe Ala Tyr Thr Lys Asp Tyr Lys Asn
290                 295                 300

Leu Gly Leu Ser Ile Lys Lys Ile Arg Glu Gln Ile Phe Glu Val Arg
305                 310                 315                 320

Asn Leu Lys Glu Ser Phe Gly Ile Glu Glu Tyr Ser Lys Ile Lys Ser
                325                 330                 335

Lys Leu Asn Thr Leu Tyr Asp Phe Val Ile Gln Asp Tyr Leu Lys Glu
                340                 345                 350

Asn Glu Glu Tyr Leu Ser Ser Cys Val Asn Ser Gln Arg Glu Met Leu
            355                 360                 365

Glu Glu Tyr Lys Glu Gln Asn Tyr Thr Lys Ile Ala Thr Asp Leu Ile
370                 375                 380

Ala Lys Leu Ser Lys Gln Phe Asn Val Ile Asp Asp Ile Cys Leu Asn
385                 390                 395                 400

Phe Glu Lys Phe Lys Thr Glu Asn Gln Lys Ala Ile Ser Gln Val Lys
                405                 410                 415

Phe Asp Val Asp Glu Arg Val Phe Gly Glu Asn Thr Val Val Ala Ala
            420                 425                 430

Leu Val Tyr Val Met Cys Arg Phe Leu Ser Glu Lys Glu Ile Asn Glu
            435                 440                 445

Phe Val Thr Gly Leu Val Asn Asn Leu Ile Asn Ile Gln Ser Leu Ile
            450                 455                 460

Glu Thr Phe Glu Glu Leu Glu Pro Asn Ser Lys Glu Leu Ser Tyr Phe
465                 470                 475                 480

Val Asn Asn Phe Glu Val Phe Lys Asn Ile Pro Asp Leu Val Tyr Glu
                485                 490                 495

Leu Gln Thr Ile Leu Thr Val Ser Lys Gln Arg Lys Ile Glu Ile Lys
                500                 505                 510

Arg Val Lys Asn Lys Asn Gln Gln Val Asp Cys Thr Tyr Thr Tyr Leu
            515                 520                 525

Glu Glu Ala Tyr Leu Leu Leu Ser Asp Asn Ser Leu Ser Phe Glu Glu
            530                 535                 540

Val Lys Asn Asp Lys Phe Leu Cys Asn Phe Leu Lys Asn Asn Ile Val
545                 550                 555                 560

Lys Ser Asn Lys Phe Ser Tyr Ile Leu Arg Tyr Asn Asn Leu Lys Asn
                565                 570                 575
```

```
Cys Lys Leu Leu Phe Lys Asn Lys Glu Phe Val Lys Tyr Val Ile Met
            580                 585                 590

Ser Gln Val Ser Lys Thr Gln Leu Glu Arg His Phe Leu Leu Ala Lys
            595                 600                 605

Thr Phe Ser Val Ser Ala Gln Ser Val Asp Glu Leu Cys Glu His Leu
            610                 615                 620

Ser Asn Ile Ser Leu Lys Thr Met Thr Ser Lys Gln Glu Ser Ala Glu
625                 630                 635                 640

Tyr Cys Glu Phe Ile Lys Ser Leu Thr Gln Leu Tyr Met Thr Ile Ile
                    645                 650                 655

Tyr Leu Thr Thr Lys Ser Leu Val Arg Ile Asn Ser Leu Tyr Cys Ile
                660                 665                 670

Ala Trp Leu Ser Tyr Glu Gln Asp Met Phe Tyr Ile Ser Lys Asn Pro
            675                 680                 685

Gln Lys Val Ile Asn Arg Phe Asn Val Val Arg Glu Asn Gln Thr Thr
            690                 695                 700

Lys Pro Asn Glu Ile Glu Tyr Asn Asn Ser Ile Thr Gln Arg Ala Leu
705                 710                 715                 720

Phe Glu Asn Lys Leu Tyr Gly Lys His Asn Glu Pro Phe Ile Thr Tyr
                    725                 730                 735

Leu Arg Glu His Phe Ile Cys Leu Asp Asn Glu Lys Thr Ile Phe Glu
                740                 745                 750

Lys Val Arg Asn His Val Met His Leu Ala Val Ile Asp Lys Val Phe
            755                 760                 765

Leu Lys Leu Glu Lys Tyr Asn Ser Lys Asp Ser Thr Tyr Phe Ser Leu
            770                 775                 780

Tyr Asn Phe Val Leu Gln Ser Leu Val Cys Asp Gly Val Asp Glu Leu
785                 790                 795                 800

Ser Tyr Cys Glu Lys Asn Phe Leu Ser Lys Gly Ile Tyr Ser Lys Asp
                    805                 810                 815

Leu Val Gln Ile Leu Asn Met Pro Phe Ala Tyr Asn Ile Ala Arg Phe
                820                 825                 830

Lys Ala Leu Thr Asn Glu Lys Ile Phe Ser Lys Val Gln Lys Phe Gly
            835                 840                 845

Asn

<210> SEQ ID NO 30
<211> LENGTH: 919
<212> TYPE: PRT
<213> ORGANISM: Ruminococcus flavefaciens
<220> FEATURE:
<221> NAME/KEY: misc_feature
<223> OTHER INFORMATION: SG11METT28958825_Rf8Mmc2

<400> SEQUENCE: 30

Met Asn Lys Lys Asn Pro Arg Glu Leu Arg Glu Ala Arg Lys Ala
1               5                   10                  15

Lys Met Lys Glu Lys Tyr Ala Ser Lys Ala Val Glu Lys Glu Val
            20                  25                  30

Ile Glu Glu Lys Ala Ala Glu Pro Lys Ser Asp Lys Asn Lys Lys
        35                  40                  45

Ser Leu Ser Lys Ala Ala Gly Leu Lys Ser Val Phe Tyr Ala Gly Glu
            50                  55                  60

Asn Leu Tyr Met Thr Ser Phe Gly Arg Gly Asn Thr Ala Val Val Glu
65                  70                  75                  80
```

-continued

```
Gln Lys Ile Asn Thr Ser Asp Tyr Ser Phe Ser Ser Met Asn Lys Ser
                85                  90                  95
Pro Asn Leu Arg Ile Asn Asn Ala Asp Glu Ile Ser Val Ser Phe Ser
            100                 105                 110
Ser Thr Arg Pro Val Val Lys Glu Asn Lys Leu Thr Ala Asp Asn Pro
            115                 120                 125
Leu His Glu Gly Lys Ser Ser Lys Pro Lys Ala Thr Gly Lys Asp Ile
130                 135                 140
Leu Gly Leu Lys Asp Thr Leu Glu Lys Arg Tyr Phe Gly Lys Val Phe
145                 150                 155                 160
Asp Asp Asn Ile His Ile Gln Ile Ile Tyr Asn Ile Leu Asp Ile Glu
                165                 170                 175
Lys Ile Leu Ala Glu Tyr Ile Thr Asn Ile Ser Val Ser Ile Asp His
            180                 185                 190
Leu Cys Asp Glu Tyr Ile Ser Asn Ile Ser Lys Tyr Glu Phe Ile Gly
            195                 200                 205
Tyr Met Ser Thr Arg Asn Thr Phe Asp Val Phe Cys Asp Pro Ser Lys
        210                 215                 220
Asn Pro Glu Leu Lys Asn Lys Ser Asn Ala Val Asn Ile Ile Asn Ser
225                 230                 235                 240
Asn Arg Asp Ile Phe Glu Lys Leu Ile Lys Ser Asn Arg Leu Gly Tyr
                245                 250                 255
Phe Gly Phe Glu Lys Glu Asp Lys Lys Arg Leu Tyr His Leu Met Ala
            260                 265                 270
Leu Ala Gly Gln Leu Arg Gln Trp Cys Phe His Asp Ala Thr Tyr Lys
            275                 280                 285
Ser Asn Asp Ile Asn Lys Glu Glu Tyr Val Lys Gly Lys Ile Arg Thr
        290                 295                 300
Trp Leu Tyr Asn Leu Asp Asn Arg Asn Leu Ala Ala Glu Tyr Tyr Asp
305                 310                 315                 320
Thr Leu Asp Tyr Phe Phe Asp Lys Arg Phe Lys Glu Ile Asn Asn Asp
                325                 330                 335
Phe Val Ser Lys Asn Ser Val Asn Leu Phe Ile Leu Lys Asp Ile Phe
            340                 345                 350
Pro Glu Glu Glu Leu Thr Glu Val Ile Lys Leu Tyr Tyr Asp Phe Ile
            355                 360                 365
Val Val Lys Ser Tyr Lys Asn Met Gly Phe Ser Ile Thr Lys Leu Arg
        370                 375                 380
Glu Lys Met Leu Glu Gln Thr Gly Ala Ala Ile Thr Ser Thr Asn
385                 390                 395                 400
Met Asp Ser Val Arg Ser Lys Leu Tyr Lys Leu Ile Asp Phe Cys Ile
                405                 410                 415
Phe Tyr Gly Tyr Tyr Lys Asp Glu Lys Lys Ser Ala Glu Asn Val Asp
            420                 425                 430
Tyr Leu Arg Ser Cys Leu Asn Glu Asp Ala Lys Glu Asn Phe Tyr Ala
            435                 440                 445
Ile Glu Ser Gln Lys Leu Trp Glu Lys Tyr Gly Lys Leu Phe Leu Asp
        450                 455                 460
Phe Cys Asn Ile Val Ser Glu Thr Asn Ile Lys Ser Leu Ser Asn Asp
465                 470                 475                 480
Val Thr Lys Lys Lys His Thr Glu Ile Leu Ser Arg Tyr Ile Asp Phe
                485                 490                 495
Glu Glu Tyr Arg Asn Ser Ser Asn Val Ser Tyr Phe Ser Lys Leu Met
```

-continued

```
                500             505             510
Tyr Val Met Cys Phe Phe Leu Asp Gly Lys Glu Ile Asn Glu Leu Leu
            515                 520                 525
Thr Thr Leu Ile Asn Lys Phe Asp Asn Ile Ser Ser Phe Ile Ala Thr
            530                 535             540
Ala Lys Glu Leu Asp Ile Asp Val Asn Phe Val Ala Asp Tyr Ser Phe
545                 550                 555                 560
Phe Asn Asp Cys Gly Lys Tyr Val Asn Glu Ile Asn Ile Val Lys Asn
                565                 570                 575
Ile Ser Arg Met Lys Lys Pro Ser Ala Lys Ala Lys Val Met Phe
                580                 585                 590
Arg Asp Ala Leu Thr Ile Leu Gly Met Pro His Asn Met Thr Glu Glu
            595                 600                 605
Gln Phe Glu Ala Glu Ile Glu Lys Leu Val Glu Val Glu Tyr Asp Val
    610                 615                 620
Thr Gly Lys Lys Ile Lys Lys Pro His Asp Tyr Arg Asn Phe Ile Cys
625                 630                 635                 640
Asn Asn Ile Ile Glu Asn Arg Arg Phe Val Tyr Ile Ile Lys Phe Cys
                645                 650                 655
Asn Pro Gly Ser Val Arg Lys Ile Ala Asp Asn Thr Ala Val Thr Lys
                660                 665                 670
Phe Val Leu Lys Arg Ile Asp Glu Lys Gln Ile Glu Arg Tyr Tyr Ile
            675                 680                 685
Ser Cys Met Glu Ala Pro Asp Val Asn Ala Ser Leu Asp Tyr Lys Ile
            690                 695                 700
Asn Gln Leu Ala Glu Met Met Lys Arg Met Asp Phe Gly Gln Phe Cys
705                 710                 715                 720
Asn Val Arg Gln Ile Ser Ser Asn Pro Ser Lys Gln Arg Lys Glu
                725                 730                 735
Arg Tyr Lys Ala Ile Val Gly Leu Tyr Leu Thr Val Val Tyr His Leu
                740                 745                 750
Val Lys Asn Leu Val Asn Val Asn Ala Arg Tyr Val Met Ala Phe His
            755                 760                 765
Ser Leu Glu Arg Asp Ala Ala Leu Tyr Asn Tyr Lys Leu Glu Lys Asn
    770                 775                 780
Tyr Thr Gly Leu Ala Lys Leu Leu Cys Asp Glu Glu Lys Ser Gln
785                 790                 795                 800
Ser Gly Tyr Leu Ala Arg Asn Lys Arg Leu Arg Glu Cys Val Lys Gln
                805                 810                 815
Asp Val Glu Asn Ala Lys Glu Leu Asp Val Gln Asn Tyr Arg Asn Asn
                820                 825                 830
Val Ala His Leu Thr Ala Ile Arg Arg Val Gly Asp Phe Val Gly Asp
            835                 840                 845
Thr Thr Lys Ile Asp Ser Tyr Phe Ala Leu Tyr His Tyr Leu Met Gln
            850                 855                 860
Arg Leu Leu Leu Glu Lys Ser Asn Ala Asp His Lys Tyr Asn Lys Gln
865                 870                 875                 880
Leu Ile Gln Trp His Thr Tyr Val Lys Asp Tyr Val Lys Ala Leu Asn
                885                 890                 895
Ser Pro Phe Gly Tyr Asn Ile Pro Arg Phe Lys Ala Leu Thr Ile Glu
                900                 905                 910
Gln Phe Phe Asp Arg Asn Glu
    915
```

<210> SEQ ID NO 31
<211> LENGTH: 882
<212> TYPE: PRT
<213> ORGANISM: Ruminococcus Sp.
<220> FEATURE:
<221> NAME/KEY: misc_feature
<223> OTHER INFORMATION: SG11METT28961912_Ru4Mmc2

<400> SEQUENCE: 31

```
Met Lys Glu Lys His Tyr Ser Lys Val Lys Ala Ala Gly Met Lys Ser
1               5                   10                  15

Ala Phe Val Asn Asn Gly Thr Val Thr Met Thr Ser Phe Gly Lys Gly
            20                  25                  30

Asn Lys Ala Ile Leu Glu Lys Glu Ile Asn Asn Gly Ile Ile Thr Asp
        35                  40                  45

Leu Gln Val Thr Asn Gln Phe Asp Val Ala Phe Ile Gly Glu Lys Lys
    50                  55                  60

Phe Asp Ile Asn Ser Lys Arg Val Lys Asn Ala Leu Ser Asp Asn Pro
65                  70                  75                  80

Val Lys Asp Asp Glu Gln Asp Val Gly Leu Asp Leu Leu His Ala Lys
                85                  90                  95

Lys Gln Leu Glu Glu Arg Tyr Phe Ser Lys Thr Phe Pro Gly Glu Asn
            100                 105                 110

Ile His Ile Gln Ile Ala Tyr Asn Ile Leu Asp Ile Lys Lys Ile Leu
        115                 120                 125

Ser Ile Tyr Ala Asn Asn Val Val Phe Ala Leu Asn Asn Leu Arg Arg
    130                 135                 140

Leu Asn Glu Val Gly Arg Glu Asn Asp Phe Ile Gly Tyr Leu Tyr Thr
145                 150                 155                 160

Gly Asn Lys Tyr Asp Asp Leu Ile Lys Asn Cys Asn Val Cys Leu Lys
                165                 170                 175

Lys Asp Asp Cys Asp Asn Ser Leu Cys Asn Asp Lys Gln Ser Arg Tyr
            180                 185                 190

Ser Trp Asn Lys Asp Ile Cys Lys Ser Thr His Lys Phe Phe Glu Tyr
        195                 200                 205

Ile Asp Lys Ile Asp Met Tyr Ala Pro Tyr Tyr Arg Glu Phe Phe Tyr
    210                 215                 220

Ser Gly Glu Phe Lys Lys Lys Asp Gly Lys Tyr Glu Glu Lys Leu
225                 230                 235                 240

Arg Ser Tyr Lys Asp Thr Tyr Asn Ile Leu Arg Leu Ile Ser Cys Leu
                245                 250                 255

Arg Gln Ser Cys Phe His Asp Gln Ile Ser Thr Thr Gly Phe Leu Phe
            260                 265                 270

Asn Pro Ile Lys Asp Val Glu Leu Lys Glu Leu Val Asp Arg Leu Tyr
        275                 280                 285

Glu Ala Lys Thr Glu Ser Ala His Asn Asn Phe Phe Asn Asn Gly
    290                 295                 300

Lys Asn Met Ser Phe Leu Phe Asp Ile Tyr Lys Ala Lys Thr Asp Glu
305                 310                 315                 320

Glu Arg Lys Lys Leu Ala Arg Glu Tyr Tyr Gly Phe Val Ile Tyr Lys
                325                 330                 335

Gln Asp Lys Asn Leu Gly Phe Ser Ile Lys Lys Leu Arg Glu Asn Met
            340                 345                 350

Leu Glu Asn Gln Lys Leu Val Tyr Ile Lys Asn Asp His Gln Tyr Asp
```

```
                355                 360                 365
Ser Val Arg Thr Lys Leu Tyr Ser Leu Leu Asp Phe Ile Leu Tyr Lys
            370                 375                 380

His Tyr Asn Asn Thr Lys Leu Gln Asp Glu Ile Val Glu Ser Leu Arg
385                 390                 395                 400

Cys Ala Tyr Thr Glu Glu Asp Lys Gln Ile Val Tyr Ser Lys Gln Ala
                405                 410                 415

Glu Ser Ser Val Leu Ala Leu Gly Asp Val Ile Asn Asn Gln Leu Ile
            420                 425                 430

Pro Lys Met Asn Gly Asp Val Ile Lys Thr Gln Arg Lys Ala Phe Ile
                435                 440                 445

Asp Arg Asn Trp Phe Glu Asp Ile Lys Leu Ser Lys Thr Ala Ser Asp
            450                 455                 460

Phe Ser Lys Ile Ile Tyr Val Leu Thr Leu Phe Leu Asp Gly Lys Glu
465                 470                 475                 480

Ile Asn Glu Leu Leu Ser Ala Leu Ile Asn Lys Leu Glu Asn Ile Ala
                485                 490                 495

Ser Phe Ile Asp Val Met Lys Asp Met Gly Ile Ala Ala Asp Phe Asn
            500                 505                 510

Lys Asp Tyr Ala Val Leu Gly Asn Ser Tyr Lys Ile Ala Asn Glu Leu
                515                 520                 525

Arg Ser Met Lys Ser Phe Val Arg Met Gln Asn Asp Ile Pro Lys Phe
            530                 535                 540

Ser Lys Gly Thr Tyr Tyr Asp Gly Ala Ser Val Leu Gly Ile Lys Lys
545                 550                 555                 560

Asn Ser Ile His Ile Glu Asn Asp Ile Asp Glu Asp Tyr Leu Asp Gly
                565                 570                 575

Phe Phe Val Glu Gly Asn Asp Asn Val Arg Asn Phe Ile Ile Asn
            580                 585                 590

Asn Val Leu Lys Ser Lys Arg Phe Leu Tyr Leu Val Arg Tyr Asn Asn
            595                 600                 605

Pro Lys Arg Ser Arg Ala Leu Ala Ser Asn Gln Glu Val Ile Lys Phe
            610                 615                 620

Val Leu Asn Gly Ile Pro Glu Thr Gln Ile Asn Arg Tyr Tyr Asn Ser
625                 630                 635                 640

Val Thr Gly Phe Asp Ser Leu Asn Ala Ser Phe Glu Glu Lys Val Asn
                645                 650                 655

Glu Leu Ser Lys Arg Ile Ser Asn Ile Asn Phe Glu Gln Phe Val Gly
            660                 665                 670

Val Lys Gln Lys Pro Lys Thr Ala Ala Glu Asn Val Glu Lys Glu Gln
            675                 680                 685

Met Lys Ala Ile Ile Gly Leu Tyr Leu Thr Val Leu Tyr Leu Leu Thr
            690                 695                 700

Lys Asn Leu Val Lys Ile Asn Ala Arg Tyr Thr Ile Ala Ile Ser Asn
705                 710                 715                 720

Leu Glu Lys Asp Thr Gln Leu His Asn Leu Pro Ser Trp Lys Asp Asn
                725                 730                 735

Pro Phe Ala Ile Ser Asp Leu Phe Val Lys Asn Lys Val Lys Asp
            740                 745                 750

Asp Trp Tyr Lys Asn Gly Asp Lys His Thr Leu Ser Asp Tyr Lys Lys
            755                 760                 765

Asn Ala Gln Lys Glu Val Phe Lys Val Tyr Arg Asn Ser Ile Ala His
            770                 775                 780
```

```
Met Thr Val Ile Thr Asp Ala Tyr Lys Tyr Leu Ser Asp Asn Ser Ser
785                 790                 795                 800

Leu Lys Val Thr Lys Ile Lys Ser Tyr Tyr Gln Ile Tyr His Ser Ile
            805                 810                 815

Met Gln Arg Val Ile Val Asn Gln Leu Lys His Asp Lys Ile Asn Leu
        820                 825                 830

Asn Asp Phe Ala Gln Lys Ser Tyr Asp Asn Ala Ile Lys Tyr Gly Ser
    835                 840                 845

Tyr Thr Lys Glu Trp Val Lys Val Leu Asn Tyr Pro Phe Ala Tyr Asn
850                 855                 860

Leu Ala Arg Tyr Lys Asn Leu Ile Asn Glu Lys Ile Phe Glu Ser Asp
865                 870                 875                 880

Arg Ser

<210> SEQ ID NO 32
<211> LENGTH: 944
<212> TYPE: PRT
<213> ORGANISM: Eubacterium siraeum
<220> FEATURE:
<221> NAME/KEY: misc_feature
<223> OTHER INFORMATION: SG11METT28962321_Eb7Mmc2

<400> SEQUENCE: 32

Met Lys Val Tyr Arg Val Cys Asp Ile Ile Phe Arg Gly Glu Ile
1               5                   10                  15

Gln Met Leu Lys Gln Ile Gly Val Lys Ser Ile Val Lys Thr Ser Lys
            20                  25                  30

Asn Lys Ile Tyr Ile Ser Asn Val Asn Glu Lys Leu Asp Lys Lys Val
        35                  40                  45

Asn Asp Thr Ser Lys Glu Val Ser Ser Phe Ala Asp Ser Ile Phe
    50                  55                  60

Asn Leu Val Phe Glu Glu Asn Lys Asn Tyr Lys Phe Glu Ala Asn
65                  70                  75                  80

Gly Leu Lys Tyr Glu Glu Glu Lys Pro Phe Leu Glu Arg Lys Asn Val
                85                  90                  95

Leu Lys Glu Lys Ile Glu Gln Ser Tyr Phe Lys Arg Asn Tyr Asn Asp
            100                 105                 110

Asn Leu Arg Val Gln Ile Ala Ser Asn Ile Met Asp Ile Gln Lys Val
        115                 120                 125

Leu Ser Phe Tyr Ile Asp Asp Val Cys Tyr Ala Ile Ser Asn Ile Tyr
130                 135                 140

Gln Asn Ala Ser Asn Asn Tyr Asn Ser Thr Thr Asp Phe Ile Gly Asn
145                 150                 155                 160

Asp Val Val His Phe Ala Asn Tyr Gly Lys Leu Asp Ser Asn Lys Lys
                165                 170                 175

Lys Asn Val Asp Ala Leu Ile Met Ala Leu Lys Glu Tyr Gly Ala Leu
            180                 185                 190

Phe Gly Gly Leu Leu Lys Tyr Asp Asn Val Leu Pro Ser Asp Glu Ser
        195                 200                 205

Ala Asp Phe Phe Ile Asp Lys Lys Thr Asn Lys Asn Tyr Arg Val
    210                 215                 220

Ala Ile Asn Asp Thr Lys Phe Ile Tyr Ser Leu Leu Arg Cys Leu Ala
225                 230                 235                 240

Leu Val Arg Asn Phe Ser Phe His Pro Asp Glu Lys Arg Asn Asn Phe
                245                 250                 255
```

-continued

Leu Tyr Gly Val Glu Asn Lys Tyr Leu Ala Asn Phe Ala Lys Asn Met
            260                 265                 270

Phe Arg Lys Lys Ile Asp Lys His Lys Glu Ser Phe Phe Asp Asn Ser
        275                 280                 285

Gln Ala Asn Asp Leu Arg Phe Leu Lys Ser Ile Tyr Pro Asn Gln Thr
    290                 295                 300

Asp Leu Gln Leu Leu Lys Glu Leu Tyr Asp Phe Thr Thr Phe Lys Asp
305                 310                 315                 320

Tyr Lys Thr Met Gly Ile Ser Ile Lys Ile Arg Glu Ile Leu Val
                325                 330                 335

Glu Lys Tyr Phe Lys Asn Asp Thr Asn Val Ser Val Gln Arg Leu Ser
            340                 345                 350

Glu Ile Lys Pro Lys Ile Asn Lys Tyr Phe Asp Phe Ile Val Tyr Lys
        355                 360                 365

Tyr Leu Asp Phe His Glu Pro Asn Val Ile Gly Phe Lys Thr Arg Leu
    370                 375                 380

Tyr Ser Val Val Gly Glu Cys Lys Asp Lys Thr Leu Thr Gly Lys Glu
385                 390                 395                 400

Arg Lys Gln Lys Ile Glu Glu Asp Arg Glu Ser Lys Phe Leu Glu Ile
                405                 410                 415

Tyr Lys Asp Ile Ala Asn Glu Ile Asp Lys Ser Asp Phe Val Lys Thr
            420                 425                 430

Lys Gly Thr Thr Tyr Phe Asp Leu Ile Lys Asn Phe Trp Val Lys Val
        435                 440                 445

Asp Ser Lys Lys Ser Thr Asn Thr Lys Asp Val Gln Tyr Lys Glu Leu
    450                 455                 460

Lys Gln Lys Phe Met Glu Glu Thr Arg Asn Ile Asn Val Ser Asp Phe
465                 470                 475                 480

Ala Ala Phe Ile Tyr Ile Leu Thr Ile Phe Leu Ser Gly Lys Glu Ile
                485                 490                 495

Asn Glu Leu Leu Asn Tyr Ile Ile Asn Lys Cys Glu Ser Thr Leu Ser
            500                 505                 510

Leu Ile Tyr Leu Asp Glu Lys Ile Ala Lys Asn Glu Asp Asp Gln Ala
        515                 520                 525

Lys Gln Asn Glu Tyr Lys Thr Asn Asn Ser Tyr Ile Cys Leu Ile Lys
    530                 535                 540

Asp Phe Cys Lys Ala Ala Lys Thr Asp Val Ala Phe Ala Lys Asn Phe
545                 550                 555                 560

Ile Arg Gln Gln Lys Leu Ser Ala Leu Gly Glu Ser Met Pro Glu Lys
                565                 570                 575

Val Thr Lys Asn Ala Ile Glu Leu Leu Gly Ser Lys Asp Val Asn Gly
            580                 585                 590

Ala Tyr Ala Leu Thr Cys Pro Gln Lys Ala Asn Lys Phe Asp Arg Arg
        595                 600                 605

Lys Asn Val Leu Lys Asn Phe Leu Arg Asn Asn Val Ala Ser Arg
    610                 615                 620

Gln Phe Asp Tyr Ile Leu Arg Tyr Val Ser Val Lys Lys Cys Arg Leu
625                 630                 635                 640

Ile Met Asn Asn Asp Ser Val Val Asn His Val Leu Asp Gln Ile Pro
                645                 650                 655

Glu Ser Lys Leu Glu Arg Tyr Tyr Glu Ile Gly Asn Thr Met Gly Gln
            660                 665                 670

-continued

```
Asn Ile Asn Arg Gln Asn Ile Val Ser His Leu Arg Lys Leu Ser Phe
            675                 680                 685

Asp Ala Leu Ile Asp Asn Lys Asn Asp Pro Lys Tyr Val Glu Tyr Leu
690                 695                 700

Lys Ala Leu Thr Gly Leu Tyr Leu Asn Ile Ala Tyr Leu Phe Ile Lys
705                 710                 715                 720

Asn Met Val Arg Thr Asn Ala Leu Tyr Ser Ile Ala Leu Ile Ala Asn
            725                 730                 735

Val Arg Asp Leu Asp Phe Ile Glu Pro Ser Thr Asp Lys Gln Lys Thr
            740                 745                 750

Glu Ile Ser Tyr Arg Asn Phe Asp Ser Val Phe Asn Phe Asn Glu
            755                 760                 765

Arg Asn Ala Val Phe Gly Lys Lys Tyr Arg Asn Lys Asn Gly Asp Ala
770                 775                 780

Val Asn Thr Glu Phe Thr Gln Gly Val Leu Asn Asn Val Lys Gln Leu
785                 790                 795                 800

Lys Asn Leu Ala Ile Glu Ile Ala Lys Ala Ser Ala Tyr Arg Asp Asn
            805                 810                 815

Gln Gly Glu Leu Lys Tyr Val Asp Ile Val Arg Leu Tyr Arg Asn Asn
            820                 825                 830

Ile Ala His Leu Thr Val Val Asn Arg Val Ala Asp Phe Val Gly Asn
            835                 840                 845

Gly Gln Ser Thr Tyr Lys Tyr Lys Asn Asp Thr Pro Ser Tyr Phe Asp
            850                 855                 860

Ile Phe Asn Phe Ser Ile Gln Ala Leu Ile Phe Glu His Val Glu Arg
865                 870                 875                 880

Lys Val Gly Gly Ile Gln Asn Thr Gly Leu Asn Asn Tyr Ile Lys Val
            885                 890                 895

Val Lys Glu Arg Gly Ser Ala Ser Arg Asp Phe Ile Lys Ile Ile Asn
            900                 905                 910

Ser Pro Phe Ala Tyr Asn Leu Ala Arg Tyr Lys Arg Leu Thr Tyr Gln
            915                 920                 925

Asn Ile Phe Glu Asp Gly Ala Asn Ile Gly Thr Arg Gly Asp Lys Lys
930                 935                 940
```

<210> SEQ ID NO 33
<211> LENGTH: 954
<212> TYPE: PRT
<213> ORGANISM: Eubacterium siraeum
<220> FEATURE:
<221> NAME/KEY: misc_feature
<223> OTHER INFORMATION: WP_005358205.1_EupMmc2

<400> SEQUENCE: 33

```
Met Gly Lys Lys Ile His Ala Arg Asp Leu Arg Glu Gln Arg Lys Thr
1               5                   10                  15

Asp Arg Thr Glu Lys Phe Ala Asp Gln Asn Lys Lys Arg Glu Ala Glu
            20                  25                  30

Arg Ala Val Pro Lys Lys Asp Ala Ala Val Ser Val Lys Ser Val Ser
            35                  40                  45

Ser Val Ser Ser Lys Lys Asp Asn Val Thr Lys Ser Met Ala Lys Ala
        50                  55                  60

Ala Gly Val Lys Ser Val Phe Ala Val Gly Asn Thr Val Tyr Met Thr
65                  70                  75                  80

Ser Phe Gly Arg Gly Asn Asp Ala Val Leu Glu Gln Lys Ile Val Asp
            85                  90                  95
```

```
Thr Ser His Glu Pro Leu Asn Ile Asp Asp Pro Ala Tyr Gln Leu Asn
            100                 105                 110

Val Val Thr Met Asn Gly Tyr Ser Val Thr Gly His Arg Gly Glu Thr
            115                 120                 125

Val Ser Ala Val Thr Asp Asn Pro Leu Arg Arg Phe Asn Gly Arg Lys
130                 135                 140

Lys Asp Glu Pro Glu Gln Ser Val Pro Thr Asp Met Leu Cys Leu Lys
145                 150                 155                 160

Pro Thr Leu Glu Lys Lys Phe Phe Gly Lys Glu Phe Asp Asp Asn Ile
            165                 170                 175

His Ile Gln Leu Ile Tyr Asn Ile Leu Asp Ile Glu Lys Ile Leu Ala
            180                 185                 190

Val Tyr Ser Thr Asn Ala Ile Tyr Ala Leu Asn Asn Met Ser Ala Asp
            195                 200                 205

Glu Asn Ile Glu Asn Ser Asp Phe Phe Met Lys Arg Thr Thr Asp Glu
            210                 215                 220

Thr Phe Asp Asp Phe Glu Lys Lys Glu Ser Thr Asn Ser Arg Glu
225                 230                 235                 240

Lys Ala Asp Phe Asp Ala Phe Glu Lys Phe Ile Gly Asn Tyr Arg Leu
            245                 250                 255

Ala Tyr Phe Ala Asp Ala Phe Tyr Val Asn Lys Lys Asn Pro Lys Gly
            260                 265                 270

Lys Ala Lys Asn Val Leu Arg Glu Asp Lys Glu Leu Tyr Ser Val Leu
            275                 280                 285

Thr Leu Ile Gly Lys Leu Arg His Trp Cys Val His Ser Glu Glu Gly
            290                 295                 300

Arg Ala Glu Phe Trp Leu Tyr Lys Leu Asp Glu Leu Lys Asp Asp Phe
305                 310                 315                 320

Lys Asn Val Leu Asp Val Val Tyr Asn Arg Pro Val Glu Glu Ile Asn
            325                 330                 335

Asn Arg Phe Ile Glu Asn Asn Lys Val Asn Ile Gln Ile Leu Gly Ser
            340                 345                 350

Val Tyr Lys Asn Thr Asp Ile Ala Glu Leu Val Arg Ser Tyr Tyr Glu
            355                 360                 365

Phe Leu Ile Thr Lys Lys Tyr Lys Asn Met Gly Phe Ser Ile Lys Lys
            370                 375                 380

Leu Arg Glu Ser Met Leu Glu Gly Lys Gly Tyr Ala Asp Lys Glu Tyr
385                 390                 395                 400

Asp Ser Val Arg Asn Lys Leu Tyr Gln Met Thr Asp Phe Ile Leu Tyr
            405                 410                 415

Thr Gly Tyr Ile Asn Glu Asp Ser Asp Arg Ala Asp Asp Leu Val Asn
            420                 425                 430

Thr Leu Arg Ser Ser Leu Lys Glu Asp Asp Lys Thr Thr Val Tyr Cys
            435                 440                 445

Lys Glu Ala Asp Tyr Leu Trp Lys Lys Tyr Arg Glu Ser Ile Arg Glu
            450                 455                 460

Val Ala Asp Ala Leu Asp Gly Asp Asn Ile Lys Lys Leu Ser Lys Ser
465                 470                 475                 480

Asn Ile Glu Ile Gln Glu Asp Lys Leu Arg Lys Cys Phe Ile Ser Tyr
            485                 490                 495

Ala Asp Ser Val Ser Glu Phe Thr Lys Leu Ile Tyr Leu Leu Thr Arg
            500                 505                 510
```

```
Phe Leu Ser Gly Lys Glu Ile Asn Asp Leu Val Thr Thr Leu Ile Asn
        515                 520                 525

Lys Phe Asp Asn Ile Arg Ser Phe Leu Glu Ile Met Asp Glu Leu Gly
    530                 535                 540

Leu Asp Arg Thr Phe Thr Ala Glu Tyr Ser Phe Phe Glu Gly Ser Thr
545                 550                 555                 560

Lys Tyr Leu Ala Glu Leu Val Glu Leu Asn Ser Phe Val Lys Ser Cys
                565                 570                 575

Ser Phe Asp Ile Asn Ala Lys Arg Thr Met Tyr Arg Asp Ala Leu Asp
                580                 585                 590

Ile Leu Gly Ile Glu Ser Asp Lys Thr Glu Asp Ile Glu Lys Met
            595                 600                 605

Ile Asp Asn Ile Leu Gln Ile Asp Ala Asn Gly Asp Lys Lys Leu Lys
            610                 615                 620

Lys Asn Asn Gly Leu Arg Asn Phe Ile Ala Ser Asn Val Ile Asp Ser
625                 630                 635                 640

Asn Arg Phe Lys Tyr Leu Val Arg Tyr Gly Asn Pro Lys Lys Ile Arg
                645                 650                 655

Glu Thr Ala Lys Cys Lys Pro Ala Val Arg Phe Val Leu Asn Glu Ile
            660                 665                 670

Pro Asp Ala Gln Ile Glu Arg Tyr Tyr Glu Ala Cys Cys Pro Lys Asn
        675                 680                 685

Thr Ala Leu Cys Ser Ala Asn Lys Arg Arg Glu Lys Leu Ala Asp Met
        690                 695                 700

Ile Ala Glu Ile Lys Phe Glu Asn Phe Ser Asp Ala Gly Asn Tyr Gln
705                 710                 715                 720

Lys Ala Asn Val Thr Ser Arg Thr Ser Glu Ala Glu Ile Lys Arg Lys
                725                 730                 735

Asn Gln Ala Ile Ile Arg Leu Tyr Leu Thr Val Met Tyr Ile Met Leu
            740                 745                 750

Lys Asn Leu Val Asn Val Asn Ala Arg Tyr Val Ile Ala Phe His Cys
        755                 760                 765

Val Glu Arg Asp Thr Lys Leu Tyr Ala Glu Ser Gly Leu Glu Val Gly
    770                 775                 780

Asn Ile Glu Lys Asn Lys Thr Asn Leu Thr Met Ala Val Met Gly Val
785                 790                 795                 800

Lys Leu Glu Asn Gly Ile Ile Lys Thr Glu Phe Asp Lys Ser Phe Ala
                805                 810                 815

Glu Asn Ala Ala Asn Arg Tyr Leu Arg Asn Ala Arg Trp Tyr Lys Leu
            820                 825                 830

Ile Leu Asp Asn Leu Lys Lys Ser Glu Arg Ala Val Val Asn Glu Phe
        835                 840                 845

Arg Asn Thr Val Cys His Leu Asn Ala Ile Arg Asn Ile Asn Ile Asn
    850                 855                 860

Ile Lys Glu Ile Lys Glu Val Glu Asn Tyr Phe Ala Leu Tyr His Tyr
865                 870                 875                 880

Leu Ile Gln Lys His Leu Glu Asn Arg Phe Ala Asp Lys Lys Val Glu
                885                 890                 895

Arg Asp Thr Gly Asp Phe Ile Ser Lys Leu Glu Glu His Lys Thr Tyr
            900                 905                 910

Cys Lys Asp Phe Val Lys Ala Tyr Cys Thr Pro Phe Gly Tyr Asn Leu
        915                 920                 925

Val Arg Tyr Lys Asn Leu Thr Ile Asp Gly Leu Phe Asp Lys Asn Tyr
```

```
                930             935             940
Pro Gly Lys Asp Asp Ser Asp Glu Gln Lys
945             950
```

<210> SEQ ID NO 34
<211> LENGTH: 933
<212> TYPE: PRT
<213> ORGANISM: Ruminococcus flavefaciens
<220> FEATURE:
<221> NAME/KEY: misc_feature
<223> OTHER INFORMATION: WP_009985792_RfpMmc2

<400> SEQUENCE: 34

```
Met Lys Lys Met Ser Leu Arg Glu Lys Arg Glu Ala Glu Lys Gln
1               5                   10                  15

Ala Lys Lys Ala Ala Tyr Ser Ala Ala Ser Lys Asn Thr Asp Ser Lys
                20                  25                  30

Pro Ala Glu Lys Lys Ala Glu Thr Pro Lys Pro Ala Glu Ile Ile Ser
                35                  40                  45

Asp Asn Ser Arg Asn Lys Thr Ala Val Lys Ala Gly Leu Lys Ser
        50                  55                  60

Thr Ile Ile Ser Gly Asp Lys Leu Tyr Met Thr Ser Phe Gly Lys Gly
65                  70                  75                  80

Asn Ala Ala Val Ile Glu Gln Lys Ile Asp Ile Asn Asp Tyr Ser Phe
                85                  90                  95

Ser Ala Met Lys Asp Thr Pro Ser Leu Glu Val Asp Lys Ala Glu Ser
                100                 105                 110

Lys Glu Ile Ser Phe Ser Ser His His Pro Phe Val Lys Asn Asp Lys
                115                 120                 125

Leu Thr Thr Tyr Asn Pro Leu Tyr Gly Gly Lys Asp Asn Pro Glu Lys
        130                 135                 140

Pro Val Gly Arg Asp Met Leu Gly Leu Lys Asp Lys Leu Glu Glu Arg
145                 150                 155                 160

Tyr Phe Gly Cys Thr Phe Asn Asp Asn Leu His Ile Gln Ile Ile Tyr
                165                 170                 175

Asn Ile Leu Asp Ile Glu Lys Ile Leu Ala Val His Ser Ala Asn Ile
                180                 185                 190

Thr Thr Ala Leu Asp His Met Val Asp Glu Asp Asp Glu Lys Tyr Leu
        195                 200                 205

Asn Ser Asp Tyr Ile Gly Tyr Met Asn Thr Ile Asn Thr Tyr Asp Val
        210                 215                 220

Phe Met Asp Pro Ser Lys Asn Ser Ser Leu Ser Pro Lys Asp Arg Lys
225                 230                 235                 240

Asn Ile Asp Asn Ser Arg Ala Lys Phe Glu Lys Leu Leu Ser Thr Lys
                245                 250                 255

Arg Leu Gly Tyr Phe Gly Phe Asp Tyr Asp Ala Asn Gly Lys Asp Lys
                260                 265                 270

Lys Lys Asn Glu Glu Ile Lys Lys Arg Leu Tyr His Leu Thr Ala Phe
                275                 280                 285

Ala Gly Gln Leu Arg Gln Trp Ser Phe His Ser Ala Gly Asn Tyr Pro
        290                 295                 300

Arg Thr Trp Leu Tyr Lys Leu Asp Ser Leu Asp Lys Glu Tyr Leu Asp
305                 310                 315                 320

Thr Leu Asp His Tyr Phe Asp Lys Arg Phe Asn Asp Ile Asn Asp Asp
                325                 330                 335
```

```
Phe Val Thr Lys Asn Ala Thr Asn Leu Tyr Ile Leu Lys Glu Val Phe
            340                 345                 350

Pro Glu Ala Asn Phe Lys Asp Ile Ala Asp Leu Tyr Tyr Asp Phe Ile
            355                 360                 365

Val Ile Lys Ser His Lys Asn Met Gly Phe Ser Ile Lys Lys Leu Arg
            370                 375                 380

Glu Lys Met Leu Glu Cys Asp Gly Ala Asp Arg Ile Lys Glu Gln Asp
385                 390                 395                 400

Met Asp Ser Val Arg Ser Lys Leu Tyr Lys Leu Ile Asp Phe Cys Ile
                405                 410                 415

Phe Lys Tyr Tyr His Glu Phe Pro Glu Leu Ser Glu Lys Asn Val Asp
            420                 425                 430

Ile Leu Arg Ala Ala Val Ser Asp Thr Lys Lys Asp Asn Leu Tyr Ser
            435                 440                 445

Asp Glu Ala Ala Arg Leu Trp Ser Ile Phe Lys Glu Lys Phe Leu Gly
            450                 455                 460

Phe Cys Asp Lys Ile Val Val Trp Val Thr Gly Glu His Glu Lys Asp
465                 470                 475                 480

Ile Thr Ser Val Ile Asp Lys Asp Ala Tyr Arg Asn Arg Ser Asn Val
                485                 490                 495

Ser Tyr Phe Ser Lys Leu Met Tyr Ala Met Cys Phe Phe Leu Asp Gly
            500                 505                 510

Lys Glu Ile Asn Asp Leu Leu Thr Thr Leu Ile Asn Lys Phe Asp Asn
            515                 520                 525

Ile Ala Asn Gln Ile Lys Thr Ala Lys Glu Leu Gly Ile Asn Thr Ala
            530                 535                 540

Phe Val Lys Asn Tyr Asp Phe Phe Asn His Ser Glu Lys Tyr Val Asp
545                 550                 555                 560

Glu Leu Asn Ile Val Lys Asn Ile Ala Arg Met Lys Lys Pro Ser Ser
                565                 570                 575

Asn Ala Lys Lys Ala Met Tyr His Asp Ala Leu Thr Ile Leu Gly Ile
            580                 585                 590

Pro Glu Asp Met Asp Glu Lys Ala Leu Asp Glu Glu Leu Asp Leu Ile
            595                 600                 605

Leu Glu Lys Lys Thr Asp Pro Val Thr Gly Lys Pro Leu Lys Gly Lys
            610                 615                 620

Asn Pro Leu Arg Asn Phe Ile Ala Asn Asn Val Ile Glu Asn Ser Arg
625                 630                 635                 640

Phe Ile Tyr Leu Ile Lys Phe Cys Asn Pro Glu Asn Val Arg Lys Ile
                645                 650                 655

Val Asn Asn Thr Lys Val Thr Glu Phe Val Leu Lys Arg Ile Pro Asp
            660                 665                 670

Ala Gln Ile Glu Arg Tyr Tyr Lys Ser Cys Thr Asp Ser Glu Met Asn
            675                 680                 685

Pro Pro Thr Glu Lys Lys Ile Thr Glu Leu Ala Gly Lys Leu Lys Asp
            690                 695                 700

Met Asn Phe Gly Asn Phe Arg Asn Val Arg Gln Ser Ala Lys Glu Asn
705                 710                 715                 720

Met Glu Lys Glu Arg Phe Lys Ala Val Ile Gly Leu Tyr Leu Thr Val
                725                 730                 735

Val Tyr Arg Val Val Lys Asn Leu Val Asp Val Asn Ser Arg Tyr Ile
            740                 745                 750

Met Ala Phe His Ser Leu Glu Arg Asp Ser Gln Leu Tyr Asn Val Ser
```

```
            755                 760                 765
Val Asp Asn Asp Tyr Leu Ala Leu Thr Asp Thr Leu Val Lys Glu Gly
770                 775                 780

Asp Asn Ser Arg Ser Arg Tyr Leu Ala Gly Asn Lys Arg Leu Arg Asp
785                 790                 795                 800

Cys Val Lys Gln Asp Ile Asp Asn Ala Lys Trp Phe Val Ser Asp
                805                 810                 815

Lys Tyr Asn Ser Ile Thr Lys Tyr Arg Asn Asn Val Ala His Leu Thr
                820                 825                 830

Ala Val Arg Asn Cys Ala Glu Phe Ile Gly Asp Ile Thr Lys Ile Asp
                835                 840                 845

Ser Tyr Phe Ala Leu Tyr His Tyr Leu Ile Gln Arg Gln Leu Ala Lys
                850                 855                 860

Gly Leu Asp His Glu Arg Ser Gly Phe Asp Arg Asn Tyr Pro Gln Tyr
865                 870                 875                 880

Ala Pro Leu Phe Lys Trp His Thr Tyr Val Lys Asp Val Val Lys Ala
                885                 890                 895

Leu Asn Ala Pro Phe Gly Tyr Asn Ile Pro Arg Phe Lys Asn Leu Ser
                900                 905                 910

Ile Asp Ala Leu Phe Asp Arg Asn Glu Ile Lys Lys Asn Asp Gly Glu
                915                 920                 925

Lys Lys Ser Asp Asp
                930

<210> SEQ ID NO 35
<211> LENGTH: 918
<212> TYPE: PRT
<213> ORGANISM: Eubacterium siraeum
<220> FEATURE:
<221> NAME/KEY: misc_feature
<223> OTHER INFORMATION: WP_041337480_RbpMmc2

<400> SEQUENCE: 35

Met Ala Lys Lys Asn Lys Met Lys Pro Arg Glu Leu Arg Glu Ala Gln
1               5                   10                  15

Lys Lys Ala Arg Gln Leu Lys Ala Ala Glu Ile Asn Asn Asn Ala Val
                20                  25                  30

Pro Ala Ile Ala Ala Met Pro Ala Ala Glu Ala Ala Pro Ala Ala
                35                  40                  45

Glu Lys Lys Lys Ser Ser Val Lys Ala Ala Gly Met Lys Ser Ile Leu
50                  55                  60

Val Ser Glu Asn Lys Met Tyr Ile Thr Ser Phe Gly Lys Gly Asn Ser
65                  70                  75                  80

Ala Val Leu Glu Tyr Glu Val Asp Asn Asn Asp Tyr Asn Lys Thr Gln
                85                  90                  95

Leu Ser Ser Lys Asp Asn Ser Asn Ile Glu Leu Cys Asp Val Gly Lys
                100                 105                 110

Val Asn Ile Thr Phe Ser Ser Arg Gly Phe Glu Ser Gly Val Glu
                115                 120                 125

Ile Asn Thr Ser Asn Pro Thr His Arg Ser Gly Glu Ser Ser Ser Val
130                 135                 140

Arg Gly Asp Met Leu Gly Leu Lys Ser Glu Leu Glu Lys Arg Phe Phe
145                 150                 155                 160

Gly Lys Asn Phe Asp Asp Asn Ile His Ile Gln Leu Ile Tyr Asn Ile
                165                 170                 175
```

```
Leu Asp Ile Glu Lys Ile Leu Ala Val Tyr Val Thr Asn Ile Val Tyr
            180                 185                 190

Ala Leu Asn Asn Met Leu Gly Glu Gly Asp Glu Ser Asn Tyr Asp Phe
        195                 200                 205

Met Gly Tyr Leu Ser Thr Phe Asn Thr Tyr Lys Val Phe Thr Asn Pro
    210                 215                 220

Asn Gly Ser Thr Leu Ser Asp Asp Lys Lys Glu Asn Ile Arg Lys Ser
225                 230                 235                 240

Leu Ser Lys Phe Asn Ala Leu Leu Lys Thr Lys Arg Leu Gly Tyr Phe
                245                 250                 255

Gly Leu Glu Glu Pro Lys Thr Lys Asp Thr Arg Ala Ser Glu Ala Tyr
            260                 265                 270

Lys Lys Arg Val Tyr His Met Leu Ala Ile Val Gly Gln Ile Arg Gln
        275                 280                 285

Cys Val Phe His Asp Lys Ser Gly Ala Lys Arg Phe Asp Leu Tyr Ser
    290                 295                 300

Phe Ile Asn Asn Ile Asp Pro Glu Tyr Arg Glu Thr Leu Asp Tyr Leu
305                 310                 315                 320

Val Asp Glu Arg Phe Asp Ser Ile Asn Lys Gly Phe Ile Gln Gly Asn
                325                 330                 335

Lys Val Asn Ile Ser Leu Leu Ile Asp Met Met Lys Gly Tyr Glu Ala
            340                 345                 350

Asp Asp Ile Ile Arg Leu Tyr Tyr Asp Phe Ile Val Leu Lys Ser Gln
        355                 360                 365

Lys Asn Leu Gly Phe Ser Ile Lys Lys Leu Arg Glu Lys Met Leu Asp
    370                 375                 380

Glu Tyr Gly Phe Arg Phe Lys Asp Lys Gln Tyr Asp Ser Val Arg Ser
385                 390                 395                 400

Lys Met Tyr Lys Leu Met Asp Phe Leu Leu Phe Cys Asn Tyr Tyr Arg
                405                 410                 415

Asn Asp Ile Ala Ala Gly Glu Ser Leu Val Arg Lys Leu Arg Phe Ser
            420                 425                 430

Met Thr Asp Asp Glu Lys Glu Gly Ile Tyr Ala Asp Glu Ala Ala Lys
        435                 440                 445

Leu Trp Gly Lys Phe Arg Asn Asp Phe Glu Asn Ile Ala Asp His Met
    450                 455                 460

Asn Gly Asp Val Ile Lys Glu Leu Gly Lys Ala Ser Asp Met Asp Phe Asp
465                 470                 475                 480

Glu Lys Ile Leu Asp Ser Glu Lys Lys Asn Ala Ser Asp Leu Leu Tyr
                485                 490                 495

Phe Ser Lys Met Ile Tyr Met Leu Thr Tyr Phe Leu Asp Gly Lys Glu
            500                 505                 510

Ile Asn Asp Leu Leu Thr Thr Leu Ile Ser Lys Phe Asp Asn Ile Lys
        515                 520                 525

Glu Phe Leu Lys Ile Met Lys Ser Ser Ala Val Asp Val Glu Cys Glu
    530                 535                 540

Leu Thr Ala Gly Tyr Lys Leu Phe Asn Asp Ser Gln Arg Ile Thr Asn
545                 550                 555                 560

Glu Leu Phe Ile Val Lys Asn Ile Ala Ser Met Arg Lys Pro Ala Ala
                565                 570                 575

Ser Ala Lys Leu Thr Met Phe Arg Asp Ala Leu Thr Ile Leu Gly Ile
            580                 585                 590

Asp Asp Lys Ile Thr Asp Asp Arg Ile Ser Glu Ile Leu Lys Leu Lys
```

```
                595                 600                 605
Glu Lys Gly Lys Gly Ile His Gly Leu Arg Asn Phe Ile Thr Asn Asn
610                 615                 620

Val Ile Glu Ser Ser Arg Phe Val Tyr Leu Ile Lys Tyr Ala Asn Ala
625                 630                 635                 640

Gln Lys Ile Arg Glu Val Ala Lys Asn Glu Lys Val Val Met Phe Val
                645                 650                 655

Leu Gly Gly Ile Pro Asp Thr Gln Ile Glu Arg Tyr Tyr Lys Ser Cys
                660                 665                 670

Val Glu Phe Pro Asp Met Asn Ser Ser Leu Gly Val Lys Arg Ser Glu
            675                 680                 685

Leu Ala Arg Met Ile Lys Asn Ile Ser Phe Asp Asp Phe Lys Asn Val
690                 695                 700

Lys Gln Gln Ala Lys Gly Arg Glu Asn Val Ala Lys Glu Arg Ala Lys
705                 710                 715                 720

Ala Val Ile Gly Leu Tyr Leu Thr Val Met Tyr Leu Leu Val Lys Asn
                725                 730                 735

Leu Val Asn Val Asn Ala Arg Tyr Val Ile Ala Ile His Cys Leu Glu
            740                 745                 750

Arg Asp Phe Gly Leu Tyr Lys Glu Ile Ile Pro Glu Leu Ala Ser Lys
            755                 760                 765

Asn Leu Lys Asn Asp Tyr Arg Ile Leu Ser Gln Thr Leu Cys Glu Leu
770                 775                 780

Cys Asp Lys Ser Pro Asn Leu Phe Leu Lys Lys Asn Glu Arg Leu Arg
785                 790                 795                 800

Lys Cys Val Glu Val Asp Ile Asn Asn Ala Asp Ser Ser Met Thr Arg
                805                 810                 815

Lys Tyr Arg Asn Cys Ile Ala His Leu Thr Val Val Arg Glu Leu Lys
            820                 825                 830

Glu Tyr Ile Gly Asp Ile Cys Thr Val Asp Ser Tyr Phe Ser Ile Tyr
            835                 840                 845

His Tyr Val Met Gln Arg Cys Ile Thr Lys Arg Glu Asn Asp Thr Lys
850                 855                 860

Gln Glu Glu Lys Ile Lys Tyr Glu Asp Asp Leu Leu Lys Asn His Gly
865                 870                 875                 880

Tyr Thr Lys Asp Phe Val Lys Ala Leu Asn Ser Pro Phe Gly Tyr Asn
                885                 890                 895

Ile Pro Arg Phe Lys Asn Leu Ser Ile Glu Gln Leu Phe Asp Arg Asn
            900                 905                 910

Glu Tyr Leu Thr Glu Lys
        915

<210> SEQ ID NO 36
<211> LENGTH: 944
<212> TYPE: PRT
<213> ORGANISM: Ruminococcus albus
<220> FEATURE:
<221> NAME/KEY: misc_feature
<223> OTHER INFORMATION: WP_074833651_RapMmc2

<400> SEQUENCE: 36

Met Ala Lys Lys Ser Lys Gly Met Ser Leu Arg Glu Lys Arg Glu Leu
1               5                   10                  15

Glu Lys Gln Lys Arg Ile Gln Lys Ala Ala Val Asn Ser Val Asn Asp
            20                  25                  30
```

```
Thr Pro Glu Lys Thr Glu Ala Asn Val Val Ser Val Asn Val Arg
        35                  40                  45

Thr Ser Ala Glu Asn Lys His Ser Lys Lys Ser Ala Ala Lys Ala Leu
 50                  55                  60

Gly Leu Lys Ser Gly Leu Val Ile Gly Asp Glu Leu Tyr Leu Thr Ser
 65                  70                  75                  80

Phe Gly Arg Gly Asn Glu Ala Lys Leu Glu Lys Lys Ile Ser Gly Asp
                 85                  90                  95

Thr Val Glu Lys Leu Gly Ile Gly Ala Phe Glu Val Ala Glu Arg Asp
            100                 105                 110

Glu Ser Thr Leu Thr Leu Glu Ser Gly Arg Ile Lys Asp Lys Thr Ala
            115                 120                 125

Arg Pro Lys Asp Pro Arg His Ile Thr Val Asp Thr Gln Gly Lys Phe
130                 135                 140

Lys Glu Asp Met Leu Gly Ile Arg Ser Val Leu Glu Lys Lys Ile Phe
145                 150                 155                 160

Gly Lys Thr Phe Asp Asp Asn Ile His Val Gln Leu Ala Tyr Asn Ile
                165                 170                 175

Leu Asp Val Glu Lys Ile Met Ala Gln Tyr Val Ser Asp Ile Val Tyr
            180                 185                 190

Met Leu His Asn Thr Asp Lys Thr Glu Arg Asn Asp Asn Leu Met Gly
            195                 200                 205

Tyr Met Ser Ile Arg Asn Thr Tyr Lys Thr Phe Cys Asp Thr Ser Asn
            210                 215                 220

Leu Pro Asp Asp Thr Lys Gln Lys Val Glu Asn Gln Lys Arg Glu Phe
225                 230                 235                 240

Asp Lys Ile Ile Lys Ser Gly Arg Leu Gly Tyr Phe Gly Glu Ala Phe
                245                 250                 255

Met Val Asn Ser Gly Asn Ser Thr Lys Leu Arg Pro Glu Lys Glu Ile
            260                 265                 270

Tyr His Ile Phe Ala Leu Met Ala Ser Leu Arg Gln Ser Tyr Phe His
            275                 280                 285

Gly Tyr Val Lys Asp Thr Asp Tyr Gln Gly Thr Thr Trp Ala Tyr Thr
            290                 295                 300

Leu Glu Asp Lys Leu Lys Gly Pro Ser His Glu Phe Arg Glu Thr Ile
305                 310                 315                 320

Asp Lys Ile Phe Asp Glu Gly Phe Ser Lys Ile Ser Lys Asp Phe Gly
                325                 330                 335

Lys Met Asn Lys Val Asn Leu Gln Ile Leu Glu Gln Met Ile Gly Glu
            340                 345                 350

Leu Tyr Gly Ser Ile Glu Arg Gln Asn Leu Thr Cys Asp Tyr Tyr Asp
            355                 360                 365

Phe Ile Gln Leu Lys Lys His Lys Tyr Leu Gly Phe Ser Ile Lys Arg
            370                 375                 380

Leu Arg Glu Thr Met Leu Glu Thr Thr Pro Ala Glu Cys Tyr Lys Ala
385                 390                 395                 400

Glu Cys Tyr Asn Ser Glu Arg Gln Lys Leu Tyr Lys Leu Ile Asp Phe
                405                 410                 415

Leu Ile Tyr Asp Leu Tyr Tyr Asn Arg Lys Pro Ala Arg Ile Glu Glu
            420                 425                 430

Ile Val Asp Lys Leu Arg Glu Ser Val Asn Asp Glu Glu Lys Glu Ser
            435                 440                 445

Ile Tyr Ser Val Glu Ala Lys Tyr Val Tyr Glu Ser Leu Ser Lys Val
```

```
                    450                 455                 460

Leu Asp Lys Ser Leu Lys Asn Ser Val Ser Gly Glu Thr Ile Lys Asp
465                 470                 475                 480

Leu Gln Lys Arg Tyr Asp Asp Glu Thr Ala Asn Arg Ile Trp Asp Ile
                    485                 490                 495

Ser Gln His Ser Ile Ser Gly Asn Val Asn Cys Phe Cys Lys Leu Ile
                500                 505                 510

Tyr Ile Met Thr Leu Met Leu Asp Gly Lys Glu Ile Asn Asp Leu Leu
                515                 520                 525

Thr Thr Leu Val Asn Lys Phe Asp Asn Ile Ala Ser Phe Ile Asp Val
                530                 535                 540

Met Asp Glu Leu Gly Leu Glu His Ser Phe Thr Asp Asn Tyr Lys Met
545                 550                 555                 560

Phe Ala Asp Ser Lys Ala Ile Cys Leu Asp Leu Gln Phe Ile Asn Ser
                565                 570                 575

Phe Ala Arg Met Ser Lys Ile Asp Asp Glu Lys Ser Lys Arg Gln Leu
                580                 585                 590

Phe Arg Asp Ala Leu Val Ile Leu Asp Ile Gly Asn Lys Asp Glu Thr
                595                 600                 605

Trp Ile Asn Asn Tyr Leu Asp Ser Asp Ile Phe Lys Leu Asp Lys Glu
                610                 615                 620

Gly Asn Lys Leu Lys Gly Ala Arg His Asp Phe Arg Asn Phe Ile Ala
625                 630                 635                 640

Asn Asn Val Ile Lys Ser Ser Arg Phe Lys Tyr Leu Val Lys Tyr Ser
                645                 650                 655

Ser Ala Asp Gly Met Ile Lys Leu Lys Thr Asn Glu Lys Leu Ile Gly
                660                 665                 670

Phe Val Leu Asp Lys Leu Pro Glu Thr Gln Ile Asp Arg Tyr Tyr Glu
                675                 680                 685

Ser Cys Gly Leu Asp Asn Ala Val Val Asp Lys Lys Val Arg Ile Glu
                690                 695                 700

Lys Leu Ser Gly Leu Ile Arg Asp Met Lys Phe Asp Asp Phe Ser Gly
705                 710                 715                 720

Val Lys Thr Ser Asn Lys Ala Gly Asp Asn Asp Lys Gln Asp Lys Ala
                725                 730                 735

Lys Tyr Gln Ala Ile Ile Ser Leu Tyr Leu Met Val Leu Tyr Gln Ile
                740                 745                 750

Val Lys Asn Met Ile Tyr Val Asn Ser Arg Tyr Val Ile Ala Phe His
                755                 760                 765

Cys Leu Glu Arg Asp Phe Gly Met Tyr Gly Lys Asp Phe Gly Lys Tyr
                770                 775                 780

Tyr Gln Gly Cys Arg Lys Leu Thr Asp His Phe Ile Glu Glu Lys Tyr
785                 790                 795                 800

Met Lys Glu Gly Lys Leu Gly Cys Asn Lys Val Gly Arg Tyr Leu
                805                 810                 815

Lys Asn Asn Ile Ser Cys Cys Thr Asp Gly Leu Ile Asn Thr Tyr Arg
                820                 825                 830

Asn Gln Val Asp His Phe Ala Val Arg Lys Ile Gly Asn Tyr Ala
                835                 840                 845

Ala Tyr Ile Lys Ser Ile Gly Ser Trp Phe Glu Leu Tyr His Tyr Val
                850                 855                 860

Ile Gln Arg Ile Val Phe Asp Glu Tyr Arg Phe Ala Leu Asn Asn Thr
865                 870                 875                 880
```

```
Glu Ser Asn Tyr Lys Asn Ser Ile Ile Lys His His Thr Tyr Cys Lys
            885                 890                 895

Asp Met Val Lys Ala Leu Asn Thr Pro Phe Gly Tyr Asp Leu Pro Arg
            900                 905                 910

Tyr Lys Asn Leu Ser Ile Gly Asp Leu Phe Asp Arg Asn Asn Tyr Leu
            915                 920                 925

Asn Lys Thr Lys Glu Ser Ile Asp Ala Asn Ser Ser Ile Asp Ser Gln
            930                 935                 940

<210> SEQ ID NO 37
<211> LENGTH: 967
<212> TYPE: PRT
<213> ORGANISM: Ruminococcus flavefaciens
<220> FEATURE:
<221> NAME/KEY: misc_feature
<223> OTHER INFORMATION: WP_075424065_Rfp2Mmc2

<400> SEQUENCE: 37

Met Ile Glu Lys Lys Ser Phe Ala Lys Gly Met Gly Val Lys Ser
1               5                   10                  15

Thr Leu Val Ser Gly Ser Lys Val Tyr Met Thr Thr Phe Ala Glu Gly
            20                  25                  30

Ser Asp Ala Arg Leu Glu Lys Ile Val Glu Gly Asp Ser Ile Arg Ser
            35                  40                  45

Val Asn Glu Gly Glu Ala Phe Ser Ala Glu Met Ala Asp Lys Asn Ala
        50                  55                  60

Gly Tyr Lys Ile Gly Asn Ala Lys Phe Ser His Pro Lys Gly Tyr Ala
65                  70                  75                  80

Val Val Ala Asn Asn Pro Leu Tyr Thr Gly Pro Val Gln Gln Asp Met
            85                  90                  95

Leu Gly Leu Lys Glu Thr Leu Glu Lys Arg Tyr Phe Gly Glu Ser Ala
            100                 105                 110

Asp Gly Asn Asp Asn Ile Cys Ile Gln Val Ile His Asn Ile Leu Asp
            115                 120                 125

Ile Glu Lys Ile Leu Ala Glu Tyr Ile Thr Asn Ala Ala Tyr Ala Val
            130                 135                 140

Asn Asn Ile Ser Gly Leu Asp Lys Asp Ile Ile Gly Phe Gly Lys Phe
145                 150                 155                 160

Ser Thr Val Tyr Thr Tyr Asp Glu Phe Lys Asp Pro Glu His His Arg
            165                 170                 175

Ala Ala Phe Asn Asn Asn Asp Lys Leu Ile Asn Ala Ile Lys Ala Gln
            180                 185                 190

Tyr Asp Glu Phe Asp Asn Phe Leu Asp Asn Pro Arg Leu Gly Tyr Phe
            195                 200                 205

Gly Gln Ala Phe Phe Ser Lys Glu Gly Arg Asn Tyr Ile Ile Asn Tyr
            210                 215                 220

Gly Asn Glu Cys Tyr Asp Ile Leu Ala Leu Ser Gly Leu Arg His
225                 230                 235                 240

Trp Val Val His Asn Asn Glu Glu Ser Arg Ile Ser Arg Thr Trp
            245                 250                 255

Leu Tyr Asn Leu Asp Lys Asn Leu Asp Asn Glu Tyr Ile Ser Thr Leu
            260                 265                 270

Asn Tyr Leu Tyr Asp Arg Ile Thr Asn Glu Leu Thr Asn Ser Phe Ser
            275                 280                 285

Lys Asn Ser Ala Ala Asn Val Asn Tyr Ile Ala Glu Thr Leu Gly Ile
```

```
            290                 295                 300
Asn Pro Ala Glu Phe Ala Glu Gln Tyr Phe Arg Phe Ser Ile Met Lys
305                 310                 315                 320

Glu Gln Lys Asn Leu Gly Phe Asn Ile Thr Lys Leu Arg Glu Val Met
                325                 330                 335

Leu Asp Arg Lys Asp Met Ser Glu Ile Arg Lys Asn His Lys Val Phe
                340                 345                 350

Asp Ser Ile Arg Thr Lys Val Tyr Thr Met Met Asp Phe Val Ile Tyr
                355                 360                 365

Arg Tyr Tyr Ile Glu Glu Asp Ala Lys Val Ala Ala Asn Lys Ser
    370                 375                 380

Leu Pro Asp Asn Glu Lys Ser Leu Ser Glu Lys Asp Ile Phe Val Ile
385                 390                 395                 400

Asn Leu Arg Gly Ser Phe Asn Asp Asp Gln Lys Asp Ala Leu Tyr Tyr
                405                 410                 415

Asp Glu Ala Asn Arg Ile Trp Arg Lys Leu Glu Asn Ile Met His Asn
                420                 425                 430

Ile Lys Glu Phe Arg Gly Asn Lys Thr Arg Glu Tyr Lys Lys Lys Asp
    435                 440                 445

Ala Pro Arg Leu Pro Arg Ile Leu Pro Ala Gly Arg Asp Val Ser Ala
    450                 455                 460

Phe Ser Lys Leu Met Tyr Ala Leu Thr Met Phe Leu Asp Gly Lys Glu
465                 470                 475                 480

Ile Asn Asp Leu Leu Thr Thr Leu Ile Asn Lys Phe Asp Asn Ile Gln
                485                 490                 495

Ser Phe Leu Lys Val Met Pro Leu Ile Gly Val Asn Ala Lys Phe Val
                500                 505                 510

Glu Glu Tyr Ala Phe Phe Lys Asp Ser Ala Lys Ile Ala Asp Glu Leu
            515                 520                 525

Arg Leu Ile Lys Ser Phe Ala Arg Met Gly Glu Pro Ile Ala Asp Ala
    530                 535                 540

Arg Arg Ala Met Tyr Ile Asp Ala Ile Arg Ile Leu Gly Thr Asn Leu
545                 550                 555                 560

Ser Tyr Asp Glu Leu Lys Ala Leu Ala Asp Thr Phe Ser Leu Asp Glu
                565                 570                 575

Asn Gly Asn Lys Leu Lys Lys Gly Lys His Gly Met Arg Asn Phe Ile
                580                 585                 590

Ile Asn Asn Val Ile Ser Asn Lys Arg Phe His Tyr Leu Ile Arg Tyr
            595                 600                 605

Gly Asp Pro Ala His Leu His Glu Ile Ala Lys Asn Glu Ala Val Val
    610                 615                 620

Lys Phe Val Leu Gly Arg Ile Ala Asp Ile Gln Lys Gln Gly Gln
625                 630                 635                 640

Asn Gly Lys Asn Gln Ile Asp Arg Tyr Tyr Glu Thr Cys Ile Gly Lys
                645                 650                 655

Asp Lys Gly Lys Ser Val Ser Glu Lys Val Asp Ala Leu Thr Lys Ile
                660                 665                 670

Ile Thr Gly Met Asn Tyr Asp Gln Phe Asp Lys Arg Ser Val Ile
    675                 680                 685

Glu Asp Thr Gly Arg Glu Asn Ala Glu Arg Lys Phe Lys Lys Ile
    690                 695                 700

Ile Ser Leu Tyr Leu Thr Val Ile Tyr His Ile Leu Lys Asn Ile Val
705                 710                 715                 720
```

```
Asn Ile Asn Ala Arg Tyr Val Ile Gly Phe His Cys Val Glu Arg Asp
                725                 730                 735

Ala Gln Leu Tyr Lys Glu Lys Gly Tyr Asp Ile Asn Leu Lys Lys Leu
            740                 745                 750

Glu Glu Lys Gly Phe Ser Ser Val Thr Lys Leu Cys Ala Gly Ile Asp
        755                 760                 765

Glu Thr Ala Pro Asp Lys Arg Lys Asp Val Glu Lys Glu Met Ala Glu
    770                 775                 780

Arg Ala Lys Glu Ser Ile Asp Ser Leu Glu Ser Ala Asn Pro Lys Leu
785                 790                 795                 800

Tyr Ala Asn Tyr Ile Lys Tyr Ser Asp Glu Lys Lys Ala Glu Glu Phe
                805                 810                 815

Thr Arg Gln Ile Asn Arg Glu Lys Ala Lys Thr Ala Leu Asn Ala Tyr
            820                 825                 830

Leu Arg Asn Thr Lys Trp Asn Val Ile Arg Glu Asp Leu Leu Arg
        835                 840                 845

Ile Asp Asn Lys Thr Cys Thr Leu Phe Arg Asn Lys Ala Val His Leu
    850                 855                 860

Glu Val Ala Arg Tyr Val His Ala Tyr Ile Asn Asp Ile Ala Glu Val
865                 870                 875                 880

Asn Ser Tyr Phe Gln Leu Tyr His Tyr Ile Met Gln Arg Ile Ile Met
                885                 890                 895

Asn Glu Arg Tyr Glu Lys Ser Ser Gly Lys Val Ser Glu Tyr Phe Asp
            900                 905                 910

Ala Val Asn Asp Glu Lys Lys Tyr Asn Asp Arg Leu Leu Lys Leu Leu
        915                 920                 925

Cys Val Pro Phe Gly Tyr Cys Ile Pro Arg Phe Lys Asn Leu Ser Ile
    930                 935                 940

Glu Ala Leu Phe Asp Arg Asn Glu Ala Ala Lys Phe Asp Lys Glu Lys
945                 950                 955                 960

Lys Lys Val Ser Gly Asn Ser
                965

<210> SEQ ID NO 38
<211> LENGTH: 7
<212> TYPE: PRT
<213> ORGANISM: Artificial Sequence
<220> FEATURE:
<223> OTHER INFORMATION: Synthetic

<400> SEQUENCE: 38

Pro Lys Lys Lys Arg Lys Val
1               5

<210> SEQ ID NO 39
<211> LENGTH: 16
<212> TYPE: PRT
<213> ORGANISM: Artificial Sequence
<220> FEATURE:
<223> OTHER INFORMATION: Synthetic

<400> SEQUENCE: 39

Lys Arg Pro Ala Ala Thr Lys Lys Ala Gly Gln Ala Lys Lys Lys Lys
1               5                   10                  15

<210> SEQ ID NO 40
<211> LENGTH: 9
<212> TYPE: PRT
```

```
<213> ORGANISM: Artificial Sequence
<220> FEATURE:
<223> OTHER INFORMATION: Synthetic

<400> SEQUENCE: 40

Pro Ala Ala Lys Arg Val Lys Leu Asp
1               5

<210> SEQ ID NO 41
<211> LENGTH: 11
<212> TYPE: PRT
<213> ORGANISM: Artificial Sequence
<220> FEATURE:
<223> OTHER INFORMATION: Synthetic

<400> SEQUENCE: 41

Arg Gln Arg Arg Asn Glu Leu Lys Arg Ser Pro
1               5                   10

<210> SEQ ID NO 42
<211> LENGTH: 38
<212> TYPE: PRT
<213> ORGANISM: Artificial Sequence
<220> FEATURE:
<223> OTHER INFORMATION: Synthetic

<400> SEQUENCE: 42

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
            20                  25                  30

Arg Asn Gln Gly Gly Tyr
        35

<210> SEQ ID NO 43
<211> LENGTH: 42
<212> TYPE: PRT
<213> ORGANISM: Artificial Sequence
<220> FEATURE:
<223> OTHER INFORMATION: Synthetic

<400> SEQUENCE: 43

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40

<210> SEQ ID NO 44
<211> LENGTH: 8
<212> TYPE: PRT
<213> ORGANISM: Artificial Sequence
<220> FEATURE:
<223> OTHER INFORMATION: Synthetic

<400> SEQUENCE: 44

Val Ser Arg Lys Arg Pro Arg Pro
1               5

<210> SEQ ID NO 45
<211> LENGTH: 8
<212> TYPE: PRT
<213> ORGANISM: Artificial Sequence
<220> FEATURE:
```

<223> OTHER INFORMATION: Synthetic

<400> SEQUENCE: 45

Pro Pro Lys Lys Ala Arg Glu Asp
1               5

<210> SEQ ID NO 46
<211> LENGTH: 8
<212> TYPE: PRT
<213> ORGANISM: Artificial Sequence
<220> FEATURE:
<223> OTHER INFORMATION: Synthetic

<400> SEQUENCE: 46

Pro Gln Pro Lys Lys Lys Pro Leu
1               5

<210> SEQ ID NO 47
<211> LENGTH: 12
<212> TYPE: PRT
<213> ORGANISM: Artificial Sequence
<220> FEATURE:
<223> OTHER INFORMATION: Synthetic

<400> SEQUENCE: 47

Ser Ala Leu Ile Lys Lys Lys Lys Lys Met Ala Pro
1               5                   10

<210> SEQ ID NO 48
<211> LENGTH: 5
<212> TYPE: PRT
<213> ORGANISM: Artificial Sequence
<220> FEATURE:
<223> OTHER INFORMATION: Synthetic

<400> SEQUENCE: 48

Asp Arg Leu Arg Arg
1               5

<210> SEQ ID NO 49
<211> LENGTH: 7
<212> TYPE: PRT
<213> ORGANISM: Artificial Sequence
<220> FEATURE:
<223> OTHER INFORMATION: Synthetic

<400> SEQUENCE: 49

Pro Lys Gln Lys Lys Arg Lys
1               5

<210> SEQ ID NO 50
<211> LENGTH: 10
<212> TYPE: PRT
<213> ORGANISM: Artificial Sequence
<220> FEATURE:
<223> OTHER INFORMATION: Synthetic

<400> SEQUENCE: 50

Arg Lys Leu Lys Lys Lys Ile Lys Lys Leu
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Synthetic

<400> SEQUENCE: 51

Arg Glu Lys Lys Lys Phe Leu Lys Arg Arg
1               5                   10

<210> SEQ ID NO 52
<211> LENGTH: 20
<212> TYPE: PRT
<213> ORGANISM: Artificial Sequence
<220> FEATURE:
<223> OTHER INFORMATION: Synthetic

<400> SEQUENCE: 52

Lys Arg Lys Gly Asp Glu Val Asp Gly Val Asp Glu Val Ala Lys Lys
1               5                   10                  15

Lys Ser Lys Lys
            20

<210> SEQ ID NO 53
<211> LENGTH: 17
<212> TYPE: PRT
<213> ORGANISM: Artificial Sequence
<220> FEATURE:
<223> OTHER INFORMATION: Synthetic

<400> SEQUENCE: 53

Arg Lys Cys Leu Gln Ala Gly Met Asn Leu Glu Ala Arg Lys Thr Lys
1               5                   10                  15

Lys

<210> SEQ ID NO 54
<211> LENGTH: 54
<212> TYPE: DNA
<213> ORGANISM: Eubacterium siraeum
<220> FEATURE:
<221> NAME/KEY: misc_feature
<223> OTHER INFORMATION: Es4Mmc2 (v267)

<400> SEQUENCE: 54
cacccgtgca aaaatgcagg ggtctaaaac tttcagagcg tcgagcagga agcc         54

<210> SEQ ID NO 55
<211> LENGTH: 54
<212> TYPE: DNA
<213> ORGANISM: Eubacterium siraeum
<220> FEATURE:
<221> NAME/KEY: misc_feature
<223> OTHER INFORMATION: Es4Mmc2 (v267)

<400> SEQUENCE: 55
cacccgtgca aaaatgcagg ggtctaaaac ttctgcgtca tggtgatgtc gacc         54

<210> SEQ ID NO 56
<211> LENGTH: 53
<212> TYPE: DNA
<213> ORGANISM: Eubacterium siraeum
<220> FEATURE:
<221> NAME/KEY: misc_feature
<223> OTHER INFORMATION: Es4Mmc2 (v267)

<400> SEQUENCE: 56
cacccgtgca aaaatgcagg ggtctaaaac agtgttttta tttcttgcaa cgg          53

<210> SEQ ID NO 57
<211> LENGTH: 54

-continued

<212> TYPE: DNA
<213> ORGANISM: Eubacterium siraeum
<220> FEATURE:
<221> NAME/KEY: misc_feature
<223> OTHER INFORMATION: Es5Mmc2 (v268)

<400> SEQUENCE: 57
cacccgtgta aaattactcg ggtctaaaac tttcagagcg tcgagcagga agcc        54

<210> SEQ ID NO 58
<211> LENGTH: 54
<212> TYPE: DNA
<213> ORGANISM: Eubacterium siraeum
<220> FEATURE:
<221> NAME/KEY: misc_feature
<223> OTHER INFORMATION: Es5Mmc2 (v268)

<400> SEQUENCE: 58
cacccgtgta aaattactcg ggtctaaaac ttctgcgtca tggtgatgtc gacc        54

<210> SEQ ID NO 59
<211> LENGTH: 53
<212> TYPE: DNA
<213> ORGANISM: Eubacterium siraeum
<220> FEATURE:
<221> NAME/KEY: misc_feature
<223> OTHER INFORMATION: Es5Mmc2 (v268)

<400> SEQUENCE: 59
cacccgtgta aaattactcg ggtctaaaac agtgttttta tttcttgcaa cgg         53

<210> SEQ ID NO 60
<211> LENGTH: 54
<212> TYPE: DNA
<213> ORGANISM: Eubacterium siraeum
<220> FEATURE:
<221> NAME/KEY: misc_feature
<223> OTHER INFORMATION: EupMmc2 (v324)

<400> SEQUENCE: 60
cacccgtgca aaatgcagg ggtctaaaac tttcagagcg tcgagcagga agcc         54

<210> SEQ ID NO 61
<211> LENGTH: 54
<212> TYPE: DNA
<213> ORGANISM: Eubacterium siraeum

<400> SEQUENCE: 61
cacccgtgca aaatgcagg ggtctaaaac ttctgcgtca tggtgatgtc gacc         54

<210> SEQ ID NO 62
<211> LENGTH: 53
<212> TYPE: DNA
<213> ORGANISM: Eubacterium siraeum

<400> SEQUENCE: 62
cacccgtgca aaatgcagg ggtctaaaac agtgttttta tttcttgcaa cgg          53

<210> SEQ ID NO 63
<211> LENGTH: 683
<212> TYPE: DNA
<213> ORGANISM: Nannochloropsis gaditana
<220> FEATURE:
<221> NAME/KEY: misc_feature
<223> OTHER INFORMATION: EMRE2EUKT373295 Nitrite Reductase Promoter

<400> SEQUENCE: 63

```
ctggtgtcgt caacagccag ctgccacaag aaagtgaaca tgcgtctatt tatgacgtca      60
ttcatcaacc accccgtttc caaacaccgt cccacgcgct gttgagagat gatttttga      120 atgccatatg gtgctcaaac atgtgcatcg acgctgtcgc acaagcagga gcgggcttgc     180
ccactcgttc ttgttaacgg cttgattcaa aatccccgcc cggaacaaaa tatgccggag    240
cgatccaacg aagcaaaagt caaccagagc ctctctttcc gtccaacacc cgtgttggtg     300
ccatgttaac aatagattca tgcatggata ggcgaagacg tgagaagtta cggagtttgg     360
gtcatgcttg cgtacatcac tcaaccctt tccccaaaaa aaatcccgc catgcgattg      420 ccttcgttgc accgcaaaac ggaaattagt tatggcgtca ttgctcaaga ttactgtttt     480
tcgacaaggt gctgcacaac cttggaagaa aactctgcaa atccgtcaat cacatgagtt    540 gtagttttt tcggcaaggc gggtgagcgt agtgaattat attccttgta aggcaaagcg    600
gatactaatt ttcacgtagt tgccctgacc tcctatgctc ggaaacgccg ccgtactgcc    660
ccacccgaac tcagatcacc agt                                              683

<210> SEQ ID NO 64
<400> SEQUENCE: 64

000

<210> SEQ ID NO 65
<211> LENGTH: 163
<212> TYPE: DNA
<213> ORGANISM: Nannochloropsis gaditana
<220> FEATURE:
<221> NAME/KEY: misc_feature
<223> OTHER INFORMATION: SRP54-full guide RNA sequence

<400> SEQUENCE: 65
cgactactga tgagtccgtg aggacgaaac gagtaagctc gtctaacccc taccaactgg      60
tcggggtttg aaaccctgc ggcaaggatg ttgctcaggc cggcatggtc ccagcctcct     120
cgctggcgcc ggctgggcaa catgcttcgg catggcgaat ggg                        163

<210> SEQ ID NO 66
<211> LENGTH: 163
<212> TYPE: DNA
<213> ORGANISM: Nannochloropsis gaditana
<220> FEATURE:
<221> NAME/KEY: misc_feature
<223> OTHER INFORMATION: Nitrate reductase-full guide RNA sequence

<400> SEQUENCE: 66
cgactactga tgagtccgtg aggacgaaac gagtaagctc gtctaacccc taccaactgg      60
tcggggtttg aaacgtaatg gtagaaggat tgggagggc cggcatggtc ccagcctcct     120
cgctggcgcc ggctgggcaa catgcttcgg catggcgaat ggg                        163

<210> SEQ ID NO 67
<211> LENGTH: 69
<212> TYPE: DNA
<213> ORGANISM: Eubacterium siraeum

<400> SEQUENCE: 67
gaactacacc cgtgcaaaat tgcaggggtc taaaacttcg gcatgagccc gtacactttc      60
cttaagaga                                                              69
```

```
<210> SEQ ID NO 68
<211> LENGTH: 68
<212> TYPE: DNA
<213> ORGANISM: Eubacterium siraeum

<400> SEQUENCE: 68
gaactacacc cgtgcagaat tgcaggggtc taaaacctgt tgaactccag gcttcctgat    60
ataggaga                                                            68

<210> SEQ ID NO 69
<211> LENGTH: 51
<212> TYPE: DNA
<213> ORGANISM: Artificial Sequence
<220> FEATURE:
<223> OTHER INFORMATION: Synthetic

<400> SEQUENCE: 69
cacccgtgca aaattgcagg ggtctaaaac ttcggcatga gaaagtacac t             51

<210> SEQ ID NO 70
<211> LENGTH: 54
<212> TYPE: DNA
<213> ORGANISM: Artificial Sequence
<220> FEATURE:
<223> OTHER INFORMATION: Synthetic

<400> SEQUENCE: 70
cacccgtgca gaatgcaggg gtctaaaacc tgttgaactc caggcttcct gata          54

<210> SEQ ID NO 71
<211> LENGTH: 54
<212> TYPE: DNA
<213> ORGANISM: Artificial Sequence
<220> FEATURE:
<223> OTHER INFORMATION: Synthetic

<400> SEQUENCE: 71
cacccgtgca aaattgcagg ggtctaaaac ttcggcatga gaaagtacac tttc          54

<210> SEQ ID NO 72
<211> LENGTH: 54
<212> TYPE: DNA
<213> ORGANISM: Artificial Sequence
<220> FEATURE:
<223> OTHER INFORMATION: Synthetic

<400> SEQUENCE: 72
cacccgtgca gaatgcaggg gtctaaaacc tgttgaactc caggcttcct gata          54

<210> SEQ ID NO 73
<211> LENGTH: 53
<212> TYPE: DNA
<213> ORGANISM: Artificial Sequence
<220> FEATURE:
<223> OTHER INFORMATION: Synthetic

<400> SEQUENCE: 73
cacccgtgca aaattgcagg ggtctaaaac ttcggcatga gaaagtacac ttt           53

<210> SEQ ID NO 74
<211> LENGTH: 54
<212> TYPE: DNA
<213> ORGANISM: Artificial Sequence
<220> FEATURE:
<223> OTHER INFORMATION: Synthetic
```

<400> SEQUENCE: 74
cacccgtgca gaatgcaggg gtctaaaacc tgttgaactc caggcttcct gata      54

<210> SEQ ID NO 75
<211> LENGTH: 50
<212> TYPE: DNA
<213> ORGANISM: Artificial Sequence
<220> FEATURE:
<223> OTHER INFORMATION: Synthetic

<400> SEQUENCE: 75
cacccgtgca aaattgcagg ggtctaaaac ttcggcatga gaaagtacac            50

<210> SEQ ID NO 76
<211> LENGTH: 54
<212> TYPE: DNA
<213> ORGANISM: Artificial Sequence
<220> FEATURE:
<223> OTHER INFORMATION: Synthetic

<400> SEQUENCE: 76
cacccgtgca gaatgcaggg gtctaaaacc tgttgaactc caggcttcct gata      54

<210> SEQ ID NO 77
<211> LENGTH: 52
<212> TYPE: DNA
<213> ORGANISM: Artificial Sequence
<220> FEATURE:
<223> OTHER INFORMATION: Synthetic

<400> SEQUENCE: 77
cacccgtgca aaattgcagg ggtctaaaac ttcggcatga gaaagtacac tt        52

<210> SEQ ID NO 78
<211> LENGTH: 54
<212> TYPE: DNA
<213> ORGANISM: Artificial Sequence
<220> FEATURE:
<223> OTHER INFORMATION: Synthetic

<400> SEQUENCE: 78
cacccgtgca gaatgcaggg gtctaaaacc tgttgaactc caggcttcct gata      54

<210> SEQ ID NO 79
<211> LENGTH: 53
<212> TYPE: DNA
<213> ORGANISM: Artificial Sequence
<220> FEATURE:
<223> OTHER INFORMATION: Synthetic

<400> SEQUENCE: 79
cacccgtgca aaattgcagg ggtctaaaac ttcggcatga gaaagtacac ttt       53

<210> SEQ ID NO 80
<211> LENGTH: 54
<212> TYPE: DNA
<213> ORGANISM: Artificial Sequence
<220> FEATURE:
<223> OTHER INFORMATION: Synthetic

<400> SEQUENCE: 80
cacccgtgca gaatgcaggg gtctaaaacc tgttgaactc caggcttcct gata      54

<210> SEQ ID NO 81
<211> LENGTH: 53

```
<212> TYPE: DNA
<213> ORGANISM: Artificial Sequence
<220> FEATURE:
<223> OTHER INFORMATION: Synthetic

<400> SEQUENCE: 81
cacccgtgca aaattgcagg ggtctaaaac ttcggcatga gaaagtacac ttt        53

<210> SEQ ID NO 82
<211> LENGTH: 54
<212> TYPE: DNA
<213> ORGANISM: Artificial Sequence
<220> FEATURE:
<223> OTHER INFORMATION: Synthetic

<400> SEQUENCE: 82
cacccgtgca gaatgcaggg gtctaaaacc tgttgaactc caggcttcct gata        54

<210> SEQ ID NO 83
<211> LENGTH: 51
<212> TYPE: DNA
<213> ORGANISM: Artificial Sequence
<220> FEATURE:
<223> OTHER INFORMATION: Synthetic

<400> SEQUENCE: 83
cacccgtgca aaattgcagg ggtctaaaac ttcggcatga gaaagtacac t          51

<210> SEQ ID NO 84
<211> LENGTH: 54
<212> TYPE: DNA
<213> ORGANISM: Artificial Sequence
<220> FEATURE:
<223> OTHER INFORMATION: Synthetic

<400> SEQUENCE: 84
cacccgtgca gaatgcaggg gtctaaaacc tgttgaactc caggcttcct gata        54

<210> SEQ ID NO 85
<211> LENGTH: 52
<212> TYPE: DNA
<213> ORGANISM: Artificial Sequence
<220> FEATURE:
<223> OTHER INFORMATION: Synthetic

<400> SEQUENCE: 85
cacccgtgca aaattgcagg ggtctaaaac ttcggcatga gaaagtacac tt         52

<210> SEQ ID NO 86
<211> LENGTH: 54
<212> TYPE: DNA
<213> ORGANISM: Artificial Sequence
<220> FEATURE:
<223> OTHER INFORMATION: Synthetic

<400> SEQUENCE: 86
cacccgtgca gaatgcaggg gtctaaaacc tgttgaactc caggcttcct gata        54

<210> SEQ ID NO 87
<211> LENGTH: 52
<212> TYPE: DNA
<213> ORGANISM: Artificial Sequence
<220> FEATURE:
<223> OTHER INFORMATION: Synthetic

<400> SEQUENCE: 87
```
cacccgtgca aaattgcagg ggtctaaaac ttcggcatga gaaagtacac tt                52

<210> SEQ ID NO 88
<211> LENGTH: 54
<212> TYPE: DNA
<213> ORGANISM: Artificial Sequence
<220> FEATURE:
<223> OTHER INFORMATION: Synthetic

<400> SEQUENCE: 88
cacccgtgca gaatgcaggg gtctaaaacc tgttgaactc caggcttcct gata           54

<210> SEQ ID NO 89
<211> LENGTH: 52
<212> TYPE: DNA
<213> ORGANISM: Artificial Sequence
<220> FEATURE:
<223> OTHER INFORMATION: Synthetic

<400> SEQUENCE: 89
cacccgtgca aaattgcagg ggtctaaaac ttcggcatga gaaagtacac tt                52

<210> SEQ ID NO 90
<211> LENGTH: 54
<212> TYPE: DNA
<213> ORGANISM: Artificial Sequence
<220> FEATURE:
<223> OTHER INFORMATION: Synthetic

<400> SEQUENCE: 90
cacccgtgca gaatgcaggg gtctaaaacc tgttgaactc caggcttcct gata           54

<210> SEQ ID NO 91
<211> LENGTH: 51
<212> TYPE: DNA
<213> ORGANISM: Artificial Sequence
<220> FEATURE:
<223> OTHER INFORMATION: Synthetic

<400> SEQUENCE: 91
cacccgtgca aaattgcagg ggtctaaaac ttcggcatga gaaagtacac t                 51

<210> SEQ ID NO 92
<211> LENGTH: 54
<212> TYPE: DNA
<213> ORGANISM: Artificial Sequence
<220> FEATURE:
<223> OTHER INFORMATION: Synthetic

<400> SEQUENCE: 92
cacccgtgca gaatgcaggg gtctaaaacc tgttgaactc caggcttcct gata           54

<210> SEQ ID NO 93
<211> LENGTH: 57
<212> TYPE: DNA
<213> ORGANISM: Artificial Sequence
<220> FEATURE:
<223> OTHER INFORMATION: Synthetic

<400> SEQUENCE: 93
cacccgtgca aaattgcagg ggtctaaaac ttcggcatga gaaagtacac tttccta        57

<210> SEQ ID NO 94
<211> LENGTH: 54
<212> TYPE: DNA
<213> ORGANISM: Artificial Sequence -continued
<220> FEATURE:
<223> OTHER INFORMATION: Synthetic

<400> SEQUENCE: 94
cacccgtgca gaatgcaggg gtctaaaacc tgttgaactc caggcttcct gata      54

<210> SEQ ID NO 95
<211> LENGTH: 51
<212> TYPE: DNA
<213> ORGANISM: Artificial Sequence
<220> FEATURE:
<223> OTHER INFORMATION: Synthetic

<400> SEQUENCE: 95
cacccgtgca aaattgcagg ggtctaaaac ttcggcatga gaaagtacac t         51

<210> SEQ ID NO 96
<211> LENGTH: 54
<212> TYPE: DNA
<213> ORGANISM: Artificial Sequence
<220> FEATURE:
<223> OTHER INFORMATION: Synthetic

<400> SEQUENCE: 96
cacccgtgca gaatgcaggg gtctaaaacc tgttgaactc caggcttcct gata      54

<210> SEQ ID NO 97
<211> LENGTH: 52
<212> TYPE: DNA
<213> ORGANISM: Artificial Sequence
<220> FEATURE:
<223> OTHER INFORMATION: Synthetic

<400> SEQUENCE: 97
cacccgtgca aaattgcagg ggtctaaaac ttcggcatga gaaagtacac tt        52

<210> SEQ ID NO 98
<211> LENGTH: 53
<212> TYPE: DNA
<213> ORGANISM: Artificial Sequence
<220> FEATURE:
<223> OTHER INFORMATION: Synthetic

<400> SEQUENCE: 98
cacccgtgca gaatgcaggg gtctaaaacc tgttgaactc caggcttcct gat       53

<210> SEQ ID NO 99
<211> LENGTH: 52
<212> TYPE: DNA
<213> ORGANISM: Artificial Sequence
<220> FEATURE:
<223> OTHER INFORMATION: Synthetic

<400> SEQUENCE: 99
cacccgtgca aaattgcagg ggtctaaaac ttcggcatga gaaagtacac tt        52

<210> SEQ ID NO 100
<211> LENGTH: 53
<212> TYPE: DNA
<213> ORGANISM: Artificial Sequence
<220> FEATURE:
<223> OTHER INFORMATION: Synthetic

<400> SEQUENCE: 100
cacccgtgca gaatgcaggg gtctaaaacc tgttgaactc caggcttcct gat       53

<210> SEQ ID NO 101
<211> LENGTH: 53
<212> TYPE: DNA
<213> ORGANISM: Artificial Sequence
<220> FEATURE:
<223> OTHER INFORMATION: Synthetic

<400> SEQUENCE: 101
cacccgtgca aaattgcagg ggtctaaaac ttcggcatga gaaagtacac ttt            53

<210> SEQ ID NO 102
<211> LENGTH: 54
<212> TYPE: DNA
<213> ORGANISM: Artificial Sequence
<220> FEATURE:
<223> OTHER INFORMATION: Synthetic

<400> SEQUENCE: 102
cacccgtgca gaatgcaggg gtctaaaacc tgttgaactc caggcttcct gata           54

<210> SEQ ID NO 103
<211> LENGTH: 55
<212> TYPE: DNA
<213> ORGANISM: Artificial Sequence
<220> FEATURE:
<223> OTHER INFORMATION: Synthetic

<400> SEQUENCE: 103
cacccgtgca aaattgcagg ggtctaaaac ttcggcatga gaaagtacac tttcc          55

<210> SEQ ID NO 104
<211> LENGTH: 54
<212> TYPE: DNA
<213> ORGANISM: Artificial Sequence
<220> FEATURE:
<223> OTHER INFORMATION: Synthetic

<400> SEQUENCE: 104
cacccgtgca gaatgcaggg gtctaaaacc tgttgaactc caggcttcct gata           54

<210> SEQ ID NO 105
<211> LENGTH: 51
<212> TYPE: DNA
<213> ORGANISM: Artificial Sequence
<220> FEATURE:
<223> OTHER INFORMATION: Synthetic

<400> SEQUENCE: 105
cacccgtgca aaattgcagg ggtctaaaac ttcggcatga gaaagtacac c              51

<210> SEQ ID NO 106
<211> LENGTH: 54
<212> TYPE: DNA
<213> ORGANISM: Artificial Sequence
<220> FEATURE:
<223> OTHER INFORMATION: Synthetic

<400> SEQUENCE: 106
cacccgtgca gaatgcaggg gtctaaaacc tgttgaactc caggcttcct gata           54

<210> SEQ ID NO 107
<211> LENGTH: 53
<212> TYPE: DNA
<213> ORGANISM: Artificial Sequence
<220> FEATURE:
<223> OTHER INFORMATION: Synthetic

```
<400> SEQUENCE: 107
cacccgtgca aaattgcagg ggtctaaaac ttcggcatga gaaagtacac ttt        53

<210> SEQ ID NO 108
<211> LENGTH: 54
<212> TYPE: DNA
<213> ORGANISM: Artificial Sequence
<220> FEATURE:
<223> OTHER INFORMATION: Synthetic

<400> SEQUENCE: 108
cacccgtgca gaatgcaggg gtctaaaacc tgttgaactc caggcttcct gata       54

<210> SEQ ID NO 109
<211> LENGTH: 53
<212> TYPE: DNA
<213> ORGANISM: Artificial Sequence
<220> FEATURE:
<223> OTHER INFORMATION: Synthetic

<400> SEQUENCE: 109
cacccgtgca aaattgcagg ggtctaaaac ttcggcatga gaaagtacac ttt        53

<210> SEQ ID NO 110
<211> LENGTH: 54
<212> TYPE: DNA
<213> ORGANISM: Artificial Sequence
<220> FEATURE:
<223> OTHER INFORMATION: Synthetic

<400> SEQUENCE: 110
cacccgtgca gaatgcaggg gtctaaaacc tgttgaactc caggcttcct gata       54

<210> SEQ ID NO 111
<211> LENGTH: 53
<212> TYPE: DNA
<213> ORGANISM: Artificial Sequence
<220> FEATURE:
<223> OTHER INFORMATION: Synthetic

<400> SEQUENCE: 111
cacccgtgca aaattgcagg ggtctaaaac ttcggcatga gaaagtacac ttc        53

<210> SEQ ID NO 112
<211> LENGTH: 54
<212> TYPE: DNA
<213> ORGANISM: Artificial Sequence
<220> FEATURE:
<223> OTHER INFORMATION: Synthetic

<400> SEQUENCE: 112
cacccgtgca gaatgcaggg gtctaaaacc tgttgaactc caggcttcct gata       54

<210> SEQ ID NO 113
<211> LENGTH: 55
<212> TYPE: DNA
<213> ORGANISM: Artificial Sequence
<220> FEATURE:
<223> OTHER INFORMATION: Synthetic

<400> SEQUENCE: 113
cacccgtgca aaattgcagg ggtctaaaac ttcggcatga gaaagtacac tttcc      55

<210> SEQ ID NO 114
```

```
<211> LENGTH: 54
<212> TYPE: DNA
<213> ORGANISM: Artificial Sequence
<220> FEATURE:
<223> OTHER INFORMATION: Synthetic

<400> SEQUENCE: 114
cacccgtgca gaatgcaggg gtctaaaacc tgttgaactc caggcttcct gata          54

<210> SEQ ID NO 115
<211> LENGTH: 51
<212> TYPE: DNA
<213> ORGANISM: Artificial Sequence
<220> FEATURE:
<223> OTHER INFORMATION: Synthetic

<400> SEQUENCE: 115
cacccgtgca aaattgcagg ggtctaaaac ttcggcatga gaaagtacac t             51

<210> SEQ ID NO 116
<211> LENGTH: 54
<212> TYPE: DNA
<213> ORGANISM: Artificial Sequence
<220> FEATURE:
<223> OTHER INFORMATION: Synthetic

<400> SEQUENCE: 116
cacccgtgca gaatgcaggg gtctaaaacc tgttgaactc caggcttcct gata          54

<210> SEQ ID NO 117
<211> LENGTH: 53
<212> TYPE: DNA
<213> ORGANISM: Artificial Sequence
<220> FEATURE:
<223> OTHER INFORMATION: Synthetic

<400> SEQUENCE: 117
cacccgtgca aaattgcagg ggtctaaaac ttcggcatga gaaagtacac ttt           53

<210> SEQ ID NO 118
<211> LENGTH: 54
<212> TYPE: DNA
<213> ORGANISM: Artificial Sequence
<220> FEATURE:
<223> OTHER INFORMATION: Synthetic

<400> SEQUENCE: 118
cacccgtgca gaatgcaggg gtctaaaacc tgttgaactc caggcttcct gata          54

<210> SEQ ID NO 119
<211> LENGTH: 56
<212> TYPE: DNA
<213> ORGANISM: Artificial Sequence
<220> FEATURE:
<223> OTHER INFORMATION: Synthetic

<400> SEQUENCE: 119
cacccgtgca aaattgcagg ggtctaaaac ttcggcatga gaaagtacac tttccg        56

<210> SEQ ID NO 120
<211> LENGTH: 54
<212> TYPE: DNA
<213> ORGANISM: Artificial Sequence
<220> FEATURE:
<223> OTHER INFORMATION: Synthetic

<400> SEQUENCE: 120
```
cacccgtgca gaatgcaggg gtctaaaacc tgttgaactc caggcttcct gata        54

<210> SEQ ID NO 121
<211> LENGTH: 51
<212> TYPE: DNA
<213> ORGANISM: Artificial Sequence
<220> FEATURE:
<223> OTHER INFORMATION: Synthetic

<400> SEQUENCE: 121
cacccgtgca aaattgcagg ggtctaaaac ttcggcatga gaaagtacac t           51

<210> SEQ ID NO 122
<211> LENGTH: 54
<212> TYPE: DNA
<213> ORGANISM: Artificial Sequence
<220> FEATURE:
<223> OTHER INFORMATION: Synthetic

<400> SEQUENCE: 122
cacccgtgca gaatgcaggg gtctaaaacc tgttgaactc caggcttcct gata        54

<210> SEQ ID NO 123
<211> LENGTH: 53
<212> TYPE: DNA
<213> ORGANISM: Artificial Sequence
<220> FEATURE:
<223> OTHER INFORMATION: Synthetic

<400> SEQUENCE: 123
cacccgtgca aaattgcagg ggtctaaaac ttcggcatga gaaagtacac ttt         53

<210> SEQ ID NO 124
<211> LENGTH: 192
<212> TYPE: DNA
<213> ORGANISM: Artificial Sequence
<220> FEATURE:
<223> OTHER INFORMATION: Synthetic

<400> SEQUENCE: 124
ttgacagcta gctcagtcct aggtataatg ctagcgctga gaactacacc cgtgtaaaat    60
tactcgggtc taaaacagtg tttttatttc ttgcaacggc actacggaac tacacccgtg   120
taaaattact cgggtctaaa acccgggaaa attatcaact tgaaaagtgg caccgagtcg   180 gtgcttttttt tt                                                      192

<210> SEQ ID NO 125
<211> LENGTH: 51
<212> TYPE: DNA
<213> ORGANISM: Artificial Sequence
<220> FEATURE:
<223> OTHER INFORMATION: Synthetic

<400> SEQUENCE: 125
cacccgtgta aaattactcg ggtctaaaac agtgttttta tttcttgcaa c           51

<210> SEQ ID NO 126
<211> LENGTH: 51
<212> TYPE: DNA
<213> ORGANISM: Artificial Sequence
<220> FEATURE:
<223> OTHER INFORMATION: Synthetic

<400> SEQUENCE: 126
cacccgtgta aaattactcg ggtctaaaac ccgggaaaat tatcaacttg a         51

<210> SEQ ID NO 127
<211> LENGTH: 51
<212> TYPE: DNA
<213> ORGANISM: Artificial Sequence
<220> FEATURE:
<223> OTHER INFORMATION: Synthetic

<400> SEQUENCE: 127
cacccgtgta aaattactcg ggtctaaaac agtgttttta tttcttgcaa t         51

<210> SEQ ID NO 128
<211> LENGTH: 51
<212> TYPE: DNA
<213> ORGANISM: Artificial Sequence
<220> FEATURE:
<223> OTHER INFORMATION: Synthetic

<400> SEQUENCE: 128
cacccgtgta aaattactcg ggtctaaaac ccgggaaaat tatcaacttg a         51

<210> SEQ ID NO 129
<211> LENGTH: 51
<212> TYPE: DNA
<213> ORGANISM: Artificial Sequence
<220> FEATURE:
<223> OTHER INFORMATION: Synthetic

<400> SEQUENCE: 129
cacccgtgta aaattactcg ggtctaaaac agtgttttta tttcttgcaa c         51

<210> SEQ ID NO 130
<211> LENGTH: 51
<212> TYPE: DNA
<213> ORGANISM: Artificial Sequence
<220> FEATURE:
<223> OTHER INFORMATION: Synthetic

<400> SEQUENCE: 130
cacccgtgta aaattactcg ggtctaaaac ccgggaaaat tatcaacttg a         51

<210> SEQ ID NO 131
<211> LENGTH: 51
<212> TYPE: DNA
<213> ORGANISM: Artificial Sequence
<220> FEATURE:
<223> OTHER INFORMATION: Synthetic

<400> SEQUENCE: 131
cacccgtgta aaattactcg ggtctaaaac agtgttttta tttcttgcaa c         51

<210> SEQ ID NO 132
<211> LENGTH: 51
<212> TYPE: DNA
<213> ORGANISM: Artificial Sequence
<220> FEATURE:
<223> OTHER INFORMATION: Synthetic

<400> SEQUENCE: 132
cacccgtgta aaattactcg ggtctaaaac ccgggaaaat tatcaacttg a         51

<210> SEQ ID NO 133
<211> LENGTH: 51
<212> TYPE: DNA
<213> ORGANISM: Artificial Sequence

```
<220> FEATURE:
<223> OTHER INFORMATION: Synthetic

<400> SEQUENCE: 133
cacccgtgta aaattactcg ggtctaaaac agtgttttta tttcttgcaa c        51

<210> SEQ ID NO 134
<211> LENGTH: 51
<212> TYPE: DNA
<213> ORGANISM: Artificial Sequence
<220> FEATURE:
<223> OTHER INFORMATION: Synthetic

<400> SEQUENCE: 134
cacccgtgta aaattactcg ggtctaaaac ccgggaaaat tatcaacttg a        51

<210> SEQ ID NO 135
<211> LENGTH: 51
<212> TYPE: DNA
<213> ORGANISM: Artificial Sequence
<220> FEATURE:
<223> OTHER INFORMATION: Synthetic

<400> SEQUENCE: 135
cacccgtgta aaattactcg ggtctaaaac agtgttttta tttcttgcaa c        51

<210> SEQ ID NO 136
<211> LENGTH: 51
<212> TYPE: DNA
<213> ORGANISM: Artificial Sequence
<220> FEATURE:
<223> OTHER INFORMATION: Synthetic

<400> SEQUENCE: 136
cacccgtgta aaattactcg ggtctaaaac ccgggaaaat tatcaacttg a        51

<210> SEQ ID NO 137
<211> LENGTH: 51
<212> TYPE: DNA
<213> ORGANISM: Artificial Sequence
<220> FEATURE:
<223> OTHER INFORMATION: Synthetic

<400> SEQUENCE: 137
cacccgtgta aaattactcg ggtctaaaac agtgttttta tttcttgcaa c        51

<210> SEQ ID NO 138
<211> LENGTH: 51
<212> TYPE: DNA
<213> ORGANISM: Artificial Sequence
<220> FEATURE:
<223> OTHER INFORMATION: Synthetic

<400> SEQUENCE: 138
cacccgtgta aaattactcg ggtctaaaac ccgggaaaat tatcaacttg a        51

<210> SEQ ID NO 139
<211> LENGTH: 51
<212> TYPE: DNA
<213> ORGANISM: Artificial Sequence
<220> FEATURE:
<223> OTHER INFORMATION: Synthetic

<400> SEQUENCE: 139
cacccgtgta aaattactcg ggtctaaaac agtgttttta tttcttgcaa c        51
```

<210> SEQ ID NO 140
<211> LENGTH: 51
<212> TYPE: DNA
<213> ORGANISM: Artificial Sequence
<220> FEATURE:
<223> OTHER INFORMATION: Synthetic

<400> SEQUENCE: 140
cacccgtgta aaattactcg ggtctaaaac ccgggaaaat tatcaacttg a        51

<210> SEQ ID NO 141
<211> LENGTH: 51
<212> TYPE: DNA
<213> ORGANISM: Artificial Sequence
<220> FEATURE:
<223> OTHER INFORMATION: Synthetic

<400> SEQUENCE: 141
cacccgtgta aaattactcg ggtctaaaac agtgttttta tttcttgcaa c        51

<210> SEQ ID NO 142
<211> LENGTH: 51
<212> TYPE: DNA
<213> ORGANISM: Artificial Sequence
<220> FEATURE:
<223> OTHER INFORMATION: Synthetic

<400> SEQUENCE: 142
cacccgtgta aaattactcg ggtctaaaac ccgggaaaat tatcaacttg a        51

<210> SEQ ID NO 143
<211> LENGTH: 51
<212> TYPE: DNA
<213> ORGANISM: Artificial Sequence
<220> FEATURE:
<223> OTHER INFORMATION: Synthetic

<400> SEQUENCE: 143
cacccgtgta aaattactcg ggtctaaaac agtgttttta tttcttgcaa t        51

<210> SEQ ID NO 144
<211> LENGTH: 51
<212> TYPE: DNA
<213> ORGANISM: Artificial Sequence
<220> FEATURE:
<223> OTHER INFORMATION: Synthetic

<400> SEQUENCE: 144
cacccgtgta aaattactcg ggtctaaaac ccgggaaaat tatcaacttg a        51

<210> SEQ ID NO 145
<211> LENGTH: 51
<212> TYPE: DNA
<213> ORGANISM: Artificial Sequence
<220> FEATURE:
<223> OTHER INFORMATION: Synthetic

<400> SEQUENCE: 145
cacccgtgta aaattactcg ggtctaaaac agtgttttta tttcttgcaa c        51

<210> SEQ ID NO 146
<211> LENGTH: 51
<212> TYPE: DNA
<213> ORGANISM: Artificial Sequence
<220> FEATURE:
<223> OTHER INFORMATION: Synthetic

<400> SEQUENCE: 146
cacccgtgta aaattactcg ggtctaaaac ccgggaaaat tatcaacttg a          51

<210> SEQ ID NO 147
<211> LENGTH: 51
<212> TYPE: DNA
<213> ORGANISM: Artificial Sequence
<220> FEATURE:
<223> OTHER INFORMATION: Synthetic

<400> SEQUENCE: 147
cacccgtgta aaattactcg ggtctaaaac agtgttttta tttcttgcaa c          51

<210> SEQ ID NO 148
<211> LENGTH: 51
<212> TYPE: DNA
<213> ORGANISM: Artificial Sequence
<220> FEATURE:
<223> OTHER INFORMATION: Synthetic

<400> SEQUENCE: 148
cacccgtgta aaattactcg ggtctaaaac ccgggaaaat tatcaacttg a          51

<210> SEQ ID NO 149
<211> LENGTH: 51
<212> TYPE: DNA
<213> ORGANISM: Artificial Sequence
<220> FEATURE:
<223> OTHER INFORMATION: Synthetic

<400> SEQUENCE: 149
cacccgtgta aaattactcg ggtctaaaac agtgttttta tttcttgcaa c          51

<210> SEQ ID NO 150
<211> LENGTH: 51
<212> TYPE: DNA
<213> ORGANISM: Artificial Sequence
<220> FEATURE:
<223> OTHER INFORMATION: Synthetic

<400> SEQUENCE: 150
cacccgtgta aaattactcg ggtctaaaac ccgggaaaat tatcaacttg a          51

<210> SEQ ID NO 151
<211> LENGTH: 51
<212> TYPE: DNA
<213> ORGANISM: Artificial Sequence
<220> FEATURE:
<223> OTHER INFORMATION: Synthetic

<400> SEQUENCE: 151
cacccgtgta aaattactcg ggtctaaaac agtgttttta tttcttgcaa c          51

<210> SEQ ID NO 152
<211> LENGTH: 51
<212> TYPE: DNA
<213> ORGANISM: Artificial Sequence
<220> FEATURE:
<223> OTHER INFORMATION: Synthetic

<400> SEQUENCE: 152
cacccgtgta aaattactcg ggtctaaaac ccgggaaaat tatcaacttg a          51

<210> SEQ ID NO 153

```
<211> LENGTH: 51
<212> TYPE: DNA
<213> ORGANISM: Artificial Sequence
<220> FEATURE:
<223> OTHER INFORMATION: Synthetic

<400> SEQUENCE: 153
cacccgtgta aaattactcg ggtctaaaac agtgttttta tttcttgcaa c          51

<210> SEQ ID NO 154
<211> LENGTH: 51
<212> TYPE: DNA
<213> ORGANISM: Artificial Sequence
<220> FEATURE:
<223> OTHER INFORMATION: Synthetic

<400> SEQUENCE: 154
cacccgtgta aaattactcg ggtctaaaac ccgggaaaat tatcaacttg a          51

<210> SEQ ID NO 155
<211> LENGTH: 51
<212> TYPE: DNA
<213> ORGANISM: Artificial Sequence
<220> FEATURE:
<223> OTHER INFORMATION: Synthetic

<400> SEQUENCE: 155
cacccgtgta aaattactcg ggtctaaaac agtgttttta tttcttgcaa c          51

<210> SEQ ID NO 156
<211> LENGTH: 51
<212> TYPE: DNA
<213> ORGANISM: Artificial Sequence
<220> FEATURE:
<223> OTHER INFORMATION: Synthetic

<400> SEQUENCE: 156
cacccgtgta aaattactcg ggtctaaaac ccgggaaaat tatcaacttg a          51

<210> SEQ ID NO 157
<211> LENGTH: 51
<212> TYPE: DNA
<213> ORGANISM: Artificial Sequence
<220> FEATURE:
<223> OTHER INFORMATION: Synthetic

<400> SEQUENCE: 157
cacccgtgta aaattactcg ggtctaaaac agtgttttta tttcttgcaa c          51

<210> SEQ ID NO 158
<211> LENGTH: 51
<212> TYPE: DNA
<213> ORGANISM: Artificial Sequence
<220> FEATURE:
<223> OTHER INFORMATION: Synthetic

<400> SEQUENCE: 158
cacccgtgta aaattactcg ggtctaaaac ccgggaaaat tatcaacttg a          51

<210> SEQ ID NO 159
<211> LENGTH: 51
<212> TYPE: DNA
<213> ORGANISM: Artificial Sequence
<220> FEATURE:
<223> OTHER INFORMATION: Synthetic

<400> SEQUENCE: 159
```
cacccgtgta aaattactcg ggtctaaaac agtgttttta tttcttgcaa c        51

<210> SEQ ID NO 160
<211> LENGTH: 51
<212> TYPE: DNA
<213> ORGANISM: Artificial Sequence
<220> FEATURE:
<223> OTHER INFORMATION: Synthetic

<400> SEQUENCE: 160
cacccgtgta aaattactcg ggtctaaaac ccgggaaaat tatcaacttg a        51

<210> SEQ ID NO 161
<211> LENGTH: 51
<212> TYPE: DNA
<213> ORGANISM: Artificial Sequence
<220> FEATURE:
<223> OTHER INFORMATION: Synthetic

<400> SEQUENCE: 161
cacccgtgta aaattactcg ggtctaaaac agtgttttta tttcttgcaa c        51

<210> SEQ ID NO 162
<211> LENGTH: 51
<212> TYPE: DNA
<213> ORGANISM: Artificial Sequence
<220> FEATURE:
<223> OTHER INFORMATION: Synthetic

<400> SEQUENCE: 162
cacccgtgta aaattactcg ggtctaaaac ccgggaaaat tatcaacttg a        51

<210> SEQ ID NO 163
<211> LENGTH: 51
<212> TYPE: DNA
<213> ORGANISM: Artificial Sequence
<220> FEATURE:
<223> OTHER INFORMATION: Synthetic

<400> SEQUENCE: 163
cacccgtgta aaattactcg ggtctaaaac agtgttttta tttcttgcaa c        51

<210> SEQ ID NO 164
<211> LENGTH: 51
<212> TYPE: DNA
<213> ORGANISM: Artificial Sequence
<220> FEATURE:
<223> OTHER INFORMATION: Synthetic

<400> SEQUENCE: 164
cacccgtgta aaattactcg ggtctaaaac ccgggaaaat tatcaacttg a        51

<210> SEQ ID NO 165
<211> LENGTH: 51
<212> TYPE: DNA
<213> ORGANISM: Artificial Sequence
<220> FEATURE:
<223> OTHER INFORMATION: Synthetic

<400> SEQUENCE: 165
cacccgtgta aaattactcg ggtctaaaac agtgttttta tttcttgcaa c        51

<210> SEQ ID NO 166
<211> LENGTH: 51
<212> TYPE: DNA

```
<213> ORGANISM: Artificial Sequence
<220> FEATURE:
<223> OTHER INFORMATION: Synthetic

<400> SEQUENCE: 166
cacccgtgta aaattactcg ggtctaaaac ccgggaaaat tatcaacttg a          51

<210> SEQ ID NO 167
<211> LENGTH: 51
<212> TYPE: DNA
<213> ORGANISM: Artificial Sequence
<220> FEATURE:
<223> OTHER INFORMATION: Synthetic

<400> SEQUENCE: 167
cacccgtgta aaattactcg ggtctaaaac agtgttttta tttcttgcaa c          51

<210> SEQ ID NO 168
<211> LENGTH: 51
<212> TYPE: DNA
<213> ORGANISM: Artificial Sequence
<220> FEATURE:
<223> OTHER INFORMATION: Synthetic

<400> SEQUENCE: 168
cacccgtgta aaattactcg ggtctaaaac ccgggaaaat tatcaacttg a          51

<210> SEQ ID NO 169
<211> LENGTH: 51
<212> TYPE: DNA
<213> ORGANISM: Artificial Sequence
<220> FEATURE:
<223> OTHER INFORMATION: Synthetic

<400> SEQUENCE: 169
cacccgtgta aaattactcg ggtctaaaac agtgttttta tttcttgcaa c          51

<210> SEQ ID NO 170
<211> LENGTH: 51
<212> TYPE: DNA
<213> ORGANISM: Artificial Sequence
<220> FEATURE:
<223> OTHER INFORMATION: Synthetic

<400> SEQUENCE: 170
cacccgtgta aaattactcg ggtctaaaac ccgggaaaat tatcaacttg a          51

<210> SEQ ID NO 171
<211> LENGTH: 51
<212> TYPE: DNA
<213> ORGANISM: Artificial Sequence
<220> FEATURE:
<223> OTHER INFORMATION: Synthetic

<400> SEQUENCE: 171
cacccgtgta aaattactcg ggtctaaaac agtgttttta tttcttgcaa c          51

<210> SEQ ID NO 172
<211> LENGTH: 51
<212> TYPE: DNA
<213> ORGANISM: Artificial Sequence
<220> FEATURE:
<223> OTHER INFORMATION: Synthetic

<400> SEQUENCE: 172
cacccgtgta aaattactcg ggtctaaaac ccgggaaaat tatcaacttg a          51
```

<210> SEQ ID NO 173
<211> LENGTH: 51
<212> TYPE: DNA
<213> ORGANISM: Artificial Sequence
<220> FEATURE:
<223> OTHER INFORMATION: Synthetic

<400> SEQUENCE: 173
cacccgtgta aaattactcg ggtctaaaac agtgttttta tttcttgcaa c          51

<210> SEQ ID NO 174
<211> LENGTH: 51
<212> TYPE: DNA
<213> ORGANISM: Artificial Sequence
<220> FEATURE:
<223> OTHER INFORMATION: Synthetic

<400> SEQUENCE: 174
cacccgtgta aaattactcg ggtctaaaac ccgggaaaat tatcaacttg a          51

<210> SEQ ID NO 175
<211> LENGTH: 36
<212> TYPE: RNA
<213> ORGANISM: Artificial Sequence
<220> FEATURE:
<223> OTHER INFORMATION: Synthetic

<400> SEQUENCE: 175
gwacuacacc ccugcaaauu ugcagggguc uaaaac                            36

<210> SEQ ID NO 176
<211> LENGTH: 36
<212> TYPE: RNA
<213> ORGANISM: Eubacterium siraeum

<400> SEQUENCE: 176
aaacuacacc cuugcaguuc ugcaaggguc ugaaac                            36

<210> SEQ ID NO 177
<211> LENGTH: 36
<212> TYPE: RNA
<213> ORGANISM: Eubacterium siraeum

<400> SEQUENCE: 177
guacuacacc ccugggauuu cacaggqguc ugaaac                            36

<210> SEQ ID NO 178
<211> LENGTH: 36
<212> TYPE: RNA
<213> ORGANISM: Eubacterium siraeum

<400> SEQUENCE: 178
gaacuacacc cgugcaaaaa ugcagggguc uaaaac                            36

<210> SEQ ID NO 179
<211> LENGTH: 36
<212> TYPE: RNA
<213> ORGANISM: Eubacterium siraeum

<400> SEQUENCE: 179
gaacuacacc cgugcaaaau ugcagggguc uaaaac                            36

<210> SEQ ID NO 180

```
<211> LENGTH: 36
<212> TYPE: RNA
<213> ORGANISM: Eubacterium siraeum

<400> SEQUENCE: 180
gaacuacacc cguguaaaau uacucggguc uaaaac                                    36

<210> SEQ ID NO 181
<211> LENGTH: 36
<212> TYPE: RNA
<213> ORGANISM: Eubacterium siraeum

<400> SEQUENCE: 181
gaacuacacc ccugcagaaa ugcuggguc ugaaac                                     36

<210> SEQ ID NO 182
<211> LENGTH: 36
<212> TYPE: RNA
<213> ORGANISM: Eubacterium siraeum

<400> SEQUENCE: 182
guacuacacc ccuguuaaau uacaggguc uaaaac                                     36

<210> SEQ ID NO 183
<211> LENGTH: 36
<212> TYPE: RNA
<213> ORGANISM: Ruminococcus flavefaciens

<400> SEQUENCE: 183
gaacuacacc ccuauaaauu uacaggguc uaaaac                                     36

<210> SEQ ID NO 184
<211> LENGTH: 36
<212> TYPE: RNA
<213> ORGANISM: Ruminococcus flavefaciens

<400> SEQUENCE: 184
gaacuacacc caugcuaaau aacaugguc uaaaac                                     36

<210> SEQ ID NO 185
<211> LENGTH: 36
<212> TYPE: RNA
<213> ORGANISM: Ruminococcus flavefaciens

<400> SEQUENCE: 185
ggacuaaacc ccucugaaaa uguggggguc ugaaac                                    36

<210> SEQ ID NO 186
<211> LENGTH: 36
<212> TYPE: RNA
<213> ORGANISM: Eubacterium siraeum

<400> SEQUENCE: 186
gcacuacacc ccccugaaac aggagggguc uaaaac                                    36

<210> SEQ ID NO 187
<211> LENGTH: 36
<212> TYPE: RNA
<213> ORGANISM: Eubacterium siraeum

<400> SEQUENCE: 187
guuuuacacc uguguaaauu caaagggguc uaaaac                                    36
```

```
<210> SEQ ID NO 188
<211> LENGTH: 36
<212> TYPE: RNA
<213> ORGANISM: Ruminococcus Sp.

<400> SEQUENCE: 188
cauuuggaac uguguaaaau uacagggguuc uaaaac                                    36

<210> SEQ ID NO 189
<211> LENGTH: 36
<212> TYPE: RNA
<213> ORGANISM: Ruminococcus Sp.

<400> SEQUENCE: 189
auuuuagaac uguguaaauu cgcaggguuc uaaaac                                     36

<210> SEQ ID NO 190
<211> LENGTH: 36
<212> TYPE: RNA
<213> ORGANISM: Ruminococcus Sp.

<400> SEQUENCE: 190
gaacuacaac ccugcuguag agcggggguuc ugaaac                                    36

<210> SEQ ID NO 191
<211> LENGTH: 36
<212> TYPE: RNA
<213> ORGANISM: Ruminococcus albus

<400> SEQUENCE: 191
cuacuauacu agugugauuu uacacuaguc uaaaac                                     36

<210> SEQ ID NO 192
<211> LENGTH: 36
<212> TYPE: RNA
<213> ORGANISM: Ruminococcus bicirculans

<400> SEQUENCE: 192
cuacuacacu ggugcgaauu ugcacuaguc uaaaac                                     36

<210> SEQ ID NO 193
<211> LENGTH: 36
<212> TYPE: RNA
<213> ORGANISM: Ruminococcus Sp.

<400> SEQUENCE: 193
cuacuacacu agugcgaauu ugcacuaguc uaaaac                                     36

<210> SEQ ID NO 194
<211> LENGTH: 36
<212> TYPE: RNA
<213> ORGANISM: Ruminococcus Sp.

<400> SEQUENCE: 194
cuacuacacu ggugcaaauu agcacuaguc uaaaac                                     36

<210> SEQ ID NO 195
<211> LENGTH: 36
<212> TYPE: RNA
<213> ORGANISM: Ruminococcus flavefaciens

<400> SEQUENCE: 195
gaacuauagu agugugaauu uacacuacuc uaaaac                                     36
```

<210> SEQ ID NO 196
<211> LENGTH: 36
<212> TYPE: RNA
<213> ORGANISM: Ruminococcus Sp.

<400> SEQUENCE: 196
acuugauacu ggguguuaaau uacacuaguc uaaaac                                    36

<210> SEQ ID NO 197
<211> LENGTH: 36
<212> TYPE: RNA
<213> ORGANISM: Ruminococcus Sp.

<400> SEQUENCE: 197
gaucagcacc cuuaccgauu cguauggguc uaagac                                    36

<210> SEQ ID NO 198
<211> LENGTH: 36
<212> TYPE: RNA
<213> ORGANISM: Ruminococcus Sp.

<400> SEQUENCE: 198
guacaacagc ccuacagauu cguagggguc ugagac                                    36

<210> SEQ ID NO 199
<211> LENGTH: 36
<212> TYPE: RNA
<213> ORGANISM: Ruminococcus flavefaciens

<400> SEQUENCE: 199
cauguaaacc ccuaacaaau gauaggggguu ugaaac                                    36

<210> SEQ ID NO 200
<211> LENGTH: 36
<212> TYPE: RNA
<213> ORGANISM: Ruminococcus flavefaciens

<400> SEQUENCE: 200
caaguaaacc ccuaccaacu ggucggggguu ugaaac                                    36

<210> SEQ ID NO 201
<211> LENGTH: 36
<212> TYPE: RNA
<213> ORGANISM: Ruminococcus flavefaciens

<400> SEQUENCE: 201
gauugaaagg auuguaaauu uacaaggucu uaaaac                                    36

<210> SEQ ID NO 202
<211> LENGTH: 36
<212> TYPE: RNA
<213> ORGANISM: Eubacterium siraeum

<400> SEQUENCE: 202
guauuaaacu acuacacccg aguaaggguc uaaaac                                    36

<210> SEQ ID NO 203
<211> LENGTH: 36
<212> TYPE: RNA
<213> ORGANISM: Eubacterium siraeum

<400> SEQUENCE: 203
auacaauuca acccgaauau aguaggguuc ucaaac                                    36

<210> SEQ ID NO 204
<211> LENGTH: 36
<212> TYPE: RNA
<213> ORGANISM: Ruminococcus Sp.

<400> SEQUENCE: 204
auuuuucacu accacuguuu uuagguggac uaaaac                                    36

<210> SEQ ID NO 205
<211> LENGTH: 36
<212> TYPE: RNA
<213> ORGANISM: Ruminococcus Sp.

<400> SEQUENCE: 205
auuuuucacu accaccgauu uuggguggac uaaaac                                    36

<210> SEQ ID NO 206
<211> LENGTH: 33
<212> TYPE: RNA
<213> ORGANISM: Eubacterium siraeum

<400> SEQUENCE: 206
acuacaacuc acgcacgccg ugaguauuaa aac                                       33

<210> SEQ ID NO 207
<211> LENGTH: 21
<212> TYPE: RNA
<213> ORGANISM: Clostridium aminophilum

<400> SEQUENCE: 207
guuuggagaa cagcccgaua u                                                    21

<210> SEQ ID NO 208
<211> LENGTH: 29
<212> TYPE: RNA
<213> ORGANISM: Eubacterium rectale

<400> SEQUENCE: 208
gugaauacag cucgauauag ugagcaaua                                            29

<210> SEQ ID NO 209
<211> LENGTH: 33
<212> TYPE: RNA
<213> ORGANISM: Herbinix hemicellulosilytica

<400> SEQUENCE: 209
gguaacaauc cccguagaca ggggaacugc aac                                       33

<210> SEQ ID NO 210
<211> LENGTH: 35
<212> TYPE: RNA
<213> ORGANISM: Lachnospiraceae bacterium NK4A179

<400> SEQUENCE: 210
gcuggagaag auagcccaag aaagagggca auaac                                     35

<210> SEQ ID NO 211
<211> LENGTH: 37
<212> TYPE: RNA
<213> ORGANISM: Leptotrichia buccalis

<400> SEQUENCE: 211
gauuuagacc accccaaaaa ugaaggggac uaaaaca                       37

<210> SEQ ID NO 212
<211> LENGTH: 36
<212> TYPE: RNA
<213> ORGANISM: Listeria newyorkensis

<400> SEQUENCE: 212
gauuuagagu accucaaaac aaaagaggac uaaaac                       36

<210> SEQ ID NO 213
<211> LENGTH: 36
<212> TYPE: RNA
<213> ORGANISM: Listeria seeligeri

<400> SEQUENCE: 213
guaagagacu accucuauau gaaagaggac uaaaac                       36

<210> SEQ ID NO 214
<211> LENGTH: 35
<212> TYPE: RNA
<213> ORGANISM: Leptotrichia shahii

<400> SEQUENCE: 214
auauagacca ccccaauauc gaaggggacu aaaac                        35

<210> SEQ ID NO 215
<211> LENGTH: 39
<212> TYPE: RNA
<213> ORGANISM: Leptotrichia wadei

<400> SEQUENCE: 215
ggauauagac caccccaaua ucgaagggga cuaaaacuu                    39

<210> SEQ ID NO 216
<211> LENGTH: 36
<212> TYPE: RNA
<213> ORGANISM: Paludibacter propionicigenes

<400> SEQUENCE: 216
cuugugaauu aucccaaaau ugaagggaac uacaac                       36

<210> SEQ ID NO 217
<211> LENGTH: 35
<212> TYPE: RNA
<213> ORGANISM: Rhodobacter capsulatus R121

<400> SEQUENCE: 217
gucacaucac cgccaagacg acggcggacu gaacc                        35

<210> SEQ ID NO 218
<211> LENGTH: 37
<212> TYPE: RNA
<213> ORGANISM: Riemerella anatipestifer

<400> SEQUENCE: 218
aguugggacu gcucucauuu ugaagggguau ucacaac                     37

<210> SEQ ID NO 219
<211> LENGTH: 36
<212> TYPE: RNA
<213> ORGANISM: Phaeodactylibacter xiamenensis

<400> SEQUENCE: 219
guccuaguca cuccucaaac cgggagccua ucggac                                    36

<210> SEQ ID NO 220
<211> LENGTH: 36
<212> TYPE: RNA
<213> ORGANISM: Psychroflexus torquis

<400> SEQUENCE: 220
guuguaacug cccuuauuuu gaaggguaaa cacagc                                    36

<210> SEQ ID NO 221
<211> LENGTH: 36
<212> TYPE: RNA
<213> ORGANISM: Prevotella sp. P5-125

<400> SEQUENCE: 221 guugug gaag guccaguuuu gaggggcuau uacaac                                   36

<210> SEQ ID NO 222
<211> LENGTH: 36
<212> TYPE: RNA
<213> ORGANISM: Prevotella sp. MA2016

<400> SEQUENCE: 222
guuguagaag cuuaucguuu ggauagguau gacaac                                    36

<210> SEQ ID NO 223
<211> LENGTH: 36
<212> TYPE: RNA
<213> ORGANISM: Porphyromonas gingivalis

<400> SEQUENCE: 223
guuggaucua cccucuauuc gaaggguaca cacaac                                    36

<210> SEQ ID NO 224
<211> LENGTH: 36
<212> TYPE: RNA
<213> ORGANISM: Prevotella saccharolytica

<400> SEQUENCE: 224
guugugucua ccuccuuuuu gagagguaaa aacagc                                    36

<210> SEQ ID NO 225
<211> LENGTH: 36
<212> TYPE: RNA
<213> ORGANISM: Prevotella buccae

<400> SEQUENCE: 225
guugcaucug ccuucuuuuu gaaagguaaa aacaac                                    36

<210> SEQ ID NO 226
<211> LENGTH: 36
<212> TYPE: RNA
<213> ORGANISM: Flavobacterium columnare

<400> SEQUENCE: 226
guugggaaag cccuuauuuu gaaggguauc uacaac                                    36

<210> SEQ ID NO 227
<211> LENGTH: 36
<212> TYPE: RNA
<213> ORGANISM: Flavobacterium branchiophilum

<400> SEQUENCE: 227
guuguaacug cccuuauuuu gaaggguaaa cacaac                                36

<210> SEQ ID NO 228
<211> LENGTH: 36
<212> TYPE: RNA
<213> ORGANISM: Capnocytophaga canimorsus

<400> SEQUENCE: 228
guuggaacug cucucauuuu ggaggguaau cacaac                                36

<210> SEQ ID NO 229
<211> LENGTH: 36
<212> TYPE: RNA
<213> ORGANISM: Bergeyella zoohelcum

<400> SEQUENCE: 229
guuggaacug cucucauuuu ggaggguaau cacaac                                36

<210> SEQ ID NO 230
<211> LENGTH: 36
<212> TYPE: RNA
<213> ORGANISM: Bacteroides pyogenes

<400> SEQUENCE: 230
guuguggaug ccacuaguuu gagugguaua gacaac                                36

<210> SEQ ID NO 231
<211> LENGTH: 36
<212> TYPE: RNA
<213> ORGANISM: Alistipes sp. ZOR0009

<400> SEQUENCE: 231
gcuguuauau cuuuaccuuu guaagggaag uacagc                                36

<210> SEQ ID NO 232
<211> LENGTH: 36
<212> TYPE: RNA
<213> ORGANISM: Fusobacterium perfoetens

<400> SEQUENCE: 232
gcuguuauau cuuuaccuuu guaagggaag uacagc                                36

<210> SEQ ID NO 233
<211> LENGTH: 30
<212> TYPE: RNA
<213> ORGANISM: Fusobacterium necrophorum

<400> SEQUENCE: 233
gacuaaaacc aaguaaauug guauuuaaac                                       30

<210> SEQ ID NO 234
<211> LENGTH: 30
<212> TYPE: RNA
<213> ORGANISM: Alistipes sp. ZOR0009

<400> SEQUENCE: 234
guuuuauucu caccuuagug aguauagucc                                       30

<210> SEQ ID NO 235
<211> LENGTH: 28
<212> TYPE: PRT
<213> ORGANISM: Unknown

```
<220> FEATURE:
<223> OTHER INFORMATION: Synthetic

<400> SEQUENCE: 235

Ala Gly Ser Leu Arg Gln Trp Ser Val His Asp Lys Gly Asn Ile Asn
1               5                   10                  15

Leu Tyr Arg Asn Asn Val Ala His Leu Lys Val Ile
            20                  25

<210> SEQ ID NO 236
<211> LENGTH: 28
<212> TYPE: PRT
<213> ORGANISM: Unknown
<220> FEATURE:
<223> OTHER INFORMATION: Synthetic

<400> SEQUENCE: 236

Ala Gly Ser Leu Arg Gln Trp Ser Val His Asn Glu Gly Asn Ile Asn
1               5                   10                  15

Leu Tyr Arg Asn Asn Val Ala His Leu Lys Val Ile
            20                  25

<210> SEQ ID NO 237
<211> LENGTH: 28
<212> TYPE: PRT
<213> ORGANISM: Unknown
<220> FEATURE:
<223> OTHER INFORMATION: Synthetic

<400> SEQUENCE: 237

Ala Gly Gln Leu Arg Gln Trp Cys Phe His Asp Ala Thr Tyr Val Gln
1               5                   10                  15

Asn Tyr Arg Asn Asn Val Ala His Leu Thr Ala Ile
            20                  25

<210> SEQ ID NO 238
<211> LENGTH: 28
<212> TYPE: PRT
<213> ORGANISM: Ruminococcus flavefaciens

<400> SEQUENCE: 238

Ala Gly Gln Leu Arg Gln Trp Ala Phe His Ser Ala Gly Asn Ile Thr
1               5                   10                  15

Lys Tyr Arg Asn Asn Val Ala His Lys Thr Ala Val
            20                  25

<210> SEQ ID NO 239
<211> LENGTH: 28
<212> TYPE: PRT
<213> ORGANISM: Bergeyella zoohelcum

<400> SEQUENCE: 239

Ile Gly Ser Leu Arg Gln Trp Ser Phe His Gly Asp Glu Lys Val Arg
1               5                   10                  15

Glu Phe Arg Asn Thr Ala Ala His Leu Asn Ala Ile
            20                  25

<210> SEQ ID NO 240
<211> LENGTH: 28
<212> TYPE: PRT
<213> ORGANISM: Unknown
<220> FEATURE:
<223> OTHER INFORMATION: Synthetic
```

-continued

```
<400> SEQUENCE: 240

Leu Ala Lys Leu Arg His Trp Cys Val His Ser Glu Lys Gly Val Thr
1               5                   10                  15

Glu Phe Arg Asn Thr Ala Ala His Leu Asn Ala Ile
            20                  25

<210> SEQ ID NO 241
<211> LENGTH: 28
<212> TYPE: PRT
<213> ORGANISM: Unknown
<220> FEATURE:
<223> OTHER INFORMATION: Synthetic

<400> SEQUENCE: 241

Ile Gly Lys Leu Arg His Trp Cys Val His Ser Glu Glu Gly Val Asn
1               5                   10                  15

Glu Phe Arg Asn Thr Val Cys His Leu Asn Ala Ile
            20                  25

<210> SEQ ID NO 242
<211> LENGTH: 28
<212> TYPE: PRT
<213> ORGANISM: Eubacterium siraeum

<400> SEQUENCE: 242

Ile Gly Lys Leu Arg His Trp Cys Val His Ser Glu Glu Gly Val Asn
1               5                   10                  15

Glu Phe Arg Asn Thr Val Cys His Leu Asn Ala Ile
            20                  25

<210> SEQ ID NO 243
<211> LENGTH: 28
<212> TYPE: PRT
<213> ORGANISM: Unknown
<220> FEATURE:
<223> OTHER INFORMATION: Synthetic

<400> SEQUENCE: 243

Ile Ala Thr Ile Arg Gln Trp Cys Ile His Phe Glu Glu Asp Ser Lys
1               5                   10                  15

Asn Phe Arg Asn Ala Val Ala His Leu Asn Pro Ile
            20                  25

<210> SEQ ID NO 244
<211> LENGTH: 28
<212> TYPE: PRT
<213> ORGANISM: Unknown
<220> FEATURE:
<223> OTHER INFORMATION: Synthetic

<400> SEQUENCE: 244

Ile Ala Thr Ile Arg Gln Trp Cys Ile His Phe Glu Glu Asp Ser Lys
1               5                   10                  15

Asn Phe Arg Asn Ala Val Ala His Leu Asn Pro Ile
            20                  25

<210> SEQ ID NO 245
<211> LENGTH: 28
<212> TYPE: PRT
<213> ORGANISM: Unknown
<220> FEATURE:
<223> OTHER INFORMATION: Synthetic

<400> SEQUENCE: 245
```

Ile Gly Ser Leu Arg Gln Trp Ile Thr His Ser Asp Glu Arg Ile Arg
1               5                   10                  15

Glu Phe Arg Asn Thr Ile Ala His Leu Gly Val Asp
            20                  25

<210> SEQ ID NO 246
<211> LENGTH: 28
<212> TYPE: PRT
<213> ORGANISM: Unknown
<220> FEATURE:
<223> OTHER INFORMATION: Synthetic

<400> SEQUENCE: 246

Leu Ser Gly Leu Arg Asn Trp Val Val His Asn Glu Val Cys Lys
1               5                   10                  15

Gln Phe Arg Asn Lys Ala Asp His Leu Glu Val Ala
            20                  25

<210> SEQ ID NO 247
<211> LENGTH: 28
<212> TYPE: PRT
<213> ORGANISM: Ruminococcus flavefaciens

<400> SEQUENCE: 247

Leu Ser Gly Leu Arg His Trp Val Val His Asn Asn Glu Val Cys Thr
1               5                   10                  15

Leu Gly Arg Asn Lys Ala Val His Leu Glu Val Ala
            20                  25

<210> SEQ ID NO 248
<211> LENGTH: 28
<212> TYPE: PRT
<213> ORGANISM: Ruminococcus albus

<400> SEQUENCE: 248

Met Ala Ser Leu Arg Gln Ser Tyr Phe His Gly Tyr Val Lys Ile Asn
1               5                   10                  15

Thr Tyr Arg Asn Gln Val Asp His Phe Ala Val Val
            20                  25

<210> SEQ ID NO 249
<211> LENGTH: 28
<212> TYPE: PRT
<213> ORGANISM: Unknown
<220> FEATURE:
<223> OTHER INFORMATION: Synthetic

<400> SEQUENCE: 249

Leu Ser Thr Val Arg Gln Phe Leu Ala His Lys Ser Asp Asp Ile His
1               5                   10                  15

Ala Phe Arg Asx Ser Ala Glu His Met Asn Ala Val
            20                  25

<210> SEQ ID NO 250
<211> LENGTH: 28
<212> TYPE: PRT
<213> ORGANISM: Unknown
<220> FEATURE:
<223> OTHER INFORMATION: Synthetic

<400> SEQUENCE: 250

Leu Ser Thr Ala Arg Asn Phe Ser Ala His Tyr Leu Asp Arg Ile Arg
1               5                   10                  15

```
Thr Phe Arg Asx Thr Ala Glu His Leu Glu Ala Leu
            20                  25

<210> SEQ ID NO 251
<211> LENGTH: 28
<212> TYPE: PRT
<213> ORGANISM: Unknown
<220> FEATURE:
<223> OTHER INFORMATION: Synthetic

<400> SEQUENCE: 251

Leu Gly Asn Leu Arg Gln Ala Met Ala His Ser Thr Glu Glu Val Arg
1               5                   10                  15

Met Tyr Arg Asn Cys Val Glu His Leu Asn Ala Val
            20                  25

<210> SEQ ID NO 252
<211> LENGTH: 28
<212> TYPE: PRT
<213> ORGANISM: Unknown
<220> FEATURE:
<223> OTHER INFORMATION: Synthetic

<400> SEQUENCE: 252

Leu Gly Lys Ala Arg Gln Met Thr Ala His Asp Leu Ala Asp Val His
1               5                   10                  15

Glu Tyr Arg Asn Cys Val Glu His Leu Ser Ala Ile
            20                  25

<210> SEQ ID NO 253
<211> LENGTH: 28
<212> TYPE: PRT
<213> ORGANISM: Unknown
<220> FEATURE:
<223> OTHER INFORMATION: Synthetic

<400> SEQUENCE: 253

Leu Gly Met Thr Arg Gln Ala Leu Ala His Asp Ser Thr Ile Thr Arg
1               5                   10                  15

Ala Phe Arg Asn Ser Val Glu His Leu Lys Ala Val
            20                  25

<210> SEQ ID NO 254
<211> LENGTH: 28
<212> TYPE: PRT
<213> ORGANISM: Unknown
<220> FEATURE:
<223> OTHER INFORMATION: Synthetic

<400> SEQUENCE: 254

Leu Gly Met Tyr Arg Gln Ala Met Ser His Glu Tyr Phe Ser Ile Arg
1               5                   10                  15

Asp Tyr Arg Asn Lys Val Ala His Lys Asn Thr Val
            20                  25

<210> SEQ ID NO 255
<211> LENGTH: 28
<212> TYPE: PRT
<213> ORGANISM: Unknown
<220> FEATURE:
<223> OTHER INFORMATION: Synthetic

<400> SEQUENCE: 255

Leu Ser Met Thr Arg Gln Ser Leu Ala His Asn Asn Ala Asp Ile Arg
```

```
                1               5                  10                  15
Gln Phe Arg Asn Lys Thr Glu His Leu Asn Ala Val
                20                  25

<210> SEQ ID NO 256
<211> LENGTH: 28
<212> TYPE: PRT
<213> ORGANISM: Unknown
<220> FEATURE:
<223> OTHER INFORMATION: Synthetic

<400> SEQUENCE: 256

Val Ser Tyr Leu Arg Asn Arg Thr Phe His Phe Lys Glu Ser Ile Ile
1               5                   10                  15

Trp Lys Arg Asx Pro Ile Ala His Leu Asn His Phe
                20                  25

<210> SEQ ID NO 257
<211> LENGTH: 28
<212> TYPE: PRT
<213> ORGANISM: Listeria seeligeri

<400> SEQUENCE: 257

Ile Ala Pro Ile Arg Asn Glu Ile Ile His Leu Lys Lys His Leu Lys
1               5                   10                  15

Glu Lys Arg Asn Asn Ile Ser His Phe Asn Tyr Leu
                20                  25

<210> SEQ ID NO 258
<211> LENGTH: 28
<212> TYPE: PRT
<213> ORGANISM: Listeria newyorkensis

<400> SEQUENCE: 258

Ile Gln Gln Ile Arg Asn Glu Val Tyr His Cys Lys Lys His Glu Lys
1               5                   10                  15

Asn Ala Arg Asn His Ile Ala His Leu Asn Tyr Leu
                20                  25

<210> SEQ ID NO 259
<211> LENGTH: 28
<212> TYPE: PRT
<213> ORGANISM: Paludibacter propionicigenes

<400> SEQUENCE: 259

Val Gln Gln Ile Arg Asn Asn Val Asn His Tyr Lys Lys Asp Met Tyr
1               5                   10                  15

Asp Ile Arg Asn His Ile Ala His Phe Asn Tyr Leu
                20                  25

<210> SEQ ID NO 260
<211> LENGTH: 28
<212> TYPE: PRT
<213> ORGANISM: Carnobacterium gallinarum

<400> SEQUENCE: 260

Val Gln Gln Ile Arg Asn Glu Ile Phe His Ser Phe Asp Lys His Gly
1               5                   10                  15

Lys Ile Arg Asx Gln Thr Ala His Leu Ser Val Leu
                20                  25

<210> SEQ ID NO 261
```

```
<211> LENGTH: 27
<212> TYPE: PRT
<213> ORGANISM: Carnobacterium gallinarum

<400> SEQUENCE: 261

Val Gln Arg Val

-continued

Glu Leu Arg Asn Tyr Ile Glu His Phe Arg Tyr Tyr
            20                  25

<210> SEQ ID NO 267
<211> LENGTH: 28
<212> TYPE: PRT
<213> ORGANISM: Lachnospiraceae bacterium NK4A179

<400> SEQUENCE: 267

Ile Tyr Ser Leu Arg Met Lys Ser Phe His Phe Lys Thr Tyr Ile Thr
1               5                   10                  15

Asp Leu Arg Lys Tyr Val Asp His Phe Arg Tyr Tyr
            20                  25

<210> SEQ ID NO 268
<211> LENGTH: 28
<212> TYPE: PRT
<213> ORGANISM: Clostridium aminophilum

<400> SEQUENCE: 268

Ile Tyr Ser Leu Arg Asn Glu Thr Phe His Phe Thr Thr Leu Ile Thr
1               5                   10                  15

Asp Val Arg Lys Tyr Val Asp His Phe Lys Tyr Tyr
            20                  25

<210> SEQ ID NO 269
<211> LENGTH: 28
<212> TYPE: PRT
<213> ORGANISM: Eubacterium rectale

<400> SEQUENCE: 269

Ile Tyr Cys Ala Arg Asn Glu Asn Phe His Phe Lys Thr Ala Ile Ile
1               5                   10                  15

Asn Leu Arg Asn Gly Ile Asp His Phe Lys Tyr Tyr
            20                  25

<210> SEQ ID NO 270
<211> LENGTH: 28
<212> TYPE: PRT
<213> ORGANISM: Lachnospiraceae bacterium MA2020

<400> SEQUENCE: 270

Leu Tyr Ala Met Arg Asn Ser Ser Phe His Phe Ser Thr Glu Ile Ile
1               5                   10                  15

Ile Phe Arg Asn Glu Ile Asp His Phe His Tyr Phe
            20                  25

<210> SEQ ID NO 271
<211> LENGTH: 28
<212> TYPE: PRT
<213> ORGANISM: Leptotrichia shahii

<400> SEQUENCE: 271

Gly Thr Asn Glu Arg Asn Arg Ile Leu His Ala Ile Ser Lys Asn Glu
1               5                   10                  15

Ser Ile Arg Asn Tyr Ile Ser His Phe Tyr Ile Val
            20                  25

<210> SEQ ID NO 272
<211> LENGTH: 28
<212> TYPE: PRT
<213> ORGANISM: Leptotrichia sp.

<400> SEQUENCE: 272

Gly Tyr Leu Leu Arg Asn Lys Ile Leu His Asn Ser Tyr Gly Asn Glu
1               5                   10                  15

Ser Ile Arg Asn Tyr Ile Ser His Phe Tyr Ile Val
            20                  25

<210> SEQ ID NO 273
<211> LENGTH: 28
<212> TYPE: PRT
<213> ORGANISM: Prevotella sp.

<400> SEQUENCE: 273

Leu Lys Met Tyr Arg Asp Leu Thr Asn His Tyr Lys Thr Tyr Leu Arg
1               5                   10                  15

Lys Ile Arg Asn Ala Phe Asp His Asn Asn Tyr Pro
            20                  25

<210> SEQ ID NO 274
<211> LENGTH: 28
<212> TYPE: PRT
<213> ORGANISM: Prevotella sp.

<400> SEQUENCE: 274

Leu Thr Glu Cys Arg Asn Phe Tyr Thr His Lys Asp Pro Tyr Leu Val
1               5                   10                  15

Ala Ile Arg Asn Ala Phe Ser His Asn Ser Tyr Asn
            20                  25

<210> SEQ ID NO 275
<211> LENGTH: 28
<212> TYPE: PRT
<213> ORGANISM: Riemerella anatipestifer

<400> SEQUENCE: 275

Leu His Ser Leu Arg Asn Tyr Tyr Ser His Tyr Lys His Lys Ile Ala
1               5                   10                  15

Ser Val Arg Asn Ala Phe Cys His Asn Gln Tyr Pro
            20                  25

<210> SEQ ID NO 276
<211> LENGTH: 28
<212> TYPE: PRT
<213> ORGANISM: Prevotella buccae

<400> SEQUENCE: 276

Leu Gln Val Leu Arg Asn Tyr Tyr Ser His Val Lys Tyr Ser Leu Lys
1               5                   10                  15

Asp Val Arg Asn Ala Phe Ser His Asn Gln Tyr Pro
            20                  25

<210> SEQ ID NO 277
<211> LENGTH: 28
<212> TYPE: PRT
<213> ORGANISM: Unknown
<220> FEATURE:
<223> OTHER INFORMATION: Synthetic

<400> SEQUENCE: 277

Leu Glu Gln Leu Arg Asn Tyr Tyr Ser His Val Lys His Ser Leu Lys
1               5                   10                  15

Asp Val Arg Asn Ala Phe Ser His Asn Gln Tyr Pro
            20                  25

<210> SEQ ID NO 278
<211> LENGTH: 28
<212> TYPE: PRT
<213> ORGANISM: Phaeodactylibacter xiamenensis

<400> SEQUENCE: 278

Leu Asn Gln Met Arg Asn Asn Tyr Ser His Tyr Ile Ser Asn Val Met
1               5                   10                  15

Gln Leu Arg Asn Lys Phe His His Asn Glu Phe Pro
            20                  25

<210> SEQ ID NO 279
<211> LENGTH: 28
<212> TYPE: PRT
<213> ORGANISM: Bacteroides pyogenes

<400> SEQUENCE: 279

Leu Gln Asp Ile Arg Asn Ala Phe Ser His Tyr His Ile Asp Leu Val
1               5                   10                  15

His Ile Arg Asn Lys Ser Ala His Asn Gln Phe Pro
            20                  25

<210> SEQ ID NO 280
<211> LENGTH: 28
<212> TYPE: PRT
<213> ORGANISM: Porphyromonas gingivalis

<400> SEQUENCE: 280

Leu Asp Phe Leu Arg Asn Asp Phe Ser His Asn Arg Leu Asp Leu Ile
1               5                   10                  15

Leu Ile Arg Asn Lys Ala Ala His Asn Gln Phe Pro
            20                  25

<210> SEQ ID NO 281
<211> LENGTH: 28
<212> TYPE: PRT
<213> ORGANISM: Porphyromonas gulae

<400> SEQUENCE: 281

Leu Asp Phe Leu Arg Asn Asp Phe Ser His Asn Arg Leu Asp Leu Ile
1               5                   10                  15

Leu Ile Arg Asn Lys Ala Ala His Asn Gln Phe Pro
            20                  25

<210> SEQ ID NO 282
<211> LENGTH: 28
<212> TYPE: PRT
<213> ORGANISM: Psychroflexus torquis

<400> SEQUENCE: 282

Ile Glu Lys Leu Arg Asp Tyr Tyr Thr His Phe Tyr His Asp Leu Ile
1               5                   10                  15

Ala Ile Arg Asn Lys Phe Ala His Asn Gln Phe Pro
            20                  25

<210> SEQ ID NO 283
<211> LENGTH: 28
<212> TYPE: PRT
<213> ORGANISM: Capnocytophaga canimorsus

<400> SEQUENCE: 283

```
Val Glu Ala Leu Arg Asn Phe Tyr Thr His Tyr Asp His Glu Leu Thr
1               5                   10                  15

Tyr Ile Arg Asn Lys Phe Ala His Asn Gln Leu Pro
            20                  25
```

<210> SEQ ID NO 284
<211> LENGTH: 28
<212> TYPE: PRT
<213> ORGANISM: Bergeyella zoohelcum

<400> SEQUENCE: 284

```
Val Arg Asp Lys Arg Asn Phe Tyr Thr His Lys Glu His Gly Leu Thr
1               5                   10                  15

Tyr Ile Arg Asn Lys Phe Ala His Asn Gln Leu Pro
            20                  25
```

<210> SEQ ID NO 285
<211> LENGTH: 28
<212> TYPE: PRT
<213> ORGANISM: Flavobacterium columnare

<400> SEQUENCE: 285

```
Ile Lys Lys Leu Arg Asp Tyr Tyr Thr His His Tyr His Lys Leu Ile
1               5                   10                  15

Ile Ile Arg Asn Lys Met Ala His Asn Gln Tyr Pro
            20                  25
```

<210> SEQ ID NO 286
<211> LENGTH: 28
<212> TYPE: PRT
<213> ORGANISM: Fusobacterium perfoetens

<400> SEQUENCE: 286

```
Tyr Ser Asp Lys Arg His Lys Leu Met His Tyr Asn Tyr Gln Leu Ala
1               5                   10                  15

Tyr Lys Arg Asn Lys Ile Cys His Leu Asn Tyr Ser
            20                  25
```

<210> SEQ ID NO 287
<211> LENGTH: 28
<212> TYPE: PRT
<213> ORGANISM: Fusobacterium necrophorum

<400> SEQUENCE: 287

```
Tyr Ser Lys Leu Arg His Ser Leu Met His Tyr Asp Tyr Gln Ile Ala
1               5                   10                  15

Asp Leu Arg Asn Phe Leu Ser His Leu Asn Tyr Ser
            20                  25
```

<210> SEQ ID NO 288
<211> LENGTH: 28
<212> TYPE: PRT
<213> ORGANISM: Anaerosalibacter massiliensis

<400> SEQUENCE: 288

```
Phe Ser Leu Arg Arg His Tyr Met Val His Tyr Asn Tyr Lys Asn Cys
1               5                   10                  15

Gln Ile Arg Asn Ser Ile Ala His Ile Asn Met Lys
            20                  25
```

RECOMBINANT VIBRIO NATRIEGENS ORGANISMS HAVING A MODIFIED OUTER MEMBRANE

CROSS-REFERENCE TO RELATED APPLICATIONS

This application claims the benefit of U.S. Provisional Application Ser. No.: 62/588,755, filed Nov. 20, 2017, which is hereby incorporated by reference in its entirety, including all Tables, Figures, and Claims.

INCORPORATION OF SEQUENCE LISTING

The material in the accompanying sequence listing is hereby incorporated by reference into this application. The accompanying sequence listing text file, name SGI2110_1_Sequence Listing.txt, was created on Oct. 4, 2018, and is 18 kb. The file can be accessed using Microsoft Word on a computer that uses Windows OS.

FIELD OF THE INVENTION

The invention relates generally to recombinant *Vibrio* sp. organisms having low levels of endotoxin versus a wild type organism while maintaining high levels of exogenous nucleic acid and protein production.

BACKGROUND OF THE INVENTION

The gram-negative bacterium *E. coli* serves as an industrial host for the production of many therapeutic recombinant proteins of pharmaceutical interest (e.g., recombinant human insulin). While *E. coli* has been used in pharmaceutical production processes since the dawn of biotech in the 1970s, one key disadvantage of this host is its production of lipopolysaccharides (LPS). Like most gram-negative bacteria *E. coli* have an outer membrane containing the potent immunostimulatory molecule lipopolysaccharide (LPS). These LPS molecules (also known as endotoxin) make up a significant portion of the outer membrane of gram-negative bacteria. These molecules are composed of three main parts: a Lipid A moiety (highly conserved among gram-negative species), a core oligosaccharide (mostly conserved), and an O-antigen polysaccharide (variable between organisms).

The immune system of vertebrates (including humans) has evolved to detect these LPS molecules and trigger an immunogenic reaction in response to their presence. Humans are very sensitive to endotoxin, which can trigger a systemic inflammatory response (or immune reaction) that can lead to organ failure, shock, and even death. As a result, biologics produced in *E. coli* are required to undergo intensive purification and quality control analyses to ensure the removal of these molecules from any injectable biologics. There are various manners of removing endotoxins that contaminate biologics and other products of interest produced in gram-negative organisms such as *E. coli*. These methods generally involve removing the endotoxin from the product by ultrafiltration, passing it through activated carbon, washing with surfactants, or anion-exchange chromatography. These methods are expensive and time consuming, and add additional time/cost to downstream processing and diminish product yield.

It would therefore be highly desirable to have an organism for the production of biologics and other molecules of interest having a lipopolysaccharide that causes a substantially reduced or eliminated immunological response in mammals, thereby eliminating much of the need for these expensive and time consuming processes to remove lipopolysaccharides and also making products made by the organisms safer for human and animal use.

SUMMARY OF THE INVENTION

The invention provides engineered or recombinant *Vibrio* sp. organisms having a genetic modification of the genes lpxL and/or lpxM. In various embodiments either one or both of the genes are genetically modified or deleted. The organisms can optionally have an exogenous nucleic acid, for cloning the exogenous nucleic acid or for expressing or producing an encoded exogenous protein or peptide. The recombinant organisms produce low amounts of endotoxin compared to a corresponding organism not comprising the genetic modification(s), which can be measured using an in vitro endotoxin assay. Therefore, molecules synthesized in or harvested from the organism present a much lower risk of endotoxicity in humans and other mammals since they will not be contaminated with endotoxin. The recombinant organisms also retain a high rate of growth and continue to be culturable even though they comprise the one or more genetic modifications. The organisms are therefore highly useful for the production of biologics, proteins, single domain antibodies, nucleic acids, and other therapeutic molecules or other molecules of interest.

The invention also provides methods of cloning a nucleic acid or of producing a protein. The methods involve culturing a *Vibrio* sp. organism having a genetic modification to the lpxL and/or lpxM gene(s). The organism optionally also has an exogenous nucleic acid sequence, which is for cloning the exogenous nucleic acid sequence or for expressing an encoded exogenous protein. In the methods the organism produces or contains substantially less endotoxin compared to a corresponding organism not comprising the genetic modification and cultivated under the same conditions. The recombinant *Vibrio* sp. organism also exhibits a growth rate of at least 60% of the growth rate of the corresponding organism when cultivated under the same conditions.

In a first aspect the invention provides a recombinant *Vibrio* sp. organism having a genetic modification of the lpxL gene or the lpxM gene. The organism has or produces substantially less endotoxin compared to a corresponding organism not having the genetic modification and cultivated under the same conditions. The recombinant *Vibrio* sp. organism can exhibit a growth rate of at least 60% of the growth rate of the corresponding organism when cultivated under the same conditions. In any of the embodiments the organism can also contain an exogenous nucleic acid for the production of the exogenous nucleic acid or for the production of an encoded exogenous protein or peptide.

In one embodiment the genetic modification is selected from a deletion, a mutation, an attenuation, a disruption, an inactivation, or a downregulation of the lpxL or lpxM genes. The organism can have an outer membrane having a modified lipopolysaccharide component. In one embodiment the organism does not have a genetic modification in any gene selected from the group consisting of: gutQ, kdsD, pagP, and lpxP. In one embodiment the organism has a growth rate of at least 70% the growth rate of a corresponding unmodified or wild type *Vibrio* sp. organism under identical conditions, or can have a growth rate as otherwise disclosed herein. In one embodiment the organism has an average endotoxin level of less than 1 EU/ml measured in an in vitro assay. The organism can have a doubling time of 55-70 minutes at 30°

C. The growth rate can be measured over a period of 8 hours or over a period of 12 hours. In a specific embodiment the genetic modification is a deletion and the organism is of the genus *Vibrio*, e.g. *Vibrio natriegens*.

In a specific embodiment the *Vibrio* sp. organism of the invention has a growth rate of at least 60% the growth rate of a wild type *Vibrio* sp. under the same growth conditions, and has an endotoxin level of less than 1 EU/ml, and a specific growth rate of at least 0.60 or 0.60-0.72 at 30° C. in LBv2 media. The organism can also have an exogenous nucleic acid for the cloning or production of the exogenous nucleic acid or for the production of an encoded heterologous protein or peptide.

In another aspect the invention provides a recombinant *Vibrio* sp. organism having an outer membrane having a modified lipopolysaccharide versus a wild type organism. The modified lipopolysaccharide can have a lipid component with a reduced number of acyl chains versus the lipid component in the wild-type organism. The recombinant organism can score substantially lower in an in vitro endotoxin assay versus the wild type organism. The recombinant organism can be any described herein that has the stated attributes.

In one embodiment the engineered *Vibrio* sp. organism of the invention has a modified LPS having a pentaacylated Lipid A. The organism can have a genetic modification to the lpx or lpxM genes. The organism can have less than 50% of the endotoxicity of an unmodified *Vibrio* sp. organism, as measured in an in vitro LPS detection assay. In another embodiment the organism has less than 5% of the endotoxicity of an unmodified *Vibrio* sp. organism, as measured in an in vitro LPS detection assay. And in yet another embodiment the organism has less than 1% of the endotoxicity of a wild type *E. coli*, as measured in an in vitro LPS detection assay.

In one aspect, the invention provides a *Vibrio* sp. organism having less than 1% of the endotoxicity of a modified *E. coli* organism that comprises the genetic deletions ΔgutQ, ΔkdsD, Δlpx, ΔlpxM, ΔpagP, ΔlpxP, and ΔeptA, as measured in an in vitro LPS detection assay. In any of the embodiment the organism can be *Vibrio natriegens*.

In another aspect the invention provides methods of cloning a nucleic acid or of producing a protein, polypeptide, or peptide. The methods involve culturing a *Vibrio* sp. organism described herein, and harvesting the cloned nucleic acid or the protein or peptide produced by the organism. In one embodiment the organism has an exogenous nucleic acid that is cloned or amplified by the organism. In another embodiment the organism has an exogenous nucleic acid encoding a protein, polypeptide, or peptide produced or expressed by the organism, and optionally secreted from the organism. The organism can be any described herein and can have any of the attributes of organisms described herein.

Section heading or sub-headings are provided solely for the convenience of the reader, and do not denote a departure from discussion or necessarily an entirely new subject matter area. Any subject matter can be discussed or disclosed under any section heading or sub-heading.

DESCRIPTION OF THE DRAWINGS

FIG. 2B provides an illustration of Lipid IV(A).

FIG. 3B presents the data in tabular format.

FIG. 7B is a graphical illustration of the ln(biomass) v. time. FIG. 7C is a graphical illustration of the linear portion of the graph in FIG. 7b.

DETAILED DESCRIPTION OF THE INVENTION

Figure 1:
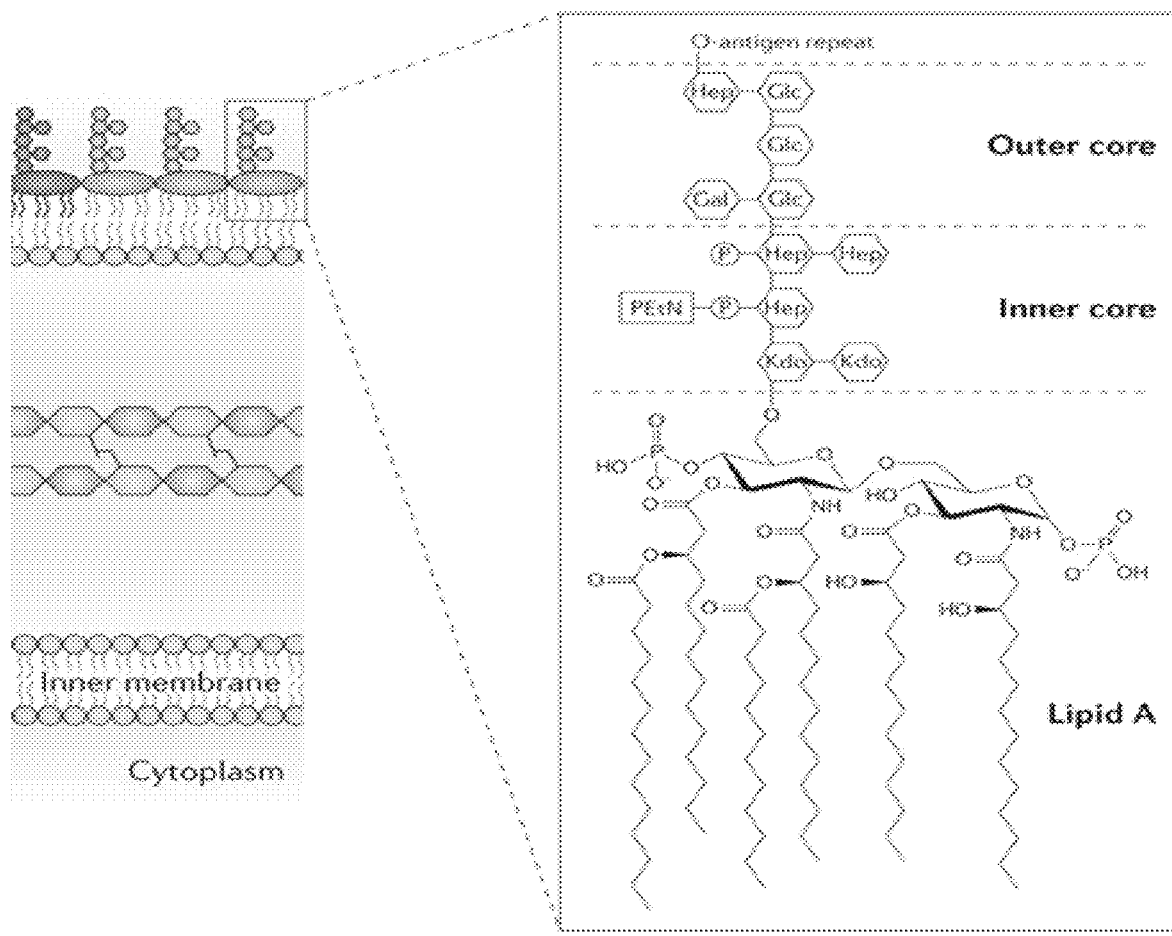
FIG. 1 provides an illustration of a membrane of a gram negative bacteria. The outer membrane is expanded for illustration of membrane components, including the Lipid A component (Okuda S., et al., Nature Reviews Microbiology, (2016) 14: 337-345).

The present invention provides a recombinant or engineered *Vibrio* sp. organism that has one or more genetic modifications affecting the lipopolysaccharide (LPS) component of its outer membrane, and the organism produces or contains substantially less endotoxin or immune-stimulatory LPS (or endotoxin) substances than the corresponding unmodified or wild-type organism cultivated under the same conditions. In some embodiments the *Vibrio* sp. organism comprises a genetic modification (e.g. a deletion, mutation, inactivation, attenuation, or downregulation) in either one or both of the lpxL and lpxM genes. The *Vibrio* sp. organism of the invention therefore allows for the production and harvesting of a biological product, such as nucleic acids, biologics, proteins, single domain antibodies, antibody fragments, and other molecules of interest in the organisms with a substantially reduced or eliminated risk of sepsis in humans or animals caused by the presence of endotoxin in the products. Single domain antibodies are antibody fragments having a single monomeric variable antibody domain and can bind specifically to a particular antigen. In various embodiments their molecular weights can be 11-16 kDa or 12-15 kDa. Biological products produced by the organisms of the invention can also be peptides and peptide hormones such as angiotensin, bradykinin, bacitracin, glucagon, vasopressin are just some examples of the peptides and hormones that can be produced in the *Vibrio* sp. organisms of the invention, as well as many other nucleic acids, protein products, polypeptide, or peptide molecules.

Persons of ordinary skill in the art know that modification of genes involved in the formation of the LPS component of the outer membrane (including lpxL and lpxM) causes gram-negative organisms to become "sick" or die, or to be unculturable, or to exhibit a greatly reduced growth rate. Such modifications therefore reduce the usefulness of the organisms by making it impracticable or impossible to produce nucleic acids or polypeptides in the organisms. It was discovered by the present inventors that when the lpxL and/or lpxM genes are genetically modified in *Vibrio* sp. organisms, the organisms surprisingly remain viable and culturable, and continue to be capable of robust growth rates while producing substantially less LPS, endotoxin, or immune-stimulatory substances that are toxic to a human or other mammal compared to that produced by an unmodified or wild-type organism. The discovery is therefore valuable for methods of producing compositions containing nucleic acids, biologics and other molecules having low levels of endotoxin. Therefore, the organisms are also useful for creating products with a greatly reduced or eliminated risk of sepsis or immune response caused by endotoxin or LPS contamination in the products, or for any other use of *Vibrio* sp. The organisms modified as described herein maintain a growth rate that is substantially as robust as the unmodified organism in spite of the modification.

*Vibrio* sp.

The invention is applicable to gram negative bacteria, such as *Vibrio* sp. The organism can also be any organism of the Family Vibrionaceae. The *Vibrio* sp. organisms of the invention can be any species of the genus *Vibrio*. Some examples of organisms in the *Vibrio* genus include, but are not limited to, *Vibrio natriegens, Vibrio cholerae, Vibrio fischeri, Vibrio parahaemolyticus, Vibrio campbellii*, and *Vibrio vulnificus*, but the invention can be applied to any *Vibrio* sp. organism, or to any combination or sub-combination of the *Vibrio* sp. organisms listed herein. In one embodiment the engineered or recombinant organisms of the invention are *Vibrio natriegens*. In another embodiment the engineered or recombinant organisms of the invention are *Vibrio cholerae*. In another embodiment the engineered or recombinant organisms of the invention are *Vibrio fischeri*. In another embodiment the engineered or recombinant organisms of the invention are *Vibrio parahaemolyticus*. In another embodiment the engineered or recombinant organisms of the invention are *Vibrio vulnificus*.

Outer Membrane and Endotoxin

Lipopolysaccharide substances (LPS), also called lipoglycans or endotoxins, consist of a lipid and a polysaccharide composed of O-antigen, an outer core and an inner core joined by a covalent bond (generally depicted in FIG. 1). They are found in the outer membrane of gram-negative bacteria and elicit a strong immune response in humans and animals (i.e. are endotoxic). LPS molecules are a major constituent of the outer membrane in gram-negative bacteria. The outer membrane can have 20-25% phospholipid and about 30% LPS substances. 3-deoxy-D-manno-octolusonic acid (Kdo) is a constituent of LPS in gram-negative bacteria and connects the core polysaccharide and Lipid A (FIG. 1). The immune response is believed to be caused by the lipid portion of the complex lipopolysaccharides, which are a major component in the outer membrane of gram-negative bacteria. The Lipid A region of the LPS is believed to be anchored to the outer membrane and may be associated with the toxicity. It is also believed that the polysaccharide portion of the outer membrane may be substantially responsible for triggering the antibacterial immune response (immunogenicity) in humans and other mammals. These components that cause this toxicity and immune response are known generally as endotoxins. Any of the organisms of the invention can therefore have an outer membrane with a modified LPS versus a corresponding unmodified or wild type *Vibrio* sp. organism.

Figure 2A:
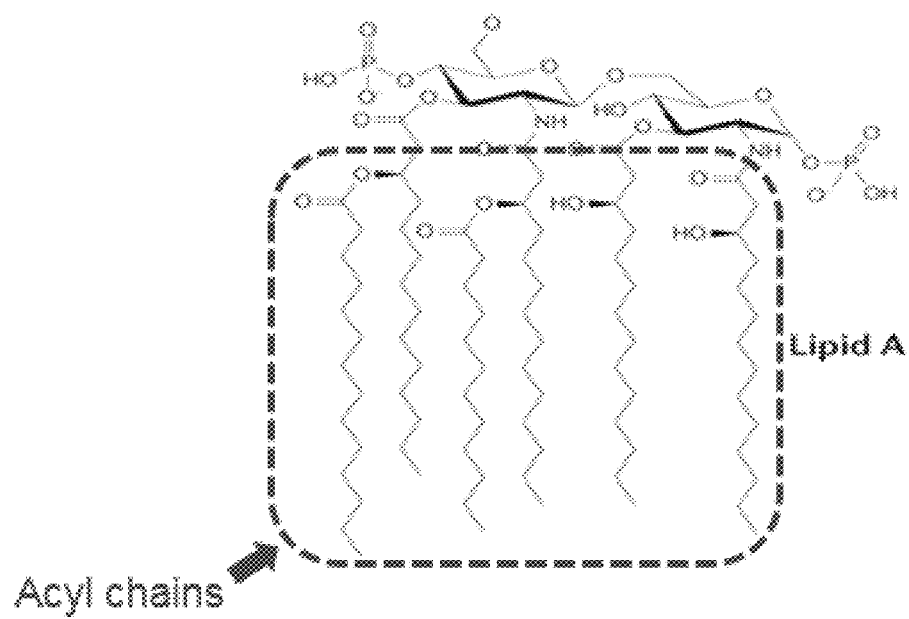
FIGS. 2A-2B, FIG. 2A provides an expanded illustration of the Lipid A component of the outer membrane of a gram negative organism, including identification of the acyl chains.
Figure 2B:
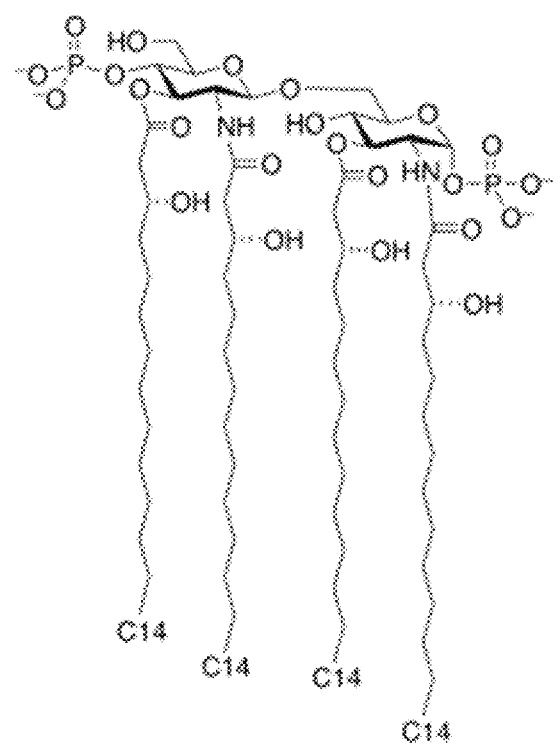

Without wanting to be bound by any particular theory it is believed that these LPS substances are present in the unmodified or wild-type organisms as the $(Kdo)_2$-Lipid A molecule, which are primarily or entirely hexaacylated (depicted generally in FIG. 2a). It is believed that by genetically modifying either one or both of the lpxL and/or lpxM genes that the Lipid A may be incompletely formed or otherwise modified to a form that may be substantially less immune stimulatory (or substantially less endotoxic) than the acylated Lipid A present in the unmodified or natural organism, and thus the recombinant organism causes a substantially lower, minimal, or no immune response (or is less endotoxic to a human, or other mammal, or bird. The recombinant organisms of the invention therefore can have a modified lipopolysaccharide component of the membrane, which in some embodiments can have a reduced number of acyl chain versus the unmodified or wild type organism. In one embodiment the acylated Lipid A in the organism of the invention can be a hexa-acylated Lipid A or a penta-acylated Lipid A. The modified lipopolysaccharides can be present in the outer membrane.

The recombinant organisms can be termed "low endotoxin," "very low endotoxin," or "endotoxin free." Therefore, products produced by methods of using these organisms (e.g. cloned nucleic acids or proteins and peptides) can avoid the lengthy and expensive endotoxin purification processes normally required, and are much safer for use in humans and animals. A low endotoxin organism (or product) is one giving an endotoxin level of 100 EU/ml or less, as determined by the endotoxin assays explained herein. A very low endotoxin organism (or product) is one giving an endotoxin level of 50 EU/ml or less, as determined by the endotoxin assays explained herein. An endotoxin free organism (or product) is one giving an endotoxin level of less than 1 EU/ml, as determined by endotoxin assays accepted in the art, for example any of those described herein.

Methods of Producing Products

The invention also provides methods of producing a biological product in a recombinant *Vibrio* sp. organism described herein. In one embodiment a biological product is a nucleic acid, which can be a DNA molecule or sequence to be amplified or cloned in the organism. In other embodiments the biological product is a protein, polypeptide, or peptide to be expressed in, and optionally secreted from, the organism. The protein, polypeptide, or peptide can be encoded by an exogenous nucleic acid in the organism. The methods involve cultivating a recombinant *Vibrio* sp. organism of the invention described herein and containing an exogenous nucleic acid to be cloned, amplified, or produced, or cultivating an organism containing an exogenous nucleic acid encoding a protein or peptide to be expressed and optionally secreted. In the methods the organism produces or contains substantially less endotoxin compared to a corresponding (wild type or unmodified) organism not having the genetic modification and cultivated under the same conditions. In the methods the recombinant *Vibrio* sp. organism can also have or exhibit a growth rate of at least 60% of the growth rate of the corresponding (wild type or unmodified) organism when cultivated under the same conditions, or have another growth rate as described herein. In the methods the recombinant organism can also produce at least 25% or at least 35% or at least 50% or at least 60% or at least 70% of the quantity of the exogenous nucleic acid to be cloned or the exogenous protein or peptide to be expressed as the corresponding organism cultivated under the same conditions and unit of time, or quantities of the nucleic acid or protein or peptide as otherwise described herein. In the methods the recombinant organism can have any of the genetic modifications described herein, and any of the characteristics of recombinant organisms described herein. Biological products produced using the recombinant cells of the invention include nucleic acids, polypeptides, peptides, and biologicals (for example any described herein), and any other molecule that can be produced in a bacterial cell.

Exogenous Nucleic Acid

The recombinant organisms of the invention can optionally comprise an exogenous nucleic acid sequence, which can be a plasmid or other vector or construct functional in the *Vibrio* sp. of the invention, or simply present on a plasmid, vector, or construct. Such plasmids are well known in the art. The exogenous nucleic acid can contain a sequence to be cloned or amplified, or can contain a sequence to be expressed as a heterologous protein or peptide.

As used herein, "exogenous" with respect to a nucleic acid or gene indicates that the nucleic acid or gene has been introduced (e.g. "transformed") into an organism, microorganism, or cell by human intervention. Typically, such an exogenous nucleic acid is introduced into a cell or organism via a recombinant nucleic acid construct. An exogenous nucleic acid can be a sequence from one species introduced into another species, i.e., a heterologous nucleic acid. A heterologous nucleic acid can also be an exogenous synthetic sequence not found in the species into which it is introduced. Further, a nucleic acid is considered exogenous if it has been introduced into a progenitor of the cell, organism, or strain under consideration.

When applied to organisms, the terms "transgenic" "transformed" or "recombinant" or "engineered" or "genetically engineered" refer to organisms that have been manipulated by introduction of an exogenous or recombinant nucleic acid sequence into the organism, or by the manipulation of native sequences, which are therefore then recombinant (e.g. by mutation of sequences, deletions, disruptions, insertions, replacements, and other manipulations described below). In some embodiments the exogenous or recombinant nucleic acid can express a heterologous protein or peptide product. A heterologous or recombinant nucleic acid molecule can be integrated into a genetically engineered/recombinant organism's genome or, in other instances, not integrated into a recombinant/genetically engineered organism's genome, or on a vector or other nucleic acid construct. As used herein, "recombinant microorganism" or "recombinant host cell" includes progeny or derivatives of the recombinant microorganisms of the disclosure. Because certain modifications may occur in succeeding generations from either mutation or environmental influences, such progeny or derivatives may not, in fact, be identical to the parent cell, but are still included within the scope of the term as used herein.

Recombinant or Engineered Organisms

In various embodiments the engineered or recombinant *Vibrio* sp. organisms of the invention comprise a genetic modification of either one or both of the lpxL and/or lpxM genes, which in one isoform have SEQ ID NOs: 1-2, respectively. A genetic modification denotes any one or more of a deletion, mutation, disruption, insertion, inactivation, attenuation, an inversion, or downregulation of a gene or other nucleic acid sequence, or any other physical change to the sequence that effects a difference in the context it occurs. An unmodified nucleic acid sequence denotes a natural or wild type sequence. The term "unmodified" can mean unmodified with respect to the gene or sequence in question, e.g. at the lpxL or lpxM genes. In various embodiments the genetic modification is a deletion or disruption of the gene.

Any genetic modification described herein can affect a demonstrable change in the organism so modified, and not be merely inconsequential to the organism's endotoxicity or growth rate. A genetic modification can decrease the organism's endotoxicity or growth rate by an amount of at least 10% or 20% or 30% or 40% or 50% or 60% or 70%. A genetic modification can also reduce the expression or activity of the modified gene by at least 10% or 25% or 40% or 50% or 70% or 90% or by 100%. And a genetic modification can increase the growth rate of the organism by at least 10% or 20% or 30% or 40% or 50% or 60% or 70%. In any of the embodiments an organism of the invention can lack one or more modification(s) that increase(s) the growth rate by any of the stated amounts. Growth rate can be measured as generation time (G), doubling time, or specific growth rate.

lpxL and lpxM genes encode fatty acid transferases involved in membrane formation. In some embodiments the recombinant or engineered organism comprises a genetic modification in either one or both of lpxL and/or lpxM gene(s). The organisms can also have (or not lack) a D-arabinose 5-phosphate isomerase (API) gene (e.g. kdsD and gutQ) and/or also have, or not lack, 2-keto-3-deoxy-D-manno-octulosonate (Kdo), any one or more of which can be natural, functional, or unmodified genes. Thus, in some embodiments the organisms of the invention can have a natural, unmodified, or wild type D-arabinose 5-phosphate isomerase (API) gene and/or a natural, unmodified, or wild type 2-keto-3-deoxy-D-manno-octulosonate (Kdo), i.e. an API or Kdo gene that has not been deleted, inactivated, disrupted, attenuated, or downregulated. In one embodiment the organism does not have a genetic modification of any gene (or any combination or sub-combination of genes) in the KDO synthesis pathway, which includes the series of enzymes that convert UDP-GlcNAc into $KDO_2$-Lipid IV(A). The organism can have wild type genes for any one of them or any combination or sub-combination of them. These enzymes include, but are not limited to, lpxD, lpxH, lpxB, lpxK, and WaaA. It can also optionally comprise a natural or unmodified transporter msbA and/or membrane protein yhjD; or in one embodiment can have only a natural, unmodified, or wild type msbA and/or yhjD gene(s) encoding a membrane protein, and have no copies of msbA or yhjD genes that are not the natural, unmodified, non-mutated, or wild type. In one embodiment the organism does not have an msbA (suppressor) mutation (e.g. has a wild type msbA gene). The recombinant organisms of the invention can also have one or more (or all) natural, unmodified, or wild type of genes involved in the synthesis and attachment of the core oligosaccharides (e.g. Waa proteins), or O-antigens (WaaL, WecA, Wzy-dependent synthesis pathways, ABC transporter-dependent pathways, and synthase-dependent pathways), and not have any non-natural or not wild type of these genes or combinations thereof.

Deletion is one type of genetic modification. A deletion can be a complete deletion or an at least partial deletion or a mutation so that the gene no longer performs its natural function and/or no longer produces a functional protein (for protein encoding genes). Thus, in some embodiments a deletion comprises a deletion of at least 10 or at least 25 or at least 50 or at least 75 or at least 100 or at least 200 or at least 300 or at least 400 or at least 500 nucleotides or at least 1000 or at least 2000 or at least 3000 or up to 5000 nucleotides. Inactivation or disruption of a gene can also be accomplished by insertion of a sequence into the gene (e.g. coding or non-coding nucleic acid sequence). A gene can also be attenuated, meaning that the gene is controlled in a manner that causes premature termination of transcription (e.g., provisional stop signaling). Downregulation of a gene is a general term meaning that the gene or nucleic acid sequence is expressed, but at a level so low that the gene or nucleic acid sequence no longer performs its natural function to a substantial degree. When a gene is a coding gene and has a modification it may no longer produce a functional protein to a substantial degree. Substantial refers to an amount that would be deemed significant to a person of ordinary skill in the context it occurs. In various embodiments a downregulated gene, or any of the genetic modifications, can be expressed at less than 50% or less than 40% or less than 30% or less than 20% or less than 10% or less than 5% or less than 1% of its expression level in a corresponding unmodified, wild type organism under similar conditions, or can be present but not expressed at all. Persons of ordinary skill with reference to this disclosure know how to perform these genetic modifications and others in a general context, and such are all considered within the scope of this disclosure. Any of these genetic modifications can also be performed in a regulatory sequence affecting expression of the gene, not necessarily in the coding region itself. The regulatory sequence can be upstream or downstream of the targeted gene. For example the deletion could be targeted to the promoter of a gene, thus preventing expression of the gene and achieving the same effect as deletion of the coding region itself. But any untranslated region associated with the gene and affecting its expression can be the target of the genetic modifications described herein. In various embodiments the *Vibrio* sp. organism of the invention does not express any lpxL gene (whether endogenous or exogenous) and/or does not express any lpxM gene (whether endogenous or exogenous).

In various embodiments *Vibrio* sp. organisms of the invention contain a deletion of either one or both of lpxL and/or lpxM, and isoforms of the genes are presented as SEQ ID Nos: 1-2. For example, in any of the embodiments the recombinant *Vibrio* sp. organisms of the invention have a genetic modification of lpxL alone, or a genetic modification if lpxM alone, or a genetic modification of both lpxL and lpxM. Any of the recombinant organisms of the invention can also have a growth rate of at least 50% or at least 55% or at least 57% or at least 60%, or at least 65% or at least 70% or at least 75% or at least 80% or at least 85% or at least 90% of the growth rate of the corresponding unmodified or wild-type *Vibrio* sp. organism under the same growth conditions, or to a *Vibrio* sp. organism that does not contain the deletion of the lpx and/or lpxM gene(s). A corresponding organism is an organism of the same type that does not have the genetic modification being examined. A corresponding organism can be a wild-type organism, or it can be wild-type or unmodified at the gene(s) being examined. In some embodiments a corresponding organism can be the same species of organism that does not have either one or both of the lpxL and/or lpxM modifications being examined as described herein. A corresponding organism can have other modifications that do not affect the trait, gene, or genetic modification being examined.

In one embodiment the engineered *Vibrio* sp. organisms of the invention has a growth rate of at least 2× or at least 3× or at least 4× or at least 5× or at least 6× the growth rate of an *E. coli* organism having a deletion of the gutQ, kdsD, lpxL, lpxM, pagP, lpxP and eptA genes, under corresponding growth conditions. The *E. coli* organism compared can also have a mutation of the msbA148 gene to enable viability in the presence of the LPS precursor lipid IV(A).

In some embodiments the engineered or recombinant *Vibrio* sp. organisms of the invention do not comprise a genetic modification of any one or more of gutQ, kdsD, pagP, lpxP, msbA148, or any sub-combination of them. The *Vibrio* sp. organisms of the invention can therefore comprise a natural, unmodified, or wild type gutQ, kdsD, pagP, or lpxP, or all four natural or wild type genes, or any combination or sub-combination of them can be natural or wild type (i.e. natural or wild type gutQ and kdsD, or gutQ and pagP, or gutQ and lpxP, or kdsD and pagP, or kdsD and lpxP, or pagP and lpxP). Any of these organisms can also comprise an unmodified, natural, or wild type msbA148 gene with any of the combinations or sub-combinations described herein.

However, in other embodiments, the engineered or recombinant *Vibrio* sp. of the invention can comprise a genetic modification in any one of gutQ, kdsD, pagP, or lpxP, or msbA148, or any combination or sub-combination of them, as described above. In some embodiments the organisms of the invention can comprise a natural or unmodified KdsD, or Kdo8P synthase, or Kdo8P phosphatase, or CMP-Kdo synthetase, or Kdo transferase (WaaA), or any combination of these genes can be natural or unmodified.

Endotoxicity

Endotoxin refers to complex lipopolysaccharide (LPS) substances present in the outer membranes of gram negative organisms such as *E. coli, Vibrio* sp., and others. These substances are collectively called "endotoxin" and are toxic to mammals and other vertebrates. Endotoxin can be released when cells are disrupted or otherwise disintegrate. Thus, when these organisms are used to clone nucleic acids or produce proteins, polypeptides, or peptides the products can be contaminated with unacceptable levels of endotoxin. The engineered or recombinant *Vibrio* sp. organisms of the invention score substantially lower in an in vitro endotoxin assay compared to a natural, unmodified, or wild type organism under the same conditions, i.e. the recombinant organisms produce or contain substantially less endotoxin or LPS substances, or are substantially less endotoxic to humans and other mammals (e.g. canines, felines, equines, bovines, or porcines). By substantially less endotoxin or less endotoxic is meant that the organism can have less than 50% or less than 40% or less than 30% or less than 20% or less than 10% or less than 5% or less than 3% or less than 2% or less than 1% or less than 0.90% or less than 0.50% or less than 0.10% of the endotoxin content compared to a corresponding unmodified or wild type *Vibrio* sp. organism (or one that does not have the genetic modification to lpxL and/or lpxM) cultivated and measured under the same conditions. The endotoxin content or concentration, or the endotoxicity of the compared organisms can be measured using any generally accepted in vitro endotoxin assay, such as any of those described herein or otherwise accepted in the field as being a valid endotoxin assay in the context, e.g. the HEKTm-Blue LPS assay, which can measure the activation of the TLR4 receptor to an endotoxin sample from an organism.

The engineered or recombinant *Vibrio* sp. organisms of the invention can also produce an endotoxin concentration of less than 50% or less than 40% or less than 30% or less than 20% or less than 10% or less than 5% or less than 1% or less than 0.50% or less than 0.10% of the endotoxin concentration produced by an unmodified or wild type *E. coli* organism (or one that does not have a genetic modification to lpxL and/or lpxM) cultivated under corresponding conditions. In some embodiments BL21(DE3) can be used as the unmodified or wild type *E. coli*. The endotoxin concentration or level can be determined using any generally accepted LPS or endotoxin assay, such as an in vitro LPS or endotoxin assay accepted in the field or described herein. Several such methods (e.g. HEK™-Blue LPS assay) are described herein.

The engineered or recombinant *Vibrio* sp. organisms of the invention can also produce an endotoxin-induced immune response of less than 50%, or less than 40%, or less than 30%, or less than 20%, or less than 10%, or less than 5%, or less than 1%, or less than 0.50%, or less than 0.10% of the response of an *E. coli* organism comprising a deletion of gutQ, kdsD, lpx, lpxM, pagP, lpxP, and eptA, or any sub-combination of them produced under the same or corresponding conditions. The compared *E. coli* organism can also comprise a compensating mutation in the msbA gene (e.g. msbA148) (*E. coli* cells having all of the above deletions and the msbA mutation are commercially available under the trademark name ClearColi®). The endotoxin-induced immune response (or endotoxicity) can be determined or measured using an in vitro LPS or endotoxin assay. The immune response or endotoxicity can be relative to, or with respect to, the immune response in a human or other mammalian cell, and can measure activation of the TLR4 receptor. [The engineered or recombinant *Vibrio* sp. organisms of the invention can also have or produce less endotoxin (in the lower amounts stated herein and above) than the aforementioned *E. coli* organisms (e.g. the "ClearColi®" organism), which endotoxin amount can be measured using an endotoxin-induced immune response as described herein.]

The engineered or recombinant *Vibrio* sp. organisms of the invention can have an average endotoxin level for purified LPS molecules of less than 50 EU/ml, or less than 25 EU/ml, or less than 15 EU/ml, or less than 10 EU/ml, or less than 5 EU/ml, or less than 5 EU/ml, or less than 4 EU/ml, or less than 3 EU/ml, or less than 2 EU/ml, or less than 1 EU/ml, or less than 0.80 EU/ml, or less than 0.70 EU/ml, or less than 0.50 EU/ml, or less than 0.30 EU/ml, or less than 0.20 EU/ml, or less than 0.10 EU/ml, as measured in an in vitro endotoxin assay. The endotoxin level can be measured according to any generally accepted method, for example those methods described herein. Any of the organisms of the invention can also have the stated endotoxin levels disclosed herein within plus or minus 10% of the stated value. In any of the embodiments the recited values for the *Vibrio* sp. organisms of the invention can be obtained while a correspondingly prepared sample of wild type or unmodified *V. natriegens* gives a value of 107 EU/ml±5% or ±10%; or while an *E. coli* having a deletion of ΔgutQ, ΔkdsD, Δlpx, ΔlpxM, ΔpagP, ΔlpxP, and ΔeptA, and a mutated msbA gene (a suppressor mutation) gives a value of 146 EU/ml±5% or ±10%.

Growth Conditions

Growth conditions for the *Vibrio* sp. organisms of the invention or for wild-type *Vibrio* sp. or other gram negative organisms, for purposes of measuring growth rates comparing relative endotoxin concentrations or levels, can be any standardized or corresponding growth conditions accepted in the field as generally equivalent. In one embodiment growth rates or other activities can be calculated or conducted in LBv2 media or LB (or LB-Miller) media, at about 30° C. or another suitable temperature. The growth conditions can be utilized to compare the growth rates between gram negative or other organisms, as is known and generally accepted in the field. In any of the embodiments a suitable media (including, but not limited to, any of those described herein) having at least 10 g NaCl/L or about 1% NaCl can be used. The media can optionally contain functional amounts glucose and/or magnesium, and can contain minimal or no calcium.

Persons of ordinary skill understand that different species (or even strains) of organisms can prefer different growth conditions. Such persons understand that growing two different organisms under their different and preferred conditions for a particular measurement provides corresponding growth conditions that accurately measure or compare a parameter. Corresponding growth conditions are those accepted in the field as those suitable for providing such accurate measurements. In some embodiments the growth rate of a *Vibrio* sp. organism can be compared to an *E. coli* organism in corresponding conditions by growing *Vibrio* sp. in LBv2 media and the *E. coli* in LB (also called LB-Miller) media, since the organisms prefer these respective media. The organisms can be grown at the same temperature, e.g. about 30° C. or about 37° C., or *Vibrio* sp. can be grown at about 30° C. and *E. coli* can be grown at about 37° C. for corresponding conditions. In one embodiment *Vibrio* sp. and *E. coli* organisms can also be compared by growing both of them in LBv2 media; in another embodiment for comparison *Vibrio* sp. can be grown in LBv2 media at about 30° C. and *E. coli* can be grown in LB (or LB-Miller) media at about 37° C. for corresponding conditions. Any of these various conditions can be used to compare any properties of the organisms, whether wild type or recombinant organisms.

Growth Rate

Genetic modification (e.g. deletion, inactivation, insertion, attenuation, inversion, disruption, or downregulation) of the lpxL and/or lpxM genes in a gram negative organism would be expected to result in an organism having a significantly lower growth rate than an unmodified wild type organism. In various embodiments the organism with a significantly lower growth rate grows at 59% or less or 60% or less or 55% or less or 50% or less or 40% or less or 30% or less of the growth rate of the unmodified or wild type organism, or that (G) at least doubles, unless the organism has a modified msbA mutation (or "suppressor mutation") that permits Lipid IV(A) transport. There are various mutations of msbA that permit of increase growth and they are known to persons of ordinary skill. Yet the present inventors discovered unexpectedly that the engineered *Vibrio* sp. organisms of the invention described herein can have a genetic modification in either one or both of the lpxL and/or lpxM genes and nevertheless remain culturable and retain a high growth rate making them useful for the production of molecules as described herein. These engineered or recombinant organisms of the invention also have the advantage of giving a substantially reduced or eliminated immune response (or are substantially less endotoxic) in humans and other mammals.

A growing population of bacteria doubles at regular intervals of time. Bacterial growth occurs by geometric progression, e.g. 1, 2, 4, 8, etc. or $2^0, 2^1, 2^2, 2^3 \ldots 2^n$ where n is the number of generations. But only part of the bacterial life cycle involves exponential growth, and bacterial growth curves thus typically have an exponential portion and a stationary portion. Growth rate can be calculated during the exponential part of the life cycle. The exponential phase of growth involves balanced growth wherein the cells are dividing regularly and growing by geometric progression. The rate of exponential growth (or the growth rate) of a bacterial culture can be expressed as generation time, or doubling time of the bacterial population. Generation time (G) is defined as the time (t) per generation (n=number of generations). Thus, the equation G=time (t) divided by (n)

expresses the doubling time or generation time. G can be expressed in minutes (or hours) or any suitable unit of time. For example, a generation time (G) of 10 minutes means that it will take 10 minutes for the population to double in size. In various embodiments the generation time can be measured by the numbers of organisms, the biomass, the O.D., or other measurements that are convenient and accepted as scientifically valid. Another common method of describing growth kinetics is the specific growth rate (SGR). The specific growth rate has units of reciprocal hours (per hr or $hr^{-1}$). Specific growth rate (SGR) and generation time (G) are related through the following mathematical formula: G=ln(2)/SGR. Thus, a large SGR will correspond with a small G, and vice versa. SGR can also be converted into doublings/hr by the formula: doubling time=ln(2) divided by the specific growth rate.

In some embodiments the engineered *Vibrio* sp. of the invention exhibits a specific growth rate of at least 0.30 $hr^{-1}$ (per hour) or at least 0.40 or at least 0.50 or at least 0.60 or at least 0.70 or at least 0.80 or at least 0.85 $hr^{-1}$ or 0.40-0.95 $hr^{-1}$ or 0.50-0.95 or 0.60-0.72 or 0.60-0.75 or 0.60-0.95, or 0.65-0.90, or 0.70-0.95, or 0.80-0.95, or 0.85-0.95, or 0.30-0.90, or 0.40-0.90, or 0.50-0.90, or 0.60-0.90, or 0.70-0.90, or 0.80-0.90 $hr^{-1}$ (per hour) which can be conveniently measured in any appropriate media and at any appropriate temperature (e.g. those listed herein). Thus, growth rate can be expressed in doublings/hr or in minutes/doubling or simply generation time, or specific growth rate (SGR). In one embodiment the doubling time of the organisms can be measured at 30° C. in LBv2 media. But any suitable media can be used, for example LB media (or LBMiller media). Growth can be assessed in any suitable container such as, for example, a fermentor or shake flask, but in one embodiment the organisms can be assessed in a culture or assay plate (e.g. a 48 well plate). The container can be flat bottomed microtiter plate, a round bottomed microtiter plate, or another appropriate vessel with wells of advantageous shape, for example flower shaped wells (e.g. FlowerPlate® microtiter plates). Any suitable container and conditions can be used to measure the growth rate. The growth rate or specific growth rate can also be assessed at various temperatures, including but not limited to, growth at about 25° C. or at about 30° C. or at about 37° C. or at about 40° C. or at about 42° C. or about 25-30° C. or 25-32° C. or 25-37° C. or about 30-37° C. or about 37-42° C. or at any temperature between 16-42° C. The growth rates disclosed herein are achievable on the media indicated herein and without any further supplementation of the media (e.g. without supplementation by arabinose 5-phosphate or glucose 6 phosphate). In some embodiments the organisms can have all wild type genes and no deletions or genetic mutations to any gene except as otherwise described herein.

In various embodiments the engineered or recombinant organisms of the invention have a doubling time of about 60 minutes, or 55-70 minutes, or 40-50 minutes, or 30-40 minutes, or less than 30 minutes at 30° C., or less than 22 minutes at 37° C., or less than 21 minutes at 42° C., all in LB or LBv2 media.

The engineered or recombinant *Vibrio* sp. organisms of the invention can grow more slowly than a corresponding or wild type organism (or one not having the genetic modification to lpxL and/or lpxM). Thus, in various embodiments the engineered or recombinant *Vibrio* sp. organisms of the invention can have a growth rate of at least 40% or at least 50%, or at least 55%, or at least 60% at least 65% or at least 70% or at least 80% or at least 85% or at least 90% or 50-70% or 55-70% or 55-65% or 55-80% or 55-90% or 60-70% or 60-65% or 60-80% or 60-90% or 60-95% or 65-90% or 70-90% or 75-90% or 55-95% or 65-95% or 70-90% or 70-95% or 75-95% of the growth rate (but also optionally less than 100% or less than 95% or less than 90% for any of them) of the corresponding or wild-type organisms (or those not having the lpx and/or lpxM modification(s)) under the same or corresponding conditions. For example, if any organism has a doubling time of 10 minutes, 65% of its growth rate can be calculated as 10/0.65=15.4 minute doubling time. Growth rates can be measured over any convenient time period of cultivation during the exponential phase, such as over 4 hours or over 6 hours or 8 hours or 9 hours or 10 hours or 12 hours or 15 hours or 18 hours or 24 hours or only from 0-3 hours or 0-4 hours or 0-6 hours or 0-8 hours or 6-8 hours or from 8-10 hours or from 8-12 hours or from 10-12 hours. Thus, the recombinant *Vibrio* sp. organisms of the invention can have a doubling time or generation time or specific growth rate of 50% or greater or 55% or greater or 60% or greater, or 65% or greater, or 70% or greater or 75% or greater or 80% or greater or 85% or greater or 90% or greater, or 95% or greater (or 55-70% or 55-65% or 55-90% or 55-95% or 60-70% or 60-65% or 60-80% or 60-90% or 60-95% or 65-90% or 65-95% or 70-90% or 75-90% or 80-90% or 75-95% or 80-95%) than the doubling time or generation time of the wild-type organism, or an organism not having the genetic modification of lpxL and/or lpxM. Doubling time can be expressed as any suitable unit of time, but doublings/hr is convenient and commonly used.

Any of the recombinant *Vibrio* sp. organisms described herein can also have a growth rate of at least 2× greater, or at least 3× greater or at least 4× greater or at least 5× greater or at least 6× greater or at least 7× greater or at least 8× greater or at least 10× greater than an *E. coli* having a deletion of ΔgutQ, ΔkdsD, Δlpx, ΔlpxM, ΔpagP, ΔlpxP, and ΔeptA, and a mutated msbA gene (a suppressor mutation). Such *E. coli* are commercially available under the trademark name ClearColi®).

Any of the engineered or recombinant *Vibrio* sp. organisms of the invention can exhibit sustained growth at higher temperatures, for example at about 40° C., or above 40° C., or at about 42° C., or above 42° C., or at about 37-42° C. or about 38-42° C., e.g. for time periods of at least 12 hours or at least 18 hours or at least 24 hours or at least 48 hours. In some embodiments the cells can be re-cultured after being exposed to the stated conditions.

Endotoxin Assay

Various methods are available for measuring the level of endotoxin in a sample or for comparing the levels of endotoxin in samples. In one embodiment the HEKTm-Blue LPS assay is used, but any in vitro endotoxin or LPS assay that is generally accepted or that has been scientifically demonstrated as reliable and is based on LPS-induced activation of a mammalian TLR4 receptor can be used. In some embodiments the endotoxin or LPS assay is a cell-based and/or colorimetric assay, like the HEKTm-Blue LPS assay. Endotoxin or LPS levels can be measured in samples of cells or in a sample of a product of cells.

The HEK-Blue™ LPS assay is a cell-based colorimetric assay for detecting endotoxin. It is based on the ability of the TLR4 receptor to recognize and be activated by LPS from gram-negative bacteria. The assay utilizes HEKBlue™-4 cells, which are highly sensitive to LPS and, in particular, to the toxic Lipid A moiety of LPS found in wild type gram negative organisms such as *Vibrio* sp. and *E. coli*. The cells used in the HEK-Blue™ LPS assay are engineered to stably express human TLR4 and an NF-kB-inducible secreted embryonic alkaline phosphatase reporter gene. In some embodiments the HEK-Blue™ LPS assay is utilized to measure or compare endotoxin activation of the TLR4 receptor in respective samples, e.g. unmodified or wild type samples versus the recombinant *Vibrio* sp. organisms of the invention, or other organisms. In various embodiments the TLR4 receptor can be a human TLR4 receptor, but animal receptors can be used for animal products. For example, a canine, feline, equine, porcine, TLR4 receptor can optionally be used when evaluating products for animals.

Monocyte activation tests (MATs) are another example of suitable and reliable endotoxin or LPS detection assays that can be used in the present invention. Monocytes contain cell-surface receptors for LPS molecules and LPS elicits a strong response from monocytes when it binds to toll-like receptor (TLR4) on the cell surface. MAT assays are in vitro assays based on this binding, which sets off a cascade of reactions resulting in the release of cytokines. These assays can be based on human whole blood. Other endotoxin tests also based on TLR4 activation can also be used in the invention.

The level of endotoxin or LPS in a sample can be expressed as endotoxin units per ml (EU/ml). In various embodiments the endotoxin or LPS assay selected can reliably measure endotoxin concentrations of about 0.1 EU/ml or less, or about 0.05 EU/ml or less, or about 0.03 EU/ml or less, or about 0.02 EU/ml or less, or about 0.01 EU/ml or less than 100 ng/ml or less than 10 ng/ml or less than 1 ng/ml or less than 0.5 ng/ml or less than 0.4 ng/ml or less than 0.3 ng/ml or less than 0.2 ng/ml or less than 0.1 ng/ml. In various embodiments other methods of measuring endotoxin level can also be used such as, for example, gel clot assays, or turbidimetric assays, or chromogenic assays, or any generally accepted method. The Examples provided herein also illustrate methods of calculating the endotoxin level of an organism or sample.

The HEK-Blue™ assay and other accepted endotoxin assays can give an endotoxin measurement in a unit of concentration, for example ug/ml or ng/ml. However, endotoxin samples can also have differing potencies. To address this the FDA established a standard endotoxin preparation expressed in units of activity instead of mass using a universal standard called the reference standard endotoxin (RSE). According to the current FDA standard, the RSE equates to 10 EU/ng (EC-6 RSE). Thus, mass units or units of concentration can be easily converted into EU/unit volume or EU. Control standard endotoxin (CSE) are also commonly provided in commercially available kits for measuring endotoxin and are secondary standards, i.e. are standardized against the RSE. CSEs are also generally accepted and widely used in the field and are useful for building standard curves for quantitation.

LPS extraction and purification methods are well known and kits are commercially available. The LPS extraction and purification methods are known in the art and are scientifically accepted, and are part of the LPS assays discussed herein for determining endotoxin levels of samples or organisms. In any of the embodiments described herein the LPS extraction method can be performed on a culture volume of 5 ml at an OD600 of 0.8-1.2 for evaluation or determination of any of the endotoxin values described herein. If desired, dilutions can be performed until a wild type or unmodified *V. natriegens* gives a value of 107±5% or ±10%; or until an *E. coli* having a deletion of ΔgutQ, ΔkdsD, Δlpx, ΔlpxM, ΔpagP, ΔlpxP, and ΔeptA, and a mutated msbA gene (suppressor mutation) gives a value of 146±5% or ±10%.

The invention also provides kits comprising a recombinant *Vibrio* sp. organism described herein, which can optionally contain a vector for cloning a nucleic acid sequence or for expressing a protein or peptide. In some embodiments the kits can also contain growth media for growing the organisms, a recovery media or buffer for growing cells after transformation and/or a positive control vector, to verify that the transformation protocol was correctly followed. The growth media, recovery media, and buffer for growing cells after transformation can be any described herein.

EXAMPLES

Example 1—Construction of *Vibrio* Strains with Δlpx, ΔlpxM, ΔeptA

This example demonstrates the preparation of a recombinant *Vibrio natriegens* organism of the invention, in this embodiment having deletions of ΔlpxL and ΔlpxM. Various methods for deleting or otherwise inactivating these genes are known to those skilled in the art.

Figure 5:
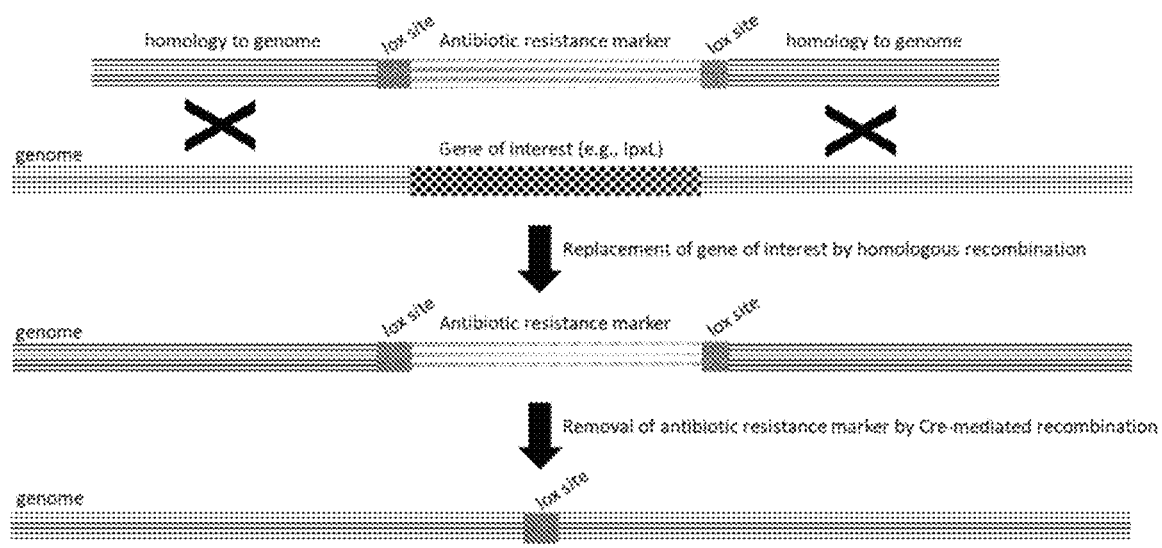
FIG. 5 is an illustration of an overview of genome engineering via natural transformation.

*Vibrio natriegens* strains were transformed with plasmid pl5a-Vc-tfoX using established electroporation or chemical transformation protocols. pl5a-Vc-tfox is a plasmid containing the pl5a origin of replication, a gene encoding the beta-lactamase protein (to confer antibiotic resistance to ampicillin and carbenicillin), and contains a copy of the *V. cholerae* tfoX gene under the control of the IPTG-inducible tac promoter. This allows inducible activation of the competence machinery and enables strain engineering via natural transformation. Briefly, cells of *V. natriegens* rendered naturally competent using known protocols were transformed with linear DNA constructs designed to delete the target genes (e.g., lpx). In one embodiment (generally depicted in FIG. 5) the construct contained an antibiotic resistance marker bounded by lox sites, flanked on either side by 3 kb of DNA homologous to the regions of the genome that are immediately upstream and downstream of the gene of interest. This construct integrates into the genome by homologous recombination, displacing the gene of interest. The antibiotic selection marker was used to distinguish transformed vs untransformed cells. Proper integration of the deletion cassette was determined by known methods such as diagnostic PCR. The antibiotic resistance marker can be removed via Cre-mediated recombination between the lox sites.

In another embodiment, deletion of these genes is performed with allelic exchange plasmids. Briefly, allelic exchange plasmids are constructed containing an origin of replication that does not replicate in *V. natriegens* (R6K), an origin of transfer (oriT) (from plasmid RP4 (a.k.a. RK2)) to enable plasmid transfer by bacterial conjugation, a negative selection marker (ccdB), and a selectable marker (chloramphenicol acyltransferase) flanked on either side by DNA (0.5-3 kb in length) that is homologous to *V. natriegens* genomic DNA that is upstream and downstream of the gene targeted for deletion. The allelic exchange plasmids can have the sequences of SEQ ID NO: 3-4. The plasmids are introduced into a conjugation-proficient *E. coli* strain (e.g., S17-1λ, pir), which can then be mobilized by conjugation into the *V. natriegens* strain. Following conjugation, cells are plated on media that only supports the growth of *V. natriegens* (to kill the *E. coli* conjugation strain) and that contains appropriate antibiotics to select for *V. natriegens* cells that took up the plasmid by conjugation. Since the plasmid is incapable of replication in *V. natriegens*, the only way *V. natriegens* cells can survive the selection is if the plasmid has integrated into the genome. The means of integration may be homologous recombination between the genome and the homologous flanking sequences on the plasmid. Double-crossover events (where the gene of interest is replaced by the selectable marker) can be identified by leveraging the negative selection cassette (ccdB) to negatively select for cells that have lost the plasmid backbone, but retain the selectable marker. The selectable marker is excised by Cre-mediated recombination, when lox recognition sites are present on either side of the marker.

Example 2: Measuring Immunogenicity of Purified Endotoxin Molecules

Various strains of *V. natriegens* and *E. coli* were selected to analyze the immunogenicity of their purified LPS molecules. For *E. coli*, we selected the commonly used TransforMax™ EPI300™ strain (Epicentre®), and a commercially available *E. coli* strain containing several gene knockouts (including ΔgutQ, ΔkdsD, Δlpx, ΔlpxM, ΔpagP, ΔlpxP, and ΔeptA, and a mutation in msbA) as a low endotoxin alternative (commercially available as ClearColi® BL21(DE3) from Lucigen®). For *V. natriegens* we selected a strain derived from the type strain of the species with ΔlpxL and ΔlpxM deletions (*V. natriegens* Δlpx, ΔlpxM) and an unmodified type strain without the deletions (*V. natriegens* wt). The type strain is defined in the International Code of Nomenclature of Bacteria and is known as the reference strain for the species, and against which subsequent strains will be compared.

LPS was purified from these strains as follows. *E. coli* strains were grown overnight at 37° C. with agitation at 200 rpm in LB-Miller media (5 g/L yeast extract, 10 g/L tryptone, 10 g/L NaCl). *V. natriegens* strains were grown overnight at 30° C. with agitation at 200 RPM in LBv2 media (LB-Miller media (5 g/L yeast extract, 10 g/L tryptone, 10 g/L NaCl) supplemented with additional 204 mM NaCl, 4.2 mM KCl, and 23.14 mM $MgCl_2$). On the following day, 1-5 ml of overnight culture was pelleted for 2 min at 17,000×g at room temperature. The supernatant was then completely removed, leaving only the wet bacterial pellet. 25 mg of each bacterial pellet was used for LPS extraction, which was performed using a commercially available LPS extraction kit according to the manufacturer's protocol (including an optional proteinase K digestion step). Samples were stored at −20° C. until further use.

Figure 6:
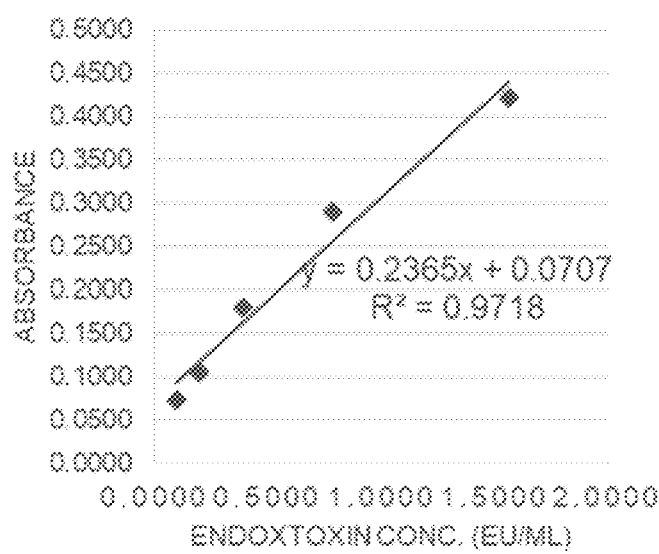
FIG. 6 provides a graph showing an example standard curve for the endotoxin assay conducted in Example 2. A linear curve is displayed.

Endotoxin-induced immunogenicity was measured using the HEK-Blue™ LPS Detection Kit (InvivoGen®) according to the manufacturer's protocol. With this kit, the presence of immune-stimulatory forms of LPS in the cell culture results in a detectable absorbance at 620-655 nm that is proportional to the amount of endotoxin present. The kit included endotoxin standard (CSE) that was used as a positive control and endotoxin-free water was used as a negative control. A standard curve was prepared from the endotoxin standard from a series of 1:2 serial dilutions (performed in duplicate and replicated on each assay plate). A series of 1:3 serial dilutions of purified LPS samples from the *E. coli* and *V. natriegens* strains were measured in duplicate. A standard curve of endotoxin concentration (EU/mL) vs. absorbance (655 nm) was plotted for the reference LPS material. A line was fit to the linear portion of the standard curve and was used to calculate the immune response of the purified LPS samples. Where the response for our samples is below or above the linear range of the standard curve, the values are presented as the highest or lowest possible values, respectively, based on the range of the standard curve. An example standard curve is shown in FIG. 6, and a linear standard curve was obtained. The endotoxin quantitation results are shown below:

TABLE 1

| Results of sample v. average endotoxin assay (EU/ml) | |
|---|---|
| wt *E. coli* | >15,000 |
| ClearColi® | 146 |
| *V. natriegens* wt | 107 |
| recombinant *V. natriegens* ΔlpxL, ΔlpxM | <0.097 |

As shown in Table 1, the recombinant *V. natriegens* of the invention gave an endotoxin assay result of only 0.097, i.e. free of endotoxin. This level was less than 1% of the unmodified (or wild type) *V. natriegens*, and less than 1% of the endotoxin reading from the commercially available, "low endotoxin" *E. coli* known as ClearColi®. It was also less than 1% of unmodified or wild type *E. coli*.

Example 3: Measuring Growth Rate of Engineered and wt Strains of *E. coli* and *V. natriegens*

The growth rates of a wt *E. coli* strain (BL21(DE3)), an LPS-engineered *E. coli* strain (ClearColi® BL21(DE3) from Lucigen®), an unmodified wt *V. natriegens* strain, and a recombinant (LPS engineered) *V. natriegens* strain of the invention (Δlpx, ΔlpxM) were determined as follows. *V. natriegens* strains were grown in LBv2 media (LB-Miller media (5 g/L yeast extract, 10 g/L tryptone, 10 g/L NaCl) supplemented with additional 204 mM NaCl, 4.2 mM KCl, and 23.14 mM $MgCl_2$), while *E. coli* strains were either grown in the recommended LB-Miller media (5 g/L yeast extract, 10 g/L tryptone, 10 g/L NaCl) or LBv2 (for comparison to *Vibrio*). Cultures grown overnight in flasks with agitation at 200 rpm to stationary phase at either 37° C. (for *E. coli*) or 30° C. (for *V. natriegens*) were re-cultured in fresh media to an OD600 of 0.1-0.3. These actively growing cultures were diluted again to an OD600 of 0.01 in their respective media, and 800 uL of each culture was added to wells of either FlowerPlate® (flower-shaped wells) or Round Well plate 48-well microtiter plates designed for use with a BioLector® I benchtop microfermentation system (m2p-labs™). The different well geometries can give rise to different growth rates, believed due to differences in sheer stress, agitation, and the rate of oxygen transfer. The cultures were grown at 30° C. at 1200 rpm with 85% humidity. Measurements of biomass (scattered light intensity), $pO_2$, and pH were recorded for all cultures at 10-minute intervals for a 12 hr period.

To determine specific growth rate, the natural logarithm was taken of all biomass measurement time points, and the slope of the linear portion from the transformation to natural log was determined. Values were calculated using the average of 5 or 6 biological replicates for the round bottom and FlowerPlates®, respectively. The error bars represent the standard deviation. The absolute growth rates are highly dependent upon the format of the experiment (e.g., growth in a microtiter plate vs. a baffled flask vs. a fermenter), but the experiment described above is useful for determining relative differences in growth rate between different strains. The growth rates are presented in FIG. 3a and in tabular form in Table 2 below:

TABLE 2

Growth data in tabular format

| Strain | Media | Growth rate (hr−1) | |
|---|---|---|---|
| | | FlowerPlate ™ | Round bottom well |
| E. coli BL21(DE3) | LB media | 0.193 | 0.597 |
| | LBv2 media | 0.471 | 0.434 |
| E. coli ClearColi ® BL21(DE3) | LB media | 0.106 | 0.16 |
| | LBv2 media | 0.089 | 0.149 |
| V. natriegens (wt) | LBv2 media | 0.758 | 0.903 |
| V. natriegens (ΔlpxL, ΔlpxM) | LBv2 media | 0.645 | 0.698 |

Figure 3A:
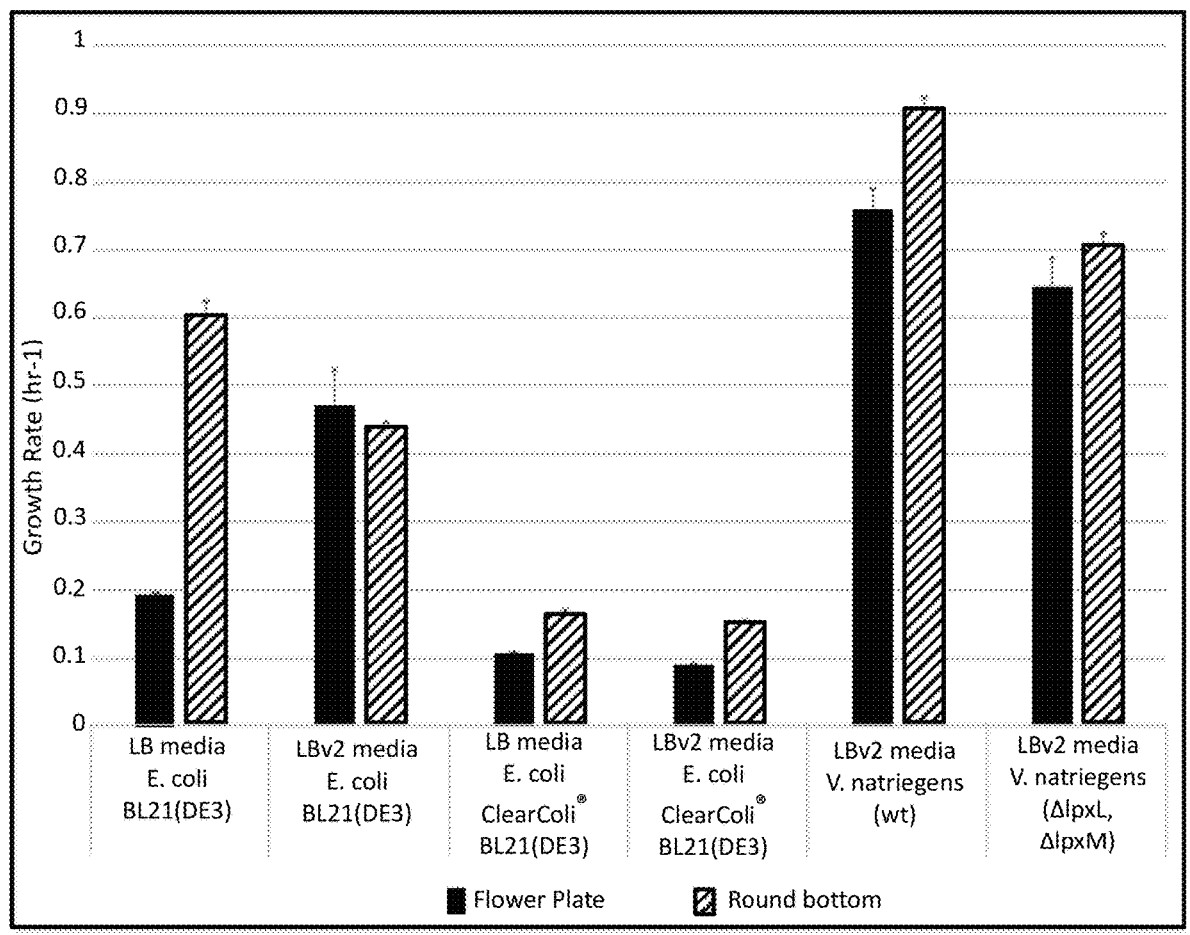
FIG. 3A-3B, FIG. 3A provides a bar graph illustrating the difference in specific growth rates of a wild type *E. coli* (BL21(DE3)), an endotoxin-reduced *E. coli* (commercially available ClearColi®), a wild type *Vibrio natriegens*, and a recombinant *Vibrio natriegens* of the invention, having a deletion of lpxL and lpxM.
Figures 3B, 4:
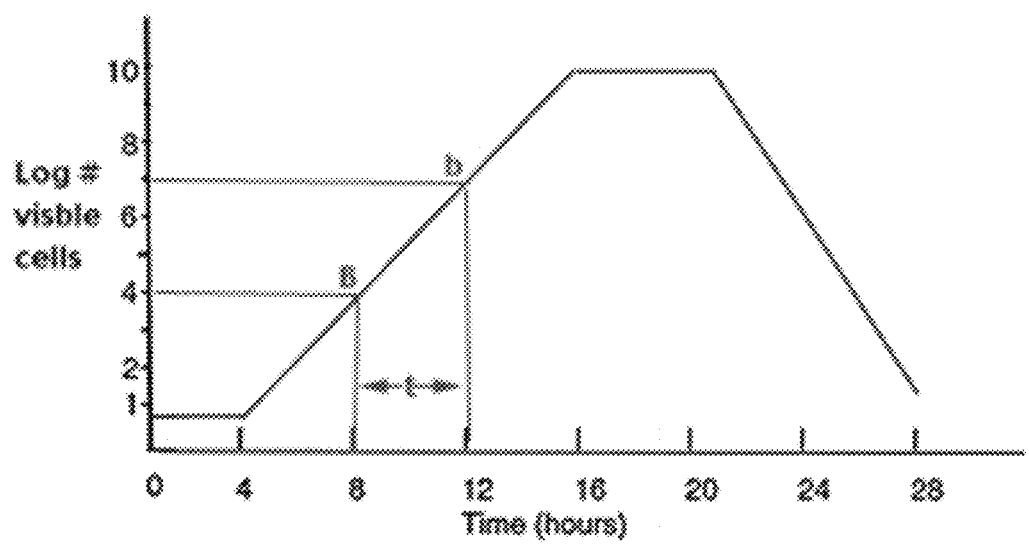
FIG. 4 is an example of calculating the growth rate of a bacterial sample and shows the exponential growth portion of the bacterial life cycle (in logarithmic format), from which readings are taken.

As illustrated in FIG. 3a and Table 2, the recombinant V. natriegens of the invention exhibited a growth rate of about 85% that of the unmodified V. natriegens organism in a FlowerPlate™ microtiter plate, and about 77.3% in a round bottom well.

The recombinant V. natriegens also exhibited a growth rate of more than 7× that of low endotoxin E. coli grown in the same media (LB(Miller) and LBv2 media) in a Flower-Plate™ microtiter plate, and more than 6× low endotoxin E. coli grown in LB media. The recombinant V. natriegens also exhibited a growth rate of more than 4.6× that of low endotoxin E. coli grown in the same media (LBv2 media) in a round bottom microtiter plate, and more than 4.3× low endotoxin E. coli grown in LB media.

Example 4—Preparation of Plasmid DNA and Single Gene Knockouts

This example shows application of the invention in an application where endotoxin contamination is of concern, which is the preparation of plasmid DNA for therapeutic or research use. This example also shows that a genetic modification or deletion to either lpxL or lpxM provides the low endotoxin benefit.

Figure 8:
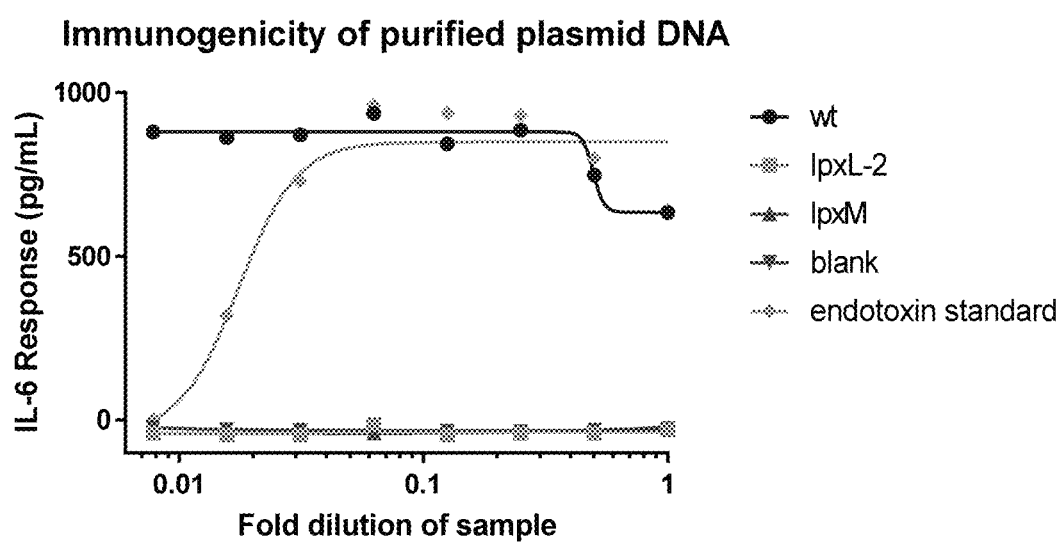
FIG. 8 is a graphical illustration showing the immunogenicity of *Vibrio* organisms having ΔlpxM and ΔlpxL deletions versus wild type organisms.

FIG. 8 shows the immunogenicity of plasmid DNA samples purified from various V. natriegens strains. Eight 1:2 serial dilutions were prepared and examined for each sample in order to measure the response across a wide range of sample concentrations. Briefly, purified plasmid preparations were prepared from bacterial cultures using QIAprep® Spin Miniprep kits (following the manufacturer's protocol) and eluted in 50 uL of the kit elution buffer. Immunogenicity of sample preps was analyzed via Monocyte Activation Test. In this test, human PBMCs isolated from human whole blood are cultured in the presence of the samples, and immunogenicity is determined by measuring the production of IL-6, a proinflammatory cytokine. IL-6 levels are determined via ELISA.

FIG. 8 shows the unmodified V. natriegens induces a strong IL-6 response across the entire dilution series. On the other hand, strains with a deletion of either lpxM or lpxL show responses that are indistinguishable from the buffer blank (negative control), demonstrating that these samples do not induce an immune response even with an undiluted plasmid preparation. A dilution series of E. coli LPS is included as an endotoxin standard (top concentration is 5 EU/mL, additional samples represent a 1:2 serial dilution series).

Example 5—Generation Time

This example provides an example of how to calculate the generation time of a bacterial population. We assume the following growth data was recorded for a bacterial population. Biomass denotes an arbitrary measurement of the amount of cells in a population, in various examples it can correspond to dry weight of cellular material, the number of cells, or the measurement of the optical density of the culture (e.g. at 600 nm), etc.).

TABLE 3

| Time (hrs) | biomass |
|---|---|
| 0.5 | 4 |
| 1 | 16 |
| 1.5 | 64 |
| 2 | 256 |
| 2.5 | 1,024 |
| 3 | 4,096 |
| 3.5 | 8,192 |
| 4 | 12,288 |
| 4.5 | 13,517 |
| 5 | 13,600 |

Figure 7A:
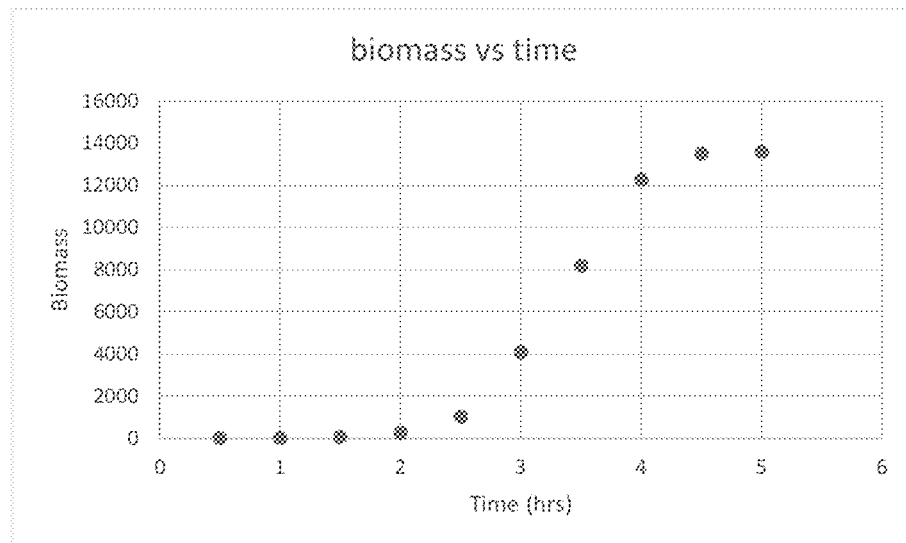
FIG. 7A-7C, FIG. 7A is a graphical illustration of a biomass v. time curve showing exponential growth.
Figure 7B:
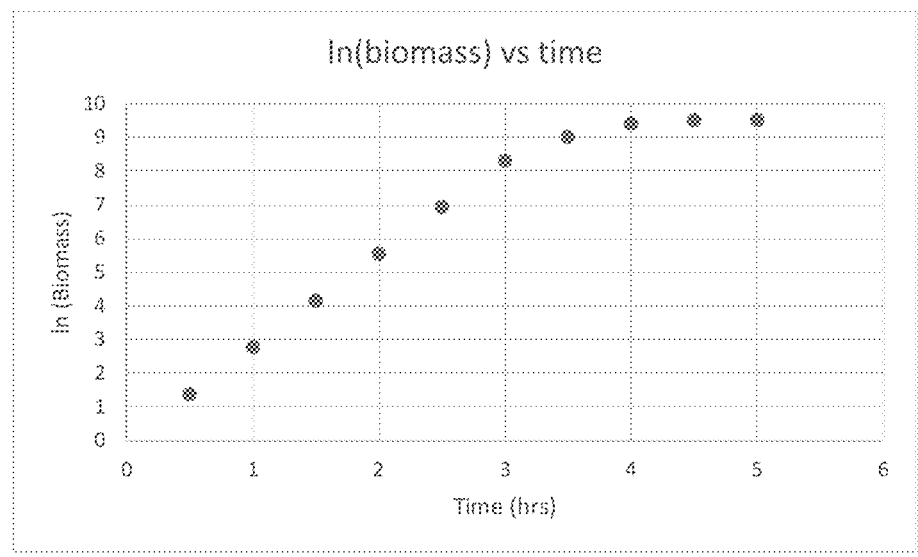
Figure 7C:
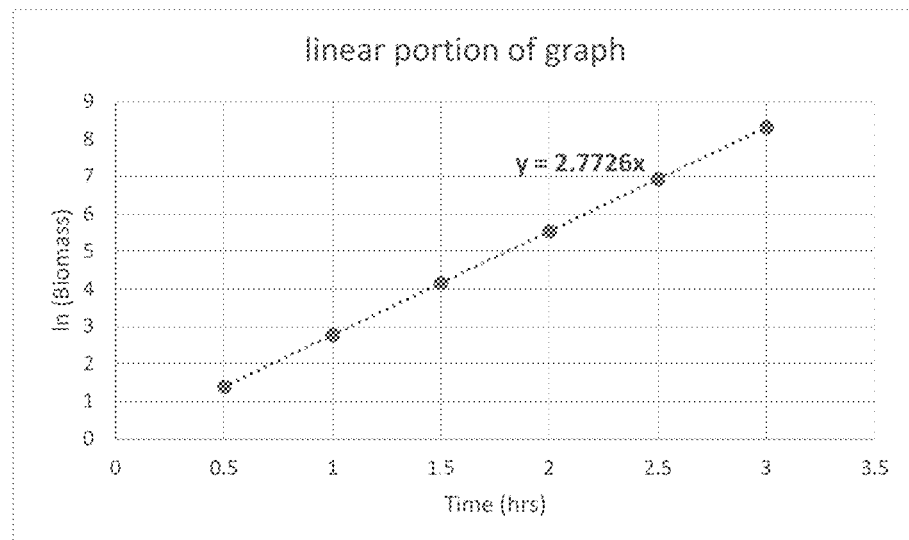

These data are plotted, giving the graph illustrated in FIG. 7a. A natural log transformation of the biomass measurements is performed and gives rise to the semi-log graph of FIG. 7b. The linear portion of the graph is identified, and a line is fit to the data, as shown in FIG. 7c. The resulting line has the formula y=2.7726x, where 2.7726 is the slope of the line. This value (2.7726) corresponds to the specific growth rate, and has units of $(hr^{-1})$ (per hour). The specific growth rate can be converted to doubling time (hours/doubling) by using the following mathematical relationship:

$$G=\ln(2)/SGR$$

where G corresponds to the doubling time, and SGR corresponds to the specific growth rate. Performing this calculation with the data:

$$G=\ln(2)/2.7726=0.249999 \text{ hours/doubling}$$

Although the invention has been described with reference to the above examples, it will be understood that modifications and variations are encompassed within the spirit and scope of the invention. Accordingly, the invention is limited only by the following claims.

The invention claimed is:

1. A recombinant *Vibrio natriegens* organism comprising:
a deletion, inactivation, or disruption of the lpxL gene or the lpxM gene,
wherein the organism produces substantially less endotoxin compared to a corresponding organism not comprising the deletion, inactivation, or disruption and cultivated under the same conditions;
wherein the recombinant *Vibrio natriegens* organism exhibits a growth rate of at least 60% of the growth rate of the corresponding organism when cultivated under the same conditions; and
wherein the organism has an endotoxin level of less than 50 EU/ml of purified lipopolysaccharide.

2. The *Vibrio* sp. organism of claim 1, wherein the organism has an outer membrane comprising a modified lipopolysaccharide component.

3. The *Vibrio* sp. organism of claim 1, wherein the organism does not comprise a deletion, inactivation, or disruption in any gene selected from the group consisting of gutQ, kdsD, pagP, and lpxP.

4. The *Vibrio natriegens* organism of claim 1, having a growth rate of at least 70% the growth rate of a corresponding unmodified *Vibrio natriegens* organism under identical conditions.

5. The *Vibrio natriegens* organism of claim 1, having an average endotoxin level of less than 1 EU/ml measured in an in vitro assay.

6. The *Vibrio natriegens* organism of claim 1, having a doubling time of 55-70 minutes at 30° C.

7. The *Vibrio natriegens* organism of claim 1, wherein the growth rate is measured over a period of 8 hours.

8. The *Vibrio natriegens* organism of claim 1, wherein the growth rate is measured over a period of 12 hours.

9. The *Vibrio natriegens* organism of claim 2, wherein the organism has a growth rate of at least 60% the growth rate of a wild type *Vibrio natriegens* under the same growth conditions, and has an endotoxin level of less than 10 EU/ml, and a specific growth rate of at least 0.60 at 30° C. in LBv2 media.

10. The *Vibrio natriegens* organism of claim 1, wherein the organism comprises an exogenous nucleic acid for the production of the exogenous nucleic acid or for the production of an encoded heterologous protein or peptide.

11. The recombinant *Vibrio natriegens* organism of claim 1, having an endotoxin level of less than 10 EU/ml measured in an in vitro assay.

12. The recombinant *Vibrio natriegens* organism of claim 11, wherein the organism exhibits a growth rate of at least 80% of the growth rate of the corresponding organism when cultivated under the same conditions.

13. The recombinant *Vibrio natriegens* organism of claim 12, having an endotoxin level of less than 1 EU/ml measured in an in vitro assay.

14. A kit comprising a recombinant *Vibrio natriegens* organism of claim 1.

15. The kit of claim 14, further comprising a vector for cloning a nucleic acid sequence or for expressing a protein or peptide.

16. The kit of claim 14, further comprising a positive control vector for verifying transformation.

17. The kit of claim 14, further comprising a growth medium for the recombinant *Vibrio natriegens* organism.

* * * * *